US012778965B2

(12) United States Patent
Gius et al.

(10) Patent No.: US 12,778,965 B2
(45) Date of Patent: Nov. 3, 2026

(54) COMBINATION CANCER THERAPY WITH PENTAAZA MACROCYCLIC RING COMPLEX AND HORMONE THERAPY AGENT

(71) Applicants: Biossil Inc., Toronto (CA); Northwestern University, Evanston, IL (US)

(72) Inventors: David R. Gius, Chicago, IL (US); Robert A. Beardsley, University City, MO (US); Jon Holmlund, Carlsbad, CA (US); Jeffery L. Keene, St. Louis, MO (US)

(73) Assignees: Biossil Inc., Toronto (CA); Northwestern University, Evanston, OH (US)

( * ) Notice: Subject to any disclaimer, the term of this patent is extended or adjusted under 35 U.S.C. 154(b) by 713 days.

(21) Appl. No.: 18/072,223

(22) Filed: Nov. 30, 2022

(65) Prior Publication Data

US 2023/0158042 A1 May 25, 2023

Related U.S. Application Data

(63) Continuation of application No. PCT/US2021/035460, filed on Jun. 2, 2021.

(60) Provisional application No. 63/033,559, filed on Jun. 2, 2020.

(51) Int. Cl.

| | |
|---|---|
| ***C01G 45/00*** | (2025.01) |
| ***A61K 31/555*** | (2006.01) |
| ***A61K 45/06*** | (2006.01) |
| ***A61P 35/00*** | (2006.01) |
| ***G01N 33/575*** | (2026.01) |

(52) U.S. Cl.
CPC ............ *A61K 31/555* (2013.01); *A61K 45/06* (2013.01); *A61P 35/00* (2018.01); *G01N 33/575* (2026.01); *G01N 2800/7028* (2013.01)

(58) Field of Classification Search
CPC ...................................................... C01G 45/00
USPC .......................................................... 556/45
See application file for complete search history.

(56) References Cited

U.S. PATENT DOCUMENTS

| | | | |
|---|---|---|---|
| 3,930,867 | A | 1/1976 | Bigelow |
| 4,001,212 | A | 1/1977 | Richman |
| 4,702,998 | A | 10/1987 | Tanaka et al. |
| 5,096,724 | A | 3/1992 | Zenner et al. |
| 5,610,293 | A | 3/1997 | Riley et al. |
| 5,624,677 | A | 4/1997 | El-Rashidy et al. |
| 5,637,578 | A | 6/1997 | Riley et al. |
| 5,874,421 | A | 2/1999 | Riley et al. |
| 5,976,498 | A | 11/1999 | Newumann et al. |
| 6,040,330 | A | 3/2000 | Hausheer et al. |
| 6,084,093 | A | 7/2000 | Riley et al. |
| 6,177,419 | B1 | 1/2001 | Campbell et al. |
| 6,180,620 | B1 | 1/2001 | Salvemini |
| 6,204,259 | B1 | 3/2001 | Riley et al. |
| 6,214,817 | B1 | 4/2001 | Riley et al. |
| 6,245,758 | B1 | 6/2001 | Stern et al. |
| 6,395,725 | B1 | 5/2002 | Salvemini |
| 6,525,041 | B1 | 2/2003 | Neumann et al. |
| 6,552,010 | B1 | 4/2003 | Bernstein |
| 6,552,040 | B1 | 4/2003 | Bernstein |
| 6,781,231 | B2 | 8/2004 | Minervini |
| 6,916,799 | B2 | 7/2005 | Fridovich et al. |
| 7,102,214 | B1 | 9/2006 | Miks et al. |
| 7,166,910 | B2 | 1/2007 | Minervini |
| 7,242,089 | B2 | 7/2007 | Minervini |
| 7,407,645 | B2 | 8/2008 | Neumann et al. |
| 7,445,641 | B1 | 11/2008 | Omberg et al. |

(Continued)

FOREIGN PATENT DOCUMENTS

| | | |
|---|---|---|
| CN | 1215919 | 5/1999 |
| CN | 2870352 | 2/2007 |

(Continued)

OTHER PUBLICATIONS

Jordan, V. C. Nature Reviews: Drug Discovery, 2, 2003, 205.*

(Continued)

*Primary Examiner* — Douglas M Willis

(74) *Attorney, Agent, or Firm* — Bryan Cave Leighton Paisner LLP

(57) ABSTRACT

A method of treating a cancer in a mammalian subject, where the cancer has multi-therapy resistance, comprises administering to the mammalian subject a therapeutically effective amount of a pentaaza macrocyclic ring complex corresponding to the Formula (I) below, optionally with administration of a further anti-cancer therapy.

(I)

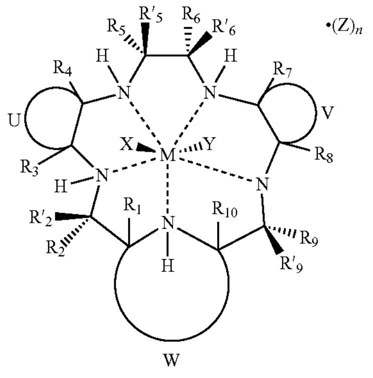

11 Claims, 53 Drawing Sheets

(56) References Cited

U.S. PATENT DOCUMENTS

| | | | |
|---|---|---|---|
| 7,981,421 | B2 | 7/2011 | Zhou et al. |
| 8,263,568 | B2 | 9/2012 | Slomczynska et al. |
| 8,444,856 | B2 | 5/2013 | Slomczynska et al. |
| 8,486,928 | B2 | 7/2013 | Riley |
| 8,808,545 | B2 | 8/2014 | Slomczynska et al. |
| 9,149,483 | B2 | 10/2015 | Keene et al. |
| 9,150,837 | B2 | 10/2015 | Salvemini et al. |
| 9,198,893 | B2 | 12/2015 | Keene et al. |
| 9,353,069 | B2 | 5/2016 | Riley |
| 9,642,861 | B2 | 5/2017 | Rothstein et al. |
| 9,738,669 | B2 | 8/2017 | Keene et al. |
| 9,738,670 | B2 | 8/2017 | Keene et al. |
| 9,855,279 | B2 | 1/2018 | Rothstein et al. |
| 10,137,133 | B2 | 11/2018 | Keene et al. |
| 10,350,193 | B2 | 7/2019 | Riley |
| 10,493,081 | B2 | 12/2019 | Keene et al. |
| 10,597,415 | B2 | 3/2020 | Keene et al. |
| 10,610,533 | B2 | 4/2020 | Rothstein et al. |
| 11,066,433 | B2 | 7/2021 | Keene et al. |
| 11,219,614 | B2 | 1/2022 | Beardsley et al. |
| 11,246,950 | B2 | 2/2022 | Beardsley et al. |
| 11,612,608 | B2 | 3/2023 | Rothstein et al. |
| 11,826,373 | B2 | 11/2023 | Keene et al. |
| 12,077,549 | B2 | 9/2024 | Keene et al. |
| 2002/0072512 | A1 | 6/2002 | Salvemini |
| 2002/0128248 | A1 | 9/2002 | Salvemini |
| 2003/0050297 | A1 | 3/2003 | Crapo |
| 2004/0132706 | A1 | 7/2004 | Salvemini |
| 2004/0219138 | A1 | 11/2004 | Salvemini |
| 2005/0101581 | A1 | 5/2005 | Reading et al. |
| 2005/0171198 | A1 | 8/2005 | Salvemini |
| 2005/0175580 | A1 | 8/2005 | Salvemini |
| 2005/0222250 | A1 | 10/2005 | Rezvani |
| 2006/0081994 | A1 | 4/2006 | Craig et al. |
| 2006/0089710 | A1 | 4/2006 | Ornberg et al. |
| 2006/0140953 | A1 | 6/2006 | Newell et al. |
| 2006/0199792 | A1 | 9/2006 | Groves et al. |
| 2006/0223808 | A1 | 10/2006 | Chackalamannil et al. |
| 2007/0148154 | A1 | 6/2007 | Weill et al. |
| 2008/0161324 | A1 | 7/2008 | Johansen et al. |
| 2008/0166000 | A1 | 7/2008 | Hsiao |
| 2008/0269185 | A1 | 10/2008 | Rothstein et al. |
| 2008/0318917 | A1 | 12/2008 | Salvemini et al. |
| 2009/0131377 | A1 | 5/2009 | Salvemini |
| 2009/0221622 | A1 | 9/2009 | Teja et al. |
| 2009/0257979 | A1 | 10/2009 | Beigelman et al. |
| 2010/0304415 | A1 | 12/2010 | Slomczynska et al. |
| 2011/0136756 | A1 | 6/2011 | Keene et al. |
| 2013/0079317 | A1 | 3/2013 | Keene et al. |
| 2014/0142065 | A1 | 5/2014 | Che et al. |
| 2017/0044193 | A1 | 2/2017 | Keene et al. |
| 2018/0042381 | A1 | 2/2018 | Grace |
| 2018/0237462 | A1 | 8/2018 | Keene et al. |
| 2019/0151331 | A1 | 5/2019 | Beardsley et al. |
| 2019/0209524 | A1 | 7/2019 | Beardsley et al. |
| 2019/0350867 | A1 | 11/2019 | Hahn |
| 2020/0000793 | A1 | 1/2020 | Falo et al. |
| 2020/0215077 | A1 | 7/2020 | Rothstein et al. |
| 2020/0376148 | A1 | 12/2020 | Beardsley et al. |
| 2021/0338686 | A1 | 11/2021 | Keene et al. |
| 2021/0347796 | A1 | 11/2021 | Keene et al. |
| 2021/0361701 | A1 | 11/2021 | Keene et al. |
| 2022/0088030 | A1 | 3/2022 | Keene et al. |
| 2022/0118119 | A1 | 4/2022 | Beardsley et al. |
| 2023/0149358 | A1 | 5/2023 | Gius et al. |

FOREIGN PATENT DOCUMENTS

| | | | |
|---|---|---|---|
| CN | 103906756 | | 7/2014 |
| CN | 108350009 | A | 7/2018 |
| CN | 109414454 | A | 3/2019 |
| CN | 110769837 | A | 2/2020 |
| EA | 010834 | | 12/2008 |
| EP | 0524161 | | 1/1993 |
| EP | 0598753 | | 3/1998 |
| EP | 2760874 | | 8/2014 |
| EP | 3388082 | | 10/2018 |
| JP | H06509566 | | 10/1994 |
| JP | 1996040941 | | 2/1996 |
| JP | 2002506445 | | 2/2002 |
| JP | 2002534382 | | 10/2002 |
| JP | 2003509423 | | 3/2003 |
| JP | 2004507487 | | 3/2004 |
| JP | 2004517113 | | 6/2004 |
| JP | 2011513333 | | 4/2011 |
| JP | 2011516610 | | 5/2011 |
| JP | 2014526562 | | 10/2014 |
| JP | 2018500347 | | 1/2018 |
| JP | 2018193302 | | 12/2018 |
| RU | 2313368 | | 9/2011 |
| WO | 1991010645 | | 7/1991 |
| WO | 1993002090 | | 2/1993 |
| WO | 1994015925 | | 7/1994 |
| WO | 95028968 | | 11/1995 |
| WO | 1996039396 | | 12/1996 |
| WO | 97006830 | | 2/1997 |
| WO | 98058636 | | 12/1998 |
| WO | 00072893 | | 12/2000 |
| WO | 01019823 | | 3/2001 |
| WO | 200158458 | | 8/2001 |
| WO | 2002053142 | | 7/2002 |
| WO | 2002058686 | | 8/2002 |
| WO | 2002071054 | | 9/2002 |
| WO | 2002100395 | | 12/2002 |
| WO | 2003024434 | | 3/2003 |
| WO | 2005042718 | | 5/2005 |
| WO | 2005060976 | | 7/2005 |
| WO | 2006078713 | | 7/2006 |
| WO | 2006083508 | | 8/2006 |
| WO | 2007139897 | | 12/2007 |
| WO | 2008027547 | | 3/2008 |
| WO | 2008045559 | | 4/2008 |
| WO | 2009111294 | | 9/2009 |
| WO | 2009134616 | | 11/2009 |
| WO | 2009143454 | | 11/2009 |
| WO | 2011113019 | | 9/2011 |
| WO | 2013048965 | | 4/2013 |
| WO | 2016102543 | | 6/2016 |
| WO | 2017025496 | A1 | 2/2017 |
| WO | 2017027728 | | 2/2017 |
| WO | 2017192740 | | 11/2017 |
| WO | 2018191676 | | 10/2018 |
| WO | 2019152661 | A1 | 8/2019 |
| WO | 2024026273 | | 2/2024 |

OTHER PUBLICATIONS

El-Mahdy, et al. Free Radical Biology & Medicine, 160, 2020, 630-642.*

Dörwald, F. Zaragoza. Side Reactions in Organic Synthesis: A Guide to Successful Synthesis Design, Weinheim: WILEY-VCH Verlag Gmbh & Co. KGaA, 2005, Preface.*

Hackam, et al. JAMA, 296(14), 2006, 1731-1732.*

Wagner, B. A., et al., Myeloperoxidase is involved in H2O2-induced apoptosis of HL-60 human leukemia cells, J. Biol. Chem, 2000, 272(29), 22461-9.

Chen, Q., et al., Pharmacologic ascorbic acid concentrations selectively kill cancer cells: action as a pro-drug to deliver hydrogen peroxide to tissues, PNAS, 2005, 102(38), 13604-9.

Rodriguez, et al., Mitochondrial or cytosolic catalase reverses the MnSOD-dependent inhibition of proliferation by enhancing respiratory chain activity, net ATP production, and decreasing the steady state levels of H2O2, Free Rad. Bio. & Med.

Alexandre, J., et al., Novel Action of Paclitaxel against Cancer Cells: Bystander Effect Mediated by Reactive Oxygen Species, Cancer Research, 2007, 67(8), 3512-3517.

Muscoli, C., et al., On the selectivity of superoxide dismutase mimetics and its importance in pharmacological studies, British Journal of Pharmacology, 2003, 140(3), 445-460.

Sawyer, D. T. et al., How super is superoxide?, Acc. Chem. Res., 1981, 14, 393-400.

(56) References Cited

OTHER PUBLICATIONS

Li, S., et al., The Role of Cellular Glutathione Peroxidase Redox Regulation in the Suppression of Tumor Cell Growth by Manganese Superoxide Dismutase, Cancer Res., 2000, 60(14), 3927-3939.

Buettner, G. R., et al., A New Paradigm: Manganese Superoxide Dismutase Influences the Production of H2O2 in Cells and Thereby Their Biological State, Free Radical Biology and Medicine, 2006, 41(8), 1338-50.

Day, B. J., Catalase and glutathione peroxidase mimics, Biochem Pharmacol, 2009, 77(3), 285-296.

Day, B. J. et al., Manganic Porphyrins Possess Catalase Activity and Protect Endothelial Cells against Hydrogen Peroxide-Mediated Injury, Arch. Biochem. & Biophysics, 1997, 347(2), 256-262.

Oberley, L. W., Mechanism of the tumor suppressive effect of MnSOD overexpression, Biomedicine & Pharmacotherapy, 2005, 59, 143-48 Mar. 19, 2005.

Rocklage et al., Manganese(II) N ,N'-Dipyridoxylethylenediamine-N , N'-diacetate 5,5'-Bis(phosphate). Synthesis and Characterization of a Paramagnetic Chelate for Magnetic Resonance Imaging Enhancement, Inorg. Chem., 1989, 28, 477-485 Sep. 29, 1988.

European Patent Office, Extended Search Report issued for 12835035.2, dated Mar. 9, 2015.

Masini et al., Prevention of antigen-induced early obstruction reaction by inhaled M40419 in actively sensitized guinea-pigs, American Journal of Respiratory and Critical Case Medicine, American Lung Associations, New York, NY, Jan. 1, 2002.

Mccarthy, A., Metaphore Pharmaceuticals, Chemistry & Biology, 2003, 10(12): 1139-1140.

Macarthur et al., Modulation of serum cytokine levels by a novel superoxide dismutase mimetic, M40401, in an *Escherichia coli* model of septic shock: Correlation with preserved circulating catecholamines, Crit. Care Med., 2003, 31(1): 237245.

Aston et al., Computer-Aided Design (CAD) of Mn(II) Complexes: Superoxide Dismutase Mimetics with Catalytic Activity Exceeding the Native Enzyme, Inorg. Chem., 2001, 40: 1779-1789.

Salvemini et al., Nonpeptidyl mimetics of superoxide dismutase in clinical therapies for diseases, Cell and Mol Life Sci, 2000, 57: 1489-1492.

Macarthur et al., Inactivation of catecholamines by superoxide gives new insights on the pathogenesis of septic shock, PNAS, 2000, 97(17): 9753-9758.

Riley, P.A., Free radicals in biology: oxidative stress and the effects of ionizing radiation, Int. J. Radiat. Biol, 1994, 65 (1): 27-33.

Shimizu et al., Neurprotection against hypoxia-ischemia in neonatal rat brain by novel superoxide dismutase mimetics, Neuroscience Letters, 2003, 346: 41-44.

Fike et al., Reactive oxygen species from NADPH oxidase contribute to altered pulmonary vascular responses in piglets with chronic hypoxia-induced pulmonary hypertension, 2008, 295(5): L881-L888.

Batinic-Haberle et al., The ortho effect makes manganese(III) meso-tetrakis(N-methylpyridinium-2-yl)porphyrin a powerful and potentially useful superoxide dismutase mimic, J Biol Chem, 1998, 273: 24521-24528.

Batinic-Haberle et al., Pure MnTBAP selectively scavenges peroxynitrite over superoxide: , Free Radic Biol Med, 2009, 46:192-201.

Day et al., Metalloporphyrins are potent inhibitors of lipid peroxidation, Free Radic Biol Med, 1999, 26: 730-736.

Day et al., A metalloporphyrin superoxide dismutase mimetic protects against paraquat-induced endothelial cell injury, in vitro, J Pharmacol Exp Ther, 1995, 275: 1227-1232.

Ferrer-Sueta et al., Reactions of Manganese Porphyrins with Peroxynitrite and Carbonate Radical Anion, J Biol Chem, 2003, 278: 27432-27438.

Kachadourian et al., Flavin-dependent antioxidant properties of a new series of meso-N,N'-dialkyl-imidazolium substituted manganese(III) porphyrins, Biochem Pharmacol, 2004, 67:77-85.

Szabo et al., Evaluation of the relative contribution of nitric oxide and peroxynitrite to the suppression of mitochondrial respiration in immunostimulated macrophages using a manganese, FEBS Letters, 1996, 381:82-86.

Thompson et al., The manganese superoxide dismutase mimetic, M40403, protects adult mice from lethal total body irradiation, Free Radical Research, 2010; 44(5): 529-540.

Tuder et al., Oxidative stree and apoptosis interative and cause emphsema due to vascular endothelial growth factor receptor blockade, Am. J. Respir. Cell Mol. Biol., 2003, 29: 88-97.

Patent Cooperation Treaty, International Search Report issued for PCT/US2012/056921 on Feb. 22, 2013, 5 pages.

Simic et al., Oxygen radicals in biology and medicine, Basic Life Sciences, 1988, vol. 49, Plenum Press, New York and London.

Weiss et al., Catalytic Efficacies of agents that dismutate superoxide, 1991, J. Cell, Biochem, Suppl. 15C, 216 Abstract C110.

Petkau, Scientific basis for the clinical use of superoxide dismutase, 1986, Cancer Treat. Rev. 13, 17.

Mccord, Superoxide dismutase: Rationale for use in ruperfusion injury and inflammation, 1986, J. Free Radicals Biol. Med, 2, 307.

Palmer et al., Nitric oxide release accounts for the biological activity of endothelium derived relaxing factor, 1987, Nature, 327, 523-526.

Riley et al., Structure-activity studies and the design of synthetic superoxide dismutase (SOD) mimetics as therapeutics, 2006, Advances in Inorganic Chemistry, 59, 233-263.

Riley et al., Synthesis, characterization, and stability of manganese(II) C-Substituted 1, 4, 7, 10, 12-Pentaazacyclopentadecane complexes exhibity superoxide dismutase activity, J. Inorg. Chem. 1996, 35: 5213-5231.

Riley et al., Toward the rational design of superoxide dismutase mimics: mechanistic studies for the elucidation of substituent effects on the catalytic activity of macrocyclic manganese(II) complexes, JACS, 1997, 119(28): 6522-6528.

Salvemini et al., M40403: Superoxied dismutase mimic, Drugs of the Future, 2000, 25(10): 1027-1033.

Salvemini et al., SOD Mimetics are coming of age, Nature Reviews, 2002, 1: 367-374.

Aykin-Burns et al., Increased levels of superoxide and H2O2 mediate the differential susceptibility of cancer cells versus normal cells to glucose deprivation, Biochem. J., 2009, 418: 29-37 2009.

Fretland et al., Superoxide Dismutase (SOD) Modulates Acetic Acid-Induced Colitis in Rodents, Gastroenterology, 1991, 100: A581 1991.

Gryglewski et al., Superoxide Anion is involved in the breakdown of Endothelium-Derived Vascular Relaxing Factor, Nature, 1986, 320: 454-456 1986.

Bannister et al., Aspects of the structure, function, and applications of Superoxide Dismutase, CRC Critical Reviews in Biochemistry, 1987, 22(2): 111-180 1987.

Newton et al., Synthesis and characterization of the Mn(II) complexof [15]aneN.sub.5, J. Coord. Chem., 1988, 19: 265-277 1988.

Bradshaw et al., A simple crab-like cyclization procedure to prepare polyaza-crowns and cyclams with one or two unsubstitute macroring Nitrogen atoms or with a Hydroxy group, J. Heterocyclic Chem, 1989, 26: 1431-1435 1989.

Krakowiak et al., Preparation of Triaza-, Tetraaza- and Peraza-Crown Compounds containing Aminoalkyl Side Groups or Unsubstituted Rin Nitrogen Atoms, J. Org. Chem, 1990, 55(10): 3364-3368 1990.

Riley et al., Stopped-flow Kinetic Analysis for Monitoring superoxide decay in aqueous systems, Analytical Biochemistry, 1991, 196: 344-349 1991.

Kurosawa et al., Cytotoxicity induced by inhibition of thioredoxin reductases via multiple signaling pathways: Role of cytosolic phospholipase A2alpha-dependent and -independent release of arachidonic acid, Journal of Cell Physiology, 219(3): 606-616 2009.

Li et al., Auranofin-mediated inhibition of PI3K/AKT/mTOR axis and anticancer activity in non-small cell lung cancer cells. Oncotarget, 7(3): 3548-3558 2016.

Meng, et al. "Potentiation of Endogenous Nitric Oxide With Superoxide Dismutase Inhibits Platelet-Mediated Thrombosis in Injured and Stenotic Arteries," JACC vol. 25, No. Jan. 1, 1995:269-75.

(56) References Cited

OTHER PUBLICATIONS

Black, et al. "Inhibition of in vivo myocardial ischemic and reperfusion injury by a synthetic manganese-based superoxide dismutase mimetic," Journal of Pharmacology and Experimental Therapeutics, Sep. 1994, 270 (3) 1208-1215.
Dennis, et al. "NADPH oxidases and reactive oxygen species at different stages of chronic hypoxia-induced pulmonary hypertension in newborn piglets," Am J Physiol Lung Cell Mol Physiol 297: L596-L607, 2009.
Cuzzocrea, et al. "Superoxide: a key player in hypertension," FASEB Journal vol. Jan. 18, 2004 pp. 94-101.
Wang, et al. "Blockade of Phencyclidine-Induced Cortical Apoptosis and Deficits in Prepulse Inhibition by M40403, a Superoxide Dismutase Mimetic," JPET, vol. 304, No. 1 pp. 266-272.
Sosman & Mier, "Biological drug duo delivers one-two tumor punch," Nature Medicine, vol. 9, No. 6, Jun. 2003 pp. 649-650.
Adringa, et al. "SOD mimics as adjuvants to chemotherapy protocols involving Adriamycin," Oxygen Society Meeting, San Antonio, TX Nov. 2002.
Coppey, et al. "Effect of M40403 treatment of diabetic rats on endoneurial blood flow, motor nerve conduction velocity and vacular function of epineurial arterioles of the sciatic nerve," British Journal of Pharmacology (2001) 134, 21-29.
GEMZAR product Sheet 1996.
Raj et al., Selective killing of cancer cells by a small molecule targeting the stress response to ROS, Nature, 475: 231-234 2016.
Tuder et al., Oxidative Stress and Apoptosis Interact and Cause Emphysema Due to Vascular Endothelial Growth Factor Receptor Blockade, Am. J. Respir. Cell Mol. Biol., 2003, 29: 88-97.
Murphy et al., Efficacy of Superoxide Dismutase Mimetic M40403 in Attenuating Radiation-Induced Oral Mucositis in Hamsters, Clin Cancer Res, 2008, 14(13): 4292-4297.
Salvemini et al., A nonpeptidyl mimic of superoxide dismutase with therapeutic activity in rats, Science, 1999, 286: 304-306.
Bannister et al., Aspects of the structure, function, and applications of superoxide dismutase, 1987, Crit. Rev. Biochem., 22, 111.
Gryglewski et al., Superoxide anion is involved in the breakdown of endothelium-derived vascular relaxing factor, 1986, Nature, 320, 454-456.
Samlowski et al., A nonpeptidyl mimic of superoxide dismutase, M40403, inhibits does-limiting hyptension associated with interleukin-2 and increases its antitumor effects, 2003, Nature Medicine, 9, 750-755.
Weiss et al., Catalytic efficacies of agents that dismutate superoxide, J. Cell. Biochem., 1991, Supplement 15C: 216 1991.
Keene, J. L., Declaration under 37 C.F.R. 1.132 May 14, 2014.
Mapuskar, et al. Mitochondrial Superoxide Dismutase in Cisplatin-Induced Kidney Injury, Antioxidants 2021, 10, 1329 16 pages.
Fike, et al. "Reactive oxygen species from NADPH oxidase contribute to altered pulmonary vascular responses in piglets with chronic hypoxia-induced pulmonary hypertension," Am J Physiol Lung Cell Mol Physiol 295: L881-L888, 2008.
Ansel, et al. Pharmaceutical Dosage Forms and Drug Delivery Systems, Published by Lippincott Williams & Wilkins p. 48-5.
Vaidya et al., Kidney Injury Molecule-1 Outperforms Traditional Biomarkers of Kidney Injury in Multi-Site Preclinical Biomarker Qualification Studies, Nat. Biotechnol, 28(5), 478-485 2010.
Miller et al., Mechanisms of Cisplatin Nephrotoxicity, Toxins, 2, 2490-2518 2010.
Kurtin, S., Myeloid Toxicity of Cancer Treatment, J. Adv. Pract. Oncol., 3(4), 209-224 2012.
Sishc et al. The superoxide dismutase mimetic GC4419 enhances tumor killing when combined with stereotactic ablative radiation, BioRxiv, , doi.org/10.1101/2020.03.10.8443 2020.
Kasten et al., Potentiation of Nitric Oxide-Mediated Vascular Relaxation by SC52608, a Superoxide Dismustas Mimic, 1995.
Patent Cooperation Treaty, International Search Report for PCT/US2018/027588, 5 pages Aug. 27, 2018.
Park et al., Synthesis and SOD activity of manganese complexes of pentaaza macrocycles containing amino-and guanidino-auxiliary, Bulletin of the Korean Chemical Society, 32(10): 3787-3789 2011.
Patent Cooperation Treaty, International Search Report for PCT/US2018/018407, 6 pages Sep. 17, 2018.
Tabata et al., Ion-Pair Extraction of Metalloporphyrins into Acetonitrile for Determination of Copper(II), Anal. Chem., 68: 758-762 1996.
Mazzucotelli, et al., Determination of trace amounts of Metalloprotein Species in Marine Mussel Samples by High Performance Liquid Chromatography with Inductively Coupled Plasma Atomic Emission Spectrometric Detection, Analyst., 116: 605-608 1991.
Furuya et al., Determination of Pheophytinatoiron(III) Chlorides by Reverse Phase High Performance Liquid Chromatography, Analytical Sciences, 3: 353-357 1987.
Zhang et al., Quantitative determination of SC-68328 in dog plasma using flow injection and tandem mass spectroscopy, Journal of Mass Spectrometry, 35(3): 354-360 2000.
Sakai et al., Liquid-Chromatographic Separation and Determination of Coproporphyrins I & III in Urine, Clinical Chemistry, 29(2): 350-353 1983.
Riley, Functional Mimics of Supeoxide Dismutase Enzymes and Therapeutic Agents, Chem. Rev., 2572-2587 1999.
Berge et al., Pharmaceutical Salts, J. Pharm. Sci., 66: 1-19 1977.
European Patent Office, European Search Report issued for EP 10179542, 4 pages Aug. 5, 2011.
Patent Cooperation Treaty, International Search Report for PCT/US2017/049960, 5pgs. Feb. 21, 2019.
Fritz et al., Intravenous vitamin C and cancer: A systematic review, Integrative Cancer Therapies, 13(4): 280-300 2014.
Mcconnell et al., Ascorbate combination therapy: New tool in the anticancer toolbox?, Science Translational Medicine, 6(222): 1-3 2014.
European Patent Office, Extended European Search Report for 16835928.9, publication 3334744, 10 pgs. Feb. 4, 2019.
Cornwell et al., Glyceryl monocaprylate/caprate as a moderate skin penetration enhancer, International Journal of Pharmaceutics, 171: 243-255 1998.
Patent Cooperation Treaty, International Search Report for PCT/US2019/016071, 4pgs. May 14, 2019.
Mapuskar et al., Mitochondrial Superoxide Increases Age-Associated Susceptability of Human Dermal Fibroblasts to Radiation and Chemotherapy, Cancer Research, 77(18): 5054-5067 2017.
Eurasian Patent Office, Search Report for 201892510, 1 page May 28, 2019.
European Patent Office, Extended Search Report for EP App. 18215666.1, 12 pages Jul. 19, 2019.
Di Paolo et al., Reduced development of experimental periodontitis by treatment with M40403, a superoxide dismutase mimetic, European Journal of Pharmacology, 51: 151-157 2005.
Mcfadden et al., M40403, a superoxide dismutase mimetic, protects cochlear hair cells from gentamicin, but not cisplatin toxicity, Toxicology and Applied Pharmacology, 186: 46-54 2003.
European Patent Office, Extended Search Report for EP App. 17793268.8, 8 pages Nov. 29, 2019.
Fath et al., Enhancement of Carboplatin-Mediated Lung Cancer Cell Killing by Simultaneous Disruption of Glutathione and Thioredoxin Metabolism, Clinical Cancer Research, 17(19): 6206-6217 2011.
Jungwirth et al., Anticancer Activity of Metal Complexes: Involvement, Antioxidants & Redox Signaling, 15(4): 1085-1127 2011.
Cao et al., Mechanisms of ferroptosis, Cell. Mol. Life Sci., 2016, 11:2195-2209 2016.
Rodman III, et al., Enhancement of Radiation Response in Breast Cancer Stem Cells by Inhibition of Thioredoxin and Glutathione Dependent Metabolism, Radiat Res., 2016, 186(4): 385-395 2016.
Samlowski et al., Evaluation of a Superoxide Dismutase Mimetic as an Adjunct to Interleukin 2 Based Cancer Therapy, Madame Curie Report, 230-249 2006.
Samlowski et al., A nonpeptidyl mimic of superoxide dismutase, M40403, inhibits dose-limiting hypotension associated with interleukin-2 and increases its antitumor effects, Nature Medicine, 9:750-755 2003.

(56) References Cited

OTHER PUBLICATIONS

Sishc et al., Superoxide dismutase mimetic GC4419 protects against radiation induced lung fibrosis, exhibits anti- tumor effects, and enhances radiation induced cell killing, 1 pg 2015.
Sishc et al., Superoxide dismutase mimetic GC4419 sensitizes non-small cell lung cancer tumors to high dose per fraction radiation and ameliorates radiation induced lung fibrosis, 1 pg 2016.
Scarbrough, P.M., Inhibitors of glucose and hydroperoxide metabolism potentiate 17AAG-induced cancer cell killing via metabolic oxidative stress, University of Iowa Theses and Dissertations 2011.
Sobhakumari et al., Susceptibility of Human Head and Neck Cancer Cells to Combined Inhibition of Glutathione and Thioredoxin Metabolism, PLOS, 7(10): e48175, 10 pgs 2012.
European Patent Office, Extended Search Report for EP App. 17847659.4, 12 pages Mar. 6, 2020.
Salvemini et al., Reply to Role of manganese superoxide dismutase in cancer, Nature Medicine, 9(9): 1103-1103 Sep. 1, 2003.
Tovmasyan et al., Radiation-Mediated tumor growth inhibition is significantly enhanced with redox-active compounds that cycle with ascorbate, Antioxidants and Redox Signaling, 29(13): 1196-1214 Nov. 1, 2018.
Sishc et al., The radioprotector GC4419 ameliorates radiation induced lung fibrosis while enhancing the response of non-small cell lung cancer tumors to high dose per fraction radiation exposures, American Association of Cancer Research, 1 pg. 2018.
Sichc et al. The superoxide dismutase mimetic GC4419 enhances tumor killing when combined with stereotactic ablative radition, BioRxiv Mar. 11, 2020.
Zhu et al. Lysine 68 acetylation directs MnSOD as a tetrameric detoxification complex versus a monomeric tumor promoter, Nature Communications Jun. 3, 2019.
European Patent Office, Extended European Search Report for 20168046.96, 16 pages Oct. 16, 2020.
Jiang et al., Role of IL-2 in cancer immunotherapy, Oncoimmunology, 5(6);E1163462 Apr. 25, 2016.
Lasry et al., Inflammatory networks underlying colorectal cancer, Nature Immunology, 17(3):230-240 Feb. 16, 2016.
Mikirova et al., Effect of high-dose intravenous vitamin C on inflammation in cancer patients, Journal of Translational Medicine, 10(189): 2 pages 2012.
Riley et al., Manganese Macrocyclic Ligand Complexes as Mimics of Superoxide Dismutase, J. Am. Chem. Soc. 116: 387-388 1994.
Pannala et al., Mechanistic Characterization of the Thioredoxin System in the Removal of Hydrogen Peroxide, Free Radic Biol Med., 78: 42-55 2015.
Kelso et al., A Mitochondria-Targeted Macrocyclic Mn(II) Superoxide Dismutase Mimetic, Chemistry & Biology, 19: 1237-1246 2012.
European Patent Office, Extended European Search Report issued for 18785213.2, 16 pages Feb. 8, 2021.
Laurent et al. Controlling Tumor Growth by Modulating Endogenous Production of Reactive Oxygen Species, Cancer Research, 65(3): 948-956 2005.
Eldor et al., Perturbation of endothelial functions by ionizing irradiation: effects on prostaglandins, chemoattractants and mitogens, Semin Thromb Hemost, 1989, 15(2): 215-225 1989.
Escribano et al., Aerosol Orgotein (Ontosein) for the Prevention of Radiotherapy-Induced Adverse Effects in Head and Neck Cancer Patients: A feasibility study, Neoplasma, 2002, 49(3): 201-209 2002.
Gridley et al., Chapter 16, Therapeutic Application of Superoxide Dismutase (SOD) (Salvemini and Cuzzocrea, eds.), 2004, 1-20 2004.
Guo et al., Prevention of Radiation-Induced Oral Cavity Mucositis by Plasmid/Liposome Delivery of the Human Manganese Superoxide Dismutase (SOD2) Transgene, Radiat. Red., 2003, 159(3): 361-370 2003.
Knox, et al., Chemotherapy-induced oral mucositis. Prevention and Management, Drugs Aging, 2000, 17(4): 257-267 2000.
Leussink et al., Pathways of Proximal Tubular Cell Death in Bismuth Nephrotoxicity, Toxicol. Appl. Pharmacol., 2002, 180(2): 100-109 2002.
Orrell, R.W., AEOL-10150 (Aeolus), Current Opinion Investig. Drugs, 2006, 7(1): 70-80 2006.
Peterson, D. E. Research advances in oral mucositis. Current Opinion Oncol., 1999, 11(4): 261-266 1999.
Plevova, P. Prevention and treatment of chemotherapy- and radiotherapy-induced oral mucositis: a review. Oral Oncol. 1999; 35(5): 453-470 1999.
Salvemini et al., Amelioration of Joint Disease in a Rat Model of Collagen-Induced Arthritis by M40403, a Superoxide Dismutase Mimetic, Arthritis & Rheumatism, 2001, 44: 2909-2921 2001.
Slikkerveer et al., Pharmacokinetics and Toxicity of Bismuth Compounds, Med. Toxicol. Adverse Drug Exp, 1989, 4(5): 303-323 1989.
Sonis, Oral Mucositis in Cancer Therapy, Support. Oncol., 2004, 2 (supple.3): 3-8 2004.
Sonis et al., Mitigating Effects of Interleukin 11 on Consecutive Courses of 5-Fiuorouracil-Induced Ulcerative Mucositis in Hamsters, Cytokine, 1997, 9(8): 605-612 1997.
Ahmad et al., Mitochondrial O.sub2. and H202 Mediate Glucose Deprivation-induced Cytotoxicity and Oxidative Stress in Human Cancer Cells, J. Bio. Chem, 2005, 280(6): 4254-4263 2005.
Sonis et al., Transforming Growth Factor-B3 Mediated Modulation of Cell Cycling and Attenuation of 5-Fiuorouracil Induced Oral Mucositis, Oral Oncol., 1997, 33(1): 47-54 1997.
Sonis et al., Defining Mechanisms of action of interleukin-11 on the progression of radiation-induced oral mucositis in hamsters, Oral Oncology, 2000, 36(4): 373-381 2000.
Cuzzocrea et al., C. Tempol, a membrane-permeable radical scavenger, reduces dinitrobenzene sulfonic acid- induced colitis, Eur J Pharmacol., 2000, 406:127-137 2001.
Murphy et al., Efficacy of superoxide dismutase mimetic M40403 in attenuating radiation-induced oral mucosisis in hamsters, Clin. Can. Res., 2008, 14(13):4292-4297 2008.
Goodman & Gilman's The Pharmacological Basis of Therapeutics, 10th Edition, McGraw Hill, 1996 1996.
Salvemini et al., A nonpeptidyl mimic of superoxide dismutase with therapeutic activity in rats, Science, 1999, 286: 304-306 1999.
Suenderhauf et al., A Physiologically Based Pharmacokinetic Model of the Minipig: Data Compilation and Model Implementation, Pharm. Res., 2013, 30(1): 1-15 2013.
Cuzzocrea et al., Protective effects of M40401, a selective superoxide dismutase mimetic, on zymosan-induced nonseptic shock, Crit. Care Med., 2004, 21(1): 157-167 2004.
Cuzzocrea et al., Reduction in the development of Cerulein-induced acute pancreatitis by treatment with M40401, a new selective superoxide dismutase mimetic, Shock, 2004, 22(3): 254-261 2004.
Anderson, C., Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC), Oral Mucositis Research Workshop, MASCC/ISOO Annual Meeting on Supportive Care in Cancer, Copenhagen, Denmark (Jun. 25, 2015) 2015.
Cotton et al., Advanced Inorganic Chemistry, Chapter 5, "Coordination Compounds", 2nd revised edn., Interscience Publishers, 1966, 139 1966.
Cotton et al., Advanced Inorganic Chemistry, Chapter 2, "Coordination Compounds", 2nd revised edn., Interscience Publishers, 1966, 35-36, 45-49 1966.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., 2016, 94(4): 869-870 2016.
Wang et al., Evidence of d-phenylglycine as delivering tool for improving I-dopa absorption, J. Biomed. Sci., 2010, 17: 71-79 2010.
Wikipedia, Cefalexin, retrieved Nov. 2, 2016, from en.wikipedia.org/wiki/Cefalexin, 6 pages 2016.
Hironaka et al., Quantitative Evaluation of PEPT1 Contribution to Oral Absorption of Cephalexin in Rats, Pharm. Res., 2009, 26(1): 40-50 2009.

(56) References Cited

OTHER PUBLICATIONS

Knütter et al., Transport of Angiotensin-Converting Enzyme Inhibitors by H+/Peptide Transporters Revisited, J. Pharma. Exp. Thera., 2008, 327(2): 432-441 2008.
Patent Cooperation Treaty, International Search Report for PCT/US2016/046599, dated Nov. 17, 2016, 5 pages Nov. 17, 2016.
Park et al., Facility case vol. and outcomes for intensity-modulated radiotherapy in head and neck cancer, Department of Therapeutic Radiology, Yale School of Medicine, 1 pg. Sep. 26, 2016.
Boero et al., Importance of Radiation Oncologist Experience Among Patients With Head-and-Neck Cancer Treated With Intensity-Modulated Radiation Therapy, Journal of Clinical Oncology, 2016, 34(7): 684-696 Mar. 1, 2015.
Ferreira et al., Effect of radiotherapy delay in overall treatment time on local control and survival in head and neck cancer: Review of the literature, Reports of Practical Oncology and Radiotherapy, 2015, 20: 328-339 May 24, 2015.
Anderson et al., Phase 1b Trial of Superoxide Dismutase Mimetic GC4419 to Reduce Chemoradiotherapy-induced Oral Mucositis in Patients with Oral Cavity or Oropharyngeal Carcinoma, Multidisciplinary Head and Neck Cancer Symposium, Scottsdale, Arizona, 17 pgs Feb. 18, 2016.
Hussan et al., A review on recent advances of enteric coating, Journal of Pharmacy, 2012, 2(6): 5-11 2012.
Strickley, R. G., Solubilizing Excipience in Oral and Injectable Formulations, Pharmaceutical Research, 2004, 21 (2): 201-230 2004.
Salvemini et al., Pharmacological manipulation of the in ammatory cascade by the superoxide dismutase mimetic, M40403, British Journal of Pharmacology, 2001, 132: 815-827 2001.
Masini et al., Reduction of antigen-induced respiratory abnormalities and airway inflammation in sensitized guinea pigs by a superoxide dismutase mimetic, Free Radical Biology & Medicine, 2005, 39: 520-531 2005.
Salvemini et al., Superoxide Dismutase Mimetics, Pulmonary Pharmacology & Therapeutics, 2002, 15: 439-447 2002.
Weiss et al., Manganese-based Superoxide Dismutase Mimetics Inhibit Neutrophil Infiltration in Vivo, Journal of Biological Chemistry, 1996, 271(42): 26149-26156 1996.
Udipi et al., Modification of inflammatory response to implated biomedical materials in vivo by surface bound superoxide dismutase mimics, Journal of Biomedical Materials Research, 1999, 1-12 1999.
Cuzzocrea et al., Protective effects of M40403, a superoxide dismutase mimetic, in a rodent model of colitis, European Journal of Pharmacology, 2001, 432: 79-89 2001.
Salvemini et al., Protective effects of superoxied dismutase mimetic nd peroxynitrite decomposition catalyst in endotoxin-indueced intestinal damage, 1999, British Journal of Pharmacology, 127(3):685-692 1999.
European Patent Office, Extended European Search Report issued for App. No. 17166668.8, 11 pages Sep. 27, 2017.
Sindoni et al., Combination of immune checkpoint inhibitors and radiotherapy: Review of the literature, Critical Reviews in Oncology/Hematology, 2017, 113: 63-70 2017.
Pardoll, D. M., The blockade of immune checkpoints in cancer immunotherapy, Nat Rev Cancer, 2012. 12(4): 252-264 Mar. 22, 2012.
Jin et al., Clinical Observation on Superoxide Dismutase in Respect of Resistance to Skin Damage Resulting from Radiation, Chinese Journal of Radiological Health, 1993, 2(3): 137 1993.
Zhou et al., Experimental Study on Superoxide Dismutase for Prophylaxis and Treatment of Inflammatory Damage to Mouth Mucosa in Animals, West China Journal of Stomatology, 1996, 14(2) 1996.
Tovmasyan et al., Anticancer therapeutic potential of Mn porphyrin/ascorbate system, Free Radical Biology and Medicine, 89:1231-1247 2015.
Rawal et al., Manganoporphyrins Increase Ascorbate-Induced Cytotoxicity by Enhancing H202 Generation, Cancer Research, 73(16):5232-5241 2013.
Batinic-Haberle et al., An educational overview of the chemistry, biochemistry and therapeutic aspects of Mn porphyrins—From superoxide dismutation to H2O2-driven pathways, Redox Biology, 5:43-65 2015.
Marzano et al., Inhibition of thioredoxin reductase by auranofin induces apoptosis in cisplatin-resistant human ovarian cancer cells, Free Radical Biology & Medicine 42: 872-881 2007.
U.S. Department of Health and Human Services, Food and Drug Administration, Center for Drug Evaluation and Research (CDER), Guidance for Industry Estimating the Maximum Safe Starting Dose in Initial Clinical Trials for Therapeutics in Adult Healthy Volunteers, 30 pages 2005.
Qian et al., Advances in the study of effects of vitamin C on tumor prevention, Youjiang Medical Journal, 36(6): 741-743 2008.
Ghosh et al., A novel manganese complex, Mn-(II) N-(2-hydroxy acetophenone) glycinate overcomes multidrug-resistance in cancer, European Journal of Pharmaceutical Sciences, 49: 737-747 2013.
Serafim et al., Regulating mitochondrial respiration in cancer in: Kanner S. (eds) Tumor Metabolome Targeting and Drug Development, Cancer Drug Discovery and Development, 45 pages 2014.
Liu et al., Mechanisms of the CDK4/6 inhibitor palbociclib (PD 0332991) and its future application in cancer treatment (Review), Oncology Reports, 36: 901-911 2018.
Friend, D. R., Review article: Issues in oral administration of locally acting glucocorticosteroids for treatment of inflammatory bowl disease, Aliment Pharmacol Therapy, 12: 591-603 1198.
Shadad et al., Gastrointestinal radiation injury: Symptoms, risk factors and mechanisms, World Journal of Gastroenterology, 19(2): 185-198 2013.
Yu et al., Intestinal stem cell injury and protection during cancer therapy, Transl Cancer Research, 2(5): 384-396 2013.
Kim et al., Antiproliferative effect of gold(I) compound auranofin through inhibition of STAT3 and telomerase activity in MDA-MB 231 human breast cancer cells, BMB Rep., 46(1): 59-64 2013.
Zou et al., Auranofin induces apoptosis by ROS-mediated ER stress and mitochondrial dysfunction and displayed synergistic lethality with piperlongumine in gastric cancer, Oncotarget, 6(34): 36505-36521 2015.
Declaration under 37 C.F.R. 1.132 of Dennis P. Riley, dated Mar. 7, 2014, and filed in U.S. Appl. No. 11/871,848, filed Mar. 3, 2014.
Declaration under 37 C.F.R. 1.132 of Douglas R. Spitz, dated Feb. 6, 2014, and filed in U.S. Appl. No. 11/871,848, filed Feb. 6, 2014.
Keene, J. L., Declaration under 37 C.F.R. 1.132 May 14, 2014 May 14, 2014.
Mikirova, et al. CAS: 158, 290966, 2012 2012.
Alexandre, et al. "Improvement of the therapeutic index of anticancer drugs by the superoxide dismutase mimic mangafodipir," Journal of the National Cancer Institute, vol. 98, No. 4, Feb. 15, 2006, pp. 236-244 Feb. 15, 2006.
Belotte, et al. "Abstract B01: Superoxide dismutase significantly reversed the development of cisplatin resistance in epithelial ovarian cancer," Acquired Resistance, Feb. 13, 2015 pp. B01-B01 Feb. 13, 2015.
Karlsson, et al. "Calmangafodipir [Ca4Mn (DPDP) 5], mangafodipir (MnDPDP) and MnPLED with special reference to their SOD mimetic and therapeutic properties," Drug Discovery Today, vol. 20, No. 4, Apr. 1, 2015 Apr. 1, 2015.
Ahmed, et al. "Tempol, a Superoxide Dismutase Mimetic Agent, Ameliorates Cisplatin-Induced Nephrotoxicity through Alleviation of Mitochondrial Dysfunction in Mice," PLOS ONE, vol. 9, No. 10, Jan. 1, 2014 Jan. 1, 2014.
Wangila, et al. "Prevention of cisplatin-induced kidney epithelial cell apoptosis with a Cu superoxide dismutase-mimetic [copper 2II (3,5-ditertiarybutylsalicylate)" 4(ethanol) 4], Toxicology In Vitro, Elsevier Science, vol. 20, No. 8 Dec. 1, 2006 pp. 1300-1312 Dec. 1, 2006.
Kobayashi, et al. "Enhancement of Anti-Cancer Activity of Cisdiaminedichloroplatinum by the Protein-Bound Polysaccharide of Coriolus Versicolor QUEL (PS-K) In Vitro," Cancer Biotherapy, vol. 9, No. 4 Jan. 1, 1994 pp. 351-358 Jan. 1, 1994.

(56) References Cited

OTHER PUBLICATIONS

Karlsson, et al. “First clinical expeirence with the magnetic resonance imaging contrast agent and superoxide dismutase mimetic mangafodipir as an adjunct in cancer chemotherapy-a translational study,” Translational Oncology, Feb. 1, 2012 pp. 32-38 Feb. 1, 2012.
Karlsson, et al. “Superior therapeutic index of calmangafodipir in comparison to mangafodipir as a chemotherapy adjunct,” Translational Oncology, Dec. 1, 2012 p. 492 Dec. 1, 2012.
Davis, et al. “Manganese Superoxide Dismutase Attenuates Cisplatin-Induced Renal Injury: Importance of Suproxide,” Journal of the American Society of Nephrology, vol. 12, No. 12, Dec. 1, 2001 pp. 2683-2690 Dec. 1, 2001.
Mohanty, et al. “Abstract 2929: GC4419 enhances the response of non-small cell lung carcinoma cell lines to cisplatin and cisplatin plus radiation through a ROS-mediated pathway : Cancer Research,” AACR Annual Meeting 2018, Jul. 1, 2018 pp. 1-4 Jul. 1, 2018.
Mapuskar, et al. “Mitochondrial Superoxide Dismutase in Cisplatin-Induced Kidney Injury,” Antioxidants, vol. 10, No. 9, Aug. 24, 2021 p. 1329 Aug. 24, 2001.
European Patent Office, Extended European Search Report for 19747505.6 publication 3746085 21 pgs. Feb. 9, 2022 Feb. 9, 2022.
Galera Therapeutics, Inc., A Phase 1 Dose Escalation Study of GC4419 in Combination With Chemoradiation for Squamous Cell Cancer of the Head & Neck, NIH U.S. National Library of Medicine, ClinicalTrials.gov,, 8 pages 2013.
Dyck et al., Immune checkpoints and their inhibition in cancer and infectious diseases, European Journal of Immunology, 47: 765-779 2017.
Zhang et al. Thioredoxin reductase inhibitors: a patent review, Expert Opinion on Therapeutic Patents, 27(5): 547-556 2017.
Elting et al., The Burdens of Cancer Therapy, Cancer, 98(7): 1531-1539 2003.
Epperly et al., Manganese Superoxide Dismutase-Plasmid/ Liposome (MnSOD-PL) Administration Protects Mice from Esophagitis Associated with Fractionated Radiation, Int. J. Cancer (Radiat. Oncol. Invest), 96: 221-231 2001.
Epperly et al., Intraoral Manganese Superoxide Dismutase-Plasmid/ Liposome (MnSOD-PL) Radioprotective Gene Therapy Decreases Ionizing Irradiation-induced Murine Mucosal Cell Cycling and Apoptosis, In Vivo, 18:401-410 2004.
Guo et al., Gene Transfer of Human Manganese Superoxide Dismutase Protects Small Intestinal Villi From Radiation Injury, J Gastrointest Surg., 7(2): 229-235 2003.
Lalla et al., Treatment of Mucositis, Including New Medications, Palliative and Supportive Care, 12(5): 348-354 2006.
Murakami, The Chemical Society of Japan, editions, Separation of Optical Isomer quarterly journal, chemical review No. 6, Scientific Societies Press, p. 212-213 (translation) 1989.
Anderson, et al. Two-Year Tumor Outcomes of Phase 2B, Randomized, Double-Blind Trial of Avasopasem Manganese (GC4419) Versus Placebo to Reduce Severe Oral Mucositis Due to Concurrent Radiation Therapy and Cisplatin for Head and Neck Cancer Published:Jun. 17, 2022DOI:https://doi.org/10.1016/j.ijrobp.2022.06.063.
Anderson, et al. Phase IIb, Randomized, Double-Blind Trial of GC4419 Versus Placebo to Reduce Severe Oral Mucositis Due to Concurrent Radiotherapy and Cisplatin For Head and Neck Cancer, Journal of Clinical Oncology 37, No. 34 (Dec. 1, 2019) 3256-3265.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., vol. 100, Issue 2, p. 427-435, Feb. 1, 2018.
ASCO Abstract Effects of GC4419 (avasopasem manganese) on chronic kidney disease in head and neck cancer patients treated with radiation and cisplatin, American Society of Clinical Oncology, 2020 2 pages.
O’Leary, et al. Loss of SOD3 (EcSOD) Expression Promotes an Aggressive Phenotype in Human Pancreatic Ductal Adenocarcinoma, Downloaded from www.clincancerres.aacrjournals.org on Jul. 17, 2020 pp. 1741-1751.
Sishc, et al. Avasopasem manganese synergizes with hypofractionated radiation to ablate tumors through the generation of hydrogen peroxide, Sci. Transl. Med. 13, May 12, 2021 pp. 1-13.
Sishc, et al. Avasopasem Manganese Protects Against Radiation Induced Oral Mucositis and Enhances the Response of Squomous Cell Carcinoma of the Head and Neck to Ionizing Radiation and Radioimmune Therapy, Astro, vol. 108, Issue 3, Suppl. S159, Nov. 1, 2020.
Sishc, et al. Abstract: The radioprotector GC4419 enhances the response of pancreatic ductal adenocarcinoma tumors to high dose per fraction radiation exposure, AACR PDAC Meeting 2019.
Steinbach, et al. Effects of GC4419 (Avasopasem Manganese) on Chronic Kidney Disease in Head and Neck Cancer Patients Treated with Radiation and Cisplatin, ASCO20 May 2020 1 pages.
Du et al., Glutathione and glutaredoxin act as a backup of human thioredoxin reductase 1 to reduce thioredoxin 1 preventing cell death by aurothioglucose, J. Biol Chem, 287(45), 38210-38219 2012.
Fan et al., Enhancement of auranofin-induced lung cancer cell apoptosis by selenocystine, a natural inhibitor of TrxR1 in vitro and in vivo, Cell Death & Disease, 5, e1191 2018.

* cited by examiner

| pMEFs (wild-type) | Myc | Ras | Myc/Ras |
|---|---|---|---|
| Control | None | None | Immort |
| $SOD^{K68R}$ | None | None | None |
| $SOD^{K68Q}$ | Immort | Immort | Immort |

FIG. 1A

| pMEFs (wild-type) | $Ras^{G12V}$ immort-alization | $Ras^{G12V}$ doubling time | $Ras^{G12V}$ soft agar growth |
|---|---|---|---|
| Control | Immort | 35 h | No |
| $SOD^{K68R}$ | None | N/A | No |
| $SOD^{K68Q}$ | Immort | 22 h | Yes |

FIG. 1C

| Group i.e., genes | Number of mice | Mice with tumor | Ave tumor weight (g) | Ave tumor size ($mm^3$) |
|---|---|---|---|---|
| MCF7 WT | 10 | 1 | 0.001 | 41 |
| MCF7 68R | 10 | 1 | 0.001 | 45 |
| MCF7 68Q | 10 | 9 | 0.73 | 960 |

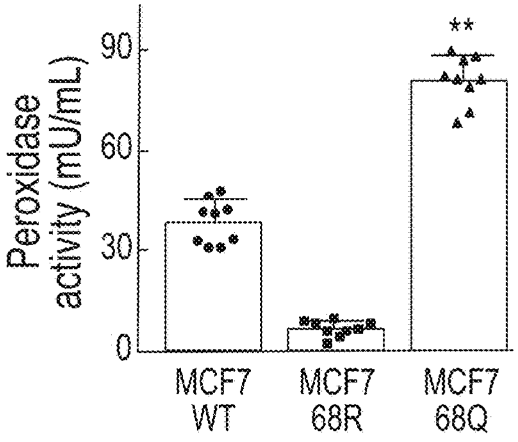
FIG. 3C
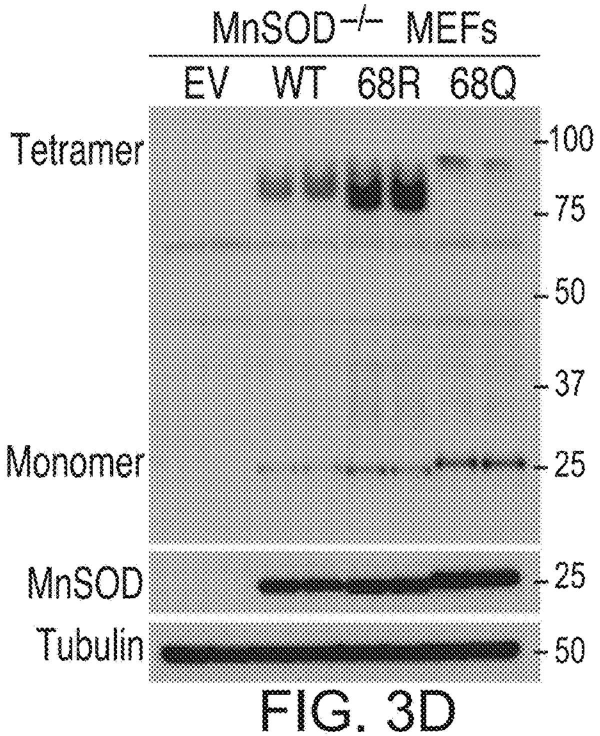
FIG. 3D
| MnSOD−/− MEFs | AdEmpty | AdMitoCat |
|---|---|---|
| MnSOD−/− | None | None |
| $MnSOD^{WT}$ | None | None |
| $MnSOD^{K68R}$ | None | None |
| $MnSOD^{K68Q}$ | Transformed | None |
FIG. 3E Theoretical
Homotetramer ~96 kDa
Monomer ~24 kDa
Actual
Tetramer 92 kDa
Monomer 25 kDa Calibration standards:
Aldolase: 158 kDa
Conalbumin: 75 kDa
Ovalbumin: 44 kDa
Ribonuclease A: 14 kDa
Aprotinin: 6.5 kDa

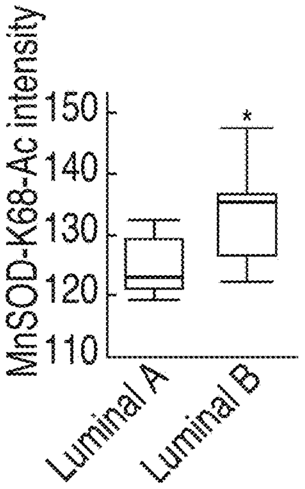
FIG. 8E
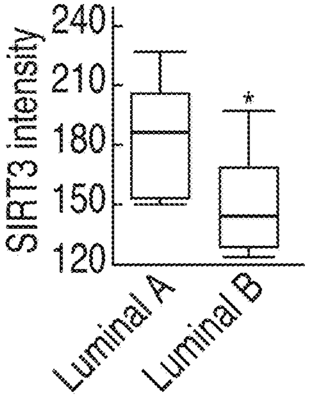
FIG. 8F
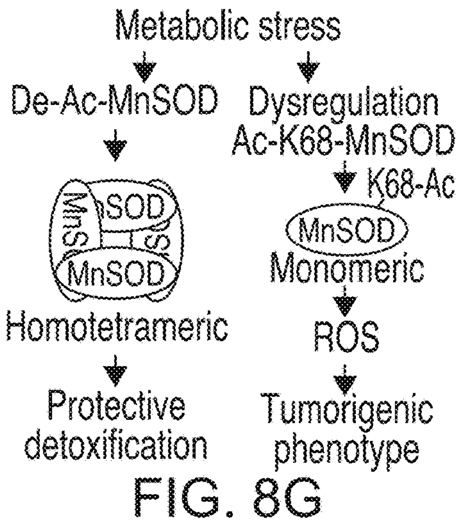
FIG. 8G
| pMEFs (lenti-Myc) | Doubling Time | Xenograft growth |
|---|---|---|
| Control | 31h | - |
| MnSOD$^{K68R}$ | 68h | - |
| MnSOD$^{K68Q}$ | 25h | ↑↑↑ |
FIG. 9A
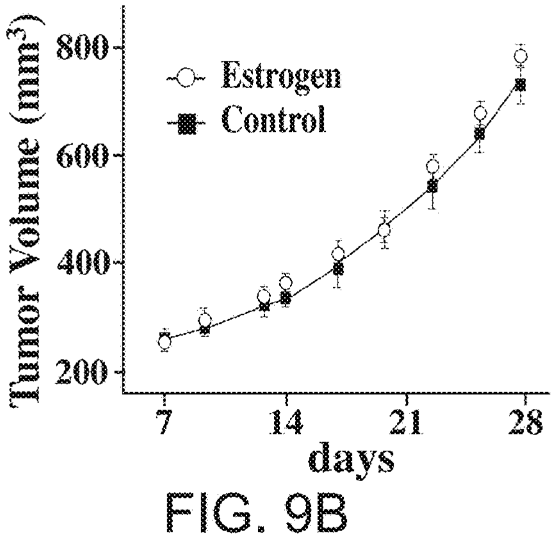
FIG. 9B

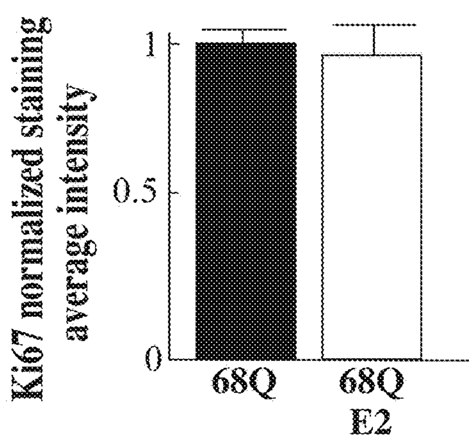
FIG. 10E
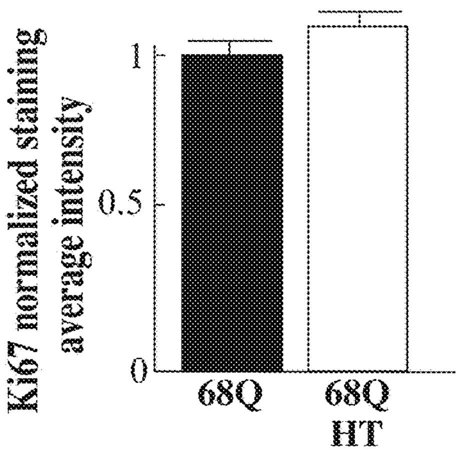
FIG. 10F
| MnSOD$^{-/-}$ MEFs | Growth Agar | Contact Inhibition | Doubling Time |
|---|---|---|---|
| Control | − | − | − |
| SOD$^{WT}$ | − | − | − |
| SOD$^{K68R}$ | − | − | − |
| SOD$^{K68Q}$ | ↑↑↑ | ↑↑↑ | ↓↓↓ |
FIG. 11A
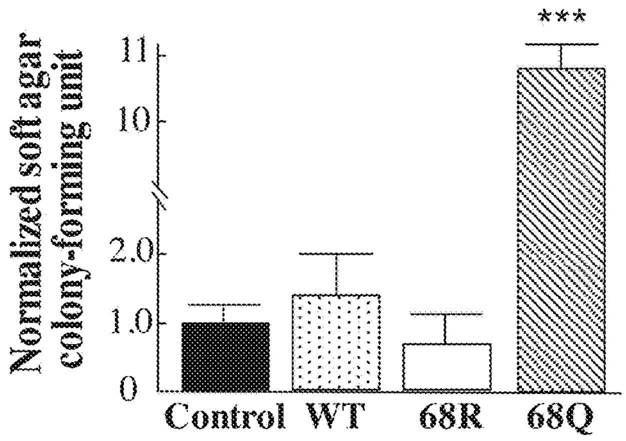
FIG. 11B

| Gene Name | Protein Identification probability | Number of unique peptides | Number of unique spectra | Number of total spectra | Percentage Lysine 68 acetylation |
|---|---|---|---|---|---|
| pET21a-MnSOD WT | 100% | 32 | 164 | 999 | 9.9% |
| pET21a-MnSOD K68TAG | 100% | 24 | 99 | 531 | 80.1% |

| Group i.e., genes | Number of mice | Mice with tumor | Ave tumor weight (g) | Ave tumor size ($mm^3$) |
|---|---|---|---|---|
| MCF7 | 10 | 0 | N/A | N/A |
| MCF7 HTR | 10 | 10 | 0.71 | 859 |

| Staining Intensity | Low | Interm | High |
|---|---|---|---|
| Luminal A | 26 | 9 | 2 |
| Luminal B | 4 | 15 | 19 |

| Staining Intensity | Low | Interm | High |
|---|---|---|---|
| Luminal A | 9 | 11 | 17 |
| Luminal B | 20 | 8 | 10 |

COMBINATION CANCER THERAPY WITH PENTAAZA MACROCYCLIC RING COMPLEX AND HORMONE THERAPY AGENT

CROSS-REFERENCE TO RELATED APPLICATIONS

This application is a by-pass continuation of PCT Application Serial Number PCT/US2021/035460, filed Jun. 2, 2021, which claims priority to U.S. Application Ser. No. 63/033,559, filed Jun. 2, 2020, the disclosure of each of which is herein incorporated by reference in its entirety.

This invention was made with government support under grant numbers 1R01CA214025-01, R01CA152601-06A1, and R01CA168292, awarded by the National Institutes of Health (NIH)/National Cancer Institute (NCI). The government has certain rights in the invention.

The present disclosure generally relates to combination therapies for cancer treatment, including administration of a pentaaza macrocyclic ring complex in combination with anti-cancer therapies including chemotherapy, radiation therapy, cell cycle inhibitors, and hormone receptor pathway inhibitors, and particularly for the treatment of cancers exhibiting a multi-therapy resistance phenotype characterized by resistance to multiple anti-cancer therapies. It further generally relates to therapies for treatment of cancers characterized by a decrease in the lysine deacetylase Sirtuin 3 (Sirt 3), an increased acetylation of manganese superoxide dismutase (MnSOD), particularly increased acetylation of lysine 68 of Mn SOD (AcK68, MnSOD-K68-Ac), or the downstream markers of these.

Transition metal-containing pentaaza macrocyclic ring complexes having the macrocyclic ring system corresponding to Formula A have been shown to be effective in a number of animal and cell models of human disease, as well as in treatment of conditions afflicting human patients.

FORMULA A

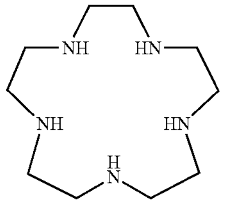

For example, in a rodent model of colitis, one such compound, GC4403, has been reported to very significantly reduce the injury to the colon of rats subjected to an experimental model of colitis (see Cuzzocrea et al., *Europ. J. Pharmacol.,* 432, 79-89 (2001)).

(4403)

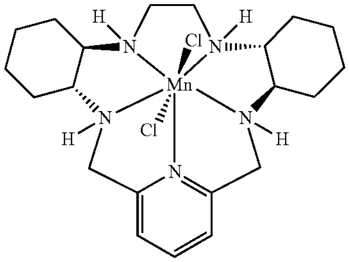

GC4403 has also been reported to attenuate the radiation damage arising both in a clinically relevant hamster model of acute, radiation-induced oral mucositis (Murphy et al., *Clin. Can. Res.,* 14(13), 4292 (2008)), and lethal total body irradiation of adult mice (Thompson et al., *Free Radical Res.,* 44(5), 529-40 (2010)). Similarly, another such compound, GC4419, has been shown to attenuate VEGFr inhibitor-induced pulmonary disease in a rat model (Tuder, et al., *Am. J. Respir. Cell Mol. Biol.,* 29, 88-97 (2003)). Additionally, another such compound, GC4401 has been shown to provide protective effects in animal models of septic shock (S. Cuzzocrea, et al., *Crit. Care Med.,* 32(1), 157 (2004) and pancreatitis (S. Cuzzocrea, et al., *Shock,* 22(3), 254-61 (2004)).

(4419)

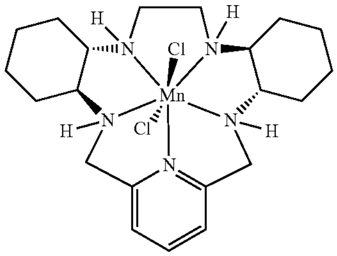

(4401)

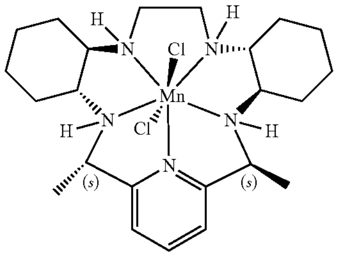

Certain of these compounds have also been shown to possess potent anti-inflammatory activity and prevent oxidative damage in vivo. For example, GC4403 has been reported to inhibit inflammation in a rat model of inflammation (Salvemini, et. al., *Science,* 286, 304 (1999)), and prevent joint disease in a rat model of collagen-induced arthritis (Salvemini et al., *Arthritis & Rheumatism,* 44(12), 2009-2021 (2001)). Yet others of these compounds, MdPAM and MnBAM, have shown in vivo activity in the inhibition of colonic tissue injury and neutrophil accumulation into colonic tissue (Weiss et al., *The Journal of Biological Chemistry,* 271(42), 26149-26156 (1996)). In addition, these compounds have been reported to possess analgesic activity and to reduce inflammation and edema in the rat-paw carrageenan hyperalgesia model, see, e.g., U.S. Pat. No. 6,180,620.

Compounds of this class have also been shown to be safe and effective in the prevention and treatment of disease in human subjects. For example, GC4419 has been shown to reduce oral mucositis in head-and-neck cancer patients undergoing chemoradiation therapy (Anderson, C., *Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC)*, Oral Mucositis Research Workshop, MASCC/ISOO Annual Meeting on Supportive Care in Cancer, Copenhagen, Denmark (Jun. 25, 2015)).

In addition, transition metal-containing pentaaza macrocyclic ring complexes corresponding to this class have shown efficacy in the treatment of various cancers. For example, certain compounds corresponding to this class have been provided in combination with agents such as paclitaxel and gemcitabine to enhance cancer therapies, such as in the treatment of colorectal cancer and lung cancer (non-small cell lung cancer) (see, e.g., U.S. Pat. No. 9,198, 893) The 4403 compound above has also been used for treatment in in vivo models of Meth A spindle cell squamous carcinoma and RENCA renal carcinoma (Samlowski et al., *Nature Medicine,* 9(6), 750-755 (2003), and has also been used for treatment in in vivo models of spindle-cell squamous carcinoma metastasis (Samlowski et al., *Madame Curie Bioscience Database* (*Internet*), 230-249 (2006)).

Endocrine therapy agents (hormone therapy agents) such as tamoxifen have proven effective in the treatment of various types of cancers, including estrogen receptor-positive breast cancer, and is also currently available as a chemopreventive agent in women with a high risk for breast cancers (Minsun Chang, *Biomolecules and Therapeutics,* 20(3):256-267 (2012)). However, a problem with certain endocrine therapy agents, such as tamoxifen, is that certain tumors may be inherently resistant (i.e. resistant to treatment before such treatment even begins), and/or an initially responsive tumor can develop resistance to the endocrine therapy agent over time (Zhu et al., *Nature Communications,* 9 (1595): 1-11(2018); Wu et al., *Cancer Research,* 78(3): 671-684 (2017)). Resistances to other types of anti-cancer therapies, such as resistance to chemotherapeutic agents, and radiation therapy, may also be inherent in, or can develop, for different types of tumors. Accordingly, the development of or inherent resistance in cancer cells to treatment can cause a relapse of the cancer in a previously treated individual, or inability to combat the cancer in an individual currently receiving the treatment.

Accordingly, a need remains for enhanced methods for cancer treatment that provide improved efficacy in the killing of cancer cells, while also reducing resistance in the cancer cells to the cancer treatment.

Briefly, therefore, aspects of the present disclosure are directed to a method of treating a cancer in a mammalian subject, the cancer being characterized as having multi-therapy resistance, the method comprising:

administering to the mammalian subject a therapeutically effective amount of a pentaaza macrocyclic ring complex corresponding to the Formula (I) below:

(I)

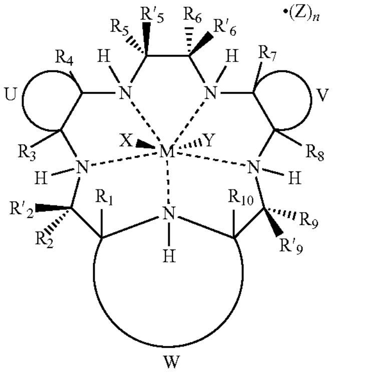

wherein

M is $Mn^{2+}$ or $Mn^{3+}$, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}$ $R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

According to another aspect, a method of treating a cancer is provided, in a mammalian subject with a tumor signature characterized by any one or more of (i) a level of sirtuin (SIRT3) protein that is below a first predetermined threshold level, (ii) a level of manganese superoxide dismutase acetylated at the lysine 68 residue (AcK68) that exceeds a second predetermined threshold level, (iii) expression levels of hypoxia-inducible factor $2_\alpha$ ($HIF2_\alpha$) that exceed a third predetermined threshold level indicative of lineage plasticity for stemness, (iv) a level of Ki-67 protein that exceeds a fourth predetermined threshold level, (v) a level of OCT4 that exceeds a fifth predetermined threshold level, (vi) a level of SOX2 that exceeds a sixth predetermined threshold level, and (vii) a ratio of monomeric to tetrameric MnSOD that exceeds a seventh predetermined threshold level, the method comprising:

administering to the mammalian subject a therapeutically effective amount of a pentaaza macrocyclic ring complex corresponding to the Formula (I).

According to another aspect, a method of treating a cancer in a mammalian subject, comprises selecting a subject that is a suitable subject for treatment with a pentaaza macrocyclic ring complex corresponding to Formula (I) below, by: obtaining a test tissue sample from the subject, the test tissue sample comprising tumor cells, assessing the test tissue sample to determine criteria comprising any one or more of (i) whether a level of sirtuin (SIRT3) protein is below a first predetermined threshold level in tumor cells of the tissue sample, (ii) whether a level of manganese superoxide dismutase acetylated at the lysine 68 residue (AcK68) exceeds a second predetermined threshold level, (iii) whether expression levels of hypoxia-inducible factor $2_{\alpha}$ ($HIF2_{\alpha}$) exceed a third predetermined threshold level indicative of lineage plasticity for stemness, (iv) whether a level of Ki-67 protein exceeds a fourth predetermined threshold level, (v) whether a level of OCT4 protein exceeds a fifth predetermined threshold level, (vi) whether a level of SOX2 protein exceeds a sixth predetermined threshold level, and (vii) whether a ratio of monomeric to tetrameric MnSOD that exceeds a seventh predetermined threshold level, and determining the subject is suitable for the treatment if either one or more of the criteria (i)-(vii) is met, and in a case where the subject is selected as suitable for treatment, administering a therapeutically effective amount of the pentaaza macrocyclic ring complex corresponding to Formula (I).

According to another aspect, a kit for treating a cancer in a mammalian subject is provided, the kit comprising an assay for analyzing a tissue sample obtained from the subject and comprising tumor cells, the assay being capable of determining criteria comprising any one or more of (i) whether a level of sirtuin (SIRT3) protein is below a first predetermined threshold level in tumor cells of the tissue sample, (ii) whether a level of manganese superoxide dismutase acetylated at the lysine 68 residue (AcK68) exceeds a second predetermined threshold level, and (iii) whether expression levels of hypoxia-inducible factor $2_{\alpha}$ ($HIF2_{\alpha}$) exceed a third predetermined threshold level indicative of lineage plasticity for stemness, (iv) whether a level of Ki-67 protein exceeds a fourth predetermined threshold level, (v) whether a level of OCT4 protein exceeds a fifth predetermined threshold level, (vi) whether a level of SOX2 protein exceeds a sixth predetermined threshold level, and (vii) whether a ratio of monomeric to tetrameric MnSOD that exceeds a seventh predetermined threshold level, and a therapeutically effective amount of the pentaaza macrocyclic ring complex corresponding to Formula (I).

According to a further aspect, a method of treating a tumor that is resistant to an anti-cancer agent in a mammalian subject afflicted therewith is provided, comprising treating the subject by administering to the subject a therapeutically effective amount of a pentaaza macrocyclic ring complex corresponding to the Formula (I).

According to a further aspect, a method of treating a tumor that is resistant to ionizing radiation therapy in a mammalian subject afflicted therewith is provided, comprising treating the subject by administering to the subject a therapeutically effective amount of a pentaaza macrocyclic ring complex corresponding to the Formula (I).

According to yet a further aspect a method of treating a cancer in a mammalian subject afflicted with the cancer is provided, where the subject has resistance to an anti-cancer therapy, and/or has a tumor signature indicative of dysregulation of the MnSOD-Ac-K68/ROS/$HIF2_{\alpha}$ axis, the method comprising: administering to the subject an anti-cancer therapy selected from the group consisting of a therapeutically effective amount of a chemotherapeutic agent, a therapeutically effective amount of a therapeutic agent that inhibits a hormone receptor pathway associated with growth or progression of the cancer, a therapeutically effective amount of a cell cycle inhibitor, and a therapeutically effective dose of ionizing radiation, and administering to the subject a therapeutically effective amount of a pentaaza macrocyclic ring complex corresponding to the Formula (I) below, prior to, concomitantly with, or after administration of the anti-cancer therapy.

According to another aspect, a method of treating and/or reducing the likelihood of, a recurrence of a cancer in a mammalian subject at risk thereof, comprises administering to the subject a therapeutically effective amount of a pentaaza macrocyclic ring complex corresponding to the Formula (I), optionally in combination with a further anti-cancer therapy.

According to another aspect, a method of treating a tumor that is resistant to an anti-cancer therapy selected from the group consisting of a chemotherapeutic agent, a therapeutic agent that inhibits a hormone receptor pathway associated with growth or progression of the cancer, a cell cycle inhibitor, and radiation therapy, in a mammalian subject, the method comprising administering to the subject a therapeutically effective amount of a pentaaza macrocyclic ring complex corresponding to the Formula (I).

According to another aspect, a method of treating a cancer in a mammalian subject afflicted with the cancer is provided, the method comprising administering to the subject a therapeutically effective amount of an anti-cancer agent selected from the group consisting of a chemotherapeutic agent, a therapeutic agent that inhibits a hormone receptor pathway associated with growth or progression of the cancer, and a cell cycle inhibitor, and administering to the subject a therapeutically effective amount of a pentaaza macrocyclic ring complex corresponding to the Formula (I) prior to, concomitantly with, or after administration of the anti-cancer agent.

According to yet another embodiment, a method of preventing and/or reducing the likelihood of occurrence and/or recurrence of a cancer in a mammalian subject at risk thereof, comprises administering to the subject of an anti-cancer agent selected from the group consisting of a chemotherapeutic agent, a therapeutic agent that inhibits a hormone receptor pathway associated with growth or progression of the cancer, and a cell cycle inhibitor, and administering to the subject a therapeutically effective amount of a pentaaza macrocyclic ring complex corresponding to the Formula (I), prior to, concomitantly with, or after administration of the anti-cancer agent. According to yet another embodiment, a method of reducing invasiveness or metastasis of a cancer in a mammalian subject afflicted with the cancer, comprises administering to the subject a therapeutically effective amount of a pentaaza macrocyclic ring complex corresponding to the Formula (I). In yet another embodiment, a method of inhibiting the development and/or progression of a stemness phenotype in a cancer in a mammalian subject afflicted with the cancer, comprises administering to the subject a therapeutically effective amount of a pentaaza macrocyclic ring complex corresponding to the Formula (I).

According to yet another embodiment, a method of treating a cancer in a mammalian subject afflicted with the cancer, or preventing and/or reducing the likelihood of occurrence and/or recurrence of a cancer in a mammalian subject at risk thereof is provided, the method comprising: determining whether the mammalian subject exhibits a biomarker indicative of expression of a K68-acetylated form of manganese superoxide dismutase (MnSOD) that exceeds a predetermined level; and in a case where it is determined that the mammalian subject exhibits the biomarker indicative of expression of the K68-acetylated form of MnSOD that exceeds the predetermined level, administering to the subject a therapeutically effective amount of a pentaaza macrocyclic ring complex corresponding to the Formula (I).

According to yet another embodiment, a method of reducing resistance to an anti-cancer therapy selected from the group consisting of therapeutic treatment with chemotherapeutic agent, treatment with a therapeutic agent that inhibits a hormone receptor pathway associated with growth or progression of the cancer, treatment with a cell cycle inhibitor, and radiation therapy, in a mammalian subject exhibiting resistance to the anti-cancer therapy, comprises administering to the subject a therapeutically effective amount of the anti-cancer therapy, and administering to the subject a therapeutically effective amount of a pentaaza macrocyclic ring complex corresponding to the Formula (I) below, prior to, concomitantly with, or after administration of the anti-cancer therapy.

BRIEF DESCRIPTION OF THE DRAWINGS

FIGS. 1*a*-1*d* are graphs and images that illustrate that mimicking acetylated lysine 68 with $MnSOD^{K68Q}$ expression promotes a transformation-permissive phenotype in vitro where: FIG. 1*a* shows immortalization, i.e., growth beyond 15 passages, of pMEFs infected with lenti-$MnSOD^{WT}$, lenti-$MnSOD^{K68R}$, and lenti-$MnSOD^{K68Q}$ and either lenti-Myc or lenti-Ras; FIG. 1*b* shows the cell lines above tested for soft agar growth (upper) and colony formation (lower panels); FIG. 1*c* shows pMEFs infected with RasG12V tested for immortalization, doubling time, and soft agar growth; FIG. 1*d* shows NIH 3T3 cells expressing $MnSOD^{WT}$, $MnSOD^{K68R}$, and $MnSOD^{K68Q}$ tested for growth in soft agar (upper) and colony formation (lower panels). Experiments done in triplicate. Scale bar: 20 μm.

FIGS. 2*a* and 2*b* show MCF7 cells expressing $MnSOD^{WT}$, $MnSOD^{K68R}$, and $MnSOD^{K68Q}$ were implanted into the hind limb of nude mice (n=10 per group) and tested for xenograft tumor growth; FIGS. 2*c* and 2*d* show MCF7 cells expressing $MnSOD^{WT}$, $MnSOD^{K68R}$, and $MnSOD^{K68Q}$, where 2c shows immunofluorescence (IF) staining for Ki-67 and DAPI, and 2d is quantified for Ki-67 intensity as determined by ImageJ analysis; FIGS. 2*e* and 2*f* show T47D cells expressing $MnSOD^{WT}$, MnSODK68R, and $MnSOD^{K68Q}$, where 2e shows IF stained for Ki-67 and DAPI, and 2f is that staining quantified for Ki-67 intensity. All experiments were done in triplicate. Error bars represent±1 SEM. A one-way ANOVA analysis with Tukey's post-analysis was used. p<0.01 and *p<0.001

FIGS. 3*a*-3*e* are images and graphs that illustrate that mimicking acetylated lysine 68 with MnSOD-$K^{68Q}$ or inducing lysine 68 acetylation by knockdown of SIRT3 deacetylase alters MnSOD conformation by decreasing the full tetrameric form and increasing the monomeric form, and generates peroxidase activity, while mimicking perpetually deacetylated lysine with $MnSOD^{K68R}$ has opposing effects, where FIG. 3*a* illustrates MCF7 (left panel) and T47D (right panel) cells expressing $MnSOD^{WT}$, $MnSOD^{K68R}$, or $MnSOD^{K68Q}$ that were analyzed by semi-native crosslinking and blotting with an anti-MnSOD antibody; FIG. 3*b* illustrates MCF7 (left) and T47D (right) cells expressing shSIRT3 to knockdown SIRT3 levels that were analyzed by crosslinking; FIG. 3*c* illustrates Flag-$MnSOD^{WT}$, Flag-$MnSOD^{K68R}$, and Flag-$MnSOD^{K68Q}$ expressed in MCF7 cells that were measured for peroxidase activity. Error bars represent±1 SEM. p<0.01; FIG. 3***d* illustrates immortalized MnSOD−/− pMEFs expressing $MnSOD^{WT}$, $MnSOD^{K68R}$, or $MnSOD^{K68Q}$ that were analyzed by semi-native crosslinking and immunoblotted with an anti-MnSOD antibody to determine levels of tetrameric and monomeric forms; and FIG. 3*e* shows MnSOD−/− pMEFs expressing $MnSOD^{WT}$, $MnSOD^{K68R}$, or $MnSOD^{K68Q}$, without or with Ad-Mito-Cat or Ad-Empty, that were measured for transformation. All experiments were done in triplicate. A one-way ANOVA statistical analysis with Tukey's post-analysis was used.

FIGS. 4*a*-4*d* show immortalized MnSOD−/− MEFs expressing Flag-$MnSOD^{WT}$ that were cultured in NAM+TSA or NAD+, separated using a 50 kDa molecular cutoff membrane, where FIG. 4*a* shows that MnSOD-K68-Ac, MnSOD, and actin immunoreactive protein levels were determined, FIG. 4*b* shows peroxidase activity, FIG. 4*c* shows MnSOD activity in <50 kDa fractions, and FIG. 4*d* shows MnSOD activity in >50 kDa fractions; FIG. 4*e* shows bacterially produced and purified recombinant MnSOD-WT and MnSOD-K68-Ac proteins were characterized by size exclusion column chromatography. Standards are shown; FIGS. 4*f* and 4*g* show elution volumes 13 and 14 mL, corresponding to peak 1 (4f) and elution volumes 16 and 17 mL, corresponding to peak 2 (4*g*) from FIG. 4*e*, that were analyzed for MnSOD and MnSOD-K68-Ac immunoblotting (top panels) or Coomassie Brilliant Blue staining (bottom panels); FIGS. 4*h* and 4*i* show that Peak 1 (elution volumes 13 and 14 mL) and peak 2 (elution volumes 16 and 17 mL) were analyzed for, as shown in FIG. 4*h*, superoxide dismutase activity, and as shown in FIG. 4*i*, peroxidase activity. All experiments were done in triplicate. Errors represent±1 SEM. *p<0.01. A t-test was used to compare means of the two groups FIGS. 5***a*-5*h* are plots that illustrate that mimicking acetylated lysine 68 with $MnSOD^{K68Q}$ expression leads to oxidative stress in human breast cancer cells while mimicking perpetually deacetylated lysine with $MnSOD^{K68R}$ has opposing effects, where

MnSOD has opposing effects, where FIGS. 6*a-c* are clonogenic cell survival experiments for, with respect to FIG. 6*a*, MCF7-MnSOD$^{WT}$, MCF7-MnSOD$^{K68R}$, and MCF7-MnSOD$^{K68Q}$ cells, with respect to FIG. 6*b*, MCF7-shCtrl and MCF7-shSIRT3 cells, and with respect to FIG. 6*c*, MCF7 and MCF7-HTR (tamoxifen resistant) cells, with and without exposure to 1 μM hydroxy-Tam for 120 h (HT), as measured by cytotoxicity; FIG. 6*d* shows MCF7 and MCF7-HTR, as well as T47D and T47D-HTR cell lysates, immunoblotted for MnSOD-K68-Ac, MnSOD, SIRT3, and actin; FIG. 6*e* shows quantification of immunoreactive MnSOD-K68-Ac protein levels for MCF7 and MCF7-HTR, as well as T47D and T47D-HTR cell lysates; FIGS. 6*f*-6*h* show clonogenic cell survival experiments for MCF7-HTR cells, where FIG. 6*f* shows such cells transfected to express MnSOD$^{WT}$, MnSOD$^{K68Q}$, or MnSOD$^{K68R}$ that were treated with 1 μM hydroxy-Tam for 120 h; FIG. 6*g* shows such cells transfected to express SIRT3$^{WT}$ or SIRT3D$^{N}$ (S3DN; deacetylation-null SIRT3 gene) that were treated with 1 μM hydroxy-Tam; FIG. 6*h* shows such cells that were treated with 5 μM of the small molecule MnSOD mimetic GC4419 for 5 days. All experiments were done in triplicate. Error bars represent±1 SEM. p<0.01, and *p<0.001. Three-armed groups were analyzed via a one-way ANOVA statistical analysis with Tukey's post-analysis, and two-armed groups were analyzed by a t-test.

FIG. 7*a* shows total MnSOD activity of MCF7 and MCF7-HTR whole-cell lysates; FIGS. 7*b* and 7*c* show MCF7 and MCF7-HTR, and T47D and T47D-HTR whole-cell homogenates assayed for, with respect to FIG. 7*b*, steady-state levels of O2·−, by MitoSox oxidation; and with respect to FIG. 7*c*, $H_2O_2$ by $CDCFH_2$ oxidation; FIG. 7*d* shows glutathione levels in MCF7 and MCF7-HTR whole-cell homogenates; FIG. 7*e* shows semi-native gel analysis of MnSOD form for MCF7 and MCF7-HTR, as well as T47D and T47D-HTR cell lysates; FIGS. 7*f*-7*h* show whole-cell homogenates of MCF7-HTR cells expressing MnSOD$^{WT}$, MnSOD$^{K68Q}$, or MnSOD$^{K68R}$ assayed for, with respect to FIG. 7*f*, steady-state levels of O2·−, with respect to FIG. 7*g*, $H_2O_2$, and with respect to FIG. 7*h*, glutathione levels; FIG. 7*i* shows MCF7 and MCF7-HTR cells that were stained for Ki-67 and DAPI; FIGS. 7*j* and 7*k* show clonogenic survival experiments for MCF7-MnSOD$^{K68Q}$ cells expressing AdMitoCat or empty vectors. In the bottom row of FIG. 7*j* and in FIG. 7*k* cells were treated with 1 μM hydroxy-Tam for 120 h. All experiments were done in triplicate. Error bars represent±1 SEM. *p<0.05 and *p<0.001. Three-armed groups analyzed via a one-way ANOVA statistical analysis with Tukey's post-analysis and two-armed groups analyzed by a t-test FIGS. 8***a* and 8*b* are a plot and images showing results for MCF7 and MCF7-HTR cells (5.0×106) that were implanted into both hind limbs of nude mice and tumor volumes that were measured for 6 weeks, where in FIG. 8*a* the error bars represent±1 SEM, and in FIG. 8*b* are shown representative images of the tumors from MCF7-HTR (left panel) and MCF7 cells (right panel) at 6 weeks.

FIGS. 9*a*-9*b* are a graph and plot illustrating that mimicking acetylation of MnSOD-K68 with expression of MnSOD$^{K68Q}$ decreased doubling time, allowed xenograft growth, and caused estrogen independence while mimicking deacetylation of MnSOD-K68 with MnSOD$^{K68R}$ had opposing effects. With respect to FIG. 9*a*, pMEFs were infected with lenti-Myc (control) and either lenti-MnSOD$^{K68R}$ or lenti-MnSOD$^{K68Q}$, cells were selected in puromycin for 14 Days; then medium was replaced every 2 days for 28 days, and cell growth rate was evaluated. Doubling time for the pMEFs-control, pMEF-Myc-MnSODK68R, and pMEF-Myc-MnSODK68Q cells (middle column) was determined by Td=(t241)*log(2)/log(q2/q1). The MCF7 cells infected with lenti-Myc (control) and either lenti-MnSOD$^{K68R}$ or lenti-MnSOD$^{K68Q}$ were also used for xenograft growth experiments where 1 million cells were implanted into both hind limbs of nude mice. The tumor volumes were measured every 3 days. The control and Myc-MnSOD$^{K68R}$ cells did not form tumors while the Myc-MnSOD$^{K68Q}$ cells formed xenograft tumors (three upward arrows represent that all 10 nude mice hind leg infections grew xenografts). With respect to FIG. 9*b*, MCF7 cells infected with lenti-MnSOD$^{K68Q}$, and selected in puromycin for 14 days, were subsequently implanted into both hind limbs of nude mice without (black squares) or with estrogen supplementation (open circles). The tumor volumes were measured every 7 days (1.0×106 cells). All experiments were done in triplicate. Error bars represent±1 SEM.

FIGS. 10*a*-10*f* are, with respect to FIGS. 10*a*-10*b*, images that illustrate MCF7 cells and MCF7-MnSOD$^{WT}$ cells stained for Ki-67 levels. Asynchronously growing cultures of, with respect to FIG. 10*a*, MCF7 and MCF7-MnSOD'AFT cells, as well as with respect to FIG. 10*b*, T47D and T47D-MnSOD'AFT cells, constructed by infection with lenti-MnSOD$^{WT}$ or the empty control lentivirus. After 24 h of growth on glass coverslips, cells were fixed and stained with anti-Ki-67 and anti-DAPI antibodies. With respect to FIGS. 10*c*-10*d*, images are shown that illustrate MCF7-MnSOD$^{K68Q}$ cells exposed to either estrogen or Tam, and stained for Ki-67. MCF7-MnSOD$^{WK68QT}$ cells were exposed to either, as shown in FIG. 10*c*, estrogen (E2) for 5 days, or as shown in FIG. 10*d*, 1 μM 4-hydroxy-Tam (HT) for 5 days. Cells were replated on glass coverslips for 24 h with same concentrations of E2 or HT. Cells were then fixed and subsequently stained with anti-Ki-67 and anti-DAPI antibodies. With respect to FIGS. 10*e*-10*f*, plots are shown that illustrate quantifications of average Ki-67 intensity in the panels shown in FIGS. 10*c* and 10*d*, and are shown in the bar graphs. All experiments were done in triplicate. Error bars represent±1 SEM. Representative IHC images are shown.

FIGS. 11*a*-11*d* are plots and images showing mimicking acetylation of MnSOD-K68 with MnSOD$^{K68Q}$ expression promotes a transformation-permissive phenotype in vitro while mimicking deacetylation of MnSOD-K68 with $MnSOD^{K68R}$ has opposing effects, where FIG. 11*a* shows MnSOD−/− MEFs that were infected with lenti-$MnSOD^{WT}$, lenti-$MnSOD^{K68R}$, and lenti-$MnSOD^{K68Q}$ and cells were cultured and selected in puromycin for 14 days. The MnSOD−/− MEFs expressing $MnSOD^{K68Q}$ exhibited a more transformed phenotype, as compared to either cells expressing $MnSOD^{K68R}$ or $MnSOD^{WT}$, well as non-infected cells (MnSOD−/−). FIG. 11*b* shows results for 100 or 250 cells from all four of these cell lines that were plated per 60 mm dish, and after 14 days cells were stained with crystal violet to determine the growth at low density. FIG. 11*c* shows results for 10,000 cells from all four of these cell lines that were plated on 0.3% agar over 0.6% base agar for 21 days, and colonies were counted. FIG. 11*d* shows results for 20,000 cells from all four of these cell lines that were plated per 60 mm dish and measured each day, and doubling time was determined by Td=(t2−t1)*log(2)/log(q2/q1). All experiments were done in triplicate. Error bars represent±1 SEM. ***p<0.001. Representative images are shown.

FIGS. 15*a*-15*e* are graphs that illustrate that the decreased MnSOD activity and increased oxidative stress in hydroxy-Tam resistant human breast cancer cells can be reversed by expression of $MnSOD^{K68R}$. With respect to FIGS. 15*a* and 15*b*, T47D cells selected for 3 months in 1 μM hydroxy-Tam were harvested, and whole-cell homogenates were used for:

in FIG. 15*a*, biochemical analysis of total MnSOD activity, and in FIG. 15*b*, biochemical analysis of glutathione levels. With respect to FIGS. 15*c*-15*e*, T47D-HTR cells were infected with lenti-MnSOD$^{WT}$, lenti-MnSOD$^{K68R}$, or lenti-MnSOD$^{K68Q}$ and harvested. Whole-cell homogenates were used for, in FIG. 15*c*, biochemical analysis of MitoSox oxidation, in FIG. 15*d*, biochemical analysis of $H_2O_2$ as detected by $CDCFH_2$ oxidation, and in FIG. 15*e*, biochemical analysis of glutathione levels. All experiments were done in triplicate. Error bars represent±1 SEM. *p<0.05, p<0.01, and *p<0.001.

In FIGS. 16*d* and 16*e*, MCF7-HTR cells, and in FIGS. 16*f* and 16*g*, T47D-HTR cells, were treated with 5 μM GC4419 and/or 1 μM 4-hydroxy-Tam for 5 days, and then stained for Ki-67 as well as DAPI. Quantifications of average Ki-67 intensity are shown in the bar graphs. All experiments were done in triplicate. Error bars represent±1 SEM. ***p<0.001. Representative images are shown.

In FIG. 17*e*, MCF7 and MCF7-HTR cells were implanted into both hind limbs of nude mice and tumor volumes were measured every 3 days for 6 weeks and the number of tumors that successfully implanted versus the total number of mice infected with MCF7 and MCF7-HTR as well as the average tumor weight and tumor size are shown. Representative images are shown. All experiments were done in triplicate. Error bars represent±1 SEM. ***p<0.001.

FIG. 18*a* shows MCF7-HTR cells that were infected with pTet-DualOn (Clontech) and selected with puromycin followed by infection with pTre-Dual2-Flag-MnSODK68R and selection with hygromycin. These cells (MCF7-HTR-Tet-On-MnSOD$^{K68Q}$ cells), without and with exposure to tetracycline, were tested by immunofluorescent imaging for both the presence of pTet-DualOn and the presence of pTre-Dual2-Flag-MnSOD$^{K68R}$. FIG. 18*b* shows the MCF7-HTR-Tet-ON-MnSOD$^{K68Q}$ cells above that were also isolated, separated by SDS-PAGE, and immunoblotted with anti-MnSOD, Flag, and Tubulin antibodies. A subgroup of human luminal B tumors exhibited high levels of MnSOD-K68-Ac.

In FIG. 19*a* LNCaP-ENZR cells were selected by continuous months of growth (greater than 3 months) in ENZ (10 μM). Extracts from these cells were immunoblotted with anti-MnSOD-K68-Ac and MnSOD antibodies. In FIG. 19*b* control and LNCaP-ENZR cells were glutaraldehyde cross-linked, harvested, and extracts were separated on SDS-PAGE, and immunoblotted with an anti-MnSOD antibody. In FIG. 19*c* extracts were assayed for MnSOD activity. Error bars are ±1 SEM. Experiments in triplicate. **p<0.01.

In FIG. 20*a*, clonogenic cell survival experiments were done in LNCaP-ENZR cells infected with lenti-MnSOD$^{K68R}$ or lenti-MnSOD$^{K68Q}$, in the presence of ENZ (10 μM). In FIG. 20*b*, clonogenic survival assays were done in LNCaP cells infected with lenti-MnSOD$^{WT}$, lenti-MnSOD$^{K68R}$, and lenti-MnSOD$^{K68Q}$, and selected with neomycin, and placed in 10 μM of ENZ for 72 hr. Error bars±1 SEM. Experiments were done in triplicate. **p<0.01.

In FIG. 21(*a*), clonogenic cell survival experiments were performed in LNCaP-ENZR (left two bars) and LNCaP-MnSOD$^{K68Q}$ (right two bars) treated with ENZ, with or without GC4419 (20 μM) for 5 days. In FIG. 21*b*, LNCaP-MnSOD$^{K68Q}$ cells, which exhibit ENZR, were implanted into hindlimbs of male nude mice and treated with GC4419 (10 mg/kg, once per week), ENZ (25 mg/kg/day), or GC4419+ENZ. Tumor volumes were measured three times a week for 46 days. For each group n=10. Error bars±1 SEM. All experiments done in triplicate. **p<0.01.

In FIG. 22*a*, samples were stained for MnSOD-K68-Ac and quantified by relative IHC staining intensity. Shaded boxes are interquartile range, whiskers are 10th-90th percentile. In FIG. 22*b*, images are provided showing MnSOD-K68-Ac staining in PIN, G3, and G4 human prostate tumor tissue samples.

In FIG. 23*a*, LNCaP-MnSOD$^{K68Q}$ cells were treated with ENZ for 3 months and immunoblotted with anti-AR and actin antibodies. In FIG. 23*b*, LNCaP cells containing the AR promoter upstream of mCherry were infected with lenti-$MnSOD^{K68Q}$ and mCherry levels were measured. Error bars are ±1 SEM.

In FIG. 24*a*, LNCaP and LNCaP-$MnSOD^{K68Q}$ cells were harvested, and immunoblotted with antibodies to $HIF2_{\alpha}$, SOX2, and Oct4 as markers of stemness, and to actin. In FIG. 24*b*, LNCaP (striped lines) and LNCaP-$MnSOD^{K68Q}$ cells (black dots) were measured by clonogenic cell survival assays with and without ENZ, and infection with a scrambled (con) or $HIF2_{\alpha}$ shRNAs. Experiments in triplicate. Error bars are ±1 SEM. * $P<0.05$.

FIGS. 25*a*-25*b* show clonogenic cell survival studies in MCF7-$MnSOD^{K68Q}$ cells exposed to either: Fulv at 100 nM (in FIG. 25*a*); or Palb at 0.5 $_{\mu}$M (in FIG. 25*b*) using standard methods. FIG. 25*c* shows MCF7-$MnSOD^{K68Q}$ cells exposed to GC4419 at (10 μM) or Palb at 0.5 $_{\mu}$M, alone or when combined. Error bars are ±1 SEM. Experiments in triplicate. *** $p<0.001$.

In FIG. 26*a*, MCF7 and MCF7-$MnSOD^{K68Q}$ cells were harvested and immunoblotted with antibodies to $HIF2_{\alpha}$, SOX2, and OCT4 as markers of stemness, and to actin. In FIG. 26*b*, MCF7 and MCF7-$MnSOD^{K68Q}$ cells were measured by clonogenic cell survival experiments, without and with Tam exposure, and infected with either a scrambled (Con) or $HIF2_{\alpha}$ shRNA. All experiments were done in triplicate. Error bars are ±1 SEM. * $p<0.05$.

FIG. 27*a* shows an immunoblot of MCF7-CispI-R cells (cisplatin-resistant cells), as compared to control (C) MCF7 cells, using anti-MnSOD-K68-Ac, MnSOD, $HIF2_{\alpha}$, or actin antibodies. In FIG. 27*b*, ROS was measured in MCF7-CispI-R cells, compared with MCF7 cells, using an Amplex Red assay. In FIG. 27*c*, MCF7 and MCF7-$MnSOD^{K68Q}$ cells were measured by clonogenic cell survival assays, without and with cisplatin exposure, and infected with scrambled (C) or $HIF2_{\alpha}$ shRNA. All experiments were done in triplicate. Error bars are ±1 SEM. * $p<0.05$.

In FIGS. 28*a*-28*b*, cell lysates of 250 nM, 500 nM, 1 μM cisplatin-resistant and 500 μM, 1 nM and 2 nM doxorubicin-resistant MCF7 cells (cultured in drug-containing media for 3 months) were collected and immunoblotted for MnSOD-K68-Ac, MnSOD, actin and tubulin. In FIGS. 28*d*-28*e*, cell lysates of 2.5 μM, 5 μM, 10 μM cisplatin-resistant and 5 nM, 10 nM and 20 nM doxorubicin-resistant T47D cells (cultured in drug-containing media for 3 months) were collected and immunoblotted for MnSOD-K68-Ac, MnSOD, actin and tubulin. In FIGS. 28*c* and 28*f*, 10,000 MCF7 or T47D cells overexpressed with empty vector, MnSOD, $MnSOD^{K68R}$ or $MnSOD^{K68Q}$ were plated in 96 well plate and treated with cisplatin (1 μM for MCF7 and 10 μM for T47D) or doxorubicin (2 nM for MCF7 and 20 nM for T47D) the next day. After 48 hours, MTT assay is conducted to determine the cell viability after chemotherapy drug treatment.

FIG. 29*a* shows $Sirt3^{-/-}$-MT-$SIRT3^{DN}$ (deacetylation activity null) and FIG. 29*b* shows that $Sirt3^{-/-}$-MT-$SIRT3_{WT}$ tumor cells ($1.0\times10^{6}$ cells) were injected bilaterally into the hind limbs of nude mice (n=10) and treated without and with 2 mg/kg GC4401 injected IP starting at day four. Mice were subsequently injected with luciferin potassium (120 mg/kg) every week and signal intensity will be quantified. Error bars represent one SD from the mean.

FIG. 30*a* shows that MCF7-$MnSOD^{WT}$, and MCF7-$MnSOD^{K68Q}$ cells were plated and exposed with 5 Gy ionizing radiation and clonogenic cell survival was determined, and FIG. 30*b* shows MCF7-$MnSOD^{K68Q}$ cells were treated with or without 5 μM GC4419 for 5 days and exposed with 5 Gy ionizing radiation and clonogenic cell survival was determined. All experiments were done in triplicate. Error bars represent±1 SEM. ***$p<0.001$. Data were analyzed by a t-test.

FIG. 31*a* shows results for LNCaP cells that were treated with 5 Gy IR on 5 consecutive days. The subsequent IRR cells (LNCaP-IRR cells), and LNCaP controls, were lysed and extracts were separated by SDS-PAGE, and immunoblotted with an anti-MnSOD-K68-Ac antibody. FIG. 31*b* shows results for the extracts assayed for MnSOD activity. All experiments were done in triplicate. Error bars are ±1 SEM. **$p<0.01$.

ABBREVIATIONS AND DEFINITIONS

Figure 1B:
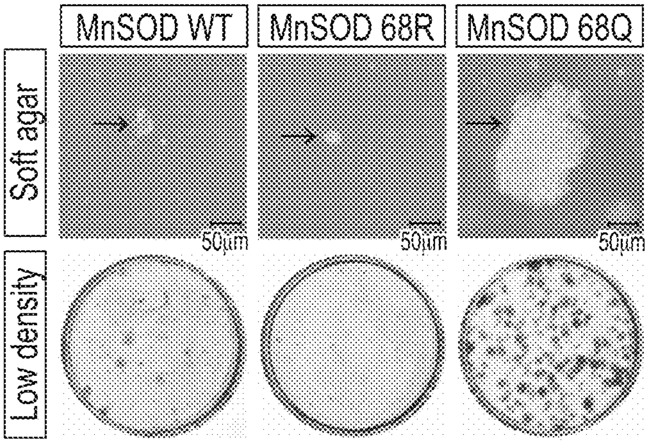

The following definitions and methods are provided to better define the present invention and to guide those of ordinary skill in the art in the practice of the present invention. Unless otherwise noted, terms are to be understood according to conventional usage by those of ordinary skill in the relevant art.

The term "AcK68" as used herein refers to the acetylated form of manganese superoxide dismutase (MnSOD) having acetylation at the K68 residue of the MnSOD protein, and may also be referred to herein as MnSOD-K68-Ac.

"Acyl" means a —COR moiety where R is alkyl, haloalkyl, optionally substituted aryl, or optionally substituted heteroaryl as defined herein, e.g., acetyl, trifluoroacetyl, benzoyl, and the like.

"Acyloxy" means a —OCOR moiety where R is alkyl, haloalkyl, optionally substituted aryl, or optionally substituted heteroaryl as defined herein, e.g., acetyl, trifluoroacetyl, benzoyl, and the like.

"Alkoxy" means a —OR moiety where R is alkyl as defined above, e.g., methoxy, ethoxy, propoxy, or 2-propoxy, n-, iso-, or tert-butoxy, and the like.

"Alkyl" means a linear saturated monovalent hydrocarbon moiety such as of one to six carbon atoms, or a branched saturated monovalent hydrocarbon moiety, such as of three to six carbon atoms, e.g., $C_1$-$C_6$ alkyl groups such as methyl, ethyl, propyl, 2-propyl, butyl (including all isomeric forms), pentyl (including all isomeric forms), and the like.

Moreover, unless otherwise indicated, the term "alkyl" as used herein is intended to include both "unsubstituted alkyls" and "substituted alkyls," the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$" when used in conjunction with a chemical moiety, such as alkyl and aralkyl, is meant to include groups that contain from x to y carbons in the chain. For example, the term $C_{x-y}$ alkyl refers to substituted or unsubstituted saturated hydrocarbon groups, including straight chain alkyl and branched chain alkyl groups that contain from x to y carbon atoms in the chain.

"Alkylene" means a linear saturated divalent hydrocarbon moiety, such as of one to six carbon atoms, or a branched saturated divalent hydrocarbon moiety, such as of three to six carbon atoms, unless otherwise stated, e.g., methylene, ethylene, propylene, 1-methylpropylene, 2-methylpropylene, butylene, pentylene, and the like.

"Alkenyl" a linear unsaturated monovalent hydrocarbon moiety, such as of two to six carbon atoms, or a branched saturated monovalent hydrocarbon moiety, such as of three to six carbon atoms, e.g., ethenyl (vinyl), propenyl, 2-propenyl, butenyl (including all isomeric forms), pentenyl (including all isomeric forms), and the like.

"Alkaryl" means a monovalent moiety derived from an aryl moiety by replacing one or more hydrogen atoms with an alkyl group.

"Alkenylcycloalkenyl" means a monovalent moiety derived from an alkenyl moiety by replacing one or more hydrogen atoms with a cycloalkenyl group.

"Alkenylcycloalkyl" means a monovalent moiety derived from a cycloalkyl moiety by replacing one or more hydrogen atoms with an alkenyl group.

"Alkylcycloalkenyl" means a monovalent moiety derived from a cycloalkenyl moiety by replacing one or more hydrogen atoms with an alkyl group.

"Alkylcycloalkyl" means a monovalent moiety derived from a cycloalkyl moiety by replacing one or more hydrogen atoms with an alkyl group.

"Alkynyl" means a linear unsaturated monovalent hydrocarbon moiety, such of two to six carbon atoms, or a branched saturated monovalent hydrocarbon moiety, such as of three to six carbon atoms, e.g., ethynyl, propynyl, butynyl, isobutynyl, hexynyl, and the like.

"Alkoxy" means a monovalent moiety derived from an alkyl moiety by replacing one or more hydrogen atoms with a hydroxy group.

"Amino" means a —$NR^aR^b$ group where $R^a$ and $R^b$ are independently hydrogen, alkyl or aryl.

"Antibody" as used herein includes an antibody of classes IgG, IgM, IgA, IgD, or IgE, or fragments or derivatives thereof, including Fab, F(ab')2, Fd, and single chain antibodies, diabodies, bispecific antibodies, and bifunctional antibodies. The antibody may be a monoclonal antibody, polyclonal antibody, affinity purified antibody, or mixtures thereof, which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety. The antibody may be a human or humanized antibody.

"Aralkyl" means a monovalent moiety derived from an alkyl moiety by replacing one or more hydrogen atoms with an aryl group.

"Aryl" means a monovalent monocyclic or bicyclic aromatic hydrocarbon moiety of 6 to 10 ring atoms e.g., phenyl or naphthyl.

"Cycle" means a carbocyclic saturated monovalent hydrocarbon moiety of three to ten carbon atoms.

"Cycloalkyl" means a cyclic saturated monovalent hydrocarbon moiety of three to ten carbon atoms, e.g., cyclopropyl, cyclobutyl, cyclopentyl, or cyclohexyl, and the like.

"Cycloalkylalkyl" means a monovalent moiety derived from an alkyl moiety by replacing one or more hydrogen atoms with a cycloalkyl group, e.g., cyclopropylmethyl, cyclobutylmethyl, cyclopentylethyl, or cyclohexylethyl, and the like.

"Cycloalkylcycloalkyl" means a monovalent moiety derived from a cycloalkyl moiety by replacing one or more hydrogen atoms with a cycloalkyl group.

"Cycloalkenyl" means a cyclic monounsaturated monovalent hydrocarbon moiety of three to ten carbon atoms, e.g., cyclopropenyl, cyclobutenyl, cyclopentenyl, or cyclohexenyl, and the like.

"Cycloalkenylalkyl" means a monovalent moiety derived from an alkyl moiety by replacing one or more hydrogen atoms with a cycloalkenyl group, e.g., cyclopropenylmethyl, cyclobutenylmethyl, cyclopentenylethyl, or cyclohexenylethyl, and the like.

"Ether" means a monovalent moiety derived from an alkyl moiety by replacing one or more hydrogen atoms with an alkoxy group.

"Halo" means fluoro, chloro, bromo, or iodo, preferably fluoro or chloro.

"Heterocycle" or "heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heteroaryl" means a monovalent monocyclic or bicyclic aromatic moiety of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

"Nitro" means —NO2.

"Multi-therapy resistance" as used herein to refer to cancer exhibiting such resistance, is characterized by resistance to two or more anti-cancer therapies, such that the cancer fails to respond to treatment therewith. Examples of such anti-cancer therapies can include chemotherapy, radiation therapy, therapy with an agent that inhibits a hormone receptor pathway such as an endocrine agent, and therapy with a cell cycle inhibitor such as a CDK4/6 inhibitor. Such failure to respond or cessation of response may be determined by any number of imaging modalities as understood by a person of ordinary skill in the art, including without limitation x-ray imaging, computerized tomography, magnetic resonance imaging, ultrasound, positron emission tomography, radionuclide imaging or visual observation, or by a plasma or tissue biomarker indicating the level of cancer activity including without limitation, PSA, PSMA, CA19-9, CA-125; or pre-treatment by ex vivo testing of cancer cells for response to the therapy by any number of methods including without limitation genomic testing, genomic screening, and ex vivo profiling.

"Organosulfur" means a monovalent moiety a —SR group where R is hydrogen, alkyl or aryl.

"Substituted alkyl," "substituted cycle," "substituted phenyl," "substituted aryl," "substituted heterocycle," and "substituted nitrogen heterocycles" means an alkyl, cycle, aryl, phenyl, heterocycle or nitrogen-containing heterocycle, respectively, optionally substituted with one, two, or three substituents, such as those independently selected from alkyl, alkoxy, alkoxyalkyl, halo, hydroxy, hydroxyalkyl, or organosulfur. Generally, the term "substituted" includes groups that are substituted with any one or more of $C_{1-4}$alkyl, $C_{2-4}$alkenyl, halogen, alcohol and/or amine.

"Thioether" means a monovalent moiety derived from an alkyl moiety by replacing one or more hydrogen atoms with an —SR group wherein R is alkyl.

As used herein, (i) the compound referred to herein and in the Figures as compound 401, 4401 or GC4401 is a reference to the same compound, (ii) the compound referred to herein and in the Figures as compound 403, 4403 or GC4403 is a reference to the same compound, (iii) the compound referred to herein and in the Figures as compound 419, 4419 or GC4419 is a reference to the same compound, and (iv) the compound referred to herein and in the Figures as compound 444, 4444 or GC4444 is a reference to the same compound.

Furthermore, the use of the term "consisting essentially of," in referring to a method of treatment, means that the method substantially does not involve providing another therapy and/or another active agent in amounts and/or under conditions that would be sufficient to provide the treatment, and which are other than the therapies and/or active agents specifically recited in the claim. Similarly, the use of the term "consisting essentially of," in referring to a kit for treatment, means that the kit substantially does not include another therapy and/or another active agent provided in amounts and/or under conditions that would be sufficient to provide the treatment, and which are other than the therapies and/or active agents specifically recited in the claim.

DETAILED DESCRIPTION

In one embodiment, aspects of the present disclosure are directed to the treatment of cancers that have multi-therapy resistance using a pentaaza macrocyclic ring complex. Cancers having multi-therapy resistance exhibit resistance to two or more anti-cancer therapies, such that the cancer fails to respond to treatment therewith. For example, the cancer may exhibit resistance to anti-cancer therapies that can include chemotherapy, radiation therapy, therapy with an agent that inhibits a hormone receptor pathway such as an endocrine agent, and therapy with a cell cycle inhibitor such as a CDK4/6 inhibitor. Cancers having such multi-therapy resistance can be difficult to treat, as they may not respond to the standard therapeutic regimens generally prescribed for the cancer. Aspects of the present disclosure are further directed to the treatment of cancers with certain tumor signatures, using a pentaaza macrocyclic ring complex, optionally in combination with another therapeutic agent.

Specifically, it has been unexpectedly discovered that certain pentaaza macrocyclic ring complexes may be capable of treating patients with cancers that are multi-therapy resistant. According to certain embodiments herein, multi-therapy resistant cancers can be characterized by having an increased level of an acetylated form of manganese superoxide dismutase (MnSOD) having acetylation at the K68 residue of the MnSOD protein, and/or reduced levels of SIRT3 protein (see, Zhu et al., Lysine 68 Acetylation Directs MnSOD as a Tetrameric Detoxification Complex Versus a Monomeric Tumor Promoter, *Nature Communications,* 10: 2399 (2019)). According to certain further aspects, it has been unexpectedly discovered that certain pentaaza macrocyclic ring complexes may be capable of treating patients with cancers that are characterized by having an increased level of expression of hypoxia-inducible factor $2_{\alpha}$ ($HIF2_{\alpha}$) that is indicative of lineage plasticity for stemness. For example, in certain embodiments, pentaaza macrocyclic ring complexes may be able to treat cancers that have an inherent resistance to certain treatment agents, and/or may be capable of reducing and even halting the development of resistance to, and thus increase the effectiveness of, certain treatment agents, such as endocrine therapy agents such as tamoxifen and/or enzalutamide, and other agents. That is, the pentaaza macrocyclic ring complexes may provide treatment, in certain aspects, to tumors that have resistance to treatment with a therapeutic agent (e.g. tamoxifen) before treatment has even begun, and/or provide treatment to tumors that have developed resistance over the course of treatment with such treatment agents.

According to other embodiments, similar effects are achieved with respect to reducing resistance to, and thus increasing effectiveness of, other therapeutic agents used to treat cancers, such as chemotherapeutic agents including cisplatin and doxorubicin, either with respect to inherent and/or acquired resistance of the tumors to the chemotherapeutic agents. According to certain other embodiments, certain pentaaza macrocyclic ring complexes described herein are capable of providing treatment as a sole therapy (i.e. without requiring administration of a further therapeutic agent, e.g. endocrine or chemotherapeutic agent), for cancers having a tumor signature characterized by a relatively high levels of, e.g., AcK68 and/or $HIF2_{\alpha}$ and/or relatively low level of SIRT3 and/or other biomarkers described herein.

According to certain embodiments, manganese superoxide dismutase (MnSOD) functions as a tumor suppressor, however, once tumorigenesis occurs, clinical data suggest MnSOD levels correlate with more aggressive human tumors, implying a potential dual function of MnSOD in the regulation of metabolism. It has been unexpectedly discovered that the MnSOD-K68 acetylation (Ac) mimic mutant (MnSODK68Q) functions as a tumor promoter. Interestingly, in various breast cancer and primary cell types the expression of MnSODK68Q is accompanied with a change of MnSOD's stoichiometry from a known homotetramer complex to a monomeric form. Biochemical experiments using the MnSOD-K68Q Ac-mimic, or physically K68-Ac (MnSOD-K68-Ac), suggest that these monomers function as a peroxidase, distinct from the established MnSOD superoxide dismutase activity. MnSODK68Q expressing cells exhibit resistance to tamoxifen (Tam) and cells selected for Tam resistance exhibited increased K68-Ac and monomeric MnSOD. These results suggest a MnSOD-K68-Ac metabolic pathway for Tam resistance, carcinogenesis and tumor progression (see, Zhu et al., Lysine 68 Acetylation Directs MnSOD as a Tetrameric Detoxification Complex Versus a Monomeric Tumor Promoter, *Nature Communications,* 10: 2399 (2019)).

According to further embodiments, it has been unexpectedly discovered that tumors having increased levels of AcK68 also exhibit disrupted cellular metabolism, increased levels of reactive oxygen species (ROS), and stabilized levels of $HIF2_{\alpha}$, which can lead to a lineage plasticity phenotype and thus tumor cells with resistance to treatment with therapeutic agents, such as prostate cancer cells with resistance to endocrine agents such as enzalutamide. In yet further embodiments, it has been unexpectedly discovered that the dysregulation and/or disruption of physiological MnSOD-K68-Ac axis can lead to a chemotherapy resistant phenotype in certain cancers, such as ER+ breast cancer, as AcK68 expression directs dysregulation of mitochondrial morphology and ultrastructure, and disrupts mitochondrial metabolism. In yet another embodiment, it has been unexpectedly discovered that dysregulation and/or disruption of physiological MnSOD-K68-Ac axis can promote lineage plasticity for stemness, which can lead to increased invasiveness and even metastasis of the cancer, and can also result in resistance of the cancer to one or more anti-cancer therapeutic agents.

According to certain embodiments, a method of treating a cancer in a mammalian subject, the cancer being characterized as having multi-therapy resistance, the method comprising: administering to the mammalian subject a therapeutically effective amount of a pentaaza macrocyclic ring complex corresponding to the Formula (I) below:

(I)

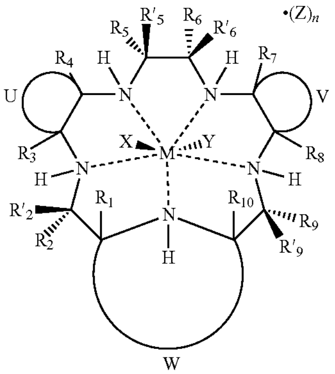

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

According to certain embodiments, the multi-therapy resistant cancer is resistant to at least two therapies selected from the group consisting of treatment with a chemotherapeutic agent, treatment with a therapeutic agent that inhibits a hormone receptor pathway, treatment with a cell cycle inhibitor, and treatment with radiation therapy. According to one embodiment, the multi-therapy resistant cancer is resistant to one or more therapies selected from the group consisting of treatment with a platinum-containing agent, treatment with an anthracycline, treatment with a hormone receptor pathway inhibitor, treatment with a cell cycle inhibitor, and treatment with radiation therapy. According to another embodiment, the multi-therapy resistant cancer is resistant to treatment with at least one of a platinum-containing chemotherapeutic agent selected from the group consisting of cisplatin, oxaliplatin, carboplatin, nedaplatin, lobaplatin, heptaplatin, dicycloplation, lipoplatin, LA-12, phosphaplatin, phenanthriplatin, prolindac, triplatin tetranitrate, picoplatin, satraplatin and/or pharmaceutically acceptable salts thereof, and/or an anthracycline chemotherapeutic agent selected from the group consisting of doxorubicin, daunorubicin, epirubicin and idarubicin, and/or pharmaceutically acceptable salts thereof.

According to yet another embodiment, the multi-therapy resistant cancer is resistant to a therapeutic agent that inhibits a hormone receptor pathway associated with growth or progression of the cancer. In one embodiment, the multi-therapy resistant cancer is resistant to a therapeutic agent that inhibits a hormone receptor pathway associated with growth or progression of the cancer targets any one or more of the estrogen receptor pathway, progesterone receptor pathway, and the androgen receptor pathway. In another embodiment, the multi-therapy resistant cancer is resistant to a therapeutic agent that targets any one or more of the estrogen receptor pathway, progesterone receptor pathway, and the androgen receptor pathway is selected from the group consisting of estrogen receptor inhibitors, estrogen receptor degraders/downregulators, selective estrogen receptor modulators (SERMs), aromatase inhibitors, GnRH agonists, androgen synthesis inhibitors, androgen receptor inhibitors, and selective progesterone receptor modulators (SPRMs). In yet another embodiment, the multi-therapy resistant cancer is resistant to a therapeutic agent targeting the estrogen receptor pathway that comprises at least one selected from the group consisting of tamoxifen, letrozole, clomifene, 4-hydroxytamoxifen, toremifene, raloxifene, nafoxidine, lasofoxifene, bazedoxifene, ospemifene, fulvestrant, brilanestrant, elacestrant, and derivatives, salts and/or prodrugs thereof.

In another embodiment, the multi-therapy resistant cancer is resistant to a therapeutic agent that targets the androgen receptor pathway that comprises any selected from the group consisting of an androgen receptor antagonist, an androgen synthesis inhibitor and an antigonadotropin. In yet another embodiment, the multi-therapy resistant cancer is resistant to a therapeutic agent that targets the androgen receptor pathway that comprises at least one selected from the group consisting of cyproterone acetate, megestrol acetate, chlormadinone acetate, spironolacone, oxendolone, osaterone acetate, flutamide, bicalutamide, nilutamide, topilutamide, enzalutamide, apalutamide, dienogest, drospirenone, medogestone, nomegestrol acetate, promegestone, trimegestone, ketoconazole, abiraterone acetate, seviteronel, aminoglutethimide, finasteride, dutasteride, episteride, alfatradial, cyproterone acetate, medrogestone, flutamide, nilutamide, bifluranol, leuprorelin, cetrorelix, allylestrenol, chlormadinone acetate, cyproterone acetate, gestonorone caproate, hydroxyprogesterone caproate, medroxyprogesterone acetate, megestrol acetate, osaterone acetate, oxendolone, estradiol, estradiol esters, ethinylestradiol, conjugated estrogens, diethylstilbestrol, and derivatives, salts and/or prodrugs thereof. In yet another embodiment, the multi-therapy resistant cancer is resistant to a therapeutic agent targeting the progesterone receptor pathway that comprises a Type 1, Type II or Type Ill selective modulator of progesterone (SPRM) that is at least one selected from the group consisting onapristone, mifepristone, lonaprisan, aglepristone, Org31710, Org31806, CDB-2914 and CDB-4124, and derivatives, salts and/or prodrugs thereof.

In yet another embodiment, the multi-therapy resistant cancer is resistant to therapy with a cell cycle inhibitor comprising a CDK4/6 inhibitor comprising at least one selected from the group of palbociclib, abemaciclib, ribociclib, and derivatives, salts and/or prodrugs thereof.

According to certain embodiments, a method of treating a cancer in a mammalian subject is provided, where the cancer comprises a tumor signature characterized by any one or more of (i) a level of sirtuin (SIRT3) protein that is below a first predetermined threshold level, (ii) a level of manganese superoxide dismutase acetylated at the lysine 68 residue (AcK68) that exceeds a second predetermined threshold level, (iii) expression levels of hypoxia-inducible factor $2_\alpha$ ($HIF2_\alpha$) that exceed a third predetermined threshold level indicative of lineage plasticity for stemness, (iv) a level of Ki-67 protein that exceeds a fourth predetermined threshold level, (v) a level of OCT4 that exceeds a fifth predetermined threshold level, (vi) a level of SOX2 that exceeds a sixth predetermined threshold level, and (vii) a ratio of monomeric to tetrameric MnSOD that exceeds a seventh predetermined threshold level, and where the method comprises administering to the mammalian subject a therapeutically effective amount of a pentaaza macrocyclic ring complex corresponding to the Formula (I) described herein. A cancer with the tumor signature meeting any of the criteria (i)-(vii) may, for example, have resistance to treatment comprising any one or more of treatment with a chemotherapeutic agent, treatment with a therapeutic agent that inhibits a hormone receptor pathway, such as an endocrine agent, treatment with a cell cycle inhibitor such as a CDK4/6 inhibitor, and treatment with ionizing radiation. According to certain embodiments, administration of the pentaaza macrocyclic ring complex can reduce the resistance of the cancer to treatment, to improve the efficacy thereof.

According to yet another embodiment, a method of treating a cancer in a mammalian subject is provided, where the method comprises selecting a subject that is a suitable subject for treatment with a pentaaza macrocyclic ring complex corresponding to Formula (I). For example, the subject may be selected on the basis of exhibit a biomarker, such as a tumor signature, indicative of a likelihood of responsiveness to such treatment. In another example, the subject may be one that has an inherent resistance to, and/or has developed resistance to, treatment comprising any one or more of treatment with a chemotherapeutic agent, treatment with a therapeutic agent that inhibits a hormone receptor pathway, such as an endocrine agent, treatment with a cell cycle inhibitor such as a CDK4/6 inhibitor, and treatment with ionizing radiation. According to one embodiment, the method can comprise selecting the subject by obtaining a test tissue sample from the subject that comprises tumor cells, and testing the tissue sample for the presence of certain biomarkers. The test tissue sample can be obtained, for example, by biopsy or other conventional method. According to certain aspects, the tissue sample is selected from a subject suffering from a type of cancer where dysregulation of any one or more of AcK68, SIRT3 and/or $HIF2_\alpha$ is implicated, as described further herein, such as for example any one or more of breast and prostate cancer. The SIRT3 may be levels of, for example, mitochondrial SIRT3. SIRT3 is a protein in humans encoded by the SIRT3 gene [sirtuin (silent mating type information regulation 2 homolog) 3 (*S. cerevisiae*)], and SIRT3 may also be referred to as NAD-dependent deacetylase sirtuin-3. The tissue sample may also be selected from a subject suffering from a type of cancer which gives rise to dysregulation of any of Ki-67 protein (also known as antigen Ki-67 or MK167, encoded by the MK167 gene), OCT4 protein (octamer-binding transcription fact 4, also known as POU5F1 (POU domain, class 5, transcription factor 1), encoded by the POU5F1 gene), and/or SOX2 protein ((sex determining region Y)-box 2, also known as SRY). According to yet another embodiment, the tissue sample may be selected from a subject suffering from a type of cancer with gives rise to dysregulation in a ratio of monomeric to tetrameric MnSOD (manganese superoxide dismutase).

According to one embodiment, the tissue sample can be tested by assessing the tissue sample to determine criteria comprising any one or more of (i) whether a level of sirtuin (SIRT3) protein is below a first predetermined threshold level in tumor cells of the tissue sample, (ii) whether a level of manganese superoxide dismutase acetylated at the lysine 68 residue (AcK68) exceeds a second predetermined threshold level, and (iii) whether expression levels of hypoxia-inducible factor $2_{\alpha}$ ($HIF2_{\alpha}$) exceed a third predetermined threshold level indicative of lineage plasticity for stemness, (iv) whether a level of Ki-67 protein exceeds a fourth predetermined threshold level, (v) whether a level of OCT4 protein exceeds a fifth predetermined threshold level, (vi) whether a level of SOX2 protein exceeds a sixth predetermined threshold level, and (vii) whether a ratio of monomeric to tetrameric MnSOD that exceeds a seventh predetermined threshold level. In yet another embodiment, a diagnostic method can be provided separately from the treatment with the pentaaza macrocyclic ring complex, the diagnostic method including analyzing the tissue sample to determine any of criteria (i)-(vii) as described herein.

For example, in one embodiment, the tissue sample can be tested to determine whether a criteria (i) is met of exhibiting a relatively low level of SIRT3, as indicated by being below a predetermined threshold level, as this low level can indicate likely responsiveness of the tumor to treatment with the pentaaza macrocyclic ring complex of Formula (I). As another example, the tissue sample can be tested to determine whether a criteria (ii) is met of the tumor cells exhibiting a relatively high level of AcK68, as indicated by exceeding a predetermined threshold level, as this high level can indicate likely responsiveness of the tumor to treatment with the pentaaza macrocyclic ring complex of Formula (I). As yet another example, the tissue sample can be tested to determine whether a criteria (iii) is met of the tumor cells exhibiting a relatively high level of $HIF2_{\alpha}$, as indicated by exceeding the predetermined threshold level, as this high level can indicate likely responsiveness of the tumor to treatment with the pentaaza macrocyclic ring complex of Formula (I). A yet another example, the tissue sample can be tested to determine whether a criteria (iv) is met of the tumor cells exhibiting a relatively high level of Ki-67 protein, as indicated by exceeding the predetermined threshold level, as this high level can indicate likely responsiveness of the tumor to treatment with the pentaaza macrocyclic ring complex of Formula (I). A yet another example, the tissue sample can be tested to determine whether a criteria (v) is met of the tumor cells exhibiting a relatively high level of OCT4 protein, as indicated by exceeding the predetermined threshold level, as this high level can indicate likely responsiveness of the tumor to treatment with the pentaaza macrocyclic ring complex of Formula (I). A yet another example, the tissue sample can be tested to determine whether a criteria (vi) is met of the tumor cells exhibiting a relatively high level of SOX2 protein, as indicated by exceeding the predetermined threshold level, as this high level can indicate likely responsiveness of the tumor to treatment with the pentaaza macrocyclic ring complex of Formula (I). A yet another example, the tissue sample can be tested to determine whether a criteria (vii) is met of the tumor cells exhibiting a relatively high ratio of monomeric to tetrameric MnSOD, as indicated by exceeding the predetermined threshold level, as this high level can indicate likely responsiveness of the tumor to treatment with the pentaaza macrocyclic ring complex of Formula (I).

Accordingly, in certain embodiments, a method of treatment can involve determining that the subject is suitable for the treatment if any one or more one of the criteria (i)-(vii) is met. In a case where the subject is selected as suitable for treatment, the method of treatment can comprise administering a therapeutically effective amount of the pentaaza macrocyclic ring complex corresponding to Formula (I), optionally in combination with a further therapeutic treatment, such as an endocrine treatment agent and/or chemotherapeutic agent, and/or other suitable agents or therapies such as those described herein.

According to certain embodiments, the levels of biomarkers such any one or more of AcK68, SIRT3 and/or $HIF2_{\alpha}$ can be determined by suitable methods, such as by immunostaining or other similar methods. In an immunostaining method, antibodies to a protein and/or moiety of interest (e.g. a specific region of a protein) are used to detect a specific target (e.g. protein) in a sample. For example, in one embodiment an antibody used for immunostaining can comprise an anti-AcK68 monoclonal antibody that specifically binds to a region (epitope) of AcK68 comprising the acetylated lysine residue. The presence of antibody bound to the protein in the sample (e.g. tissue or cells) can be determined by a variety of methods, including by tagging or labelling the antibody with a moiety that can be detected, such as a fluorescent dye detectable by a fluorescence detector, and/or peroxidase that can be developed to give a colored product that is detectable by methods such as light microscopy, as well as other methods. According to further aspects, one or more secondary antibodies may be used that are labelled and/or tagged with a detectable moiety (e.g. peroxidase or fluorescent dye) and that binds the primary antibody that targets the protein of interest in the sample. According to even further aspects, the primary antibody can be labelled with a small molecule that interacts with a high affinity binding partner that is linked to an enzyme or fluorescent moiety, such as by using biotin-streptavidin interaction. Examples of immunostaining methods can include immunohistochemistry (IHC) methods for staining tissue samples, or immunocytochemistry staining methods for staining cells. Other techniques that can be used to implement and/or complement immunostaining techniques can include flow cytometry techniques, western blotting, enzyme-linked immunoabsorbent assays (ELISA) and immuno-electron microscopy. According to certain embodiments, immunoprecipitation methods that use antibodies to separate out target proteins from a sample for further analysis (e.g. by coupling to beads) can also be used. According to further embodiments, other indirect methods of determining levels of the target proteins of interest, such as by determining levels of activity of the proteins, or by determining other factors indicative of expression, protein activation and/or de-activation.

According to one embodiment, selecting the subject for treatment comprises determining levels of AcK68 by an immunostaining method, comprising contacting the tissue with an anti-Ack68 monoclonal antibody, and determining the levels of anti-AcK68 monoclonal antibody that bind to AcK68 in the tissue sample. According to another embodiment, selecting the subject for treatment comprises determining levels of SIRT3 protein by an immunostaining method, comprising contacting the tissue with an anti-SIRT3 monoclonal antibody, and determining the levels of anti-SIRT3 monoclonal antibody that bind to SIRT3 in the tissue sample. In yet another embodiment, selecting the subject for treatment comprises determining levels of $HIF2_{\alpha}$ protein by an immunostaining method, comprising contacting the tissue with an anti-$HIF2_{\alpha}$ monoclonal antibody, and determining the levels of anti-$HIF2_{\alpha}$ monoclonal antibody that bind to $HIF2_{\alpha}$ in the tissue sample. In yet another embodiment, selecting the subject for treatment comprises determining levels of Ki-67 protein by an immunostaining method, comprising contacting the tissue with an anti-Ki-67 monoclonal antibody, and determining the levels of anti-Ki-67 monoclonal antibody that bind to Ki-67 in the tissue sample. In yet another embodiment, selecting the subject for treatment comprises determining levels of OCT4 protein by an immunostaining method, comprising contacting the tissue with an anti-OCT4 monoclonal antibody, and determining the levels of anti-OCT4 monoclonal antibody that bind to OCT4 in the tissue sample. In another embodiment, selecting the subject for treatment comprises determining levels of SOX2 protein by an immunostaining method, comprising contacting the tissue with an anti-SOX2 monoclonal antibody, and determining the levels of anti-SOX2 monoclonal antibody that bind to SOX2 in the tissue sample. In another embodiment, selecting the subject for treatment comprises determining levels of tetrameric and monomeric SOD protein by an immunostaining method, comprising contacting the tissue with an anti-tetrameric SOD monoclonal antibody, and determining the levels of anti-tetrameric SOD monoclonal antibody that bind to tetrameric SOD in the tissue sample, contacting the tissue with an anti-monomeric SOD monoclonal antibody, and determining the levels of anti-monomeric SOD monoclonal antibody that bind to monomeric SOD in the tissue sample, and determine a ratio of monomeric to tetrameric MnSOD.

According to one embodiment, a kit for treating a cancer in a mammalian subject is provided. According to certain aspects, the kit comprises an assay for analyzing a tissue sample obtained from the subject and comprising tumor cells, where the assay is capable of determining criteria comprising any one or more of (i) whether a level of sirtuin (SIRT3) protein is below a first predetermined threshold level in tumor cells of the tissue sample, (ii) whether a level of manganese superoxide dismutase acetylated at the lysine 68 residue (AcK68) exceeds a second predetermined threshold level, (iii) whether expression levels of hypoxia-inducible factor $2_{\alpha}$ ($HIF2_{\alpha}$) exceed a third predetermined threshold level indicative of lineage plasticity for stemness, whether a level of Ki-67 protein exceeds a fourth predetermined threshold level, (v) whether a level of OCT4 protein exceeds a fifth predetermined threshold level, (vi) whether a level of SOX2 protein exceeds a sixth predetermined threshold level, and (vii) whether a ratio of monomeric to tetrameric MnSOD that exceeds a seventh predetermined threshold level. According to further aspects, the kit can further comprise a therapeutically effective amount of the pentaaza macrocyclic ring complex corresponding to Formula (I), for treatment of the cancer in the event that any of the criteria (i)-(vii) are met as determined by the assay.

In one embodiment, the assay comprises an immunostaining assay, such as an immunohistochemistry assay or assay corresponding to any of the immunostaining techniques described herein, for determining the levels of target protein in the tissue sample. In further embodiments, the assay can comprise an anti-AcK68 antibody that is capable of selectively binding to AcK68 to determine levels thereof. In another embodiment, the assay can comprise an anti-SIRT3 antibody that is capable of selectively binding to SIRT3 to determine levels thereof in the tissue sample. In another embodiment, the assay can comprise an anti-$HIF2_{\alpha}$ antibody that is capable of selectively binding to $HIF2_{\alpha}$ to determine levels thereof in the tissue sample. In another embodiment, the assay can comprise an anti-Ki-67 antibody that is capable of selectively binding to Ki-67 to determine levels thereof in the tissue sample. In another embodiment, the assay can comprise an anti-OCT4 antibody that is capable of selectively binding to OCT4 to determine levels thereof in the tissue sample. In yet another embodiment, the assay can comprise an anti-SOX2 antibody that is capable of selectively binding to SOX2 to determine levels thereof in the tissue sample. In yet another embodiment, the assay can comprise an anti-monomeric MnSOD antibody that is capable of selectively binding to monomeric MnSOD to determine levels thereof in the tissue sample, and an anti-tetrameric MnSOD antibody that is capable of selectively binding to tetrameric MnSOD to determine levels thereof in the tissue sample.

The assay may alternatively or additionally comprise tests utilizing techniques other than immunostaining for directly or indirectly assessing the target protein levels. In yet further embodiments, the kit can further comprise instructions for any one or more of utilizing the assay for determination of target protein levels, instructions for assessing whether any of criteria (i)-(vii) are met based on the results of the assay, and/or instructions for administration of the pentaaza macrocyclic ring complex. In further embodiments, the kit can comprise instruments and/or reagents for obtaining a tissue sample from the subject. The kit can also comprise one or more tools and/or reagents for preparing a tissue sample for analysis, such as tools and/or reagents for forming a formalin-fixed paraffin-embedded tissue section. The kit can also comprise one or more tools and/or reagents for carrying out the analysis of the tissue, such as one or more of primary antibodies, secondary antibodies, labels, blocking reagents, buffers, dyes, peroxidases, developing reagents, etc. In yet another embodiment, a diagnostic kit can be provided separately from the pentaaza macrocyclic ring complex, the diagnostic kit including the assay for analyzing the tissue sample to determine any of criteria (i)-(vii) as described herein, for example in a case where diagnosis is performed separately from treatment.

According to one embodiment, the levels of one or more of the biomarkers (i)-(vii), such as levels of AcK68, SIRT3 and/or $HIF2_{\alpha}$ are compared to threshold levels to determine whether a subject is afflicted with a type of tumor that would benefit from treatment with the pentaaza macrocyclic ring complex of Formula (I), either alone or in combination with a further therapeutic agent. That is, the levels of the target proteins (e.g. AcK68, SIRT3 and/or $HIF2_{\alpha}$) as determined in tumor cells obtained from a subject can be compared to predetermined threshold levels to determine whether any of the criteria (i)-(vii) are met. In one embodiment, the comparison to the threshold levels can involve evaluating a ratio of a detected level of any one or more of the target proteins in tumor cells, to a level in "normal" or non-cancerous tissue, of the same tissue type. For example, the threshold value may be met when a ratio of the detected value to the "normal" value is at or exceeds a predetermined value. In another embodiment, the comparison to the threshold levels can involve comparison of a value of a detected level of any one or more of the target proteins in tumor cells, to a value of a level in "normal" or non-cancerous tissue, of the same tissue type, such as for example a comparison to a predetermined level exceeding a standard deviation of the level for "normal" or non-cancerous tissue. Other comparisons of the detected level to a threshold level can also be provided. For example, other metrics of the threshold level can be provided based on the level at which resistance of tumors to treatment is observed. In one embodiment, the threshold levels are levels that deviate from average levels of the respective target proteins, in non-cancerous tissue of the same tissue type, obtained from a plurality of different individuals. For example, the average levels may be the average for the respective protein targets as measured in non-cancerous (normal) tissue obtained from at least 6 different individuals, with tissue type that is the same as that of the cancerous tissue (e.g., cancerous breast tissue is compared to non-cancerous breast tissue, etc.). The average levels for each respective target protein can comprise a normal score for that target protein in the respective tissue type as tested.

According to certain embodiments, the threshold level for comparison to the detected levels of target protein in tumor cells can be set at a level that is indicative of levels where treatment with the pentaaza macrocyclic ring complex would be beneficial. In one embodiment, the threshold level for the respective target proteins can be set according to the relation of the detected level of the target protein in tumor cells to the standard deviation from the normal score of that protein in non-cancerous tissue. That is, the threshold level can be set to be a level that is at least one half of one standard deviation from the normal score, at least one standard deviation from the normal score, at least one and a half standard deviations from the normal score, at least two standard deviations from the normal score, at least two and a half standard deviations from the normal score, at least three standard deviations from the normal score, at least four standard deviations from the normal score, and/or at least five standard deviations from the normal score. Accordingly, detected levels of one or more target proteins that are outside the predetermined threshold would be indicative of tumor tissue that may be responsive to treatment with the pentaaza macrocyclic ring complex. According to yet another embodiment, the normal score can comprise an average as obtained across a large population, such as for example values for members of a large population, for a particular type of immunostaining assay, to provide a reference value that can be referred to in subsequent determinations. According to further embodiments, the threshold levels for any one or more of the target proteins (e.g. AcK68, SIRT3, and/or $HIF2_{\alpha}$) may be set according to alternative diagnostic methods and/or diagnostic correlations that provide a correlation between target levels and suitability of treatment. For example, the threshold levels may be set according to methods that provide a substantially equivalent result to the immunostaining methods described herein, which methods may be equivalent in that they provide an assessment of levels of target protein to allow for a determination as to whether the tumor cells are resistant to anti-cancer treatment agents (e.g. based on SIRT3, AcK68 and/or $HIF2_{\alpha}$ levels, or other diagnostic results).

According to certain embodiments, the levels of any one or more of the target proteins (e.g. AcK68, SIRT3 and/or $HIF2_{\alpha}$) in tumor cells are determined by an immunostaining technique. According to certain aspects, the levels of the target proteins can be compared to respective threshold levels determined according the same immunostaining technique, such as by obtaining levels for non-cancerous tissue of the same tissue type as the tumor cells (e.g., breast cancer cells, prostate cancer cells), from at least 6 different individuals, to determine a normal score. According to one embodiment, the first predetermined threshold level for sirtuin (SIRT3) protein activity in tumor tissue is a level that is lower than one standard deviation from a normal score for non-cancerous tissue of the same type as the tumor tissue, where the normal score is determined by taking the average of at least 6 non-cancerous tissue samples of the same tissue type from at least 6 different individuals, as determined by immunostaining. According to another embodiment, the second predetermined threshold level for manganese superoxide dismutase acetylated at the lysine 68 residue (AcK68) is a level that is higher than one standard deviation from a normal score for non-cancerous tissue of the same type as the tumor tissue, where the normal score is determined by taking the average of at least 6 non-cancerous tissue samples of the same type from at least 6 different individuals, as determined by immunostaining. According to yet another embodiment, the third predetermined threshold level for expression levels of hypoxia-inducible factor $2_{\alpha}$ ($HIF2_{\alpha}$) is a level that is higher than one standard deviation from a normal score for non-cancerous tissue of the same type as the tumor tissue, where the normal score is determined by taking the average of at least 6 non-cancerous tissue samples of the same type from at least 6 different individuals, as determined by immunostaining. According to another embodiment, the fourth predetermined threshold level for expression levels of Ki-67 protein is a level that is higher than one standard deviation from a normal score for non-cancerous tissue of the same type as the tumor tissue, where the normal score is determined by taking the average of at least 6 non-cancerous tissue samples of the same type from at least 6 different individuals, as determined by immunostaining. According to another embodiment, the fifth predetermined threshold level for expression levels of OCT4 protein is a level that is higher than one standard deviation from a normal score for non-cancerous tissue of the same type as the tumor tissue, where the normal score is determined by taking the average of at least 6 non-cancerous tissue samples of the same type from at least 6 different individuals, as determined by immunostaining. According to another embodiment, the sixth predetermined threshold level for expression levels of SOX2 protein is a level that is higher than one standard deviation from a normal score for non-cancerous tissue of the same type as the tumor tissue, where the normal score is determined by taking the average of at least 6 non-cancerous tissue samples of the same type from at least 6 different individuals, as determined by immunostaining. According to a further embodiment, the seventh predetermined threshold level for the ration of expression levels of monomeric MnSOD protein to expression levels of tetrameric MnSOD protein is a level that is higher than one standard deviation from a normal score for non-cancerous tissue of the same type as the tumor tissue, where the normal score is determined by taking the average of at least 6 non-cancerous tissue samples of the same type from at least 6 different individuals, as determined by immunostaining. In other embodiments, the respective threshold levels may be set at a different multiple and/or fraction of the standard deviation from the normal score, or according to other correlation, as described above.

According to one embodiment, the methods of treatment herein can comprise administration of an anti-cancer therapy such as ionizing radiation therapy and/or a therapeutic anti-cancer agent comprising any one of more of a chemotherapeutic agent, a therapeutic agent that inhibits a hormone receptor pathway associated with growth or progression of the cancer, (e.g., a hormone therapy agent such as an endocrine agent), and treatment with a cell cycle inhibitor (e.g. a CDK4/6 inhibitor) prior to, concomitantly with, or after administration of the pentaaza macrocyclic ring complex of Formula (I). Such further therapeutic agents can also be included as a part of any kits described herein, for example to provide a co-therapy with the pentaaza macrocyclic ring complex of Formula (I), and/or the kit can include instructions for administration of the therapy.

In one embodiment, the anti-cancer therapeutic agent comprises a chemotherapeutic agent comprising any of a platinum-containing chemotherapeutic agent and an anthracycline chemotherapeutic agent, and/or a combination thereof can also be provided. In a further embodiment, the therapeutic agent comprises at least one of a platinum-containing chemotherapeutic agent selected from the group consisting of cisplatin oxaliplatin, carboplatin, nedaplatin, lobaplatin, heptaplatin, dicycloplation, lipoplatin, LA-12, phosphaplatin, phenanthriplatin, prolindac, triplatin tetranitrate, picoplatin, satraplatin and/or pharmaceutically acceptable salts thereof, and/or an anthracycline chemotherapeutic agent selected from the group consisting of doxorubicin, daunorubicin, epirubicin and idarubicin, and/or pharmaceutically acceptable salts thereof.

According to yet another embodiment, the therapeutic anti-cancer agent can comprise a therapeutic agent that inhibits a hormone receptor pathway associated with growth or progression of the cancer (e.g. an endocrine therapy agent). According to one embodiment, the therapeutic agent that inhibits a hormone receptor pathway associated with growth or progression of the cancer targets any one or more of the estrogen receptor pathway, progesterone receptor pathway, and the androgen receptor pathway (e.g., hormone therapy agent and/or endocrine agent). For example, the therapeutic agent that targets any one or more of the estrogen receptor pathway, progesterone receptor pathway, and the androgen receptor pathway can comprise any selected from the group consisting of estrogen receptor inhibitors, estrogen receptor degraders/downregulators, selective estrogen receptor modulators (SERMs), aromatase inhibitors, and GnRH agonists, and combinations thereof can also be provided. According to one embodiment, the therapeutic agent targeting the estrogen receptor pathway comprises at least one selected from the group consisting of tamoxifen, letrozole, clomifene, 4-hydroxytamoxifen, toremifene, raloxifene, nafoxidine, lasofoxifene, bazedoxifene, ospemifene, fulvestrant, brilanestrant, elacestrant, and derivatives, salts and/or prodrugs thereof. According to another embodiment, the therapeutic agent targeting the androgen receptor pathway comprises any selected from the group consisting of an androgen receptor antagonist, an androgen synthesis inhibitor and an antigonadotropin. For example, the therapeutic agent that targets the androgen receptor pathway can comprise at least one selected from the group consisting of cyproterone acetate, megestrol acetate, chlormadinone acetate, spironolacone, oxendolone, osaterone acetate, flutamide, bicalutamide, nilutamide, topilutamide, enzalutamide, apalutamide, dienogest, drospirenone, medogestone, nomegestrol acetate, promegestone, trimegestone, ketoconazole, abiraterone acetate, seviteronel, aminoglutethimide, finasteride, dutasteride, episteride, alfatradial, cyproterone acetate, medrogestone, flutamide, nilutamide, bifluranol, leuprorelin, cetrorelix, allylestrenol, chlormadinone acetate, cyproterone acetate, gestonorone caproate, hydroxyprogesterone caproate, medroxyprogesterone acetate, megestrol acetate, osaterone acetate, oxendolone, estradiol, estradiol esters, ethinylestradiol, conjugated estrogens, diethylstilbestrol, and derivatives, salts and/or prodrugs thereof. According to another embodiment, the therapeutic agent targeting the progesterone receptor pathway can comprise a Type I, Type II or Type III selective modulator of progesterone (SPRM) that is at least one selected from the group consisting onapristone, mifepristone, lonaprisan, aglepristone, Org31710, Org31806, CDB-2914 and CDB-4124, and derivatives, salts and/or prodrugs thereof (see also Antiprogestins in Breast Cancer Treatment: Are We Ready? by Lanari et al., Endocrine-Related Cancer (2012) 19 R35-R500. According to yet another embodiment, the anti-cancer therapeutic agent comprises a cell cycle inhibitor such as a CDK4/6 inhibitor, such as at least one selected from the group consisting of palbociclib, abemaciclib, ribociclib, and derivatives, salts and/or prodrugs thereof In one embodiment, a method of treating a tumor that is resistant to a therapeutic anti-cancer agent, such as any one or more of a chemotherapeutic agent, a therapeutic agent that inhibits a hormone receptor pathway, and a cell cycle inhibitor in a mammalian subject afflicted therewith is provided. For example, the tumor that is resistant to the anti-cancer agent may be one having the tumor having a tumor signature characterized by any one or more of (i) a level of sirtuin (SIRT3) protein that is below a first predetermined threshold level, (ii) a level of K68-acetylated manganese superoxide dismutase ($MnSOD^{K68}$) that exceeds a second predetermined threshold level, (iii) expression levels of hypoxia-inducible factor $2_{\alpha}$ ($HIF2_{\alpha}$) exceeds a third predetermined threshold level indicative of lineage plasticity for stemness, (iv) a level of Ki-67 protein that exceeds a fourth predetermined threshold level, (v) a level of OCT4 protein that exceeds a fifth predetermined threshold level, (vi) a level of SOX2 protein that exceeds a sixth predetermined threshold level, and (vii) a ratio of monomeric to tetrameric MnSOD that exceeds a seventh predetermined threshold level. That is, the tumor signature characterized by any of (i)-(vii) may be indicative of resistance of tumor cells to treatment by the anti-cancer agent.

According to certain aspects, the method can comprise selecting a subject that is a suitable subject for treatment, by obtaining a test tissue sample from the patient, the test tissue sample comprising tumor cells, and assessing the tissue sample to determine criteria comprising any one or more of (i) whether a level of sirtuin (SIRT3) protein activity is below a first predetermined threshold level in tumor cells of the tissue sample, (ii) whether a level of manganese superoxide dismutase acetylated at the lysine 68 residue (AcK68) exceeds a second predetermined threshold level, and (iii) whether expression levels of hypoxia-inducible factor $2_{\alpha}$ ($HIF2_{\alpha}$) exceeds a third predetermined threshold level indicative of lineage plasticity for stemness, (iv) whether a level of Ki-67 protein that exceeds a fourth predetermined threshold level, (v) whether a level of OCT4 protein that exceeds a fifth predetermined threshold level, (vi) whether a level of SOX2 protein that exceeds a sixth predetermined threshold level, and (vii) whether a ratio of monomeric to tetrameric MnSOD that exceeds a seventh predetermined threshold level. The method further comprises determining that the subject is suitable for the treatment if one or more of the criteria (i)-(vii) is met. According certain aspects, in a case where the subject is selected as suitable for treatment, the method can comprise treating the subject by administering to the subject a therapeutically effective amount of a pentaaza macrocyclic ring complex corresponding to the Formula (I), optionally with a further therapeutic agent such as any described herein. Alternatively, or additionally, a diagnostic method can be performed to determine whether a tumor is resistant to an anti-cancer agent such as any one or more of a chemotherapeutic agent, a therapeutic agent that inhibits a hormone receptor pathway, and a cell cycle inhibitor, by assessing the tissue to determine whether any of the criteria (i)-(vii) are met, without requiring administration of the pentaaza macrocyclic ring complex according to Formula (I). The treatment and/or diagnostic can also be implemented by a kit comprising an assay to assess any of criteria (i)-(vii), such as any kit described herein. In one embodiment, the method can further comprise administration of an anti-cancer agent prior to, concomitantly with, or after administration of the pentaaza macrocyclic ring complex of Formula (I), where the chemotherapeutic agent can be any described herein. The anti-cancer agent can also be provided as a part of a kit for performing the treatment method, and/or the kit can comprise instructions for administration of the chemotherapeutic agent as a part of treatment.

According to another aspect, a method of treating a tumor that is resistant to ionizing radiation therapy in a mammalian subject afflicted therewith is provided. For example, the tumor that is resistant to radiation therapy may be one having a tumor signature characterized by any one or more of (i) a level of sirtuin (SIRT3) protein that is below a first predetermined threshold level, (ii) a level of K68-acetylated manganese superoxide dismutase ($MnSOD^{K68}$) that exceeds a second predetermined threshold level, (iii) expression levels of hypoxia-inducible factor $2_{\alpha}$ ($HIF2_{\alpha}$) exceeds a third predetermined threshold level indicative of lineage plasticity for stemness, (iv) a level of Ki-67 protein that exceeds a fourth predetermined threshold level, (v) a level of OCT4 protein that exceeds a fifth predetermined threshold level, (vi) a level of SOX2 protein that exceeds a sixth predetermined threshold level, and (vii) a ratio of monomeric to tetrameric MnSOD that exceeds a seventh predetermined threshold level. That is, the tumor signature characterized by any of (i)-(vii) may be indicative of resistance of tumor cells to treatment by ionizing radiation. According to certain embodiments, a method of treatment can comprise selecting a subject that is a suitable subject for treatment, by obtaining a test tissue sample from the subject, the test tissue sample comprising tumor cells, and assessing the tissue sample to determine criteria comprising any one or more of (i) whether a level of sirtuin (SIRT3) protein activity is below a first predetermined threshold level in tumor cells of the tissue sample, (ii) whether a level of manganese superoxide dismutase acetylated at the lysine 68 residue (AcK68) exceeds a second predetermined threshold level, (iii) whether expression levels of hypoxia-inducible factor $2_{\alpha}$ ($HIF2_{\alpha}$) exceeds a third predetermined threshold level indicative of lineage plasticity for stemness, (iv) whether a level of Ki-67 protein that exceeds a fourth predetermined threshold level, (v) whether a level of OCT4 protein that exceeds a fifth predetermined threshold level, (vi) whether a level of SOX2 protein that exceeds a sixth predetermined threshold level, and (vii) whether a ratio of monomeric to tetrameric MnSOD that exceeds a seventh predetermined threshold level. According to certain aspects, it is determined that the subject is suitable for the treatment if one or more of the criteria (i)-(vii) is met. According to further aspects, in a case where the subject is selected as suitable for treatment, the method can comprise treating the subject by administering to the subject a therapeutically effective amount of a pentaaza macrocyclic ring complex corresponding to the Formula (I). That is, according to certain aspects, the pentaaza macrocyclic ring complex corresponding to Formula (I) can be administered to reduce resistance of the cancer/tumor to radiation therapy involving ionizing radiation. Accordingly, in certain embodiments, the method can further comprise administering ionizing radiation to the subject, such as in a course of radiation therapy, either prior to, concomitantly with, or after administration of the pentaaza macrocyclic ring complex, such as for example according to and/or in combination with any of the radiation administration/radiation therapy methods described further herein. In certain further embodiments, an addition anti-cancer therapeutic agent can also be provided, such as any one or more of a chemotherapeutic agent, a therapeutic agent that inhibits a hormone receptor pathway (e.g. an endocrine agent), and a cell cycle inhibitor, including any of those described herein.

According to one embodiment, a method of treating a cancer in a mammalian subject afflicted with the cancer, comprises administering to the subject an anti-cancer therapy selected from the group consisting of a therapeutically effective amount of a chemotherapeutic agent, a therapeutically effective amount of a therapeutic agent that inhibits a hormone receptor pathway associated with growth or progression of the cancer (e.g. an endocrine agent), a therapeutically effective amount of a cell cycle inhibitor, and a therapeutically effective dose of ionizing radiation, and administering to the subject a therapeutically effective amount of a pentaaza macrocyclic ring complex corresponding to the Formula (I), prior to, concomitantly with, or after administration of the therapeutic agent. For example, according to certain aspects, the pentaaza macrocyclic ring complex may reduce the resistance of the tumor cells to, or otherwise enhance the effectiveness of, the anti-cancer therapeutic agent. According to yet another embodiment, a method of treating and/or reducing the likelihood of a recurrence of a cancer in a mammalian subject at risk thereof, comprises administering to the subject a therapeutically effective amount of a pentaaza macrocyclic ring complex corresponding to the Formula (I), optionally in combination with a further anti-cancer therapy, such as an anti-cancer therapeutic agent (e.g. chemotherapeutic agent or endocrine agent). For example, according to certain aspects, the administration of the pentaaza macrocyclic ring complex may be effective to treat a recurrence of a cancer in a subject, such as a recurrence of a tumor that is resistant to other therapies, and/or may reduce the likelihood that a recurrence of a tumor occurs, by reducing the likelihood of developing resistance to the therapy.

According to yet another embodiment, a method of treating a tumor that is resistant to a an anti-cancer therapy selected from the group consisting of a chemotherapeutic agent, a therapeutic agent that inhibits a hormone receptor pathway associated with growth or progression of the cancer, a cell cycle inhibitor, and radiation therapy, in a mammalian subject, comprises administering to the subject a therapeutically effective amount of a pentaaza macrocyclic ring complex corresponding to the Formula (I), optionally in combination with the anti-cancer therapy, such as an anti-cancer therapeutic agent. In yet a further embodiment, resistance of a tumor to a therapeutic agent can be determined according to the methods described herein, such as by determining whether the criteria (i)-(vii) herein are met. Furthermore, the methods described herein can additionally comprising administration of any one or more of the anti-cancer therapeutic agents herein either prior to, concomitantly with, or after, administration of the pentaaza macrocyclic ring complex. Kits comprising an assay, such as those described herein for determining the criteria (i)-(vii), with or without the pentaaza macrocyclic ring complex and/or further therapeutic agent, can also be provided as a diagnostic and/or treatment kit, to implement any part of the entirety of the method described herein.

Accordingly, in certain embodiments, the pentaaza macrocyclic ring complexes described herein may advantageously treat and/or reduce the likelihood of recurrence or relapse of certain cancers, either as provided in combination with an anti-cancer therapy such as an anti-cancer therapeutic agent and/or to reduce the resistance of cancer cells to treatment with the anti-cancer therapy and/or anti-cancer therapeutic agent.

According to one embodiment, a method of treating a cancer in a mammalian subject afflicted with the cancer comprises administering to the subject a therapeutically effective amount of an endocrine therapy agent, and administering to the subject a therapeutically effective amount of a pentaaza macrocyclic ring complex corresponding to the Formula (I) below, prior to, concomitantly with, or after administration of the endocrine therapy agent. For example, the endocrine therapy agent and pentaaza macrocyclic ring complex can comprise a combination therapy administered for treating cancer in the afflicted individual.

According to yet another embodiment, a method of reducing the likelihood of recurrence of a cancer in a mammalian subject at risk thereof, comprises administering to the subject a therapeutically effective amount of an endocrine therapy agent, and administering to the subject a therapeutically effective amount of a pentaaza macrocyclic ring complex corresponding to the Formula (I), prior to, concomitantly with, or after administration of the endocrine therapy agent. For example, a method for reducing the likelihood of recurrence can comprising administering a combination therapy of the endocrine therapy agent and pentaaza macrocyclic ring complex, to a subject at risk for recurrence of the cancer and/or experiencing a relapse of the cancer. According to another embodiment, the subject may be one that is in remission from a cancer, with the combination therapy being administered to reduce the likelihood of the recurrence of the cancer.

According to yet another embodiment, the predetermined thresholds use in the determination of criteria (i)-(vii) can be set in relation to an average or median level of the target proteins in the general population, such that the predetermined threshold correlates with therapeutically significant amounts of the target proteins (e.g., SIRT3, AcK68 and/or $HIF2_{\alpha}$), such as a therapeutically significant extent of K68-acetylation. In one embodiment, the predetermined threshold for AcK68 is a level where significant peroxidase activity occurs that is indicative of K68-acetylation and/or presence of monomeric MnSOD form. In another embodiment, the predetermined threshold levels of the target proteins can correlate to levels that are indicative of increased resistance to anti-cancer therapy, such as endocrine therapy and/or chemotherapy, and/or increased risk of cancer recurrence and/or cancer growth or proliferation in the subject.

According to yet another embodiment, a method of reducing resistance to an anti-cancer therapy such as an endocrine therapy and/or chemotherapy in a mammalian subject having resistance to the anticancer therapy agent, comprises administering to the subject a therapeutically effective amount of anti-cancer therapeutic agent, and administering to the subject a therapeutically effective amount of a pentaaza macrocyclic ring complex corresponding to the Formula (I), prior to, concomitantly with, or after administration of the anti-cancer therapeutic agent. For example, the pentaaza macrocyclic ring complex may be capable of reducing and/or reversing the resistance that is either inherent in, and/or has developed in, cancer cells, to a particular anti-cancer therapy, such as a particular endocrine therapy agent and/or chemotherapeutic agent, such that efficacy of treatment with the endocrine therapy agent and/or chemotherapeutic agent is increased and/or restored. According to one embodiment, the combination therapy can be provided in a case where the mammalian subject has inherent resistance to, and/or had developed resistance to, endocrine therapy, for example as a result of receiving an endocrine therapy treatment regimen to treat a cancer which with the mammalian subject is afflicted. According to another embodiment, the combination therapy can be provided in a case where the mammalian subject has developed resistance to endocrine therapy as a result of receiving an endocrine therapy treatment regimen to reduce the likelihood of recurrence of a cancer for which the mammalian subject is at risk. According to another embodiment, the combination therapy can be provided in a case where the mammalian subject has developed resistance to chemotherapy as a result of receiving a chemotherapy treatment regimen to treat a cancer which with the mammalian subject is afflicted. According to certain aspects, the pentaaza macrocyclic ring complex is capable of unexpectedly and advantageously restoring susceptibility of cancer cells to the anti-cancer therapeutic agent (e.g. endocrine therapy agent and/or chemotherapy agent), such that treatment with the anti-cancer therapeutic agent can be achieved.

According to one embodiment, the cancer and/or tumor that may be treated and/or likelihood of recurrence decreased according to any of the methods herein may be one selected from the group consisting of breast cancer, prostate cancer, testicular cancer, glioma, glioblastoma, head and neck cancer, ovarian cancer, endometrial cancer, hepatocellular carcinoma, desmoid tumors, pancreatic carcinoma, melanoma, and renal cell carcinoma (see also the article SIRT3 is a Mitochondrial-Localized Tumor Suppressor Required for Maintenance of Mitochondrial Integrity and Metabolism during Stress, by Kim et al, Cancer Cell, Vol. 16, 41-52 (2010)). According to certain embodiments, the cancer may be one that is known to be treatable and/or receptive to treatment with one or more of an endocrine therapy agent and/or chemotherapeutic agent, although in other embodiments other cancers may also be treated and/or prevented. According to one embodiment, the cancer that is treated and/or prevented according to any of the methods herein is a hormone receptor-positive (HR+) breast cancer. According to yet another embodiment, the cancer is any of luminal A type breast cancer and/or luminal B type breast cancer. For example, in one embodiment, the cancer is a luminal B type breast cancer. According to yet another embodiment, the cancer comprises cancer cells that exhibit increased levels of an acetylated form of manganese superoxide dismutase (MnSOD) having acetylation at the K68 residue of the MnSOD protein, and/or reduced levels of SIRT3 protein, and/or increased levels of $HIF2_{\alpha}$, which are hallmarks of disrupted dismutase function associated with resistance to endocrine therapy and/or chemotherapy. According to yet another embodiment, the cancer and/or tumor that may be treated and/or for which the likelihood of recurrence may be decreased, may be a hormone receptor-positive (HR+) cancer, such as an estrogen receptor-positive (ER+) cancer, progesterone receptor-positive (PR+) cancer and/or an androgen receptor-positive (AR+) cancer.

According to yet another embodiment, the methods described herein can further comprise a step of performing an evaluation of the mammalian subject to identify whether they would benefit from treatment with the pentaaza macrocyclic ring complex as a part of a combination therapy, and administering the pentaaza macrocyclic ring complex as a part of a combination therapy in response to results of the evaluation. For example, the evaluation can comprise determining whether the mammalian subject is afflicted with and/or at risk for developing recurrence of a cancer having any of characteristics described therein, such as a cancer that is treatable by an anti-cancer agent such as endocrine therapy agent and/or chemotherapeutic agent, a cancer that has inherent and/or acquired resistance to treatment with the anti-cancer agent such as the endocrine therapy agent and/or chemotherapeutic agent, and/or a cancer that exhibits hallmarks of disrupted dismutase function (e.g. any of the criteria (i)-(vii) described herein), among other characteristics that can indicate that administration of the pentaaza macrocyclic ring complex would be advantageous. Once the subject is identified as one that would benefit from the treatment, as belonging to a population that would be receptive to the treatment, the pentaaza macrocyclic ring complex can be administered to improve the efficacy of the anti-cancer treatment (e.g. endocrine therapy treatment and/or chemotherapy treatment). According to certain embodiments, the pentaaza macrocyclic ring complex can be administered in a therapeutically effective amount that results in an increase in cancer response corresponding to any selected from the group consisting of reduced tumor volume, reduced tumor growth rate, increased survival of the mammalian subject, reduced occurrence and/or extent of metastasis, and reduced proliferation of cancer cells, and/or decreased cancer complications. Furthermore, the methods herein can comprise additional cancer treatments in combination with any of the treatments described herein, such as any of radiation therapy, immunotherapy, and/or administration of a further chemotherapeutic or other anti-cancer agent.

Transition Metal Pentaaza Macrocyclic Ring Complex

In one embodiment, the pentaaza macrocyclic ring complex corresponds to the complex of Formula (I):

(I)

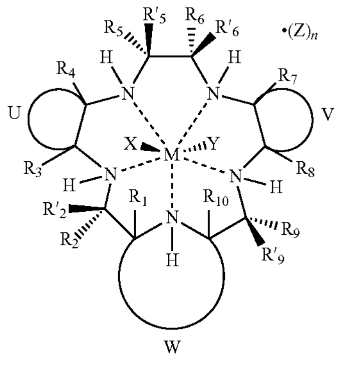

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

As noted above in connection with the pentaaza macrocyclic ring complex of Formula (I), M is $Mn^{2+}$ or $Mn^{3+}$. In one particular embodiment in which the pentaaza macrocyclic ring complex corresponds to Formula (I), M is $Mn^{2+}$. In another particular embodiment in which the pentaaza macrocyclic ring complex corresponds to Formula (I), M is $Mn^{3+}$.

In the embodiments in which one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are hydrocarbyl, for example, suitable hydrocarbyl moieties include, but are not limited to alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and aralkyl. In one embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, or heterocyclyl. More preferably in this embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl (e.g., $C_1$-$C_6$ alkyl, more typically $C_1$-$C_4$ alkyl). Thus, for example, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ may be independently hydrogen, methyl, ethyl, propyl, or butyl (straight, branched, or cyclic). In one preferred embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl.

In one preferred embodiment in which the pentaaza macrocyclic ring complex corresponds to Formula (I), $R_1$, $R_2$, $R'_2$, $R_3$, $R_4$, $R_5$, $R'_5$, $R_7$, $R_8$, $R_9$, $R'_9$, and $R_{10}$ are each hydrogen and one of $R_6$ and $R'_6$ is hydrogen and the other of $R_6$ and $R'_6$ is methyl. In this embodiment, for example, $R_1$, $R_2$, $R'_2$, $R_3$, $R_4$, $R_5$, $R'_5$, $R_6$, $R_7$, $R_8$, $R_9$, $R'_9$, and $R_{10}$ may each be hydrogen while $R'_6$ is methyl. Alternatively, for example, $R_1$, $R_2$, $R'_2$, $R_3$, $R_4$, $R_5$, $R'_5$, $R'_6$, $R_7$, $R_8$, $R_9$, $R'_9$, and $R_{10}$ may each be hydrogen while $R_6$ is methyl. In another preferred embodiment in which the pentaaza macrocyclic ring complex corresponds to Formula (I), $R_1$, $R_3$, $R_4$, $R_5$, $R'_5$, $R'_6$, $R_7$, $R_8$, and $R_{10}$ are each hydrogen, one of $R_2$ and $R'_2$ is hydrogen and the other of $R_2$ and $R'_2$ is methyl, and one of $R_9$ and R's is hydrogen and the other of $R_9$ and R's is methyl. In this embodiment, for example, $R_1$, $R'_2$, $R_3$, $R_4$, $R_5$, $R'_5$, $R_7$, $R_8$, $R_9$, and $R_{10}$ may each be hydrogen while $R_2$ and R's are methyl. Alternatively, for example, $R_1$, $R_2$, $R_3$, $R_4$, $R_5$, $R'_5$, $R_7$, $R_8$, $R'_9$, and $R_{10}$ may each be hydrogen while $R'_2$ and $R_9$ are methyl. In another embodiment in which the pentaaza macrocyclic ring complex corresponds to Formula (I), $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

In certain embodiments the U and V moieties are independently substituted or unsubstituted fused cycloalkyl moieties having 3 to 20 ring carbon atoms, more preferably 4 to 10 ring carbon atoms. In a particular embodiment, the U and V moieties are each trans-cyclohexanyl fused rings.

In certain embodiments the W moiety is a substituted or unsubstituted fused heteroaromatic moiety. In a particular embodiment, the W moiety is a substituted or unsubstituted fused pyridino moiety. Where W is a substituted fused pyridino moiety, for example, the W moiety is typically substituted with a hydrocarbyl or substituted hydrocarbyl moiety (e.g., alkyl, substituted alkyl) at the ring carbon atom positioned para to the nitrogen atom of the heterocycle. In a one preferred embodiment, the W moiety is an unsubstituted fused pyridino moiety.

As noted above, X and Y represent suitable ligands which are derived from any monodentate or polydentate coordinating ligand or ligand system or the corresponding anion thereof (for example benzoic acid or benzoate anion, phenol or phenoxide anion, alcohol or alkoxide anion). For example, X and Y may be selected from the group consisting of halo, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, among other possibilities. In one embodiment, X and Y if present, are independently selected from the group consisting of halo, nitrate, and bicarbonate ligands. For example, in this embodiment, X and Y, if present, are halo ligands, such as chloro ligands.

Furthermore, in one embodiment X and Y correspond to $—O—C(O)—X_1$, where each $X_1$ is $—C(X_2)(X_3)(X_4)$, and each $X_1$ is independently substituted or unsubstituted phenyl or $—C(—X_2)(—X_3)(—X_4)$;

each $X_2$ is independently substituted or unsubstituted phenyl, methyl, ethyl or propyl;

each $X_3$ is independently hydrogen, hydroxyl, methyl, ethyl, propyl, amino, $—X_5C(=O)R_{13}$ where $X_5$ is NH or O, and $R_{13}$ is C1-C18 alkyl, substituted or unsubstituted aryl or C1-C18 aralkyl, or $—OR_{14}$, where $R^{14}$ is C1-C18 alkyl, substituted or unsubstituted aryl or C1-C18 aralkyl, or together with $X_4$ is (=O); and each $X_4$ is independently hydrogen or together with $X_3$ is (=O).

In yet another embodiment, X and Y are independently selected from the group consisting of charge-neutralizing anions which are derived from any monodentate or polydentate coordinating ligand and a ligand system and the corresponding anion thereof; or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

In the pentaaza macrocyclic ring complex corresponding to Formula (I), Z is a counterion (e.g., a charge-neutralizing anion), wherein n is an integer from 0 to 3. In general, Z may correspond to counterions of the moieties recited above in connection for X and Y.

In combination, among certain preferred embodiments are pentaaza macrocyclic ring complexes corresponding to Formula (I) wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl;

U and V are each trans-cyclohexanyl fused rings;

W is a substituted or unsubstituted fused pyridino moiety;

X and Y are ligands; and

Z, if present, is a charge-neutralizing anion.

More preferably in these embodiments, M is $Mn^{2+}$; $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl; U and V are each trans-cyclohexanyl fused rings; W is an unsubstituted fused pyridino moiety; and X and Y are independently halo ligands (e.g., fluoro, chloro, bromo, iodo). Z, if present, may be a halide anion (e.g., fluoride, chloride, bromide, iodide).

In yet another embodiment, the pentaaza macrocyclic ring complex is represented by Formula (II) below:

(II)

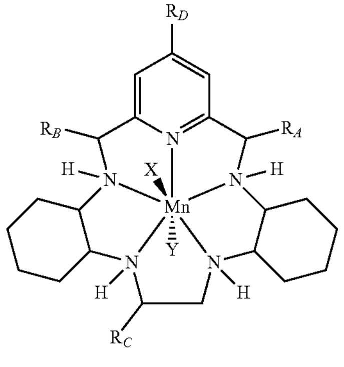

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl.

Furthermore, in one embodiment, the pentaaza macrocyclic ring complex is represented by Formula (III) or Formula (IV):

(III)

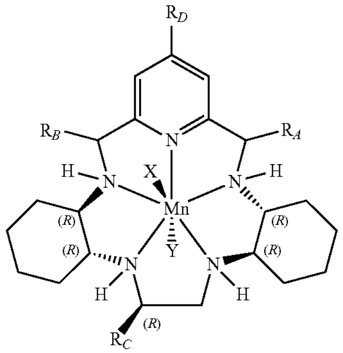

(IV)

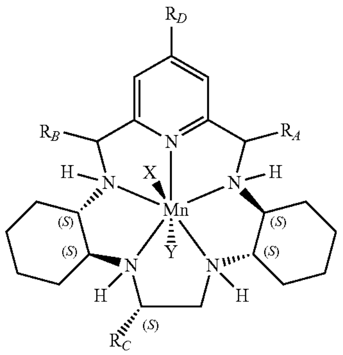

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl.

In yet another embodiment, the pentaaza macrocyclic ring complex is a compound represented by a formula selected from the group consisting of Formulae (V)-(XVI):

(V)

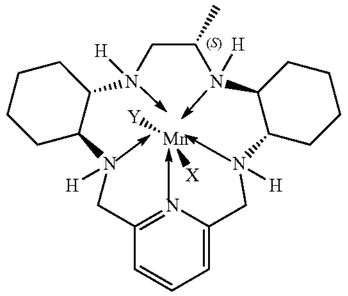

(4459)

(VI)

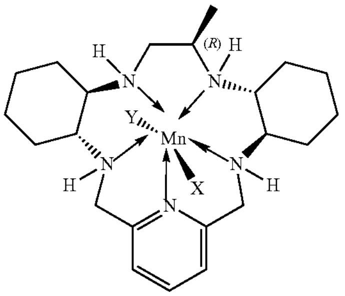

(4444)

(VII)

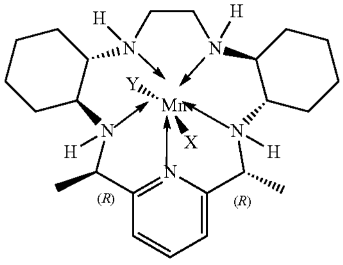

(4498)

(VIII)

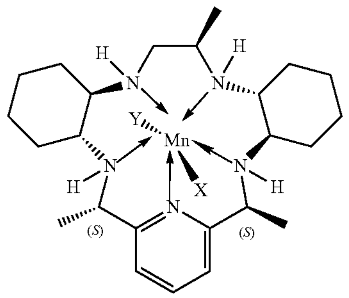

(4401)

(IX)

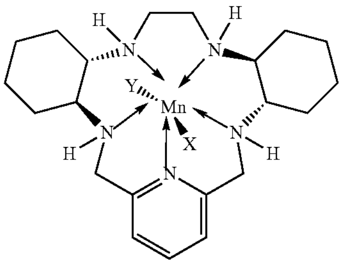

(4419)

-continued (X)

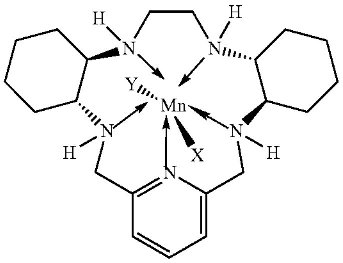

(4403)

(XI)

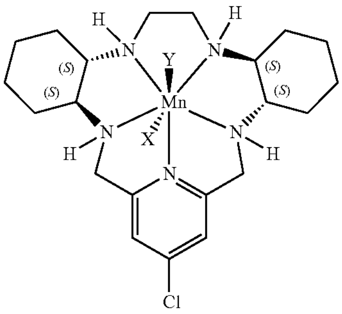

(XII)

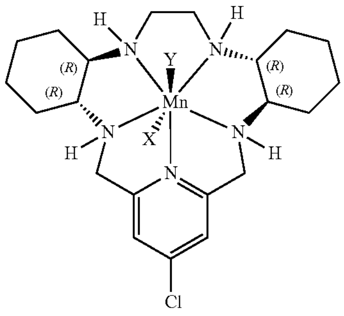

(XIII)

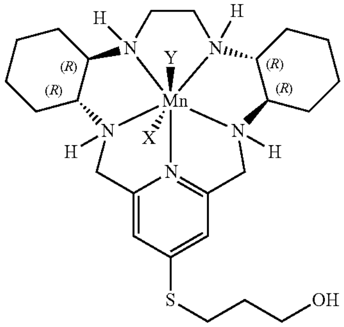

(XIV)

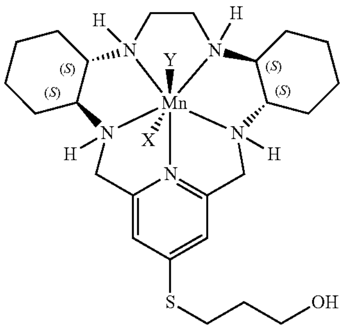

-continued (XV)

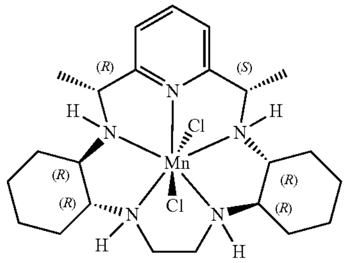

(XVI)

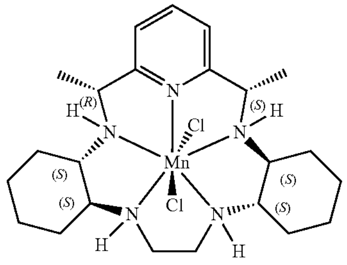

In one embodiment, X and Y in any of the formulae herein are independently selected from the group consisting of fluoro, chloro, bromo and iodo anions. In yet another embodiment, X and Y in any of the formulae herein are independently selected from the group consisting of alkyl carboxylates, aryl carboxylates and arylalkyl carboxylates. In yet another embodiment, X and Y in any of the formulae herein are independently amino acids.

In one embodiment, the pentaaza macrocyclic ring complex has the following Formula (IA):

(IA)

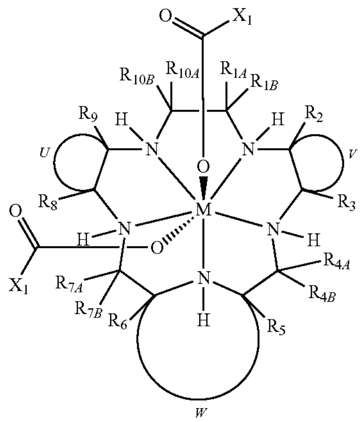

wherein

M is $Mn^{2+}$ or $Mn^{3+}$;

$R_{1A}$, $R_{1B}$, $R_2$, $R_3$, $R_{4A}$, $R_{4B}$, $R_5$, $R_6$, $R_{7A}$, $R_{7B}$, $R_8$, $R_9$, $R_{10A}$, and $R_{10B}$ are independently hydrogen, hydrocarbyl, substituted hydrocarbyl, heterocyclyl, an amino acid side chain moiety, or a moiety independently selected from the group consisting of $—OR_{11}$, $—NR_{11}R_{12}$, $—COR_{11}$, $—CO_2R_{11}$, $—C(=O)NR_{11}R_{12}$, $—SR_{11}$, $—SOR_{11}$, $—SO_2R_{11}$, $—SO_2NR_{11}R_{12}$, $—N(OR_{11})(R_{12})$, $—P(=O)(OR_{11})(OR_{12})$, $—P(=O)(OR_{11})(R_{12})$, and $—OP(=O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_5$ and $R_6$ attached to the carbon atoms which are both part of the heterocycle and the macrocycle are absent; wherein each $X_1$ is independently substituted or unsubstituted phenyl or —C(—$X_2$)(—$X_3$)(—$X_4$);

each $X_2$ is independently substituted or unsubstituted phenyl or alkyl;

each $X_3$ is independently hydrogen, hydroxyl, alkyl, amino, —$X_5$C(═O)$R_{13}$ where $X_5$ is NH or O, and $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_1$alkyl, substituted or unsubstituted aryl or $C_1$-$C_{18}$ aralkyl, or together with $X_4$ is (═O);

each $X_4$ is independently hydrogen or together with $X_3$ is (═O); and the bonds between the transition metal M and the macrocyclic nitrogen atoms and the bonds between the transition metal M and the oxygen atoms of the axial ligands —OC(═O)$X_1$ are coordinate covalent bonds.

In one embodiment, within Formula (IA), and groups contained therein, in one group of compounds $X_1$ is —C(—$X_2$)(—$X_3$)(—$X_4$) and each $X_2$, $X_3$, and $X_4$, in combination, corresponds to any of the combinations identified in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | ═O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | ═O ($X_3$ and $X_4$ in combination) | |

Furthermore, within embodiment (IA), and groups contained therein, in one group of compounds $X_1$ is C(—$X_2$)(—$X_3$)(—$X_4$), and $X_3$ is —$X_5$C(═O)$R_{13}$, such that the combinations of $X_2$, $X_3$ and $X_4$ include any of the combinations identified in the following table:

| Combination | $X_2$ | $X_3$ | $X_4$ |
|---|---|---|---|
| 1 | Ph | NHC(═O)$R_{13}$ | H |
| 2 | Ph | OC(═O)$R_{13}$ | H |
| 3 | $CH_3$ | NHC(═O)$R_{13}$ | H |
| 4 | $CH_3$ | OC(═O)$R_{13}$ | H |

-continued where $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl.

In one embodiment, the pentaaza macrocyclic ring complex corresponding to Formula (IA) is one of the complexes Formula (IE), such as ($IE_{R1}$), ($IE_{S1}$), ($IE_{R2}$), ($IE_{S2}$), ($IE_{R3}$), or ($IE_{S3}$):

($IE_{R1}$)

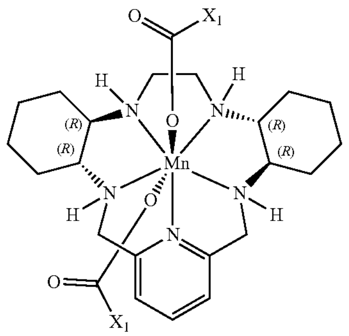

($IE_{S1}$)

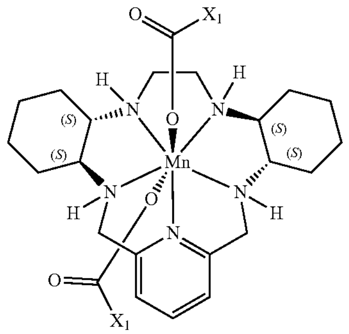

($IE_{R2}$)

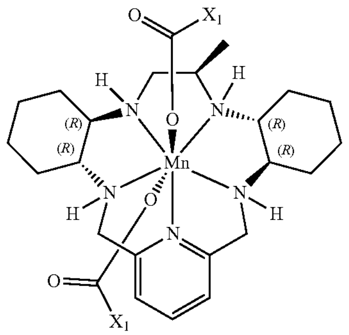

-continued ($IE_{S2}$)

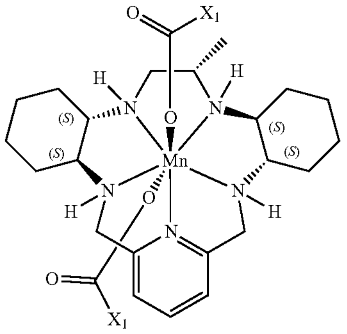

($IE_{R3}$)

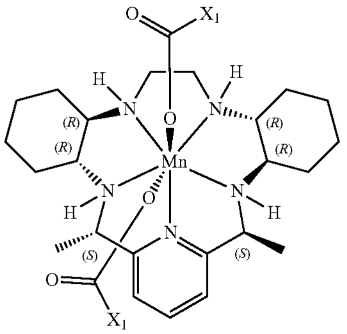

($IE_{S3}$)

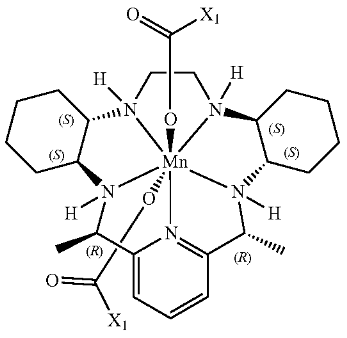

wherein

M is $Mn^{+2}$ or $Mn^{+3}$;

each $X_1$ is independently substituted or unsubstituted phenyl or —$C(X_2)(X_3)(X_4)$;

each $X_2$ is independently substituted or unsubstituted phenyl, methyl, ethyl, or propyl;

each $X_3$ is independently hydrogen, hydroxyl, methyl, ethyl, propyl, amino, or together with $X_4$ is =O;

each $X_4$ is independently hydrogen or together with $X_3$ is =O; and the bonds between the manganese and the macrocyclic nitrogen atoms and the bonds between the manganese and the oxygen atoms of the axial ligands —OC(O)$X_1$ are coordinate covalent bonds.

In one embodiment, each $X_1$ is —$C(X_2)(X_3)(X_4)$ and each —$C(X_2)(X_3)(X_4)$ corresponds to any of combinations 1 to 9 appearing in the table for Formula (IA) above.

In yet another embodiment, the X and Y in pentaaza macrocyclic ring complex of Formula (I) correspond to the ligands in Formulas (IA) or (IE). For example, X and Y in the complex of Formula (I) may correspond to —O—C(O)—$X_1$, where $X_1$ is as defined for the complex of Formula (IA) and (IE) above.

In one embodiment, the pentaaza macrocyclic ring complexes corresponding to Formula (I) (e.g., of Formula (I) or any of the subsets of Formula (I) corresponding to Formula (II)-(XIV), (IA) and (IE)), can comprise any of the following structures:

(4419)

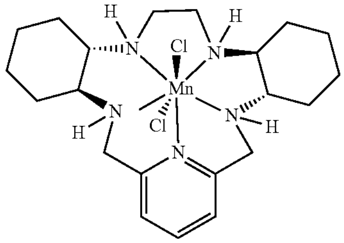

, (4403)

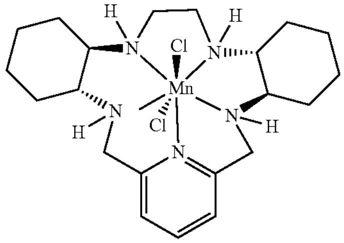

, (4401)

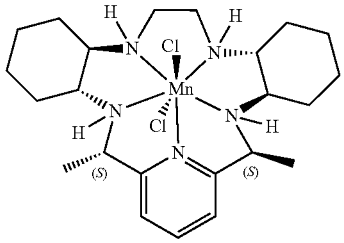

, (4498)

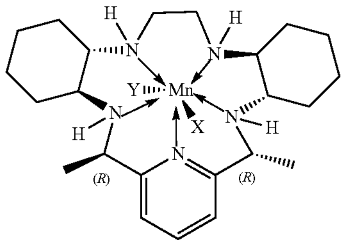

,

GC4444

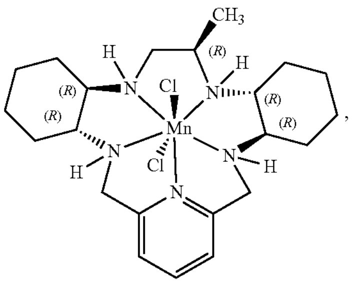

,

-continued

GC4702

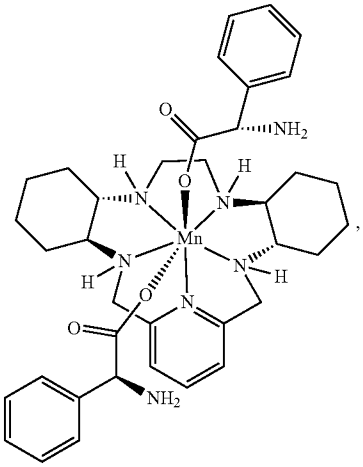

GC4711

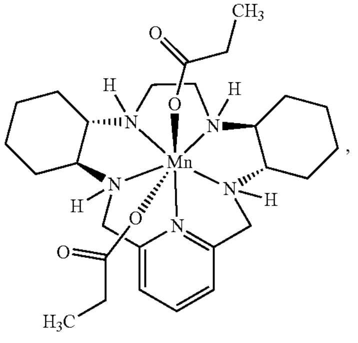

In one embodiment, the pentaaza macrocyclic ring complexes for use in the methods and compositions described herein include those corresponding to Formulae (2), (3), (4), (5), (6), and (7):

2

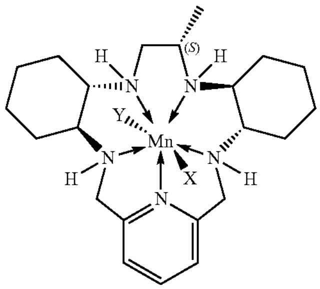

3

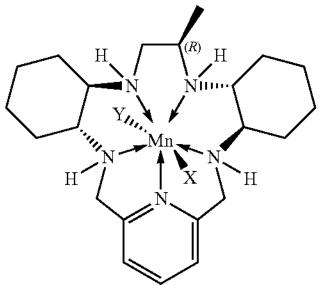

-continued

4

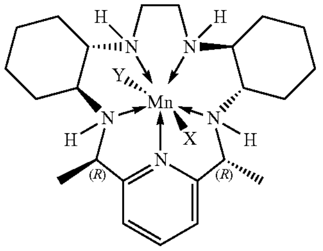

5

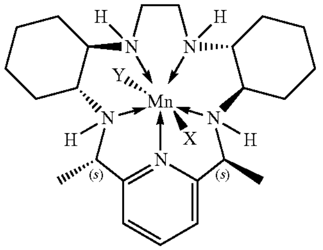

6

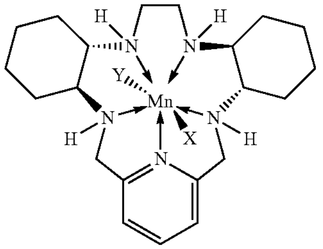

7

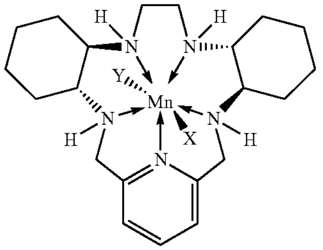

wherein X and Y in each of Formulae (2), (3), (4), (5), (6), and (7) are independently ligands. For example, according to one embodiment, the pentaaza macrocyclic ring complex for use in the methods and compositions described herein include those corresponding to Formulae (2), (3), (4), (5), (6), and (7) with X and Y in each of these formulae being halo, such as chloro. Alternatively, X and Y may be ligands other than chloro, such as any of the ligands described above.

In another embodiment, the pentaaza macrocyclic ring complex corresponds to Formula (6) or Formula (7):

6

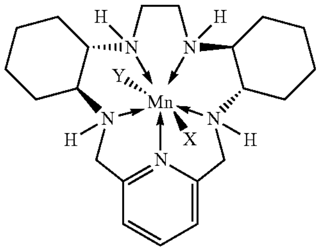

-continued

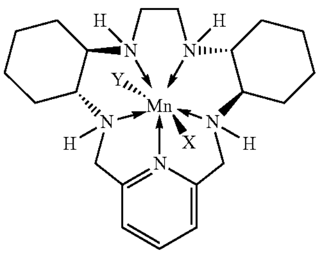

7

The chemical structures of 6 (such as the dichloro complex form described, for example, in Riley, D. P., Schall, O. F., 2007, Advances in Inorganic Chemistry, 59: 233-263) and of 7 herein (such as the dichloro complex form of 7), are identical except that they possess mirror image chirality; that is, the enantiomeric structures are non-superimposable.

For example, the pentaaza macrocyclic ring complex may correspond to at least one of the complexes below:

(4403)

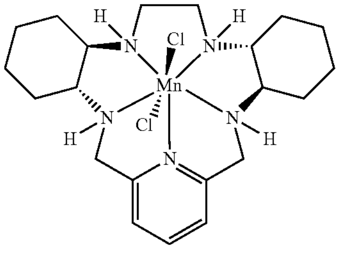

(4419)

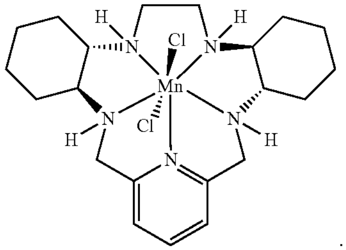

In yet another embodiment, the pentaaza macrocyclic ring complex may correspond to at least one of the complexes below, and/or an enantiomer thereof:

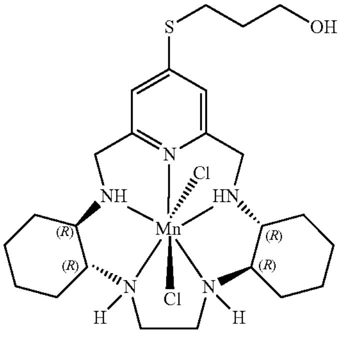

-continued

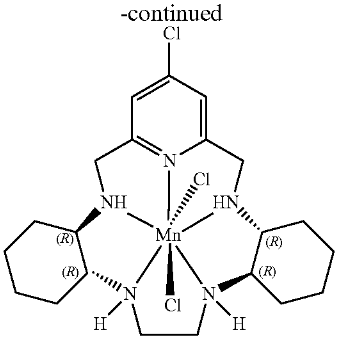

In one embodiment, the enantiomeric purity of the pentaaza macrocyclic ring complex is greater than 95%, more preferably greater than 98%, more preferably greater than 99%, and most preferably greater than 99.5%. As used herein, the term "enantiomeric purity" refers to the amount of a compound having the depicted absolute stereochemistry, expressed as a percentage of the total amount of the depicted compound and its enantiomer. In one embodiment, the diastereomeric purity of the pentaaza macrocyclic ring complex is greater than 98%, more preferably greater than 99%, and most preferably greater than 99.5%. As used herein, the term "diastereomeric purity" refers to the amount of a compound having the depicted absolute stereochemistry, expressed as a percentage of the total amount of the depicted compound and its diastereomers. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC). Similarly, enantiomeric purity can be determined by any analytical method capable of quantitatively distinguishing between a compound and its enantiomer. Examples of suitable analytical methods for determining enantiomeric purity include, without limitation, optical rotation of plane-polarized light using a polarimeter, and HPLC using a chiral column packing material.

In one embodiment, a therapeutically effective amount of the pentaaza macrocyclic ring complex may be an amount sufficient to provide a peak plasma concentration of at least 0.1 μM when administered to a patient. For example, in one embodiment, the pentaaza macrocyclic ring complex may be administered in an amount sufficient to provide a peak plasma concentration of at least 1 μM when administered to a patient. In yet another embodiment, the pentaaza macrocyclic ring complex may be administered in an amount sufficient to provide a peak plasma concentration of at least 10 μM when administered to a patient. Generally, the pentaaza macrocyclic ring complex will not be administered in an amount that would provide a peak plasma concentration greater than 40 μM when administered to a patient. For example, the pentaaza macrocyclic ring complex may be administered in an amount sufficient to provide a peak plasma concentration in the range of from 0.1 μM to 40 μM in a patient. As another example, the pentaaza macrocyclic ring complex may be administered in an amount sufficient to provide a peak plasma concentration in the range of from 0.5 μM to 20 μM in a patient. As another example, the pentaaza macrocyclic ring complex may be administered in an amount sufficient to provide a peak plasma concentration in the range of from 1 μM to 10 μM in a patient.

In yet another embodiment, a dose of the pentaaza macrocyclic ring complex that is administered per kg body weight of the patient may be at least 0.1 mg/kg, such as at least 0.2 mg/kg. For example, the dose of the pentaaza macrocyclic ring complex that is administered per kg body weight of the patient may be at least 0.5 mg/kg. As another example, the dose of the pentaaza macrocyclic ring complex that is administered per kg body weight of the patient may be at least 1 mg/kg. In another example, the pentaaza macrocyclic compound that is administered per kg body weight may be at least 2 mg/kg, such as at least 3 mg/kg, and even at least about 15 mg/kg, such as at least 24 mg/kg and even at least 40 mg/kg. Generally, the dose of the pentaaza macrocyclic ring complex that is administered per kg body weight of the patient will not exceed 1000 mg/kg. For example the dose of the pentaaza macrocyclic ring complex that is administered per kg body weight of the patient may be in the range of from 0.1 to 1000 mg/kg, such as from 0.2 mg/kg to 40 mg/kg, such as 0.2 mg/kg to 24 mg/kg, and even 0.2 mg/kg to 10 mg/kg. As another example, the dose of the pentaaza macrocyclic ring complex that is administered per kg body weight may be in a range of from 1 mg/kg to 1000 mg/kg, such as from 3 mg/kg to 1000 mg/kg, and even from 5 mg/kg to 1000 mg/kg, such as 10 mg/kg to 1000 mg/kg. As another example, the dose of the pentaaza macrocyclic ring complex that is administered per kg body weight may be in a range of from 2 mg/kg to 15 mg/kg. As yet another example, the dose of the pentaaza macrocyclic ring complex that is administered per kg body weight may be in a range of from 3 mg/kg to 10 mg/kg. As another example, the dose of the pentaaza macrocyclic ring complex that is administered per kg body weight of the patient may be in the range of from 0.5 to 5 mg/kg. As yet a further example, the dose of the pentaaza macrocyclic ring complex that is administered per kg body weight of the patient may be in the range of from 1 to 5 mg/kg.

In one embodiment, the dosages and/or plasma concentrations discussed above may be particularly suitable for the pentaaza macrocyclic ring complex corresponding to GC4419, although they may also be suitable for other pentaaza macrocyclic ring complexes. In addition, one or ordinary skill in the art would recognize how to adjust the dosages and/or plasma concentrations based on factors such as the molecular weight and/or activity of the particular compound being used. For example, for a pentaaza macrocyclic ring complex having an activity twice that of GC4419, the dosage and/or plasma concentration may be halved, or for a pentaaza macrocyclic ring complex having a higher molecular weight that GC4419, a correspondingly higher dosage may be used.

The dosing schedule of the pentaaza macrocyclic ring complex can similarly be selected according to the intended treatment. For example, in one embodiment, a suitable dosing schedule can comprise dosing a patient at least once per week, such as at least 2, 3, 4, 5, 6 or 7 days per week (e.g., daily), during a course of treatment. As another example, in one embodiment, the dosing may be at least once a day (qd), or even at least twice a day (bid). In one embodiment, the course of treatment with the pentaaza macrocyclic ring complex may last at least as long as a course of treatment with an anti-cancer therapeutic agent, such as endocrine agent (e.g. tamoxifen or 4-hydroxytamoxifen) and/or chemotherapeutic agent and may even exceed the duration during which the anti-cancer therapeutic agent is provided. The course of therapy with the pentaaza macrocyclic ring complex may also start on the same date as treatment with the endocrine therapy agent, or may start sometime after initial dosing with the anti-cancer therapeutic agent, as is discussed in more detail below. For example, in one embodiment, for an anti-cancer therapeutic agent that is administered for a course of therapy lasting at least a day, two days, three days, four days, five days, six days, one week, two weeks, three weeks, a month, two months, three months, four months, five months, six months, the pentaaza macrocyclic ring complex may be administered for a course of therapy lasting at least at least a day, two days, three days, four days, five days, six days, one week, two weeks, three weeks, a month, two months, three months, four months, five months, six months.

Anti-Cancer Therapeutic Agent

According to one embodiment, an anti-cancer therapeutic agent is provided as a part of the treatment method(s) herein, in combination with the pentaaza macrocyclic compound. Anti-cancer therapeutic agents may be any one or more of a therapeutic agent that inhibits a hormone receptor pathway associated with growth or progression of the cancer (e.g. endocrine agents, which may be referred to as hormone therapy agents), and/or a chemotherapy agent. The endocrine agents are compounds that are capable of blocking or interfering with the effects of hormones on cancer cells (Lumachi et al., *Curr Med Chem,* 18(4) 513-522 (2011); Awan et al., *Curr Oncol,* 25(4): 285-291 (2018)). Cancer and/or tumor cells that contain hormone receptors and/or that depend on hormones for growth may be particularly responsive to endocrine therapy, such as for example estrogen receptor positive (ER positive) cells that use estrogen to grow. According to one embodiment, the therapeutic agent that inhibits a hormone receptor pathway associated with growth or progression of the cancer targets any one or more of the estrogen receptor pathway, the progesterone receptor pathway, and the androgen receptor pathway. For example the therapeutic agent that targets any one or more of the estrogen receptor pathway, progesterone receptor pathway, and the androgen receptor pathway can comprises any one or more of estrogen receptor inhibitors, estrogen receptor degraders/downregulators, selective estrogen receptor modulators (SERMs), aromatase inhibitors, GnRH agonists, androgen synthesis inhibitors, androgen receptor inhibitors, and selective progesterone receptor modulators (SPRMs). According to another embodiment, the endocrine therapy agent comprises a SERM compound selected from the group consisting of tamoxifen, letrozole, clomifene, 4-hydroxytamoxifen, toremifene, raloxifene, nafoxidine, lasofoxifene, bazedoxifene, ospemifene, fulvestrant, brilanestrant, elacestrant, and derivatives, salts and/or prodrugs thereof. According to yet another embodiment, the endocrine therapy agent comprises a SERM compound having a triphenylethylene structure, and/or a benzothiophene structure. According to yet a further embodiment, the endocrine therapy agent comprises a SERM that is any one selected from the group consisting of tamoxifen, 4-hydroxytamoxifen, and derivatives, prodrugs and/or salts thereof.

According to yet another embodiment, the anti-cancer therapeutic agent targets the androgen receptor pathway, and comprises any one or more of an androgen receptor antagonist, an androgen synthesis inhibitor and an antigonadotropin. For example, the therapeutic agent that targets the androgen receptor pathway can comprise at least one selected from the group consisting of cyproterone acetate, megestrol acetate, chlormadinone acetate, spironolacone, oxendolone, osaterone acetate, flutamide, bicalutamide, nilutamide, topilutamide, enzalutamide, apalutamide, dienogest, drospirenone, medogestone, nomegestrol acetate, promegestone, trimegestone, ketoconazole, abiraterone acetate, seviteronel, aminoglutethimide, finasteride, dutasteride, episteride, alfatradial, cyproterone acetate, medrogestone, flutamide, nilutamide, bifluranol, leuprorelin, cetrorelix, allylestrenol, chlormadinone acetate, cyproterone acetate, gestonorone caproate, hydroxyprogesterone caproate, medroxyprogesterone acetate, megestrol acetate, osaterone acetate, oxendolone, estradiol, estradiol esters, ethinylestradiol, conjugated estrogens, diethylstilbestrol, and derivatives, salts and/or prodrugs thereof.

According to yet another embodiment, the anti-cancer therapeutic agent targets the progesterone receptor pathway, and comprises any one or more comprises a Type I, Type II or Type III selective modulator of progesterone (SPRM) that is at least one selected from the group consisting onapristone, mifepristone, lonaprisan, aglepristone, Org31710, Org31806, CDB-2914 and CDB-4124, and derivatives, salts and/or prodrugs thereof.

According to yet another embodiment, the anti-cancer therapeutic agent comprises a chemotherapeutic agent, such as any of a platinum-containing chemotherapeutic agent and an anthracycline chemotherapeutic agent. For example, the chemotherapeutic agent can comprise any of a platinum-containing chemotherapeutic agent selected from the group consisting of cisplatin, oxaliplatin, carboplatin, nedaplatin, lobaplatin, heptaplatin, dicycloplation, lipoplatin, LA-12, phosphaplatin, phenanthriplatin, prolindac, triplatin tetranitrate, picoplatin, satraplatin and/or pharmaceutically acceptable salts thereof, and/or an anthracycline chemotherapeutic agent selected from the group consisting of doxorubicin, daunorubicin, epirubicin and idarubicin, and/or pharmaceutically acceptable salts thereof. Other chemotherapeutic agents described elsewhere herein may also be suitable.

According to yet another embodiment, the anti-cancer therapeutic agent comprises a cell cycle inhibitor such as a CDK4/6 inhibitor, such as any selected from the group consisting of group of palbociclib, abemaciclib, ribociclib, and derivatives, salts and/or prodrugs thereof.

The dose of the anti-cancer therapeutic agent can be selected according to the treatment to be provided and the particular anti-cancer therapeutic agent being used. The dosing schedule of the anti-cancer therapeutic agent can similarly be selected according to the intended treatment and the anti-cancer therapeutic agent being provided. For example, in one embodiment, a suitable dosing schedule can comprise dosing a patient at a frequency of once or twice per day, two days, three days, four days, five days, six days, per week, per two weeks, per three weeks or per month.

Timing of Administration

In one embodiment, a course of therapy with pentaaza macrocyclic ring complex, optionally with the anti-cancer therapeutic agent can comprise one or multiple doses of the agent and/or complex, according to the treatment to be provided. In one embodiment, a course of therapy comprising one or multiple doses can comprise administering a dose of the pentaaza macrocyclic complex a predetermined period of time before administration of the anti-cancer therapeutic agent. For example, the course of therapy can comprise administering an initial dose and optionally one or more subsequent doses of the anti-cancer therapeutic agent, with the onset of dosing with the pentaaza macrocyclic ring complex being performed a predetermined period of time before the initial anti-cancer therapeutic agent. In another embodiment, a course of therapy comprising one or multiple doses can comprise administering a dose of the pentaaza macrocyclic complex after a predetermined period of time has elapsed since administration of a dose of anti-cancer therapeutic agent. That is, the course of therapy can comprise administering an initial dose and optionally one or more subsequent doses of the anti-cancer therapeutic agent, with the onset of dosing with the pentaaza macrocyclic ring complex being delayed for a predetermined period of time after the initial anti-cancer therapeutic agent.

In one embodiment, at least one of the doses of the pentaaza macrocyclic ring complex during the course of therapy, is administered at least one week, at least 5 days, at least 3 days, at least 2 days, at least 1 day at least 12 hours, at least 8 hours, at least 4 hours, at least 2 hours, at least 1 hour and/or at least 30 mins before administration of the anti-cancer therapeutic agent. In another embodiment, the at least one of the doses of the pentaaza macrocyclic ring complex during the course of therapy, is administered at least one week, at least 5 days, at least 3 days, at least 2 days, at least 1 day at least 12 hours, at least 8 hours, at least 4 hours, at least 2 hours, at least 1 hour and/or at least 30 mins after administration of the anti-cancer therapeutic agent. Furthermore, the timing of the at least one dose of the pentaaza macrocyclic ring complex may also apply to a plurality of doses provided during the course of therapy, such as at least 25%, at least 50%, at least 75%, at least 90%, and even substantially all of the doses provided during the course of therapy.

Other Cancer Therapies

In one embodiment, the treatment provided herein can further comprise treatment with another therapy other than those specifically described above, such as for example one or more of a radiation therapy, immunotherapy and/or another chemotherapeutic treatment. For example, in one embodiment, a radiation therapy may be administered to the subject prior to, concomitantly with, or after administration of one or more of the pentaaza macrocyclic ring complex optionally with the anti-cancer therapeutic agent. Further detailed description of radiation therapies and other chemotherapies suitable for the treatment of cancer are provided below.

In one embodiment, a radiation therapy can be administered concomitantly with administration of one or more of the pentaaza macrocyclic ring complex and optional anti-cancer therapeutic agent. For example, one or more of the anti-cancer therapeutic agent and pentaaza macrocyclic ring complexes may be administered during a course of radiation therapy, such as in between, before or after, or on the same day as dosing with radiation, such that the subject is receiving radiation therapy concurrently with one or more of the anti-cancer therapeutic agent and pentaaza macrocyclic ring complex.

In yet another embodiment, the pentaaza macrocyclic ring complex and optional anti-cancer therapeutic agent, can be administered in the absence of any other cancer treatment. As demonstrated further in the examples below, it has been unexpectedly discovered that the pentaaza macrocyclic ring complexes are capable of enhancing the response to and/or efficacy of anti-cancer therapies such as endocrine therapies and chemotherapies, even when administered without radiation therapy. Accordingly, in one embodiment, the cancer treatment provided to the subject may consist essentially of the pentaaza macrocyclic ring complex and optional anti-cancer therapeutic agent, without radiation exposure (i.e. without administering a radiation dose or dose fraction). For example, the combination of the pentaaza macrocyclic ring complex and optionally the anti-cancer therapeutic agent may be administered to a subject that is not receiving radiation therapy, and/or a subject that has not received any radiation therapy for at least one day, such as at least one week and/or at least one month.

Methods of Administration

According to one embodiment, the anti-cancer therapeutic agent, is administered as a co-therapy or combination therapy with the pentaaza macrocyclic ring complex. Co-therapy or combination therapy according to the methods described herein is intended to embrace administration of each compound in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent, or single or multiple parenteral administrations, or other routes of administration and dosage forms. When administered in combination, therefore, the therapeutic agents (i.e., the pentaaza macrocyclic ring complex and/or the anti-cancer therapeutic agent) can be formulated as separate compositions that are administered at the same time or sequentially at different times, or the therapeutic agents can be given as a single composition. Pharmaceutical compositions and formulations are discussed elsewhere herein.

It is not necessary that the pentaaza macrocyclic ring complex and the anti-cancer therapeutic agent be administered simultaneously or essentially simultaneously; the agents and compounds may be administered in sequence. The advantage of a simultaneous or essentially simultaneous administration, or sequential administration, is well within the determination of the skilled clinician. For instance, while a pharmaceutical composition or formulation comprising an anti-cancer therapeutic agent may be advantageous for administering first in the combination for one particular treatment, prior to administration of the pentaaza macrocyclic ring complex, prior administration of the pentaaza macrocyclic ring complex may be advantageous in another treatment. It is also understood that the instant combination of the pentaaza macrocyclic ring complex and the anti-cancer therapeutic agent may be used in conjunction with other methods of treating cancer (typically cancerous tumors) including, but not limited to, radiation therapy and surgery, or other chemotherapy. It is further understood that another active agent, such as a cytostatic or quiescent agent, or antiemetic agent, if any, may be administered sequentially or simultaneously with any or all of the other synergistic therapies.

Thus, embodiments of the therapeutic method include wherein a pentaaza macrocyclic ring complex and an anti-cancer therapeutic agent, and combinations thereof, are administered simultaneously or sequentially. For instance, aspects of the present disclosure encompass a method for the treatment of cancer wherein a pentaaza macrocyclic ring complex and an anti-cancer therapeutic agent are administered simultaneously or sequentially. Other active agents can also be administered simultaneously or sequentially with the pentaaza macrocyclic ring complex and the anti-cancer therapeutic agent.

As noted above, if the pentaaza macrocyclic ring complex and the anti-cancer therapeutic agent are not administered simultaneously or essentially simultaneously, then the initial order of administration of the components may be varied. Thus, for example, the anti-cancer therapeutic agent may be administered first, followed by the administration of the pentaaza macrocyclic ring complex; or the pentaaza macrocyclic ring complex may be administered first, followed by the administration of the anti-cancer therapeutic agent. This alternate administration may be repeated during a single treatment protocol. Other sequences of administration to exploit the effects described herein are contemplated, and other sequences of administration of other active agents can also be provided.

In one embodiment, the subject is pre-treated with the anti-cancer therapeutic agent, followed by administration of the pentaaza macrocyclic ring complex, or vice versa. In accordance with such embodiments, the pentaaza macrocyclic ring complex may be administered at least 1 hour, and even at least 3 days, after administration of the anti-cancer therapeutic agent, or vice versa. For example, in one embodiment, the pentaaza macrocyclic ring complex is administered between 1 hour and 3 days after administration of the anti-cancer therapeutic agent, or vice versa. In another embodiment, for example, the pentaaza macrocyclic ring complex is administered between 1 hour and 1 day after administration of the anti-cancer therapeutic agent, or vice versa. For example, the pentaaza macrocyclic ring complex may be administered within 1 hour, 2 hours, 3 hours, 4 hours, 5 hours, 6 hours, 12 hours, 18 hours, 24 hours, 36 hours, 48 hours, one week, 2 weeks, 3 weeks, 4 weeks, 6 weeks, 8 weeks, 9 weeks, 10 weeks or 12 weeks after administration of the anti-cancer therapeutic agent, or vice versa. In these and other embodiments, the anti-cancer therapeutic agent may be administered in multiple doses leading up to administration of the pentaaza macrocyclic ring complex, or vice versa.

Alternatively, the subject may be pre-treated with the pentaaza macrocyclic ring complex, followed by administration of the anti-cancer therapeutic agent, or vice versa. In accordance with such embodiments, the pentaaza macrocyclic ring complex may be administered within at least 1 plasma half-life of the anti-cancer therapeutic agent, such as within 4 plasma half-lives of the anti-cancer therapeutic agent, or vice versa. For example, the pentaaza macrocyclic ring complex may be administered within 1, 2, or 3 plasma half-lives of the other anti-cancer therapeutic agent, or vice versa.

In other alternative embodiments, the subject may be pre-treated with the anti-cancer therapeutic agent, followed by administration of the pentaaza macrocyclic ring complex, which is further followed by one or more additional administrations of the anti-cancer therapeutic agent, or vice versa. For example, the subject could be pre-treated with a dose of anti-cancer therapeutic agent, followed by administration of a dose of pentaaza macrocyclic ring complex, which is then followed by the administration of additional (or partial) dose of the same or different anti-cancer therapeutic agent, which may be further followed by another dose of pentaaza macrocyclic ring complex. Further, the subject could be pre-treated with a partial or full dose of pentaaza macrocyclic ring complex, followed by administration of an anti-cancer therapeutic agent, which is then followed by administration of an additional (or partial) dose of pentaaza macrocyclic complex.

As described in further detail below, the combinations of the disclosure may also be co-administered with other well-known therapeutic agents that are selected for their particular usefulness against the condition that is being treated. Combinations may alternatively be used sequentially with known pharmaceutically acceptable agent(s) when a multiple combination formulation is inappropriate.

In one embodiment, the pentaaza macrocyclic ring complex and/or the anti-cancer therapeutic agent can generally be administered according to therapeutic protocols that may be known for these agents. For example, the administration of the various components can be varied depending on the disease being treated and the effects of pentaaza macrocyclic ring complex and anti-cancer therapeutic agent on that disease. Also, in accordance with the knowledge of the skilled clinician, the therapeutic protocols (e.g., dosage amounts and times of administration) can be varied in view of the observed effects of the administered therapeutic agents (i.e., pentaaza macrocyclic ring complex, anti-cancer therapeutic agent) on the patient, and in view of the observed responses of the disease to the administered therapeutic agents.

Also, in general, the pentaaza macrocyclic ring complex and/or the anti-cancer therapeutic agent do not have to be administered in the same pharmaceutical composition, and may, because of different physical and chemical characteristics, have to be administered by different routes. For example, the pentaaza macrocyclic ring complex may be administered orally to generate and maintain good blood levels thereof, while the anti-cancer therapeutic agent may be administered intravenously or via transfusion, or vice versa. The mode of administration may include, where possible, in the same pharmaceutical composition, or in separate pharmaceutical compositions (e.g., two or three separate compositions). Furthermore, once the initial administration has been made, then based upon the observed effects, the dosage, modes of administration and times of administration can be modified.

The particular choice of pentaaza macrocyclic ring complex and the anti-cancer therapeutic agent, and other related therapies (such as radiation, immunotherapy, or other chemotherapies), will depend upon the diagnosis of the attending physicians and their judgment of the condition of the patient and the appropriate treatment protocol.

Thus, in accordance with experience and knowledge, the practicing physician may modify each protocol for the administration of a component (the pentaaza macrocyclic ring complex and the anti-cancer therapeutic agent) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The products of which the combination are composed may be administered simultaneously, separately or spaced out over a period of time so as to obtain the maximum efficacy of the combination; it being possible for each administration to vary in its duration from a rapid administration to a relatively continuous perfusion of either component (in separate formulations or in a single formulation). As a result, for the purposes of the present disclosure, the combinations are not exclusively limited to those which are obtained by physical association of the constituents, but also to those which permit a separate administration, which can be simultaneous or spaced out over a period of time.

Accordingly, administration of the components described herein can occur as a single event or over a time course of treatment. For example, the pentaaza macrocyclic ring complex and/or the anti-cancer therapeutic agent can be administered (simultaneously or in sequence) hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the patient in need of such treatment. Alternatively, the compounds and agents can be administered hourly, daily, weekly, bi-weekly, or monthly, for a period of several weeks, months, years, or over the lifetime of the patient as a prophylactic measure.

The dose or amount of pharmaceutical compositions including the pentaaza macrocyclic ring complex and/or the anti-cancer therapeutic agent administered to the patient should be an effective amount for the intended purpose, i.e., treatment or prophylaxis of one or more of the diseases, pathological disorders, and medical conditions discussed herein, particularly cancer. Generally speaking, the effective amount of the composition administered can vary according to a variety of factors such as, for example, the age, weight, sex, diet, route of administration, and the medical condition of the patient in need of the treatment. Specifically preferred doses are discussed more fully herein. It will be understood, however, that the total daily usage of the compositions described herein will be decided by the attending physician or veterinarian within the scope of sound medical judgment.

As noted above, the combinations can be co-administered (via a co-formulated dosage form or in separate dosage forms administered at about the same time). The combinations can also be administered separately, at different times, with each agent in a separate unit dosage form. Numerous approaches for administering the anti-cancer therapeutic agent and pentaaza macrocyclic ring complex can be readily adapted for use in the present disclosure. The pharmaceutical compositions may be delivered orally, e.g., in a tablet or capsule unit dosage form, or parenterally, e.g., in an injectable unit dosage form, or by some other route. For systemic administration, for example, the drugs can be administered by, for example, intravenous infusion (continuous or bolus). The compositions can be used for any therapeutic or prophylactic treatment where the patient benefits from treatment with the combination.

The specific therapeutically effective dose level for any particular patient will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. If desired, the effective daily doses may be divided into multiple doses for purposes of administration. Consequently, single dose compositions may contain such amounts or submultiples to make up the daily dose.

In one embodiment, suitable or preferred doses for each of the components are employed in the methods or included in the compositions described herein. Preferred dosages for the pentaaza macrocyclic ring complex, for instance, may be within the range of 10 to 500 mg per patient per day. However, the dosage may vary depending on the dosing schedule, which can be adjusted as necessary to achieve the desired therapeutic effect. It should be noted that the ranges of effective doses provided herein are not intended to limit the disclosure and represent exemplary dose ranges. The most preferred dosage will be tailored to the individual subject, taking into account, among other things, the particular combinations employed, and the patient's age, sex, weight, physical condition, diet, etc., as is understood and determinable by one of ordinary skill in the art without undue experimentation.

Treatment of cancer, or cancer therapies, described herein includes achieving a therapeutic benefit, however the therapy may also be administered to achieve a prophylactic benefit. Therapeutic benefits generally refer to at least a partial eradication or amelioration of the underlying disorder being treated. For example, in a cancer patient, therapeutic benefit includes (partial or complete) eradication or amelioration of the underlying cancer. Also, a therapeutic benefit is achieved with at least partial, or complete, eradication or amelioration of one or more of the physiological symptoms associated with the underlying disorder such that an improvement is observed in the patient, notwithstanding the fact that the patient may still be afflicted with the underlying disorder. For prophylactic benefit, a method of the disclosure may be performed on, or a composition of the invention administered to, a patient at risk of developing cancer, or to a patient reporting one or more of the physiological symptoms of such conditions, even though a diagnosis of the condition may not have been made.

Cancer Treatment Methods

In general, any subject having, or suspected of having, a cancer or other proliferative disorder may be treated using the compositions and methods of the present disclosure. Subjects receiving treatment according to the methods described herein are mammalian subjects, and typically human patients. Other mammals that may be treated according to the present disclosure include companion animals such as dogs and cats, farm animals such as cows, horses, and swine, as well as birds and more exotic animals (e.g., those found in zoos or nature preserves). In one embodiment of the disclosure, a method is provided for the treatment of cancerous tumors, particularly solid tumors. Advantageously, the methods described herein may reduce the development of tumors, reduce tumor burden, or produce tumor regression in a mammalian host. Cancer patients and individuals desiring cancer prophylaxis can be treated with the combinations described herein.

Cancer and tumors generally refer to or describe the physiological condition in mammals that is typically characterized by unregulated cell growth. By means of the pharmaceutical combinations, co-formulations, and combination therapies of the present disclosure, various tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

In one embodiment, the tumor or cancer is chosen from adenoma, angio-sarcoma, astrocytoma, epithelial carcinoma, germinoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Thus, for example, the present disclosure provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

For example, particular leukemias that can be treated with the combinations and methods described herein include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas can also be treated with the combinations and methods described herein. Lymphomas are generally neoplastic transformations of cells that reside primarily in lymphoid tissue. Lymphomas are tumors of the immune system and generally are present as both T cell- and as B cell-associated disease. Among lymphomas, there are two major distinct groups: non-Hodgkin's lymphoma (NHL) and Hodgkin's disease. Bone marrow, lymph nodes, spleen and circulating cells, among others, may be involved. Treatment protocols include removal of bone marrow from the patient and purging it of tumor cells, often using antibodies directed against antigens present on the tumor cell type, followed by storage. The patient is then given a toxic dose of radiation or chemotherapy and the purged bone marrow is then re-infused in order to repopulate the patient's hematopoietic system.

Other hematological malignancies that can be treated with the combinations and methods described herein include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

In one embodiment, the methods and pharmaceutical compositions described herein are used to treat a cancer that is any of breast cancer, melanoma, oral squamous cell carcinoma, lung cancer including non-small cell lung cancer, renal cell carcinoma, colorectal cancer, prostate cancer, brain cancer, spindle cell carcinoma, urothelial cancer, bladder cancer, colorectal cancer, head and neck cancers such as squamous cell carcinoma, and pancreatic cancer. According to yet another embodiment, the cancer that is treated any one selected from the group consisting of breast cancer, prostate cancer, testicular cancer, glioma, glioblastoma, head and neck cancer, ovarian cancer, endometrial cancer, hepatocellular carcinoma, desmoid tumors, pancreatic carcinoma, melanoma, and renal cell carcinoma.

According to one embodiment, the cancer treatment involves administering one or both of the anti-cancer therapeutic agent and the pentaaza macrocyclic ring complex in a therapeutically effective amount that results in an increase in cancer response corresponding to any selected from the group consisting of reduced tumor volume, reduced tumor growth rate, increased survival of the mammalian subject, reduced occurrence and/or extent of metastasis, and reduced proliferation of cancer cells, and/or may decrease cancer complications.

Pharmaceutical Formulations

Another aspect of the present disclosure relates to the pharmaceutical compositions comprising the combinations described herein, together with a pharmaceutically acceptable excipient. The pharmaceutical compositions include the pentaaza macrocyclic ring complex (e.g., those corresponding to Formula (I)), and optionally at least anti-cancer therapeutic agent, and combinations thereof, as discussed above, typically formulated as a pharmaceutical dosage form, optionally in combination with a pharmaceutically acceptable carrier, additive or excipient. In one embodiment, for example, the pharmaceutical composition comprises a pentaaza macrocyclic ring complex, anti-cancer therapeutic agent and a pharmaceutically acceptable excipient. Pharmaceutical compositions according to the present disclosure may be used in the treatment of cancer.

The pharmaceutical compositions described herein are products that result from the mixing or combining of more than one active ingredient and include both fixed and non-fixed combinations of the active ingredients. Fixed combinations are those in which the active ingredients, e.g., a pentaaza macrocyclic ring complex and an anti-cancer therapeutic agent, are administered to a patient simultaneously in the form of a single entity or dosage. Other active agents may also be administered as a part of the single entity or dosage, or may be separately administered Non-fixed combinations are those in which the active ingredients, e.g., a pentaaza macrocyclic ring complex and an anti-cancer therapeutic agent, are administered to a patient as separate entities either simultaneously, concurrently or sequentially with no specific intervening time limits, wherein such administration provides effective levels of the compounds in the body of the patient. The latter also applies to cocktail therapy, e.g., the administration of three or more active ingredients.

The above-described pentaaza macrocyclic ring complex and/or the anti-cancer therapeutic agent may be dispersed in a pharmaceutically acceptable carrier prior to administration to the mammal; i.e., the components described herein are preferably co-formulated. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route, and in accordance with the conventional route of administration. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in combination with the compositions of the present disclosure are well known to those of ordinary skill in the art and are selected based upon a number of factors: the particular compound(s) and agent(s) used, and its/their concentration, stability and intended bioavailability; the subject, its age, size and general condition; and the route of administration. Suitable non-aqueous, pharmaceutically-acceptable polar solvents include, but are not limited to, alcohols (e.g., a-glycerol formal, 6-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(6-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyester,polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, DE, polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$ to $C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, di methylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

In some embodiments, oils or non-aqueous solvents may be employed in the formulations, e.g., to bring one or more of the compounds into solution, due to, for example, the presence of large lipophilic moieties. Alternatively, emulsions, suspensions, or other preparations, for example, liposomal preparations, may be used. With respect to liposomal preparations, for example, any known methods for preparing liposomes may be used. See, for example, Bangham et al., J. Mol. Biol, 23: 238-252 (1965) and Szoka et al., Proc. Natl Acad. Sci 75: 4194-4198 (1978), incorporated herein by reference. Thus, in one embodiment, one or more of the compounds are administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines. Ligands may also be attached to the liposomes, for instance, to direct these compositions to particular sites of action.

Other pharmaceutically acceptable solvents for use in the pharmaceutical compositions described herein are well known to those of ordinary skill in the art, and are identified in The Chemotherapy Source Book (Williams & Wilkens Publishing), *The Handbook of Pharmaceutical Excipients*, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, New York, 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, New York, 1980), Remington's Pharmaceutical Sciences (A. Gennaro, ed., 19th ed.) (Mack Publishing, Easton, PA, 1995), The United States Pharmacopeia 24, The National Formulary 19, (National Publishing, Philadelphia, PA, 2000), and A. J. Spiegel et al., Use of Non-aqueous Solvents in Parenteral Products, Journal of Pharmaceutical Sciences, Vol. 52, No. 10, pp. 917-927 (1963).

Formulations containing the pentaaza macrocyclic ring complex and/or the anti-cancer therapeutic agent may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions orformulation products employ the pentaaza macrocyclic ring complex and/or and the anti-cancer therapeutic agent within accepted dosage ranges.

In one embodiment, a formulation is provided that contains the anti-cancer therapeutic agent as a part of liquid dosage form, such as a sterile liquid dosage form suitable for injection. For example, the liquid form containing the anti-cancer therapeutic agent in combination with one or more further ingredients, such as edetate disodium (EDTA). In one embodiment, the liquid form can comprise EDTA in an amount suitable to act as a preservative and/or metal-chelating agent, such as an amount of about 0.025%. The liquid form can further comprise water, and may also comprise a pH adjuster, such as sodium bicarbonate, for pH adjustment in the range of pH 5.5 to 7.0. In one embodiment, the pentaaza macrocyclic ring complex can also be provided as a part of a sterile liquid dosage form suitable for injection, either in the same liquid dosage form with the anti-cancer therapeutic agent or as a separate dosage form.

Formulations for certain pentaaza macrocyclic ring complexes are also described in, for example, in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041 (each of which is hereby incorporated herein by reference in its entirety).

It is contemplated that co-formulations of the pentaaza macrocyclic ring complex and the anti-cancer therapeutic agent may employ conventional formulation techniques for these components individually, or alternative formulation routes, subject to compatibility and efficacy of the various components, in combination.

The above-described pharmaceutical compositions including the pentaaza macrocyclic compound and/or the anti-cancer therapeutic agent may additionally include one or more additional pharmaceutically active components. Suitable pharmaceutically active agents that may be included in the compositions according to aspects of the present invention include, for instance, antiemetics, anesthetics, antihypertensives, antianxiety agents, anticlotting agents, anticonvulsants, blood glucose-lowering agents, decongestants, antihistamines, antitussives, antineoplastics, beta blockers, anti-inflammatory agents, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's Disease agents, antibiotics, anti-depressants, and antiviral agents. The individual components of such combinations may be administered either sequentially or simultaneously in separate or combined pharmaceutical formulations.

In yet another embodiment, a kit may be provided that includes a pentaaza macrocyclic ring complex and optionally the anti-cancer therapeutic agent, for treatment of a condition such as cancer, and/or to reduce the likelihood of recurrence of cancer. For example, the kit may comprise a first vessel or container having therein a formulation comprising the pentaaza macrocyclic ring complex, such as an oral or injectable formulation of the pentaaza macrocyclic ring complex, and a second vessel or container having therein a formulation comprising the anti-cancer therapeutic agent, such as an injectable formulation of anti-cancer therapeutic agent. The kit may further comprise a label or other instructions for administration of the active agents, recommended dosage amounts, durations and administration regimens, warnings, listing of possible drug-drug interactions, and other relevant instructions, such as a label instructing therapeutic regimens (e.g., dosing, frequency of dosing, etc.) corresponding to any of those described herein.

Combination Treatment with Cancer Therapy

In one embodiment, the pentaaza macrocyclic ring complex and/or the anti-cancer therapeutic agent can be administered in combination with another cancer therapy, to provide therapeutic treatment. For example, the pentaaza macrocyclic ring complex and/or the anti-cancer therapeutic agent may be administered as a part of a radiation therapy treatment regime.

In general, the temporal aspects of the administration of the pentaaza macrocyclic ring complex and/or the anti-cancer therapeutic agent may depend for example, on the particular radiation therapy that is selected, or the type, nature, and/or duration of the radiation exposure. Other considerations may include the disease or disorder being treated and the severity of the disease or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors. For example, the compounds may be administered in various embodiments before, during, and/or after the administration of the radiation therapy (e.g., before, during or after exposure to and/or before, during or after a course of radiation therapy comprising multiple exposures and/or doses). By way of another example, the compounds may be administered in various embodiments before, during, and/or after an exposure to radiation. In one embodiment, the radiation therapy can comprise comprising any selected from the group consisting of gamma irradiation, proton therapy, heavy ion therapy, brachytherapy, radionuclide therapy, conformal radiation therapy, intensity modulated radiation therapy, stereotactic body radiation therapy, stereoablative radiation therapy, and gamma knife therapy, whether delivered as standard fractionation, hypofractionation, accelerated fractionation or decelerated fractionation and variations thereof.

If desired, the effective dose can be divided into multiple doses for purposes of administration; consequently, single dose compositions may contain such amounts or submultiples thereof to make up the dose.

In one embodiment, for example, the pentaaza macrocyclic ring complex and/or the anti-cancer therapeutic agent are administered to the patient prior to or simultaneous with the radiation exposure. In another embodiment, for example, the components are administered to the patient prior to, but not after, the radiation exposure. In yet another embodiment, one or more of the pentaaza macrocyclic ring complex and/or the anti-cancer therapeutic agent are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the radiation exposure, such as an initial radiation exposure in a course of radiation treatment, or prior to another dose or dose fraction of radiation that is one of the doses or dose fractions of radiation in the course of treatment. In still other embodiments, for example, the pentaaza macrocyclic ring complex and/or the anti-cancer therapeutic agent are administered to the patient after the radiation exposure; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the radiation exposure, which may be a dose or dose fraction of radiation in a multi-dose course of radiation therapy, or may be the single or final dose or dose fraction of radiation in the radiation therapy.

In one embodiment, the pentaaza macrocyclic ring complex and/or the anti-cancer therapeutic agent are administered as a part of a course of therapy that includes the radiation therapy. In radiation therapy, a patient receives a dose or dose fraction of ionizing radiation to kill or control the growth of cancerous cells. The dose or dose fraction of radiation may be directed at a specific part of the body, and the beam of radiation may also be shaped according to a predetermined treatment regimen, to reduce deleterious effects on parts of the body not afflicted with cancer. A typical course of radiation therapy may include one or a plurality of doses or dose fractions of radiation, which can be administered over the course of days, weeks and even months. A total "dose" of radiation given during a course of radiation therapy typically refers to the amount of radiation a patient receives during the entire course of radiation therapy, which doses may be administered as dose "fractions" corresponding to multiple radiation exposures in the case where the total dose is administered over several sessions, with the sum of the fractions administered corresponding to the overall dose.

In one embodiment, at least one of the pentaaza macrocyclic ring complex and/or the anti-cancer therapeutic agent are administered within a predetermined time period before or after a radiation exposure, such as a before or after a radiation dose or dose fraction. For example, the pentaaza macrocyclic ring complex and/or the anti-cancer therapeutic agent may be administered within 1 week, 48 hours, 24 hours, 12 hours, 6, hours, 2 hours, 1 hour or even within 30 minutes of the patient receiving the radiation exposure, such as the dose or dose fraction (either before or after the radiation exposure corresponding to the radiation dose or dose fraction). Other durations between the radiation exposure and administration of the compound that result in the enhanced the killing of cancer cells may also be suitable. In one embodiment, one or more of the pentaaza macrocyclic ring complex and/or the anti-cancer therapeutic agent may be administered before the radiation exposure, and the remaining one or more of the pentaaza macrocyclic ring complex and/or the anti-cancer therapeutic agent can be administered after the radiation exposure. One or more of the pentaaza macrocyclic ring complex and the anti-cancer therapeutic agent may also be administered both before and after administration of a radiation exposure.

In one embodiment, a course of radiation therapy includes a plurality of radiation doses or dose fractions given over a predetermined period of time, such as over the course of hours, weeks, days and even months, with the plural doses or dose fractions being either of the same magnitude or varying. That is, a course of radiation therapy can comprise the administration of a series of multiple doses or dose fractions of radiation. In one embodiment, the pentaaza macrocyclic ring complex and/or the anti-cancer therapeutic agent can be administered before one or more radiation doses or dose fractions in the series, such as before each radiation dose or dose fraction, or before some number of the radiation doses or dose fractions. Furthermore, the administration of the pentaaza macrocyclic ring complex and/or the anti-cancer therapeutic agent during the course of radiation therapy can be selected to enhance the cancer treating effects of the radiation therapy, such as by sensitizing cancer cells to the radiation therapy. In one embodiment, the pentaaza macrocyclic ring complex and/or the anti-cancer therapeutic agent are administered within a predetermined duration before or after of each dose or dose fraction, such as the predetermined duration discussed above. In another embodiment, the pentaaza macrocyclic ring complex and/or the anti-cancer therapeutic agent are administered within a predetermined duration of time before or after only select doses or dose fractions. In yet another embodiment, at least one of the pentaaza macrocyclic ring complex and/or the anti-cancer therapeutic agent is administered within a predetermined duration of time before the doses, while another of the pentaaza macrocyclic ring complex and/or the anti-cancer therapeutic agent is administered within a predetermined duration of time after the doses or dose fraction. In a further embodiment, at least one of the pentaaza macrocyclic ring complex and/or the anti-cancer therapeutic agent is administered only within the predetermined duration before or after select doses or dose fractions, while another of the pentaaza macrocyclic ring complex and/or the anti-cancer therapeutic agent is administered only within the predetermined duration before or after doses or dose fractions other than the select doses or dose fractions.

A suitable overall dose to provide during a course of therapy can be determined according to the type of treatment to be provided, the physical characteristics of the patient and other factors, and the dose fractions that are to be provided can be similarly determined. In one embodiment, a dose fraction of radiation that is administered to a patient may be at least 1.8 Gy, such as at least 2 Gy, and even at least 3 Gy, such as at least 5 Gy, and even at least 6 Gy. In yet another embodiment, a dose fraction of radiation that is administered to a patient may be at least 10 Gy, such as at least 12 Gy, and even at least 15 Gy, such as at least 18 Gy, and even at least 20 Gy, such as at least 24 Gy. In general, a dose fraction of radiation administered to a patient will not exceed 54 Gy. Furthermore, it should be noted that, in one embodiment, a dose fraction delivered to a subject may refer to an amount delivered to a specific target region of a subject, such as a target region of a tumor, whereas other regions of the tumor or surrounding tissue may be exposed to more or less radiation than that specified by the nominal dose fraction amount.

In yet another embodiment, the pentaaza macrocyclic ring complex and/or the anti-cancer therapeutic agent are administered as a part of a course of therapy that includes administration of an additional chemotherapeutic agent. In chemotherapy, chemotherapeutic agents are administered to a patient to kill or control the growth of cancerous cells. A typical course of chemotherapy may include one or a plurality of doses of one or more chemotherapeutic agents, which can be administered over the course of days, weeks and even months. Chemotherapeutic agents can include at least one of: alkylating antineoplastic agents such as nitrogen mustards (e.g. cyclophosphamide, chlorambucil), nitrosoureas (e.g. n-nitroso-n-methylurea, carmustine, semustine), tetrazines (e.g. dacarbazine, mitozolimide), aziridines (e.g. thiotepa, mytomycin); anti-metabolites such as anti-folates (e.g. methotrexate and pemetrexed), fluoropyrimidines (e.g., fluorouracil, capecitabine), anthracyclines (e.g. doxorubicin, daunorubicin, epirubicin), deoxynucleoside analogs (e.g. cytarabine, gemcitabine, decitabine) and thiopurines (e.g., thioguanine, mercaptopurine); anti microtubule agents such as taxanes (e.g. paclitaxel, docetaxel); topoisomerase inhibitors (e.g. etoposide, doxorubicin, mitoxantrone, teniposide); and antitumor antibiotics (e.g. bleomycin, mitomycin). For example, the chemotherapeutic agent may be selected from the group consisting of all-trans retinoic acid, arsenic trioxide, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine. The administration of many of the chemotherapeutic agents is described in the "Physicians' Desk Reference" (PDR), e.g., 1996 edition (Medical Economics Company, Montvale, N.J. 07645-1742, USA).

In one embodiment, the pentaaza macrocyclic ring complex and/or the anti-cancer therapeutic agent are administered as a part of a course of therapy that includes an additional chemotherapeutic agent selected from the group consisting of cisplatin, doxorubicin, bleomycin, and paclitaxel. Furthermore, in one embodiment, the additional chemotherapeutic agent may be selected from the group consisting of a taxane, an anticancer antibiotic, and an anthracycline. Other chemotherapeutic agents can include arsenic trioxide and 5-FU, which agents can also be used in the methods and compositions described herein. (Alexandre et al., Cancer Res. 67: (8), 3512-3517 (2007); Yen et al., J. Clin. Invest. 98 (5), 1253-1260 (1996); Masuda et al., Cancer Chemother. Pharmacol. 47(2), 155-160 (2001)).

According to yet another embodiment, the additional chemotherapeutic agent can include at least one of an antimetabolite anti-cancer agents and antimitotic anti-cancer agents, and combinations thereof, which may include some of the agents described above and well as other agents described further herein. Various antimetabolite and antimitotic agents may be employed in the methods and compositions described herein.

Antimetabolic agents typically structurally resemble natural metabolites, which are involved in normal metabolic processes of cancer cells such as the synthesis of nucleic acids and proteins. The antimetabolites, however, differ enough from the natural metabolites such that they interfere with the metabolic processes of cancer cells. In the cell, antimetabolites are mistaken for the metabolites they resemble, and are processed by the cell in a manner analogous to the normal compounds. The presence of the "decoy" metabolites prevents the cells from carrying out vital functions and the cells are unable to grow and survive. For example, antimetabolites may exert cytotoxic activity by substituting these fraudulent nucleotides into cellular DNA, thereby disrupting cellular division, or by inhibition of critical cellular enzymes, which prevents replication of DNA.

In one embodiment, therefore, the antimetabolite agent is a nucleotide or a nucleotide analog. In certain embodiments, for example, the antimetabolite agent may comprise purine (e.g., guanine or adenosine) or analogs thereof, or pyrimidine (cytidine or thymidine) or analogs thereof, with or without an attached sugar moiety.

Suitable antimetabolite agents for use in the present disclosure may be generally classified according to the metabolic process they affect, and can include, but are not limited to, analogues and derivatives of folic acid, pyrimidines, purines, and cytidine. Thus, in one embodiment, the antimetabolite agent(s) is selected from the group consisting of cytidine analogs, folic acid analogs, purine analogs, pyrimidine analogs, and combinations thereof.

In one particular embodiment, for example, the antimetabolite agent is a cytidine analog. According to this embodiment, for example, the cytidine analog may be selected from the group consisting of cytarabine (cytosine arabinodside), azacitidine (5-azacytidine), and salts, analogs, and derivatives thereof.

In another particular embodiment, for example, the antimetabolite agent is a folic acid analog. Folic acid analogs or antifolates generally function by inhibiting dihydrofolate reductase (DHFR), an enzyme involved in the formation of nucleotides; when this enzyme is blocked, nucleotides are not formed, disrupting DNA replication and cell division. According to certain embodiments, for example, the folic acid analog may be selected from the group consisting of denopterin, methotrexate (amethopterin), pemetrexed, pteropterin, raltitrexed, trimetrexate, and salts, analogs, and derivatives thereof.

In another particular embodiment, for example, the antimetabolite agent is a purine analog. Purine-based antimetabolite agents function by inhibiting DNA synthesis, for example, by interfering with the production of purine containing nucleotides, adenine and guanine which halts DNA synthesis and thereby cell division. Purine analogs can also be incorporated into the DNA molecule itself during DNA synthesis, which can interfere with cell division. According to certain embodiments, for example, the purine analog may be selected from the group consisting of acyclovir, allopurinol, 2-aminoadenosine, arabinosyl adenine (ara-A), azacitidine, azathiprine, 8-aza-adenosine, 8-fluoro-adenosine, 8-methoxy-adenosine, 8-oxo-adenosine, cladribine, deoxycoformycin, fludarabine, gancylovir, 8-aza-guanosine, 8-fluoro-guanosine, 8-methoxy-guanosine, 8-oxo-guanosine, guanosine diphosphate, guanosine diphosphate-beta-L-2-aminofucose, guanosine diphosphate-D-arabinose, guanosine diphosphate-2-fluorofucose, guanosine diphosphate fucose, mercaptopurine (6-MP), pentostatin, thiamiprine, thioguanine (6-TG), and salts, analogs, and derivatives thereof.

In yet another particular embodiment, for example, the antimetabolite agent is a pyrimidine analog. Similar to the purine analogs discussed above, pyrimidine-based antimetabolite agents block the synthesis of pyrimidine-containing nucleotides (cytosine and thymine in DNA; cytosine and uracil in RNA). By acting as "decoys," the pyrimidine-based compounds can prevent the production of nucleotides, and/or can be incorporated into a growing DNA chain and lead to its termination. According to certain embodiments, for example, the pyrimidine analog may be selected from the group consisting of ancitabine, azacitidine, 6-azauridine, bromouracil (e.g., 5-bromouracil), capecitabine, carmofur, chlorouracil (e.g. 5-chlorouracil), cytarabine (cytosine arabinoside), cytosine, dideoxyuridine, 3'-azido-3'-deoxythymidine, 3'-dideoxycytidin-2'-ene, 3'-deoxy-3'-deoxythymidin-2'-ene, dihydrouracil, doxifluridine, enocitabine, floxuridine, 5-fluorocytosine, 2-fluorodeoxycytidine, 3-fluoro-3'-deoxythymidine, fluorouracil (e.g., 5-fluorouracil (also known as 5-FU), gemcitabine, 5-methylcytosine, 5-propynylcytosine, 5-propynylthymine, 5-propynyluracil, thymine, uracil, uridine, and salts, analogs, and derivatives thereof. In one embodiment, the pyrimidine analog is other than 5-fluorouracil. In another embodiment, the pyrimidine analog is gemcitabine or a salt thereof.

In certain embodiments, the antimetabolite agent is selected from the group consisting of 5-fluorouracil, capecitabine, 6-mercaptopurine, methotrexate, gemcitabine, cytarabine, fludarabine, pemetrexed, and salts, analogs, derivatives, and combinations thereof. In other embodiments, the antimetabolite agent is selected from the group consisting of capecitabine, 6-mercaptopurine, methotrexate, gemcitabine, cytarabine, fludarabine, pemetrexed, and salts, analogs, derivatives, and combinations thereof. In one particular embodiment, the antimetabolite agent is other than 5-fluorouracil. In a particularly preferred embodiment, the antimetabolite agent is gemcitabine or a salt or thereof (e.g., gemcitabine HCl (Gemzar®)).

Other antimetabolite agents may be selected from, but are not limited to, the group consisting of acanthifolic acid, aminothiadiazole, brequinar sodium, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, Wellcome EHNA, Merck & Co. EX-015, fazarabine, fludarabine phosphate, N-(2'-furanidyl)-5-fluorouracil, Daiichi Seiyaku FO-152, 5-FU-fibrinogen, isopropyl pyrrolizine, Lilly LY-188011; Lilly LY-264618, methobenzaprim, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, tiazofurin, Erbamont TIF, tyrosine kinase inhibitors, Taiho UFT and uricytin, among others.

In one embodiment, the chemotherapeutic agent comprises an antimitotic agent that is a microtubule inhibitor or a mictrotubule stabilizer. In general, microtubule stabilizers, such as taxanes (some of which are also described above) and epothilones, bind to the interior surface of the beta-microtubule chain and enhance microtubule assembly by promoting the nucleation and elongation phases of the polymerization reaction and by reducing the critical tubulin subunit concentration required for microtubules to assemble. Unlike mictrotubule inhibitors, such as the *vinca* alkaloids, which prevent microtubule assembly, the microtubule stabilizers, such as taxanes, decrease the lag time and dramatically shift the dynamic equilibrium between tubulin dimers and microtubule polymers towards polymerization. In one embodiment, therefore, the microtubule stabilizer is a taxane or an epothilone. In another embodiment, the microtubule inhibitor is a *vinca* alkaloid.

One element of the therapy described herein may include the use of a taxane or derivative or analog thereof, some of which have also been discussed above. In one embodiment, the taxane may be a naturally derived compound or a related form, or may be a chemically synthesized compound or a derivative thereof, with antineoplastic properties. The taxanes are a family of terpenes, including, but not limited to paclitaxel (Taxol®) and docetaxel (Taxotere®), which are derived primarily from the Pacific yew tree, *Taxus brevifolia*, and which have activity against certain tumors, particularly breast and ovarian tumors. In one embodiment, the taxane is docetaxel or paclitaxel. Paclitaxel is a preferred taxane and is considered an antimitotic agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions.

Also included are a variety of known taxane derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; deoxygenated paclitaxel compounds such as those described in U.S. Pat. No. 5,440,056; and taxol derivatives described in U.S. Pat. No. 5,415,869. As noted above, it further includes prodrugs of paclitaxel including, but not limited to, those described in WO 98/58927; WO 98/13059; and U.S. Pat. No. 5,824,701. The taxane may also be a taxane conjugate such as, for example, paclitaxel-PEG, paclitaxel-dextran, paclitaxel-xylose, docetaxel-PEG, docetaxel-dextran, docetaxel-xylose, and the like. Other derivatives are mentioned in "Synthesis and Anticancer Activity of Taxol Derivatives," D. G. I. Kingston et al., Studies in Organic Chemistry, vol. 26, entitled "New Trends in Natural Products Chemistry" (1986), Atta-ur-Rabman, P. W. Ie Quesne, Eds. (Elsevier, Amsterdam 1986), among other references. Each of these references is hereby incorporated by reference herein in its entirety.

Various taxanes may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267) (each of which is hereby incorporated by reference herein in its entirety), or obtained from a variety of commercial sources, including for example, Sigma-Aldrich Co., St. Louis, MO.

Alternatively, the antimitotic agent can be a microtubule inhibitor; in one preferred embodiment, the microtubule inhibitor is a *vinca* alkaloid. In general, the *vinca* alkaloids are mitotic spindle poisons. The *vinca* alkaloid agents act during mitosis when chromosomes are split and begin to migrate along the tubules of the mitosis spindle towards one of its poles, prior to cell separation. Under the action of these spindle poisons, the spindle becomes disorganized by the dispersion of chromosomes during mitosis, affecting cellular reproduction. According to certain embodiments, for example, the *vinca* alkaloid is selected from the group consisting of vinblastine, vincristine, vindesine, vinorelbine, and salts, analogs, and derivatives thereof.

The antimitotic agent can also be an epothilone. In general, members of the epothilone class of compounds stabilize microtubule function according to mechanisms similar to those of the taxanes. Epothilones can also cause cell cycle arrest at the G2-M transition phase, leading to cytotoxicity and eventually apoptosis. Suitable epithiolones include epothilone A, epothilone B, epothilone C, epothilone D, epothilone E, and epothilone F, and salts, analogs, and derivatives thereof. One particular epothilone analog is an epothilone B analog, ixabepilone (Ixempra™).

In certain embodiments, the antimitotic anti-cancer agent is selected from the group consisting of taxanes, epothilones, *vinca* alkaloids, and salts and combinations thereof. Thus, for example, in one embodiment the antimitotic agent is a taxane. More preferably in this embodiment the antimitotic agent is paclitaxel or docetaxel, still more preferably paclitaxel. In another embodiment, the antimitotic agent is an epothilone (e.g., an epothilone B analog). In another embodiment, the antimitotic agent is a vinca alkaloid.

In one embodiment, at least one of the pentaaza macrocyclic ring complex and/or the anti-cancer therapeutic agent are administered within a predetermined time period before or after a dose of an additional chemotherapeutic agent is administered. For example, the pentaaza macrocyclic ring complex and/or the anti-cancer therapeutic agent may be administered within 1 week, 48 hours, 24 hours, 12 hours, 6, hours, 2 hours, 1 hour or even within 30 minutes of the patient receiving the dose of the additional chemotherapeutic agent (either before or after the dose of chemotherapeutic agent). Other durations between the additional chemotherapeutic agent dose and administration of the components that result in the enhanced the killing of cancer cells may also be suitable. In one embodiment, one or more of the pentaaza macrocyclic ring complex and/or the anti-cancer therapeutic agent may be administered before the dose of the additional chemotherapeutic agent, and the remaining one or more of the pentaaza macrocyclic ring complex and/or the anti-cancer therapeutic agent can be administered after the dose of the additional chemotherapeutic agent. One or more of the pentaaza macrocyclic ring complex and/or the anti-cancer therapeutic agent may also be administered both before and after administration of the dose of additional chemotherapeutic agent.

In one embodiment, a course of chemotherapy includes a singular dose of the additional chemotherapeutic agent. In another embodiment, a course of chemotherapy includes a plurality of doses of the additional chemotherapeutic agent given over a predetermined period of time, such as over the course of hours, weeks, days and even months. The plural doses may be either of the same magnitude or varying, and can include doses of the same or different chemotherapeutic agents and/or a combination of chemotherapeutic agents. The administration of the pentaaza macrocyclic ring complex and/or the anti-cancer therapeutic agent during the course of chemotherapy can be selected to enhance the cancer treating effects of the chemotherapy, such as by increasing intracellular levels of hydrogen peroxide to promote oxidative stress in the cancer cells. In one embodiment, the pentaaza macrocyclic ring complex and/or the anti-cancer therapeutic agent are administered within a predetermined duration before or after each dose, such as the predetermined duration discussed above. In another embodiment, the pentaaza macrocyclic ring complex and/or anti-cancer therapeutic agent are administered within a predetermined duration of time before or after only select doses. In yet another embodiment, at least one of the pentaaza macrocyclic ring complex and/or the anti-cancer therapeutic agent are administered within a predetermined duration of time before the doses, while another of the pentaaza macrocyclic ring complex and/or the anti-cancer therapeutic agent are administered within a predetermined duration of time after the doses. In a further embodiment, at least one of the pentaaza macrocyclic ring complex and/or the anti-cancer therapeutic agent is administered only within the predetermined duration before or after select doses, while another of the pentaaza macrocyclic ring complex and/or the anti-cancer therapeutic agent is administered only within the predetermined duration before or after doses other than the select doses.

In yet another embodiment, at least one of the pentaaza macrocyclic ring complex and/or the anti-cancer therapeutic agent is administered in combination with both a radiation therapy and a chemotherapy involving administration of an additional chemotherapeutic agent.

EXAMPLES

The following non-limiting examples are provided to further illustrate aspects of the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

The mitochondrial sirtuin, SIRT3, acts as a tumor suppressor (TS) protein that targets several metabolic proteins for deacetylation, including manganese superoxide dismutase (MnSOD)[1,2,3,4], to protect against metabolic damage[5]. Research[1,6], has shown that acetylation of MnSOD disrupts normal cellular and mitochondrial metabolism, leading to a tumor-permissive phenotype, suggesting that MnSOD is an adaptive enzyme responding to cellular oxidative stress[7,8,9]. It has been proposed that the acetylation of MnSOD is a mechanistic link between the cellular and organismal physiology of aging, energy status, and metabolic stressors, such as reactive oxygen species (ROS), carcinogenesis, and resistance to anticancer agents[2,3,4,8]; however, the mechanism by which MnSOD acetylation directs these processes remains unclear.

Mammalian MnSOD is a mitochondrial matrix-localized, homotetrameric, antioxidant enzyme with four identical subunits each harboring a Mn2+ atom[10]; the primary function of MnSOD is to scavenge superoxide generated from different metabolic processes. While multiple MnSOD acetylation sites have been identified, recent publications seem to suggest that the acetylation status of lysine 68 in the MnSOD subunit (K68) is central to the regulation of MnSOD superoxide dismutase activity[1,6,8,9,11,12,13]. However, the specific cell biological, biochemical, and/or physiological significance of MnSOD acetylation, and the underlying molecular mechanism regulating MnSOD detoxification activity and mitochondrial metabolism, remains to be fully determined. Thus, it has been proposed that MnSOD is a mitochondrial signaling hub that regulates how cells adapt to ROS-induced metabolic stress in addition to directing mitochondrial metabolism[14], which may play an important role in late-onset diseases[2,5].

Mice lacking Sirt3, and thus containing acetylated MnSOD (MnSOD-Ac), developed tumors[7], implying that SIRT3 may function as a tumor suppressor (TS). Female mice lacking Sirt3 spontaneously develop estrogen-positive (ER+), poorly differentiated, high Ki-67 mammary gland tumors that appear to be similar to human luminal B breast malignancies, which are often diagnosed in older women[2,5,7,15]. As compared to luminal A ER+ breast cancers, luminal B subtypes tend to have increased proliferation markers and, most importantly, can exhibit an endocrine-resistant phenotype[5]. Mice that have a monoallelic knockout for MnSOD (MnSOD+/−) exhibit decreased MnSOD activity, increased oxidative stress, and decreased life span, as well as aging-related phenotypes, especially carcinogenesis[16]. This in vitro and in vivo evidence supports the possibility that there is a link between the mitochondrial acetylome, as directed by SIRT3, and ROS detoxification, mitochondrial metabolism, and carcinogenesis. Furthermore, the examples herein suggest that, under specific physiological conditions when K68 becomes acetylated, MnSOD may function as a tumor promoter, consistent with data implying that MnSOD levels positively correlate with aggressive tumor phenotypes. In this regard, several publications in the last few years have shown a connection between disruption of the MnSOD-Ac axis and human illnesses[4], including aging[34], neurodegeneration[35] cardiovascular disease[36], and insulin resistance[37].

The Examples herein present data showing that the acetylation status of MnSOD, specifically K68, directs ROS detoxification activity, as well as connects metabolic stress and mitochondrial reparative pathways that maintain metabolic balance. The results show that MnSOD exists in both homotetrameric and monomeric forms, which function as a superoxide dismutase and a peroxidase, respectively. The results further show that the homotetramer is a TS, whereas the monomer, as modeled by enforced MnSOD$^{K68Q}$ expression, functions as a tumor promoter. The results show that acetylation status may be associated with tumor stage, and that acetylated K68 (AcK68) is elevated in multiple human tumor types. The results further show that acetylation status at the AcK68 site is associated with and induces resistance to specific and multiple cancer therapies, and with cancer cell stemness phenotype which is likewise associated with therapy resistance and cancer metastasis. Finally, the results support that mimicking deacetylation of K68, whether by expression of an acetylation-resistant MnSOD or pharmacologically with a manganese pentaazamacrocyclic mimetic of MnSOD (dismutase mimetic) can inhibit growth of AcK68-positive tumors, reduce cancer cell and tumor resistance to therapy, and reduce cancer cell stemness.

Example 1

$MnSOD^{K68Q}$ Expression Promotes a Transformation Phenotype.

MnSOD is a TS in vitro and in vivo[17,18], as well as in human tumor samples[19]. However, correlative findings in human tumor samples suggest that while MnSOD may function as a TS during the early stages of tumor initiation, once tumorigenesis progresses, MnSOD levels positively correlate with more aggressive human tumors[20], suggesting that specific isoforms of MnSOD, including potentially the acetylated lysine 68 form of MnSOD (MnSOD-K68-Ac, AcK68), may function as a tumor promoter. In addition, it also appears that, under specific conditions, there is a link between dysregulated MnSOD, aberrant cellular ROS levels[2,22,23], and resistance to tamoxifen (Tam)-induced cytotoxicity. These and other findings[24] suggest a mechanistic link between mitochondrial redox/ROS balance and the biology of ER+ breast cancer.

To test this hypothesis, MnSOD K68 acetylation mimic ($MnSOD^{K68Q}$) and deacetylation mimic ($MnSOD^{K68R}$) mutants were made where the substitution of lysine 68 with a glutamine (Q) stably mimics an acetylated amino acid state, while substitution with an arginine (R) stably mimics a deacetylated8. To determine if $MnSOD^{K68Q}$, a site-directed mutant that genetically mimics AcK68, may function as a tumor promoter, lenti-$MnSOD^{K68R}$ or lenti-$MnSOD^{K68Q}$ vectors were co-infected into wild-type (WT) primary mouse embryonic fibroblasts (pMEFs) with lentiviral expression of either c-Myc or Ras. In these experiments, at least two oncogenes, i.e., c-Myc and Ras (WT Ras gene)[25], are required to immortalize and/or transform primary cells. pMEFs infected with lenti-$MnSOD^{K68Q}$, and either c-Myc or Ras, became immortalized (i.e., divided beyond 15 cell passages), as well as cells infected with both genes (FIG. 1*a*, bottom row). In contrast, infection with lenti-$MnSOD^{K68R}$ did not immortalize WT pMEFs infected with c-Myc or Ras, and interestingly, $MnSOD^{K68R}$ prevented immortalization in cells infected with both genes (FIG. 1*a*, middle row). As a control, pMEFs were immortalized by c-Myc and Ras together, but not with c-Myc or Ras alone (FIG. 1*a*, top row). In addition, pMEFs infected with lenti-$MnSOD^{K68Q}$ exhibited a more transformed in vitro phenotype as determined by growth in soft agar (FIG. 1*b*, top panel), a measure of anchorage-independent growth; increased colony formation when plated at low density (bottom panel), a measure of proliferative capacity; decreased doubling time, a measurement of proliferation rate (FIG. 9*a*, middle column); and the formation of xenograft tumors, a measure of an in vivo tumorigenic permissive phenotype (FIG. 9*a*, right column).

Figure 1D:
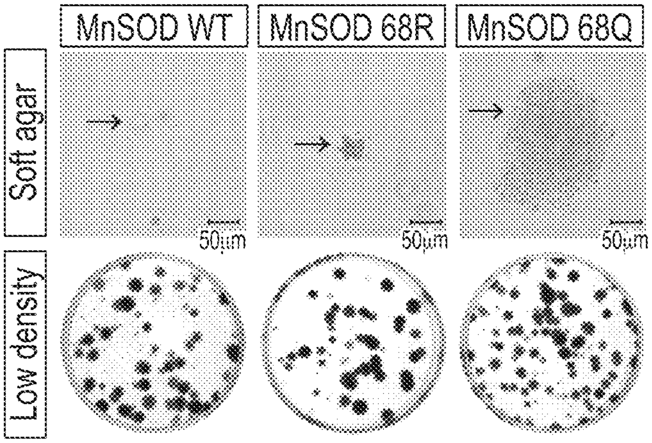

To further characterize the link between MnSOD and its function, TS versus tumor promoter, pMEFs were co-infected with oncogenic lenti-$Kras^{G12V}$ (i.e., the oncogenic Kras gene) and lenti-$MnSOD^{WT}$, lenti-$MnSOD^{K68R}$, or lenti-$MnSOD^{K68Q}$. The pMEFs expressing $MnSOD^{K68Q}$ were immortalized (FIG. 1*c*, bottom row, second column), as well as exhibited a more transformed in vitro phenotype, as measured by doubling time in culture (22 versus 35 h, third column) and growth in soft agar (bottom row, right column). Interestingly, infection with lenti-$MnSOD^{K68R}$, the deacetylation mimic MnSOD mutant, prevented immortalization when co-infected with lenti-$Kras^{G12V}$ (middle row, second column). Finally, these experiments were repeated in immortalized NIH 3T3 cells, an established in vitro model, to determine in vitro transformation, and NIH 3T3 cells expressing MnSODK68Q exhibited increased growth in soft agar (FIG. 1*d*, upper panels) and colony formation when plated at low density (bottom panels). Accordingly, it was shown that mimicking acetylated lysine 68 with $MnSOD^{K68Q}$ expression promotes a transformation-permissive phenotype in vitro, decreased doubling time and allowed xenograft growth, while mimicking deacetylation of MnSOD-K68 with $MnSOD^{K68R}$ had opposing effects.

MnSODK68Q Increases In Vitro and Xenograft Proliferation.

Figures 2A, 2B:
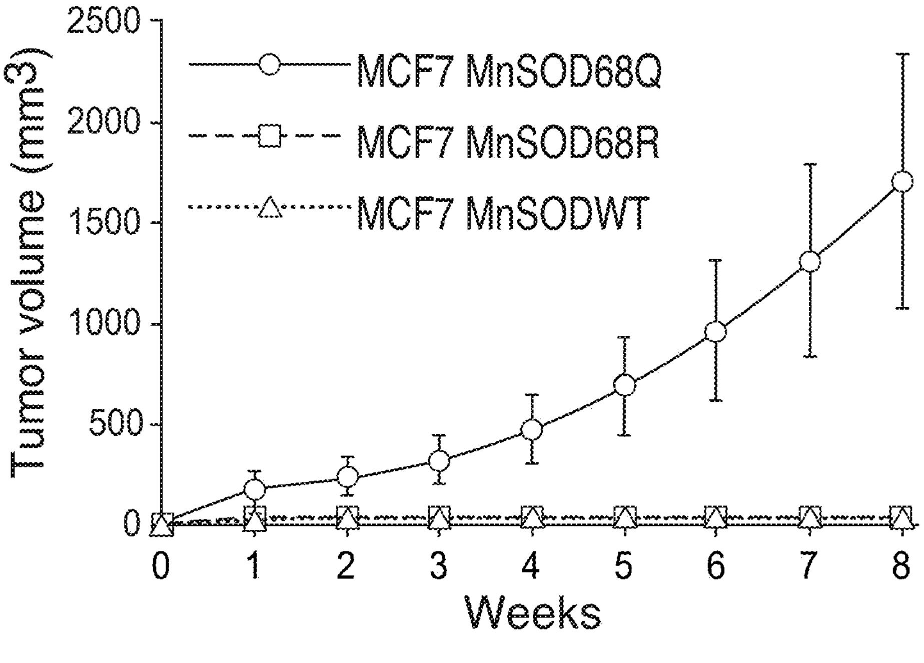
FIGS. 2*a*-2*f* are graphs and plots that illustrate that mimicking acetylated lysine 68 with $MnSOD^{K68Q}$ expression increases xenograft tumor growth and in vitro proliferation while mimicking perpetually deacetylated lysine with $MnSOD^{K68R}$ has opposing effects, where

To determine the role of $MnSOD^{K68Q}$ expression on tumor growth properties, human mammary ER+ MCF7 tumor cells infected with lenti-$MnSOD^{WT}$, lenti-$MnSOD^{K68R}$, or lenti-$MnSOD^{K68Q}$ were engrafted into nude mice. Normally, MCF7 cells will not grow in nude mice without estrogen supplementation; however, MCF7 cells infected with lenti-$MnSOD^{K68Q}$ (MCF7-$MnSOD^{K68Q}$) grew tumors in nude mice without estrogen supplementation (FIG. 2*a, b*). In contrast, MCF7 cells infected with lenti-$MnSOD^{WT}$ (MCF7-$MnSOD^{WT}$) or lenti-$MnSOD^{K68R}$ (MCF7-$MnSOD^{K68R}$) did not form tumors (FIG. 2*a, b*). These results suggest increased growth characteristics in xenograft tumors that express $MnSOD^{K68Q}$; however, this could also reflect estrogen-independent growth properties. To address this, MCF7-$MnSOD^{K68Q}$ cells were injected into the hind limbs of nude mice, and these xenograft experiments showed that estrogen supplementation did not alter the tumor growth curve (FIG. 9*b*).

Figure 10A:
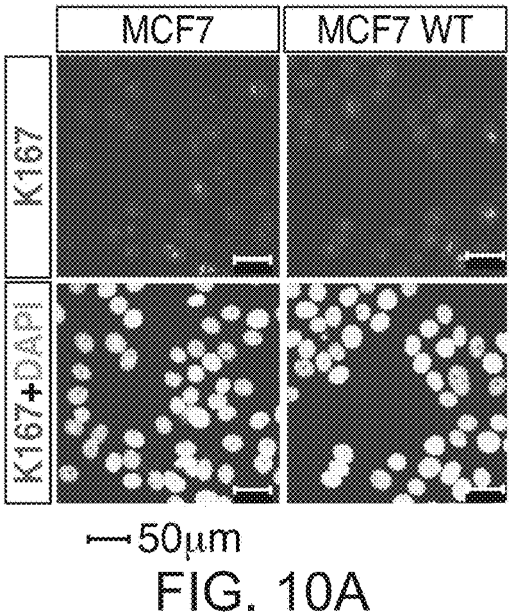
Figure 10B:
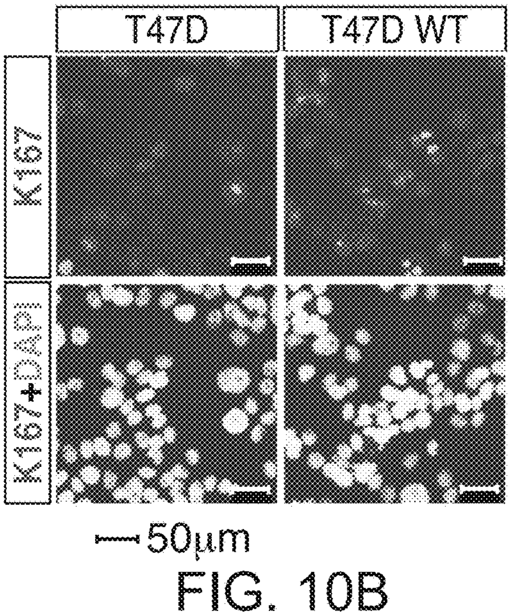
Figure 10C:
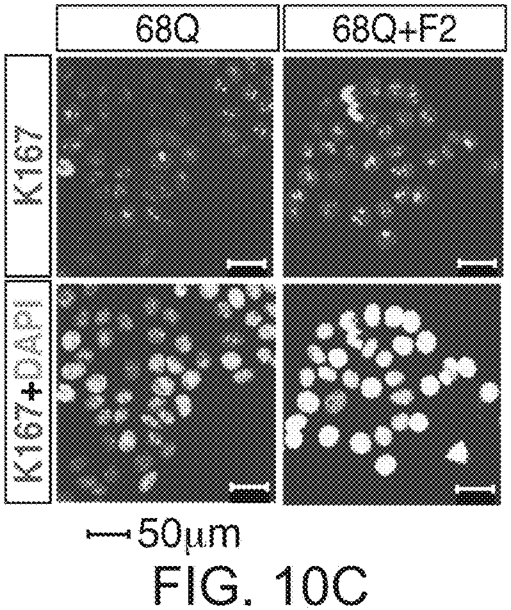
Figure 10D:
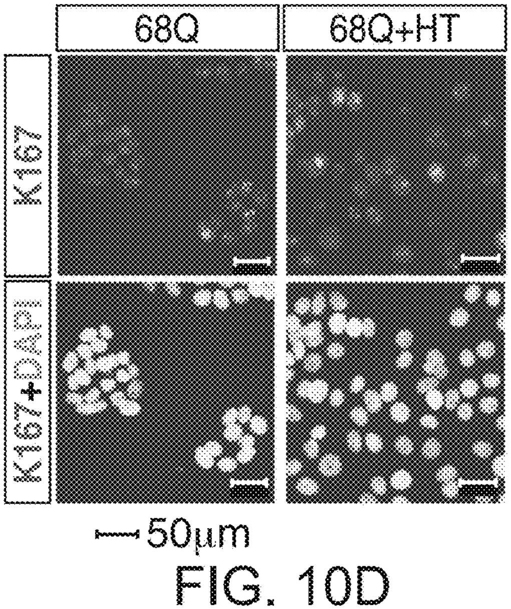

Luminal B ER+ breast cancer cells are more aggressive and display increased proliferation, as measured by Ki-67 staining, compared to luminal A cancer cells[5]. Tumors in mice lacking Sirt3, which contain MnSOD-Ac, display a luminal B-like tumor signature, including increased Ki-67[5]. Consistent with these observations, MCF7-$MnSOD^{K68Q}$ cells stained with an anti-Ki-67 antibody showed a significant increase in Ki-67 immunofluorescence (IF) staining, as compared to MCF7-$MnSOD^{K68R}$ or MCF7-$MnSOD^{WT}$ cells (FIG. 2*c*) and quantified using ImageJ analysis (FIG. 2*d*). MCF7-$MnSOD^{WT}$ cells exhibited the same Ki-67 staining as the control, non-infected MCF7 cells (FIG. 10*a*). In addition, experiments using a second ER+ human breast cancer cell line, T47D, also showed increased Ki-67 staining for T47D-$MnSOD^{K68Q}$ as compared to T47D-$MnSOD^{K68R}$ and T47D-$MnSOD^{WT}$ cells (FIG. 2*e, f*). T47D-$MnSOD^{WT}$ cells exhibited the same Ki-67 staining as the control, non-infected T47D cells (FIG. 10*b*). Finally, MCF7-$MnSOD^{K68Q}$ cells exhibited similar Ki-67 staining when exposed to either estrogen (FIG. 10*c, e*) or Tam (FIG. 10*d, f*). Accordingly, it was shown that mimicking acetylated lysine 68 with $MnSOD^{K68Q}$ expression increases xenograft tumor growth and in vitro proliferation and caused estrogen independence, while mimicking perpetually deacetylated lysine with $MnSOD^{K68R}$ has opposing effects.

$MnSOD^{K68Q}$ is a Monomer that Exhibits Peroxidase Activity.

Figure 3A:
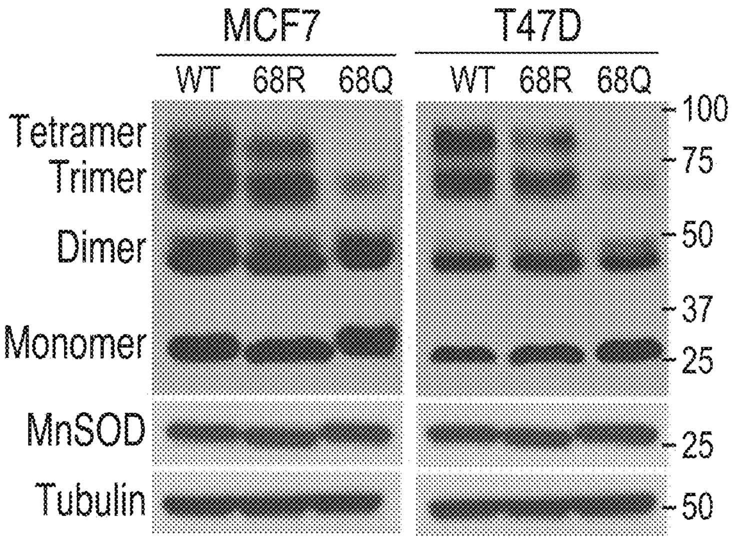
Figure 3B:
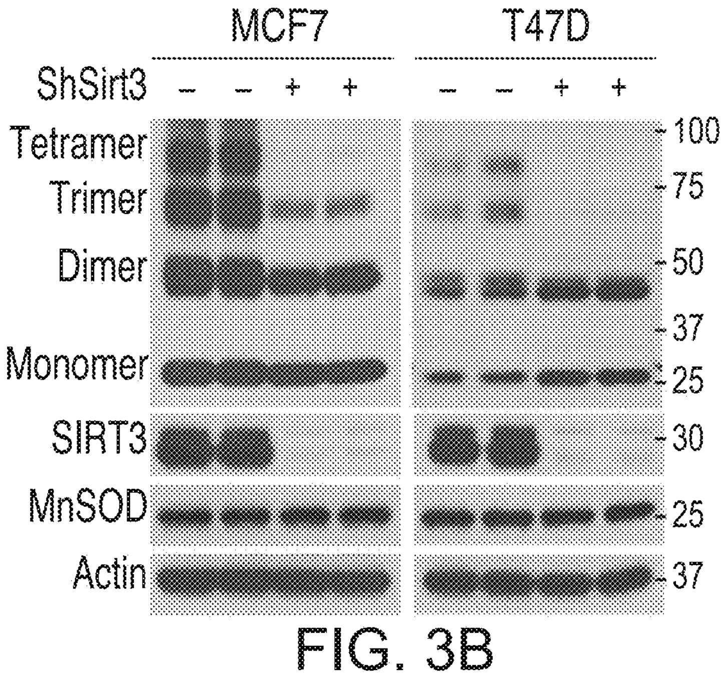

MnSOD consists of four subunits that form a homotetramer, each binding a manganese ion (~88 kDa)[3,10] To determine if the acetylation status of lysine 68 (K68) alters the conformation of MnSOD, as well as its activity, MCF7-$MnSOD^{WT}$, MCF7-$MnSOD^{K68R}$, and MCF7-$MnSOD^{K68Q}$ cells were harvested and cell lysates were crosslinked with glutaraldehyde, followed by sodium dodecyl sulfate polyacrylamide gel electrophoresis (SDS-PAGE) and immunoblotting with an anti-MnSOD antibody. These experiments showed that cells expressing $MnSOD^{K68Q}$ exhibited a significant decrease in the tetrameric form of MnSOD (FIG. 3*a*, left panel), with a slight increase in both the dimeric and monomeric forms. Similar results were also observed in T47D-MnSOD$^{K68Q}$ cells (right panel). In addition, these experiments were repeated in MCF7 and T47D cells infected with lenti-shSIRT3 which inhibits SIRT3 deacetylation of K68, and these cells also showed a significant decrease in the tetrameric form of MnSOD (FIG. 3*b*), in contrast to little or no change in the oligomerization status of MnSOD in the control cells.

It has been previously shown that MnSOD, under specific conditions and when significantly overexpressed, can exhibit peroxidase activity[26]; however, the mechanism to explain this observation is unknown. In this regard, a peroxidase assay showed that MnSOD$^{K68Q}$ mutant Immunoprecipitated (IPed) from MCF7 cells functions as a peroxidase (FIG. 3*c*). In contrast, IPed MnSOD$^{K68R}$ exhibited significantly less peroxidase activity (i.e., a roughly 50-fold difference), suggesting that this peroxidase activity may require acetylation of K68 (FIG. 3*c*). Finally, experiments confirmed that the MnSOD−/− MEFs expressing MnSOD$^{K68Q}$ exhibited a significant decrease in tetrameric MnSOD, as compared to cells expressing MnSOD$^{WT}$ or MnSOD$^{K68R}$ (FIG. 3*d*).

Figure 11C:
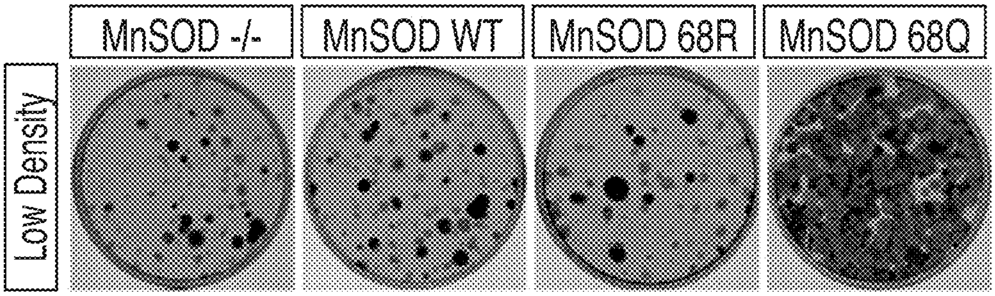
Figure 11D:
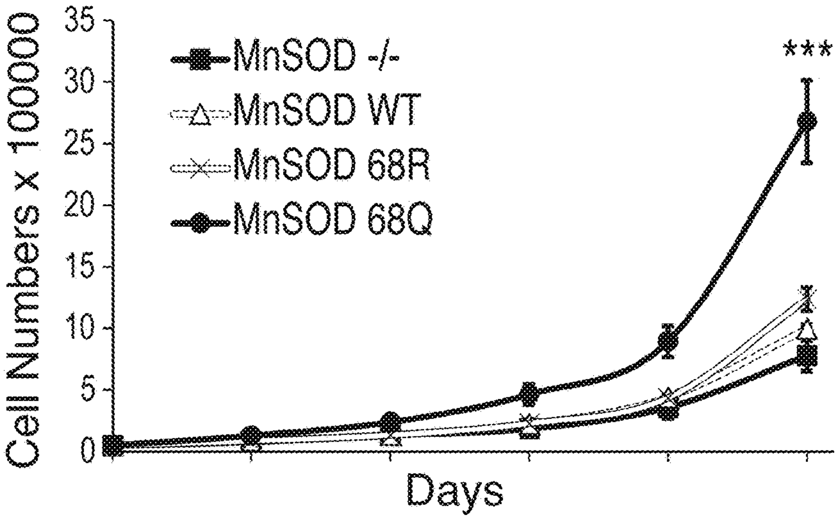

In the experiments above, it is shown that MnSOD$^{K68Q}$, which is a genetic mutant that functions as a mimic for AcK68, leads to a tumor promoting phenotype (FIG. 1*a, b*). To more rigorously address this idea, immortalized, but not transformed, MnSOD−/− MEFs were infected with the MnSOD site-directed mutants described above. These experiments showed that MnSOD−/− MEFs infected with only lenti-MnSOD$^{K68Q}$, (i.e., a single gene) exhibited a more transformed phenotype (FIG. 3*e*, middle column), as compared to cells infected with lenti-empty vector, lenti-MnSOD$^{WT}$, or lenti-MnSOD$^{K68R}$ (FIG. 11*a*), as measured by growth in soft agar, contact inhibition, and doubling time (FIGS. 11*b-d*). Since these results were done in cells lacking MnSOD, it seems reasonable that MnSOD$^{K68Q}$ functions as an in vitro tumor promoter.

Finally, if MnSOD$^{K68Q}$ acts as a peroxidase, then removing cellular hydrogen peroxide, which is a necessary and required substrate for peroxidase activity, might prevent its ability to function as a peroxidase, as well as a tumor promoter. In this regard, co-infection with lenti-MnSOD$^{K68R}$ and AdMitoCat, which expresses catalase and decreases cellular hydrogen peroxide, prevented transformation (FIG. 3*e*, right column). Since it is shown that immortalized MnSOD−/− MEFs can be transformed by infection with MnSOD$^{K68Q}$, these results suggest that MnSOD$^{K68Q}$, which enriches for monomeric MnSOD, is potentially an in vitro tumor promoter that requires hydrogen peroxide. Accordingly, it was shown that mimicking AcK68 with MnSOD$^{K68Q}$ or inducing AcK68 by knockdown of SIRT3 deacetylase alters MnSOD conformation by decreasing the full tetrameric form and increasing the monomeric form, and generates peroxidase activity, while mimicking perpetually deacetylated lysine 68 with MnSOD$^{K68R}$ has opposing effects. It was also shown that mimicking acetylation of MnSOD-K68 with MnSOD$^{K68Q}$ expression promotes a transformation-permissive phenotype in vitro while mimicking deacetylation of MnSOD-K68 with MnSOD$^{K68R}$ has opposing effects.

MnSOD-K68-Ac Exhibits Peroxidase Activity.

Figure 12A:
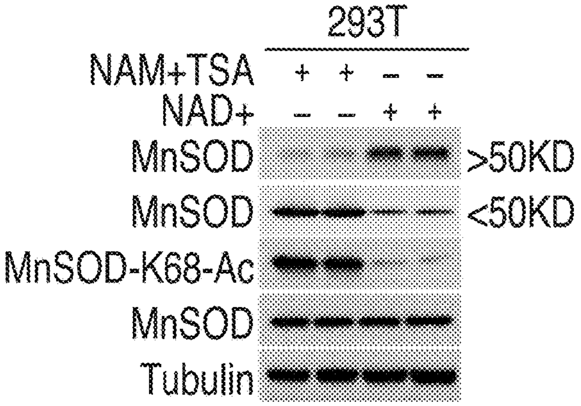
FIGS. 12*a*-12*c* are images and plots that illustrate that the biochemical acetylation of MnSOD-K68 shifts the size of MnSOD from tetrameric to smaller forms including monomeric and produces peroxidase activity. With respect to FIG. 12*a,* 293T cells were transfected with plasmids expressing Flag-$MnSOD^{WT}$ and treated with either 10 mM NAM and 1 μM TSA, or 10 mM NAD+, harvested at 40 h, and IPed with anti-Flag antibody. The IPed samples were separated using 50 kDa centrifugal filters and protein extracts above and below 50 kDa were isolated, followed by immunoblotting with anti-MnSOD, MnSOD-K68-Ac, and actin antibodies. With respect to FIG. 12*b*, the samples expressing Flag-$MnSOD^{WT}$ and treated with 10 mM NAM and 1 μM TSA or 10 mM NAD+ were separated using 50 kDa centrifugal filters. Samples were subsequently run on a semi-native gel and immunoblotted with an anti-MnSOD antibody. With respect to FIG. 12*c*, MnSOD−/− immortalized MEFs were transfected with plasmids expressing Flag-$MnSOD^{WT}$ and treated with either 10 mM NAM and 111M TSA, or 10 mM NAD+, and cells were harvested at 40 h and IPed with anti-Flag antibody. The IPed samples were separated using 50 kDa centrifugal filters and protein exacts above 50 kDa were isolated, and purified proteins were then used for biochemical analysis of peroxidase activity. All experiments were done in triplicate. Error bars represent±1 SEM. Representative images are shown.

The data presented above showed enrichment of monomeric MnSOD (FIG. 3*a*) and peroxidase activity (FIG. 3*c*) upon expression of MnSOD$^{K68Q}$ to mimic K68-Ac. However, it is also essential to show how the physical acetylation of K68 affects enzymatic activity. To initially address this issue, an established tissue culture system was used that enriches for acetylated K68 in one mode, versus for deacetylated in another mode. In this system, transfected MnSOD−/− MEFs with FLAG-MnSOD$^{WT}$ were followed by the exposure to (i) 10 mM nicotinamide (NAM) and 1 μM trichostatin A (TSA), to inhibit SIRT3 deacetylase activity and enrich for AcK68, or (ii) 10 mM NAD+, to activate SIRT3 activity and enrich for deacetylated K68. As expected, whole-cell extracts harvested 40 h after transfection and IPed with an anti-FLAG antibody showed that NAM/TSA exposure increased MnSOD-K68-Ac (FIG. 4*a*, top row, left two lanes), while NAD+exposure minimized MnSOD-K68-Ac (right two lanes). Similar results were observed in 293T cells (FIG. 12*a*). The MnSOD-K68-Ac antibody specificity (Abcam, Inc, ab137037) was validated by two different methods[12].

Figure 4A:
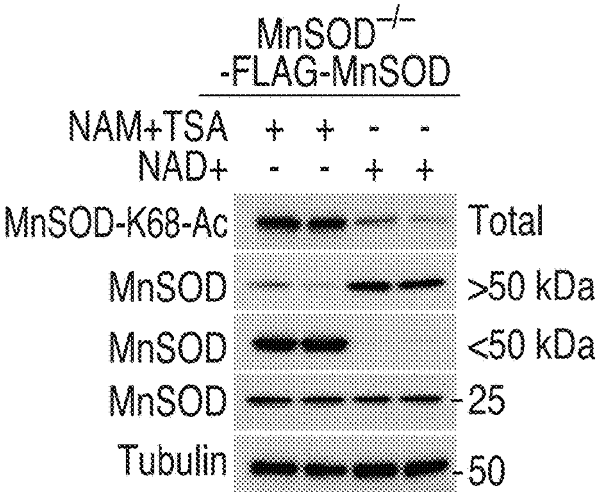
FIGS. 4*a*-4*i* are images and plots that illustrate that the biochemical acetylation of MnSOD-K68 shifts the size of MnSOD from tetrameric to smaller forms including monomeric, and that the tetrameric forms exhibit dismutase activity while the smaller forms exhibit peroxidase activity, where.
Figure 12B:
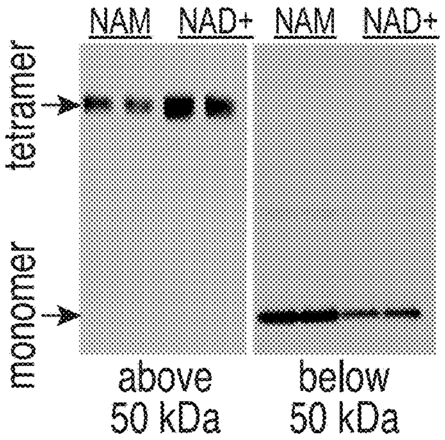

These samples were subsequently separated, using a spin column, into fractions above or below 50 kDa. Immunoblotting with an anti-MnSOD antibody, the sample from cells grown in NAM/TSA showed an enrichment of MnSOD in the <50 kDa fraction, suggesting that most of the MnSOD is in the dimeric or monomeric form, with minimal MnSOD in the >50 kDa fraction (FIG. 4*a,* 2nd and 3rd row, left two lanes). The enrichment of the monomeric MnSOD was confirmed when the <50 kDa fraction was run on a semi-native gel followed by immunoblotting for MnSOD (FIG. 12*b*, left two lanes) with minimal tetrameric MnSOD in the >50 kDa fraction (right panel, left two lanes). In contrast, MnSOD from cells grown in NAD+ showed increased levels of MnSOD in the >50 kDa fraction (FIG. 4*a,* 2nd and 3rd row, right two lanes), with enrichment of tetrameric MnSOD in the >50 kDa fraction (FIG. 12*b*, right panel, right two lanes). These experiments confirm that samples enriched for AcK68 contain predominantly monomeric MnSOD, and those with deacetylated MnSOD-K68 contain predominantly tetrameric MnSOD.

Figure 4B:
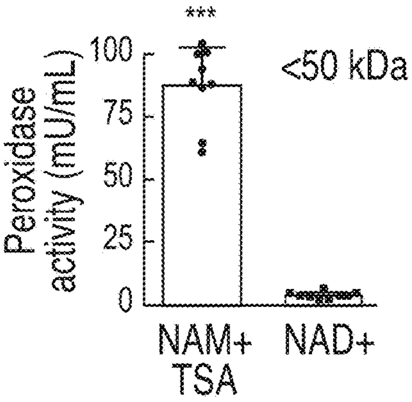
Figure 4C:
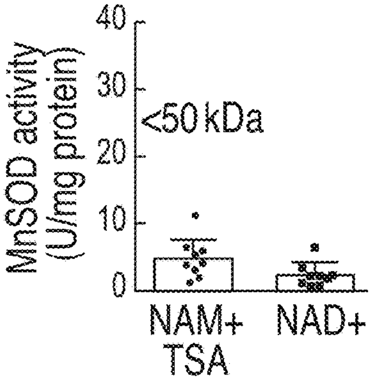
Figure 4D:
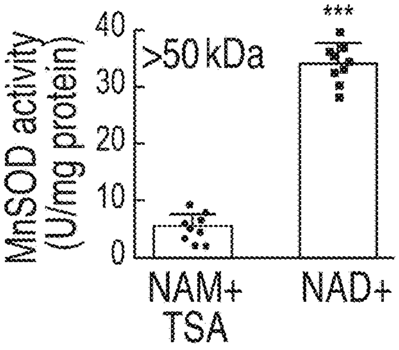
Figure 12C:
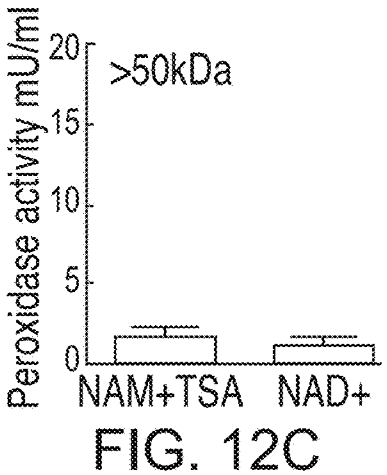

Biochemical analysis of the <50 kDa fraction from cells exposed to NAM/TSA (i.e., enriched for MnSOD-K68-Ac and monomeric MnSOD) showed elevated peroxidase activity compared to the <50 kDa fraction from cells treated with NAD+(FIG. 4*b*). In contrast, MnSOD from both<50 kDa fractions exhibited minimal MnSOD detoxification activity (FIG. 4*c*). Analysis of the >50 kDa fraction from cells treated with NAD+(i.e., enriched for tetrameric MnSOD) exhibited elevated MnSOD detoxification activity compared to cells exposed to NAM/TSA (FIG. 4*d*). There was little MnSOD peroxidase activity in the >50 kDa fraction from cells treated with either NAD+ or NAM/TSA (FIG. 12*c*). Accordingly, it was shown that the biochemical acetylation of MnSOD-K68 shifts the size of MnSOD from tetrameric to smaller forms including monomeric and produces peroxidase activity.

Figure 4E:
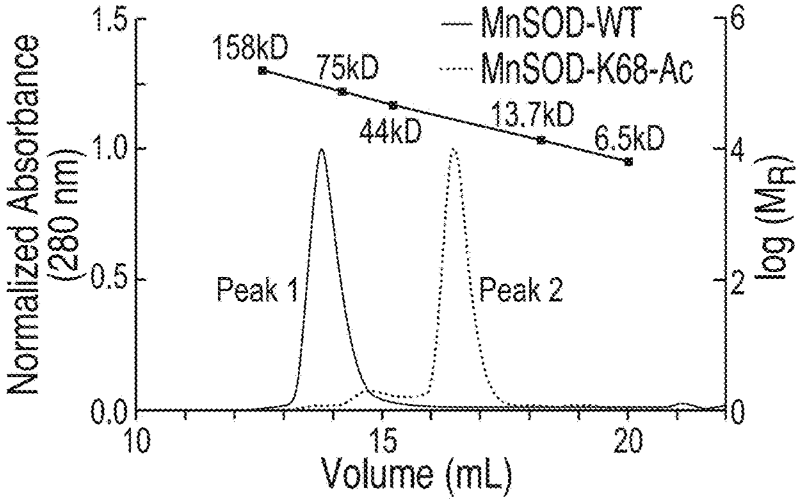
Figure 13A:
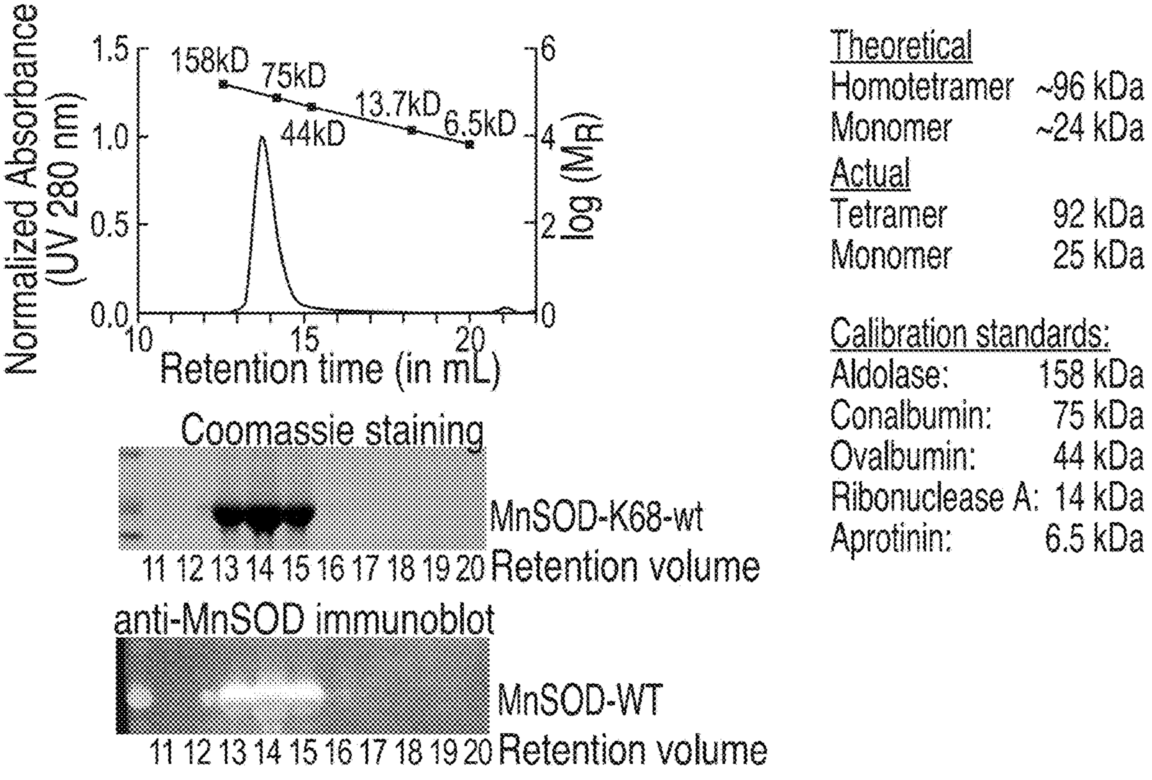
FIGS. 13*a*-13*f* are images and plots that illustrate that MnSOD-K68 acetylation shifts the size of MnSOD from tetrameric to smaller forms including monomeric. BL21 (DE3) bacteria were transformed with pET21a-$MnSOD^{WT}$, or pEVOL-AcKRS together with pET21a-$MnSOD^{K68TAG}$. Cells were harvested and lysed, and eluted protein were run over a Superdex 20 Increase 10/300 GL column and fractions1' 2' 3, and these samples were subsequently used for further analysis. With respect to FIG. 13*a*, shown is a chromatogram from the size exclusion column of purified protein from bacteria carrying pET21a-MnSODwT (top panel), retention volumes fractions 11 through 20 were further analyzed by either Coomassie staining (middle panel) or immunoblotted with anti-MnSOD antibody (lower panel) to confirm MnSOD levels. With respect to FIG. 13*b*, shown is a chromatogram of purified protein from bacteria carrying pEVOL-AcKRS and pET21a-$MnSOD^{K68TAG}$, all the fractions were further analyzed by either Coomassie staining (middle panel) or immunoblotted with an anti-MnSOD-K68-Ac antibody (lower panel) The raw data are presented with the y-axis as mAU (280 nm) to show that peak 2 is smaller than peak 1 which is likely due to the slightly less protein run on the Superdex 200 Increase 10/300 GL column (5.5 mg vs. 4.8 mg). With respect to FIG. 13 *c*, three separate MnSOD-K68-WT samples were analyzed via mass spectroscopy and 32 exclusive unique peptides, 164 spectra, and 999 total spectra, 100% coverage which is an average of each run. With respect to FIG. 13*d*, three separate MnSOD-K68-Ac samples showed 24 exclusive unique peptides, 99 unique spectra, 531 total spectra were identified, 95% coverage which is an average of each run. With respect to FIG. 13*e*, a table shows the average percentage of total number of unique K68 acetylated peptides, as a ratio of the total number of unique peptides. The data for total number of unique peptides, unique spectra, and total spectra from bacteria expressing pET21a-$MnSOD^{WT}$ or expressing pET21a-$MnSOD^{K68TAG}$ are also shown. With respect to FIG. 13*f*, Peak 1 (volumes 13, 14 ml) and peak 2 (volumes 16, 17 ml) were separated by SDS-PAGE and immunoblotted with anti-MnSOD-K68-Ac antibody. All experiments done in triplicate. Representative images are shown.
Figure 13B:
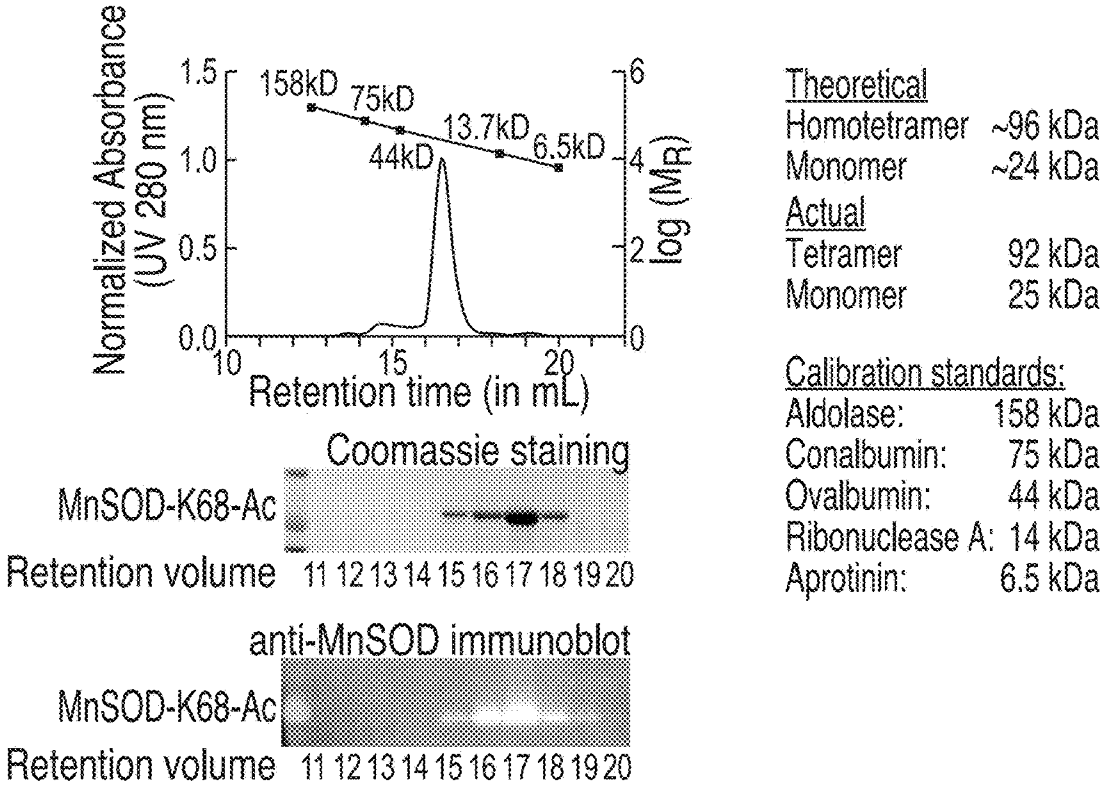

A second method was also used to determine how the biochemical acetylation of MnSOD-K68 alters enzymatic activity. Recombinant MnSOD-K68-Ac was produced in *E. coli* transformed with both pEVOL-AcKRS, which expresses an acetyl-lysyl-tRNA synthetase/tRNA$^{CUA}$ pair from *M. barkeri*, and pET21a-MnSOD$^{K68TAG}$, a MnSOD bacterial expression vector that allows the site-specific incorporation of N-(ε)-acetyl-1-lysine into K68. The bacterially expressed proteins from the control (carrying pET21a-MnSOD$^{WT}$) and acetylated form (carrying pET21a-MnSOD$^{K68TAG}$) were purified by nickel affinity columns followed by size exclusion chromatography (SEC)[13,27,28] Purified wild-type MnSOD from bacteria eluted at a volume roughly corresponding to 92 kDa (FIG. 4*e*, peak 1) on SEC consistent with the size of its known homotetrameric complex (FIG. 13*a*, full chromatogram), as shown by others (Knyphausen et al., 2016)[13]. Purified MnSOD-K68-Ac from bacteria carrying pEVOL-AcKRS and pET21a-MnSOD$^{K68TAG}$ eluted at a volume consistent with the monomeric form of MnSOD (FIG. 4*e*, peak 2) roughly corresponding to 25 kDa (FIG. 13*b*, full chromatogram).

Figure 4F:
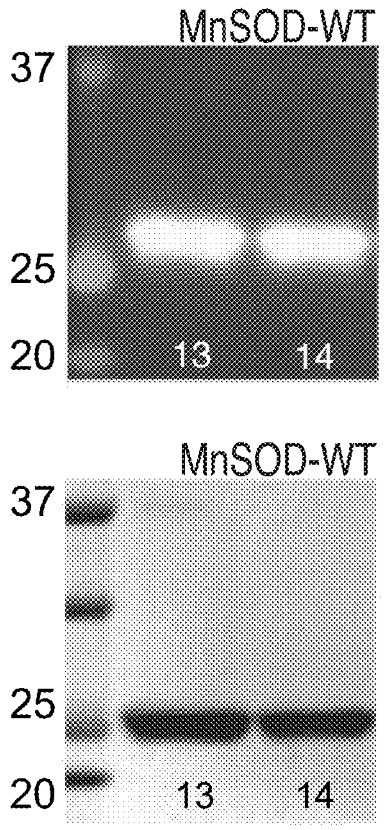
Figure 4G:
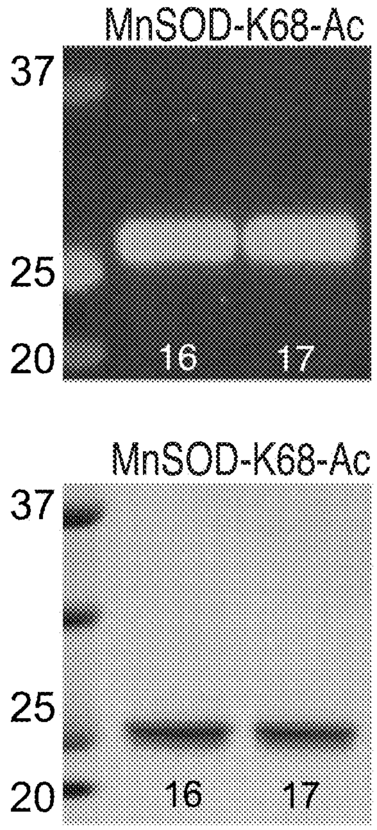
Figure 13C:
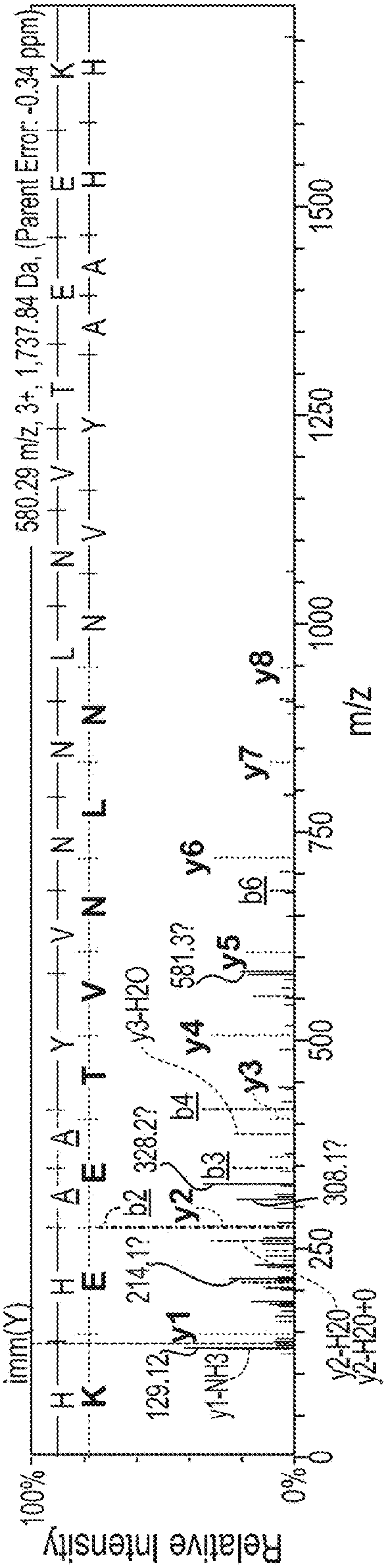
Figure 13D:
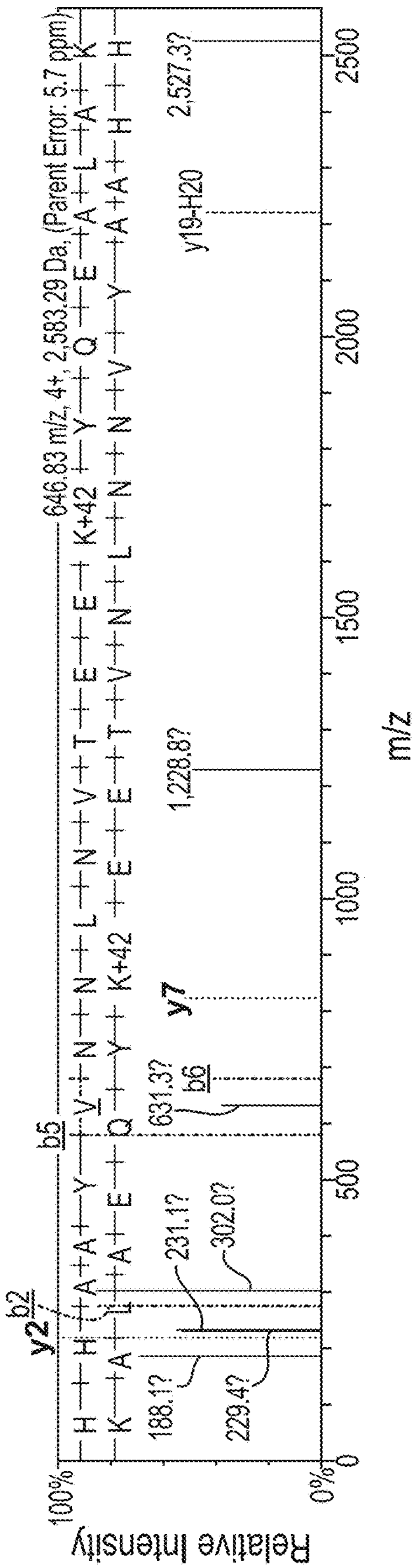
Figures 13E, 13F:
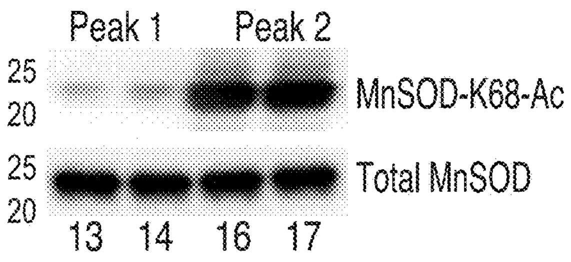

Prior to further analysis, two eluted fractions corresponding to peak 1 (elution volumes 13 and 14 mL) and peak 2 (elution volumes 16 and 17 mL) were analyzed to confirm MnSOD. Immunoblotting (FIG. 4*f*, top panel) and Coomassie staining (bottom panel) for purified wild-type bacterial expressed protein confirmed the presence of MnSOD. Similar experiments also confirmed the presence of MnSOD in bacteria carrying pET21a-MnSOD$^{K68TAG}$ (FIG. 4*g*, top and bottom panel). These samples were also analyzed via mass spectrometry (FIG. 13*c-e*) and by staining with the anti-MnSOD-K68-Ac antibody (FIG. 13*f*) confirming that peak 2 is enriched for MnSOD-K68-Ac protein. Accordingly, it was shown that MnSOD-K68 acetylation shifts the size of MnSOD from tetrameric to smaller forms including monomeric.

Figure 4H:
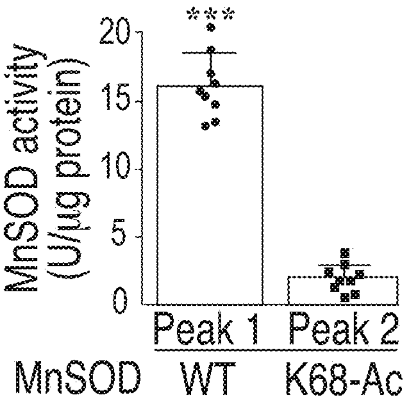
Figure 4I:
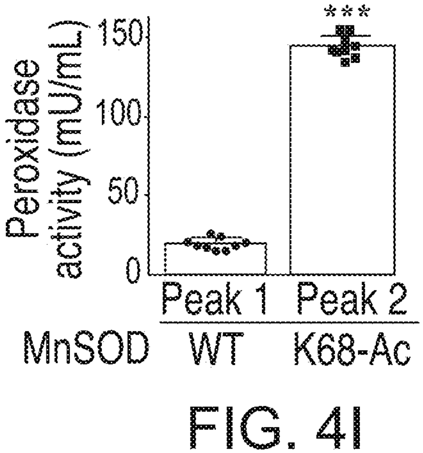

Purified protein samples from the bacteria cells expressing pET21a-MnSOD$^{WT}$ (elution volumes 13 and 14 mL) showed significant superoxide dismutase activity (FIG. 4*h*, left bar) with minimal peroxidase activity (FIG. 4*i*, left bar). In contrast, recombinant MnSOD-K68-Ac protein from bacterial cells expressing pET21a-MnSOD$^{K68TAG}$ (elution volumes 16 and 17 mL) exhibited minimal superoxide activity (FIG. 4*h*, right bar) and significant peroxidase activity (FIG. 4*i*, right bar). These biochemical results show two different methods to isolate MnSOD where K68 is either physically acetylated (bacterial expression system) or enriched for K68 acetylation (transfection expression system) to confirm a switch to monomeric MnSOD and exhibits a peroxidase enzymatic function. Accordingly, it was shown that the biochemical acetylation of MnSOD-K68 shifts the size of MnSOD from tetrameric to smaller forms including monomeric, and that the tetrameric forms exhibit dismutase activity while the smaller forms exhibit peroxidase activity.

MnSOD-K68-Ac Increases Oxidative Stress in Breast Cells.

Figures 5A, 5B, 5C, 5D, 5E, 5F, 5G, 5H:
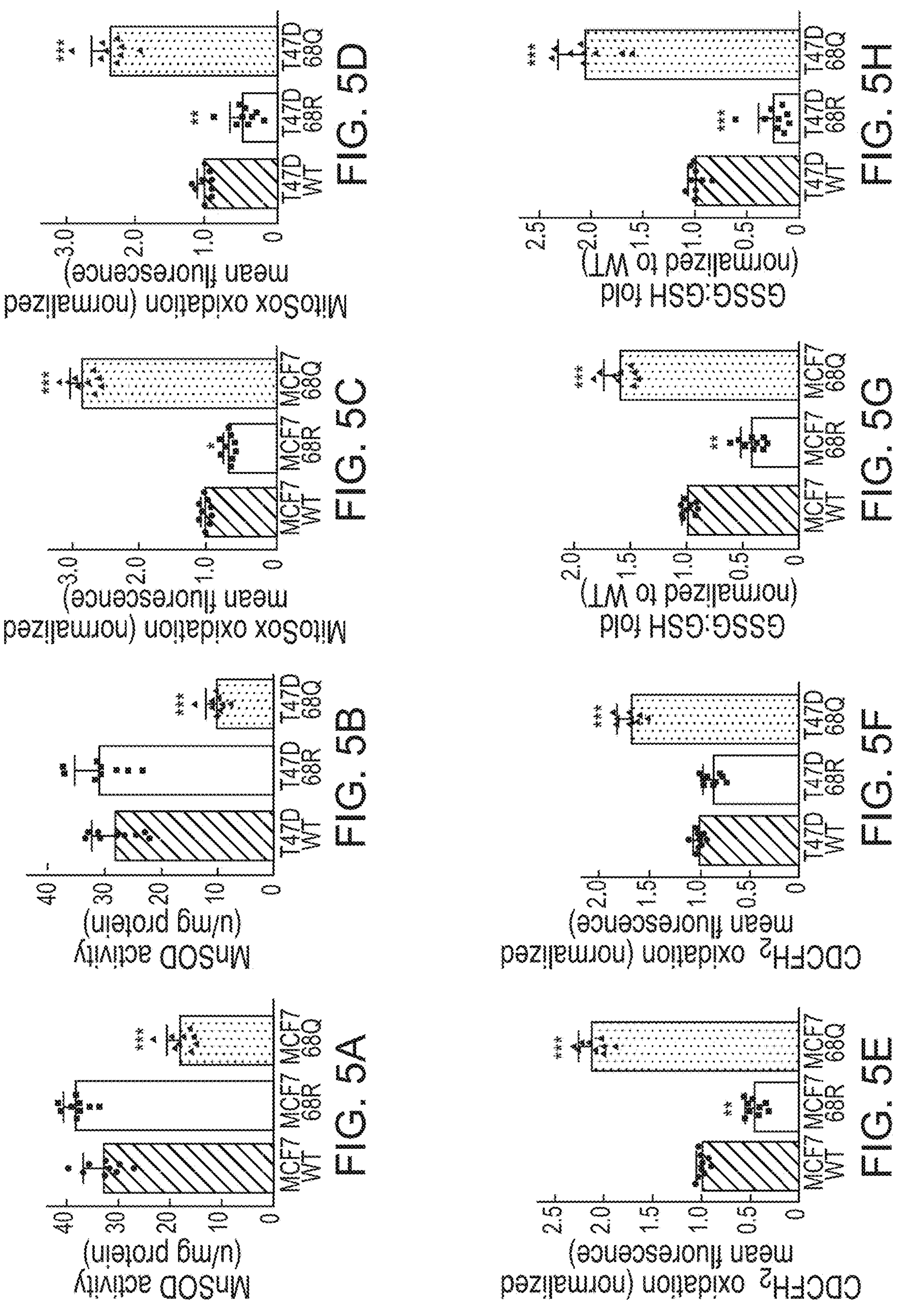
FIGS. 5*a* and 5*b* show MnSOD activity, with FIG. 5*a* showing MCF7-$MnSOD^{WT}$, MCF7-$MnSOD^{K68R}$, and MCF7-$MnSOD^{K68Q}$, and FIG. 5*b* showing T47D-$MnSOD^{WT}$, T47D-$MnSOD^{K68R}$, and T47D-$MnSOD^{K68Q}$ in whole-cell homogenates.
FIGS. 5*c* and 5*d* showing steady-state levels of superoxide that were measured in, as shown in FIG. 5*c*, MCF7-$MnSOD^{WT}$, MCF7-$MnSOD^{K68R}$, and MCF7-$MnSOD^{K68Q}$, and as shown in FIG. 5*d*, T47D-$MnSOD^{WT}$, T47D-$MnSOD^{K68R}$, and T47D-$MnSOD^{K68Q}$ cells.
FIGS. 5*e* and 5*f* show $H_2O_2$ levels that measured in these cells by $CDCFH_2$ oxidation via flow cytometry.
FIGS. 5*g* and 5*h* show the ratio of oxidized glutathione (GSSG) to reduced glutathione (GSH) levels measured in whole-cell homogenates of these cells. All experiments were done in triplicate. Error bars represent±1 SEM. *p<0.05, p<0.01, and *p<0.001. A one-way ANOVA statistical analysis with Tukey's post-analysis was used.

The MCF7-MnSOD$^{K68Q}$ (FIG. 5*a*) and T47D-MnSODK68Q (FIG. 5*b*) cells, which constitutively express MnSOD$^{K68Q}$, also exhibited a significant decrease in MnSOD superoxide detoxification activity, consistent with that shown by others[6,12] Since the primary function of MnSOD is to detoxify mitochondrial superoxide (O2·−), the mitochondrial oxidation/reduction status was measured in MCF7 and T47D cells expressing the various MnSOD acetylation mutants. Among these cell lines, MCF7-MnSOD$^{K68Q}$ and T47D-MnSOD$^{K68Q}$ cells exhibited a significant increase in: (1) MitoSox oxidation, a measure of mitochondrial O2·− (FIG. 5*c, d*); (2) CDCFH2 oxidation, a measure of cellular hydroperoxide levels (FIG. 5*e, f*); and (3) GSSG/GSH ratio, a measure of cellular oxidative stress (FIG. 5*g, h*), as compared to the MCF7-MnSOD$^{K68R}$, T47D-MnSOD$^{K68R}$, and control cell lines. Accordingly, it was shown that mimicking acetylated lysine 68 with MnSOD$^{K68Q}$ expression leads to oxidative stress in human breast cancer cells while mimicking perpetually deacetylated lysine with MnSOD$^{K68R}$ has opposing effects.

Tumor Cells Expressing MnSOD K68Q Exhibit Tam Resistance.

It has previously been shown that there is a link between dysregulated MnSOD[29,30,31] and aberrant cellular ROS levels and/or oxidative stress, due to several different mechanisms[23,32], and resistance to endocrine therapy. Based on these previous publications, and the results above identifying MnSOD$^{K68Q}$ as an in vitro tumor promoter, it seems reasonable that, similar to other oncogenes, enforced expression of MnSOD$^{K68Q}$ may also lead to, either indirectly or directly, resistance to Tam.

Figure 6A:
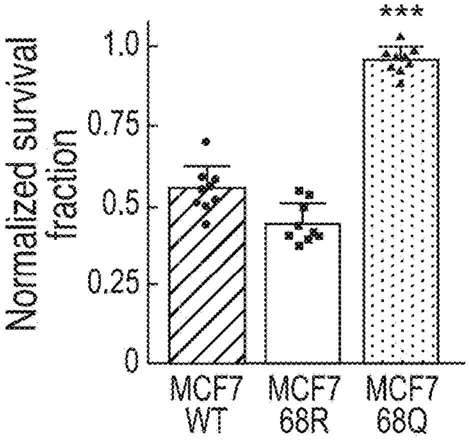
FIGS. 6*a*-6*h* are plots and images that illustrate that acetylation or mimicking acetylation of MnSOD-K68 in breast cancer cells makes them hydroxy-Tam-resistant while mimicking deacetylation of MnSOD-K68 or pharmacologically mimicking the activity of deacetylated lysine 68
Figure 6B:
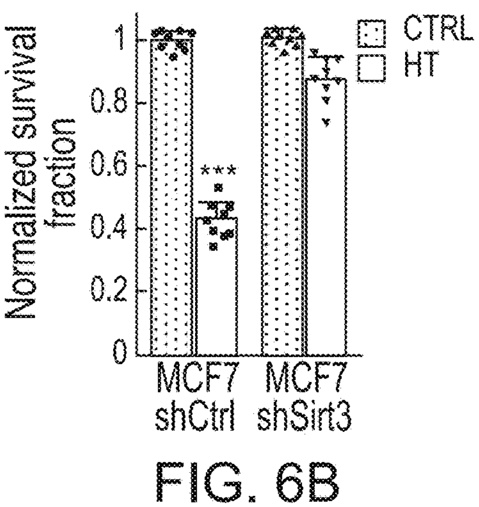
Figure 14A:
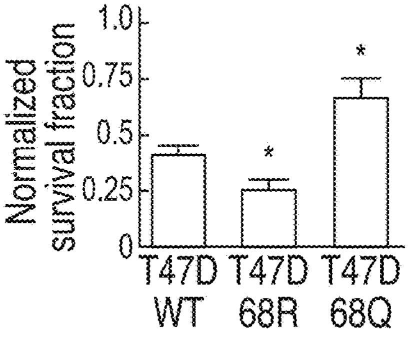
FIGS. 14*a*-14*g* are images and plots that illustrate that loss of SIRT3-induced MnSOD-K68 deacetylation leads to hydroxy-Tam resistance, and that such resistance is associated with increased lysine acetylation in human breast cancer cells, while mimicking deacetylation of MnSOD-K68 or pharmacologically mimicking the activity of deacetylated lysine 68 MnSOD with a manganese pentaazamacrocyclic dismutase mimetic has opposing effects. With respect to FIG. 14*a*, T47D-$MnSOD^{WT}$, T47D-$MnSOD^{K68R}$, and T47D-$MnSOD^{K68D}$ permanent cell lines were selected for hydroxy-Tam resistance in 1 μM for 3 months, and clonogenic cell survival experiments were completed. With respect to FIG. 14*b*, T47D-shCtrl and SIRT3 knockdown T47D-shSIRT3 permanent cell lines were exposed to 1 μM 4-hydroxy-Tam For 24 h (HT), and clonogenic cell survival experiments were done. With respect to FIG. 14*c*, T47D and T47D-HTR cells, with and without exposure to 1 μM 4-hydroxy-Tam for 24 h (HT), were measured for hydroxy-Tam response by clonogenic survival experiments. With respect to FIG. 14*d*, MCF7 cells (left), and T47D cells (right) were cultured in regular DMEM containing 1 μM hydroxy-Tam for 3 months (HT). The cell lysates were analyzed by immunoblotting with anti-MnSOD-K122-Ac (validated as a SIRT3 deacetylation target in Tao et al., 2010, Cancer Cell), anti-MnSOD, anti-OSCP-K139-Ac (validated as a SIRT3 deacetylation target in Tao et al., 2010, Cancer Cell), anti-OSCP, anti-IDH2K413-Ac (validated as a SIRT3 deacetylation target in Someya et al., 2010, Cancer Cell), anti-IDH2, and anti-actin. With respect to FIG. 14*e*, T47D-HTR cells were infected with lenti-$MnSOD^{WT}$, lenti-$MnSOD^{K68}$D, or lenti-$MnSOD^{K68R}$ and treated with 1 μM 4-HT for 24 h, followed by clonogenic cell survival assays. With respect to FIG. 14*f*, T47D-HTR cells were infected with lenti-$SIRT^{WT}$ (S3) or lenti-$SIRT^{DN}$ (S3DN; dominant-negative deacetylation-null gene) and treated with 1 μM hydroxy-Tam for 24 h, followed by clonogenic cell survival assays. With respect to FIG. 14*g*, T47D-HTR cells were incubated with 5 μM GC4419 for 5 days, followed by clonogenic cell survival assays. All experiments were done in triplicate. Error bars represent±1 SEM. *p<0.05, p<0.01, and *p<0.001.
Figure 14B:
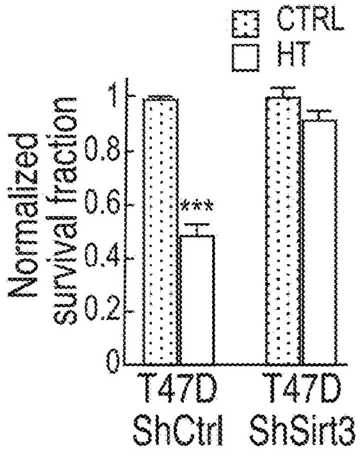

To test this idea, MCF7, MCF7-MnSOD$^{K68R}$, and MCF-MnSOD$^{K68Q}$ cells were treated with 1 μM hydroxy-Tam for 5 days, and clonogenic survival assays were performed. The results of these experiments showed that MCF7 (FIG. 6*a*) and T47D (FIG. 14*a*) cells constitutively expressing MnSOD$^{K68Q}$ exhibited significant resistance to the cytotoxicity of hydroxy-Tam, as compared to cells expressing MnSOD$^{K68WT}$ or MnSOD$^{K68R}$. In addition, MCF7 (FIG. 6*b*) and T47D (FIG. 14*b*) cells expressing shSIRT3, which results in increased cellular MnSOD-K68-Ac, also exhibited resistance to hydroxy-Tam cytotoxicity. These experiments indicate a link between MnSOD$^{K68Q}$ expression and hydroxy-Tam-resistant tumor cells. These results also add to the literature implicating the role of the MnSOD pathway[29,30,31], as well as ROS levels[23,32], in Tam resistance.

Tam-Resistant Breast Cells Exhibit a MnSOD-K68-Ac Signature.

Figure 6C:
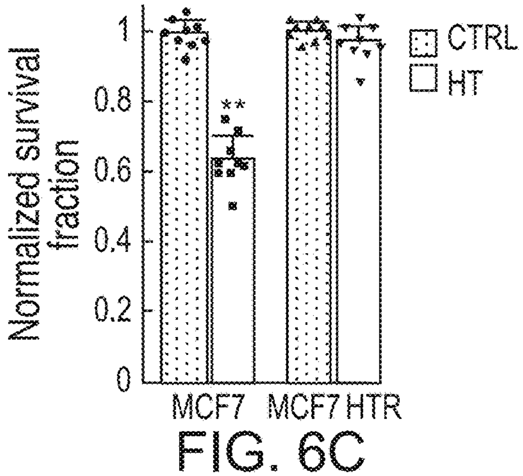
Figure 6D:
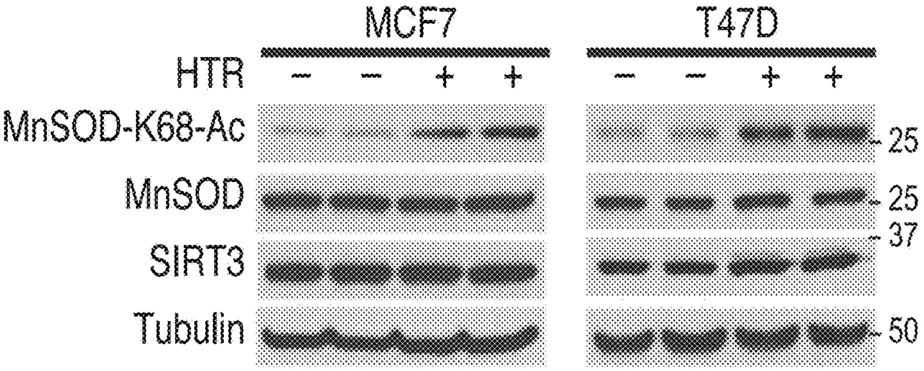
Figure 6E:
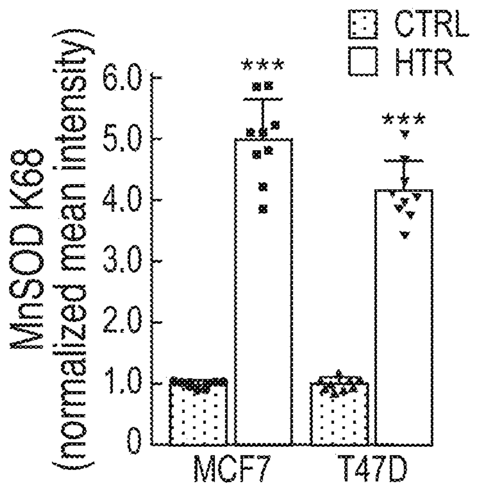
Figure 14C:
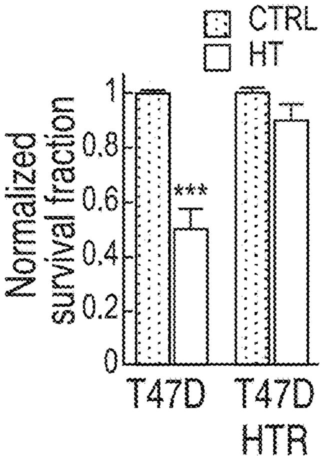
Figure 14D:
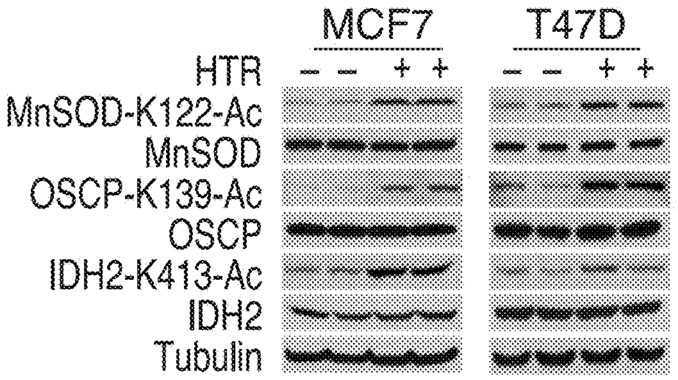

Since breast cancer cells expressing MnSOD$^{K68Q}$ exhibited resistance in vitro to Tam-induced cytotoxicity, it seems that MCF7 cells selected for resistance to hydroxy-Tam could also display a MnSOD-K68-Ac signature. To address this idea, MCF7 (FIG. 6*c*) and T47D (FIG. 14*c*) cells were cultured in the presence of 1 μM hydroxy-Tam for 3 months to generate hydroxy-Tam-resistant (HTR) cells. Both MCF7-HTR and T47D-HTR cells showed an increase in MnSOD-K68-Ac (FIG. 6*d, e*). In addition, staining with antibodies for several other SIRT3 deacetylation targets (MnSOD-K122-Ac, IDH2-K413-Ac, and OSCP-K139-Ac), which are a proxy for SIRT3 activity, also showed increased acetylation (FIG. 14*d*), suggesting decreased SIRT3 activity. The results of these experiments indicate that ER+ breast cancer cell lines selected for resistance to Tam exhibit a MnSOD-K68-Ac signature, which may also serve as a potential molecular biomarker.

Tam Resistance is Reversed by Mimicking Lysine 68 Deacetylation with MnSOD$^{K68R}$ Expression or MnPAM Dismutase Mimetic.

Figure 6F:
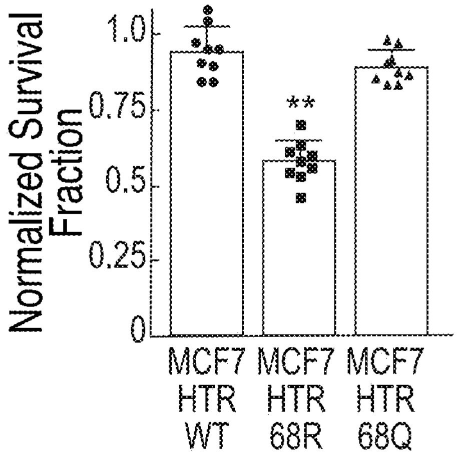
Figure 6G:
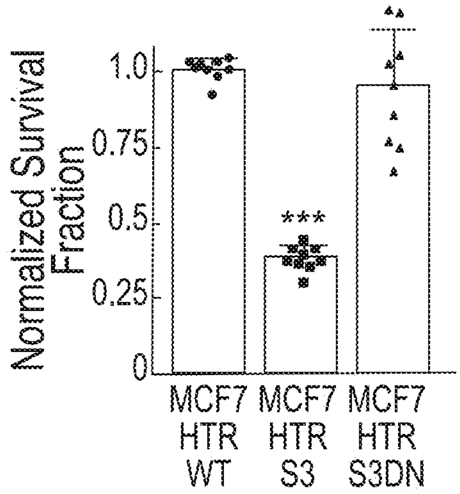
Figure 6H:
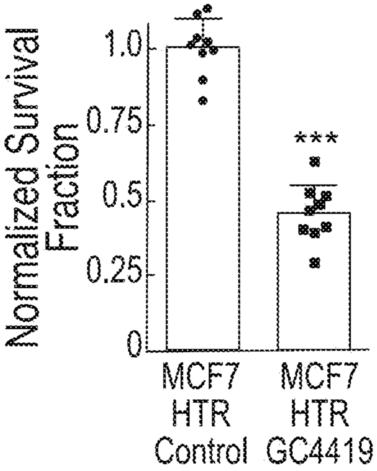
Figure 14E:
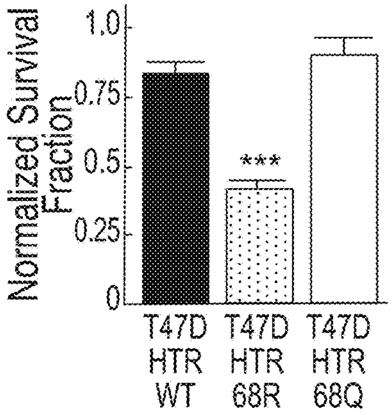
Figure 14F:
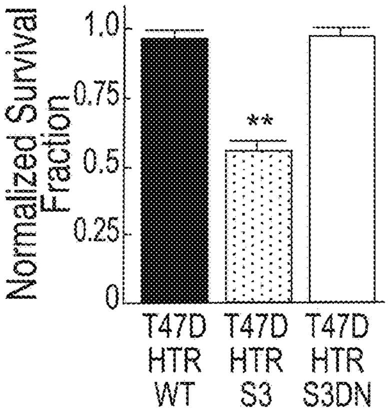
Figure 14G:
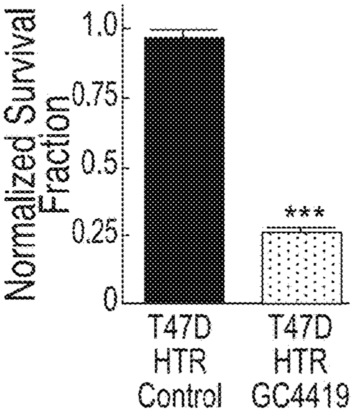

To further show that MnSOD-K68-Ac is a potential marker of Tam resistance, HTR cells were infected with lenti-MnSOD$^{WT}$, lenti-MnSOD$^{K68Q}$, and lenti-MnSOD$^{K68R}$, and hydroxy-Tam resistance was measured by clonogenic cell survival assays. The results showed that infection with lenti-MnSOD$^{K68R}$, but not with lenti-MnSOD$^{WT}$ or lenti-MnSOD$^{K68Q}$, reversed the hydroxy-Tam resistance (FIG. 6*f* and FIG. 14*e*). Furthermore, when MCF7-HTR and T47D-HTR cells were infected with lenti-SIRT3$^{WT}$ (FIG. 6*g* and FIG. 14*f*), which will result in MnSOD deacetylation, or treated with 5 μM GC4419 (FIG. 6*h* and FIG. 14*g*), a manganese pentaaza macrocyclic ring complex (MnPAM) that catalytically converts superoxide to hydrogen peroxide via same the catalytic mechanism used by homotetrameric MnSOD, they became sensitive to hydroxy-Tam. These results suggest that MnSOD-K68-Ac is a potential molecular biomarker and/or tumor signature for resistance to Tam. These results also show that cells having hydroxy-Tam resistance can be treated and/or the hydroxy-Tam resistance can be reversed by pharmacologically providing MnPAM such as GC4419. Accordingly, it was shown that acetylation or mimicking acetylation of MnSOD-K68 in breast cancer cells makes them hydroxy-Tam-resistant while mimicking deacetylation of MnSOD-K68 or pharmacologically mimicking the activity of deacetylated lysine 68 MnSOD with a manganese pentaazamacrocyclic dismutase mimetic has opposing effects. It was also shown that loss of SIRT3-induced MnSOD-K68 deacetylation leads to hydroxy-Tam resistance, and that such resistance is associated with increased lysine acetylation in human breast cancer cells, while mimicking deacetylation of MnSOD-K68 or pharmacologically mimicking the activity of deacetylated lysine 68 MnSOD with a manganese pentaazamacrocyclic dismutase mimetic has opposing effects.

Tam Exposure Increases Oxidative Stress and Monomeric MnSOD.

Figure 7A:
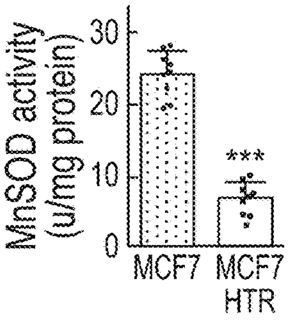
FIGS. 7*a*-7*k* are images and plots that illustrate that hydroxy-Tam exposure-induced resistance to hydroxy-Tam (HTR) is associated with loss of the tetrameric MnSOD and activity, increased monomeric form, increased oxidative stress, and increased proliferation, while mimicking perpetually deacetylated lysine with MnSOD$^{K68R}$ in the HTR cancer cells reversed these effects, where.
Figure 7B:
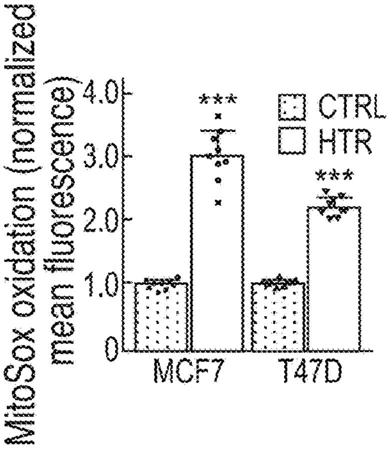
Figure 7C:
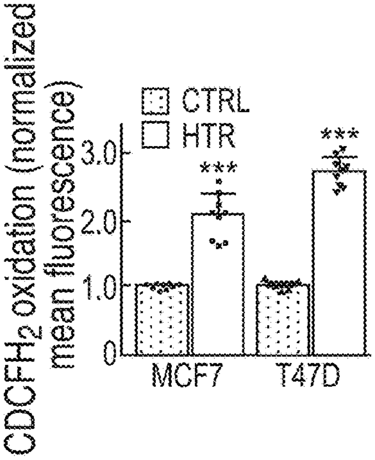
Figure 7D:
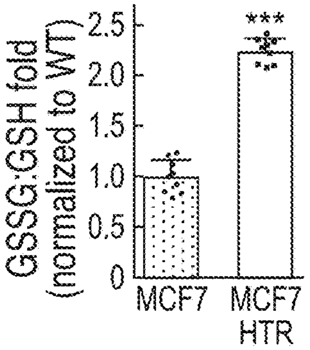
Figure 7E:
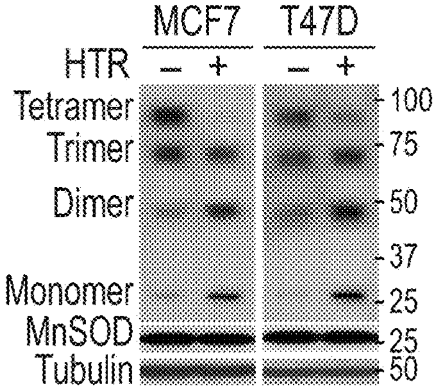
Figure 15A:
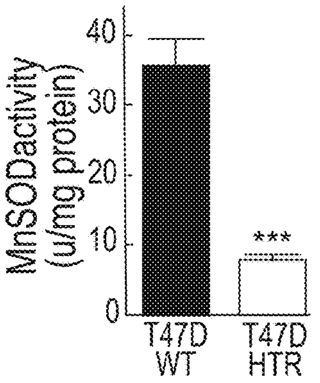
Figure 15B:
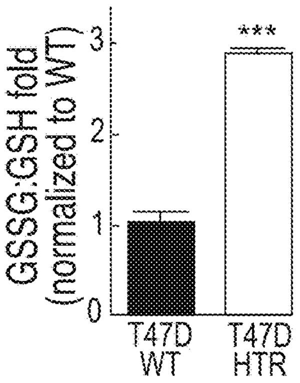

MnSOD activity is tightly correlated with mitochondrial metabolism, and HTR cells exhibit a MnSOD-K68-Ac (AcK68) signature (FIG. 6*d, e*); thus the mitochondrial metabolic profile in HTR ER+ breast cancer cells was determined. In this regard, MCF7-HTR (FIG. 7*a*) and T47D-HTR (FIG. 15*a*) cells exhibited a decrease in MnSOD activity, an increase in mitochondrial superoxide levels (FIG. 7*b*), and increased cellular hydroperoxide, as measured by CDCFH2 oxidation (FIG. 7*c*), as well as an increase in the GSSG/GSH ratio (FIG. 7*d* and FIG. 15*b*). Finally, monomeric MnSOD is enriched in MCF7-HTR and T47D-HTR cells (FIG. 7*e*), which is consistent with the decrease in MnSOD activity (FIG. 7*a*) and increase in MnSOD-K68-Ac (FIG. 6*d*), as compared to control MCF7 and T47D cells.

Figure 7F:
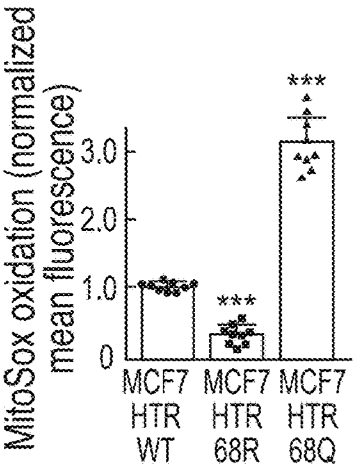
Figure 7G:
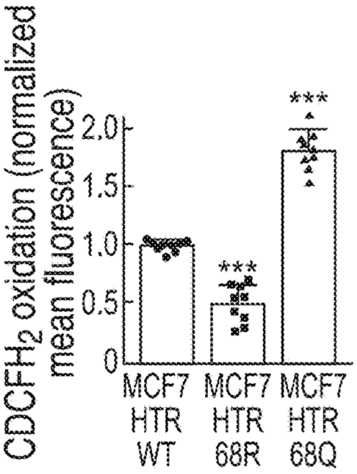
Figure 7H:
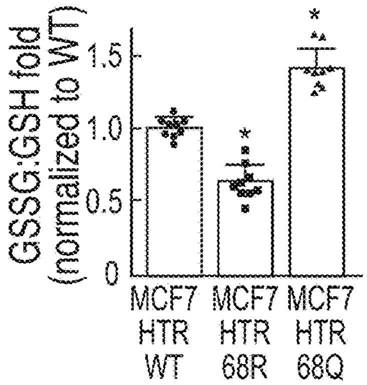
Figure 15C:
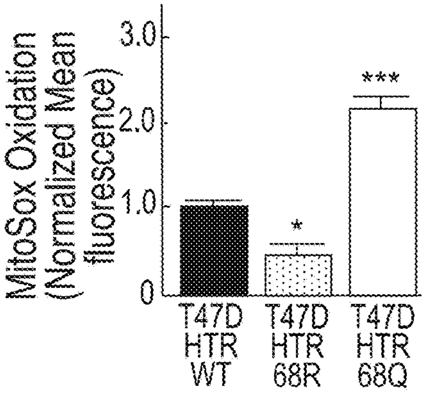
Figure 15D:
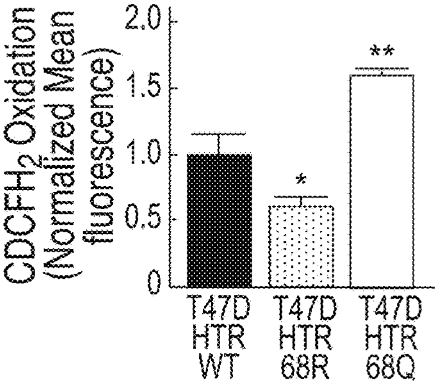
Figure 15E:
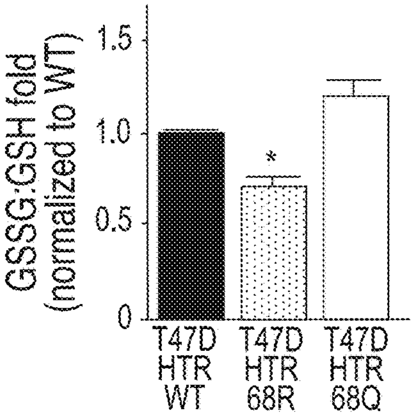

Furthermore, to determine if this increased oxidative stress in HTR cells is due to the acetylation status of MnSOD-K68, MCF7-HTR and T47D-HTR cells were infected with lenti-MnSOD$^{WT}$, lenti-MnSOD$^{K68R}$, and lenti-MnSOD$^{K68Q}$. These experiments showed that enforced expression of MnSOD$^{K68R}$ reversed the increase in mitochondrial superoxide (FIG. 7*f* and FIG. 15*c*), intracellular hydroperoxide (FIG. 7*g* and FIG. 15*d*), and GSSG/GSH ratio (FIG. 7*h* and FIG. 15*e*), as compared to cells expressing MnSOD$^{K68Q}$ or MnSOD$^{WT}$. These data show that HTR increases MnSOD-K68-Ac, indicating that there may be a Tam resistance tumor signature that also includes changes in cellular ROS profiles, which has been shown by others[23,30]. Accordingly, it was shown that decreased MnSOD activity and increased oxidative stress in hydroxy-Tam resistant human breast cancer cells can be reversed mimicking deacetylation of MnSOD-K68.

Tam-Resistant MCF7 and T47D Cells Exhibit Increased Ki-67.

Figure 2C:
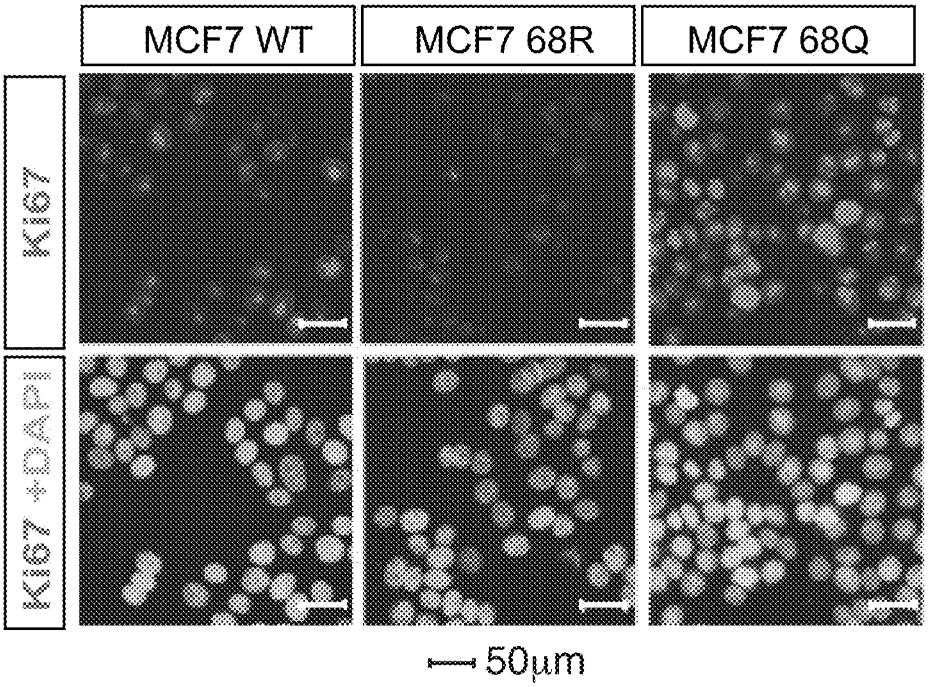
Figure 2D:
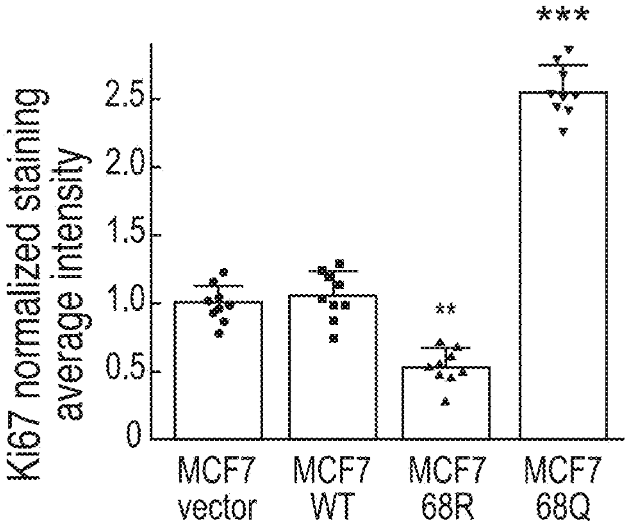
Figure 2E:
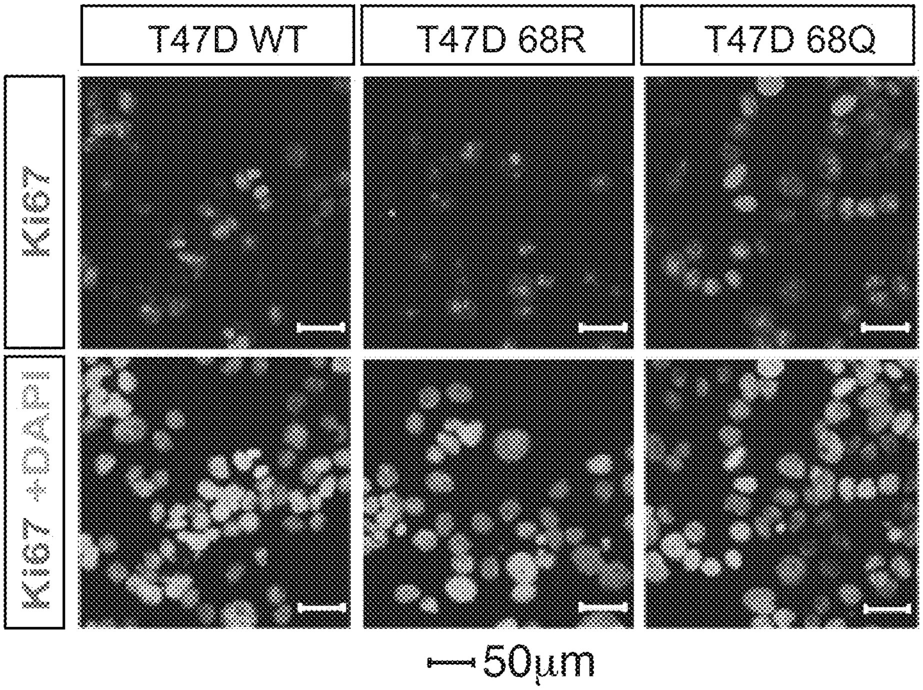
Figure 2F:
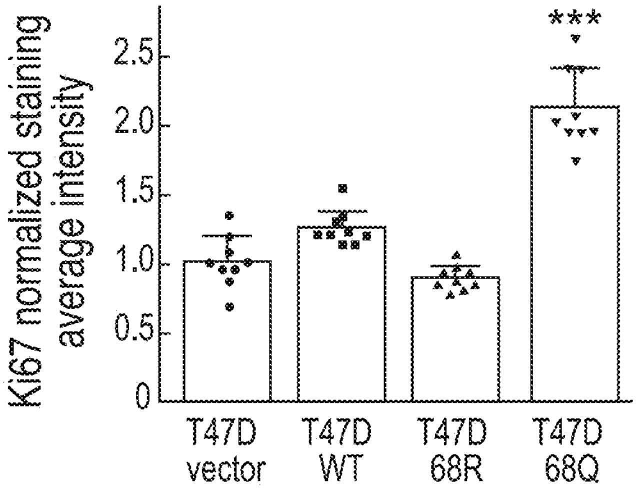
Figure 7I:
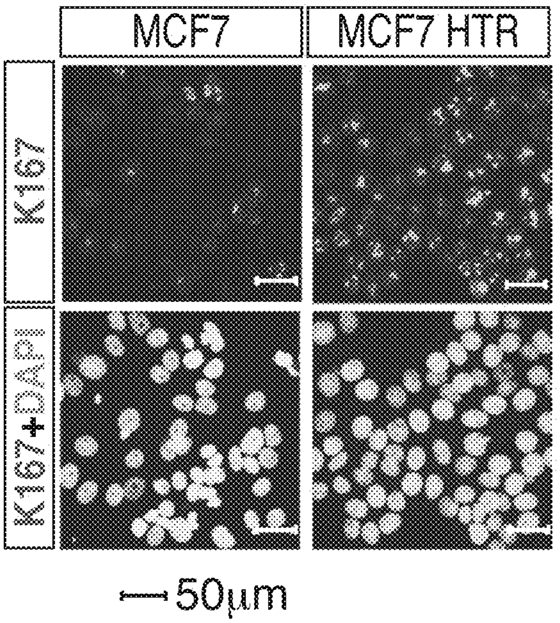
Figure 16A:
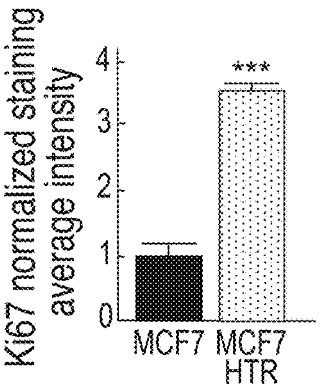
FIGS. 16*a*-16*g* are images and plots that illustrate that Ki-67 levels were increased in hydroxy-Tam resistant (HTR) breast cancer cells, and that pharmacologically mimicking the activity of deacetylated lysine 68 MnSOD with a manganese pentaazamacrocyclic dismutase mimetic decreased Ki-67 levels in the HTR cells, and made them sensitive to hydroxy-Tam cytotoxicity. With respect to FIG. 16*a*, the data from FIG. 7*i*, where MCF7-HTR cells were stained for Ki-67, as well as DAPI, were counted with ImageJ and quantified for average Ki-67 intensity as shown in the bar graph. With respect to FIGS. 16*b* and 16*c*, T47D and T47D-HTR cells were stained for Ki-67 as well as DAPI, and particles in the nucleus were counted with ImageJ and quantified for average Ki-67 intensity as shown in the bar graph.
Figure 16B:
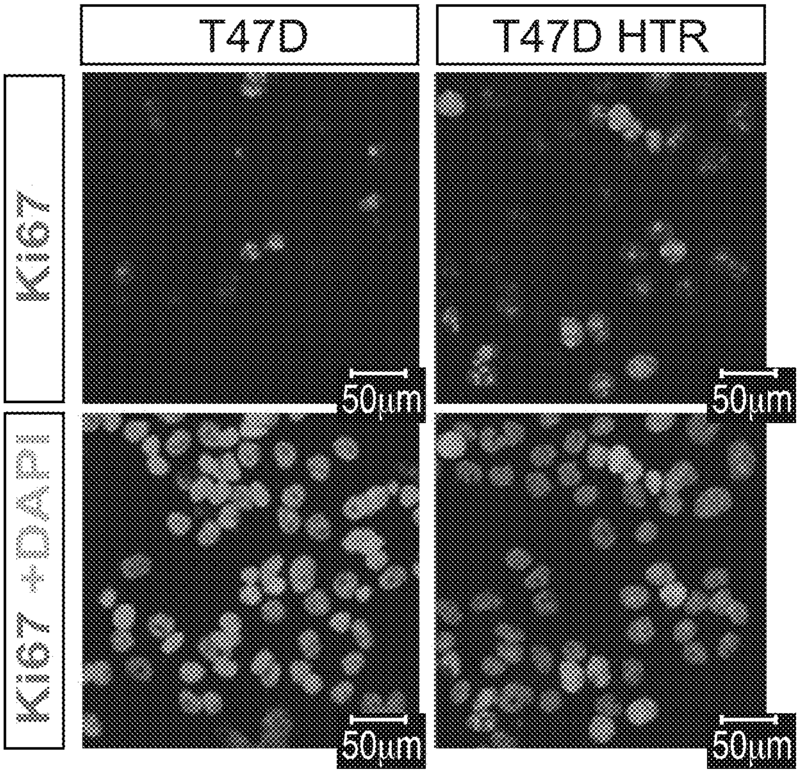
Figure 16C:
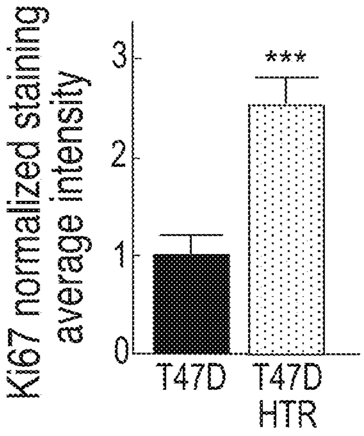
Figure 16D:
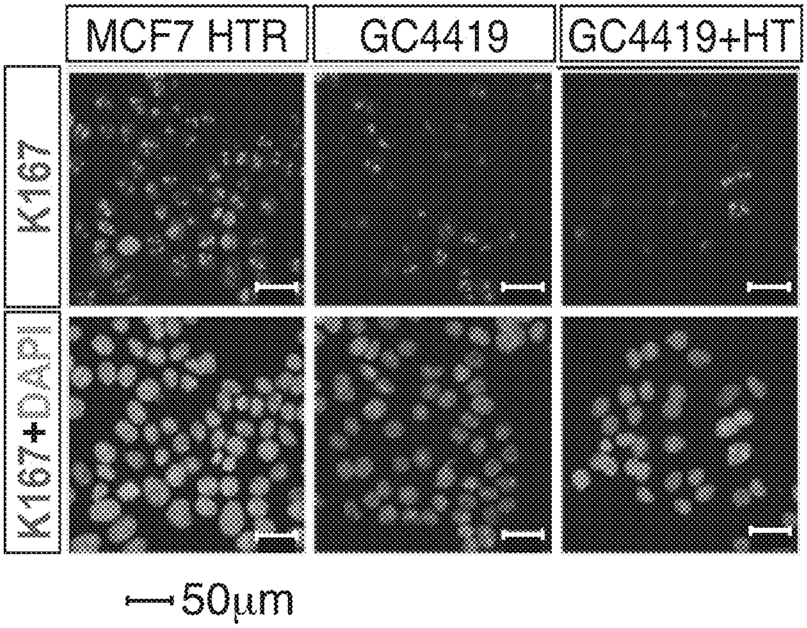
Figure 16E:
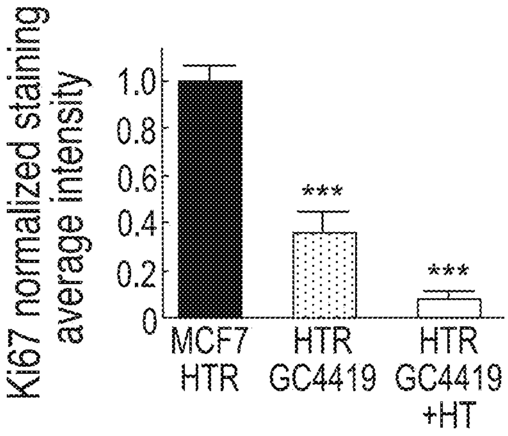
Figure 16F:
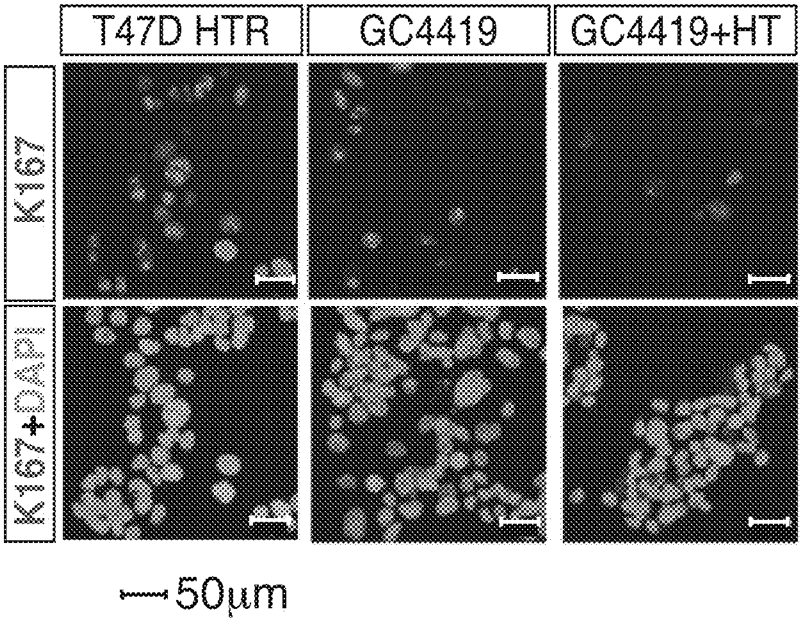
Figure 16G:
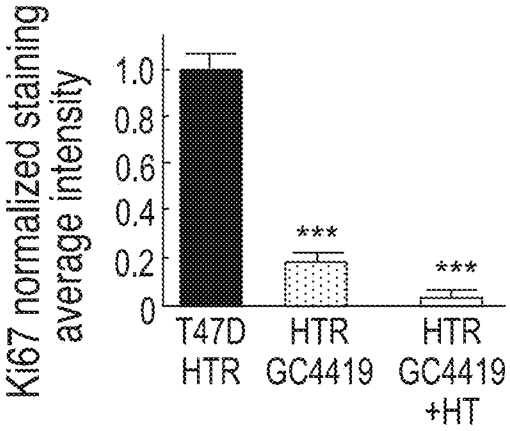
Figure 17A:
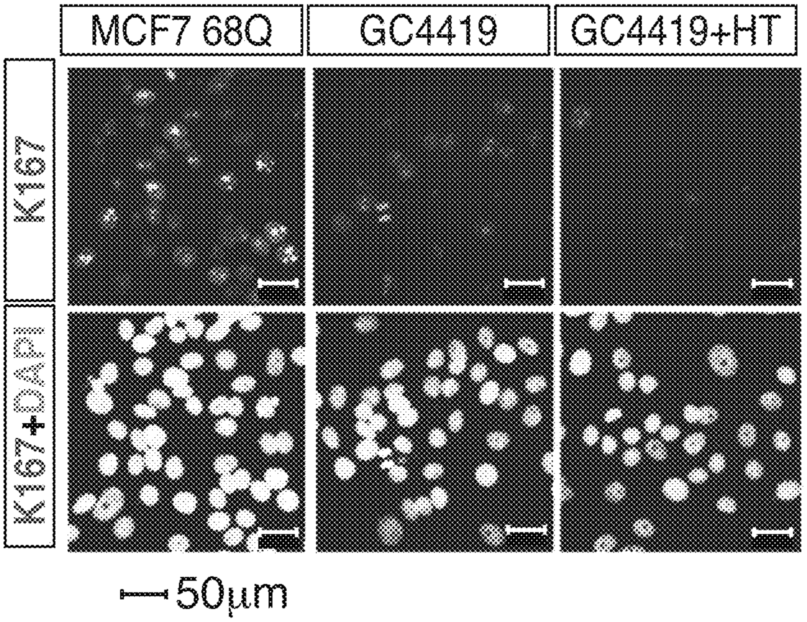
FIGS. 17*a*-17*e* are images and plots that illustrate that pharmacologically mimicking the activity of deacetylated lysine 68 MnSOD with a manganese pentaazamacrocyclic dismutase mimetic decreased Ki-67 levels in MCF7 and T47D cells expressing MnSOD$^{K68Q}$. MCF7-MnSOD$^{K68Q}$ cells (in FIGS. 17*a* and 17*b*) and T47D-MnSOD$^{K68Q}$ cells (in FIGS. 17*c* and 17*d*) were treated with 5 μM GC4419 and/or 1 μM 4-hydroxy-Tam for 5 days, and then stained for Ki-67 as well as DAPI. Quantifications of average Ki-67 intensity are shown in the bar graphs.
Figure 17B:
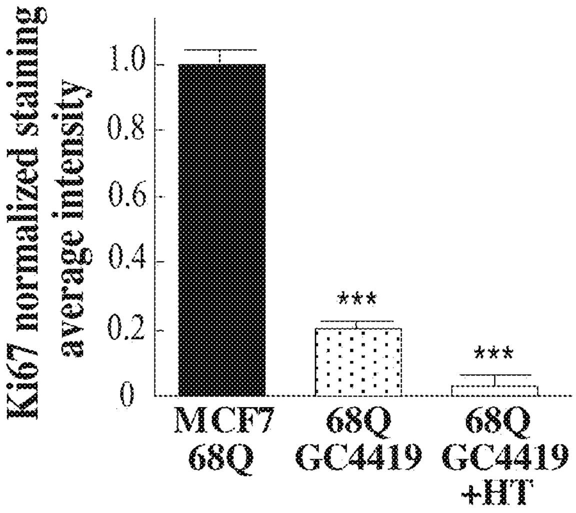
Figure 17C:
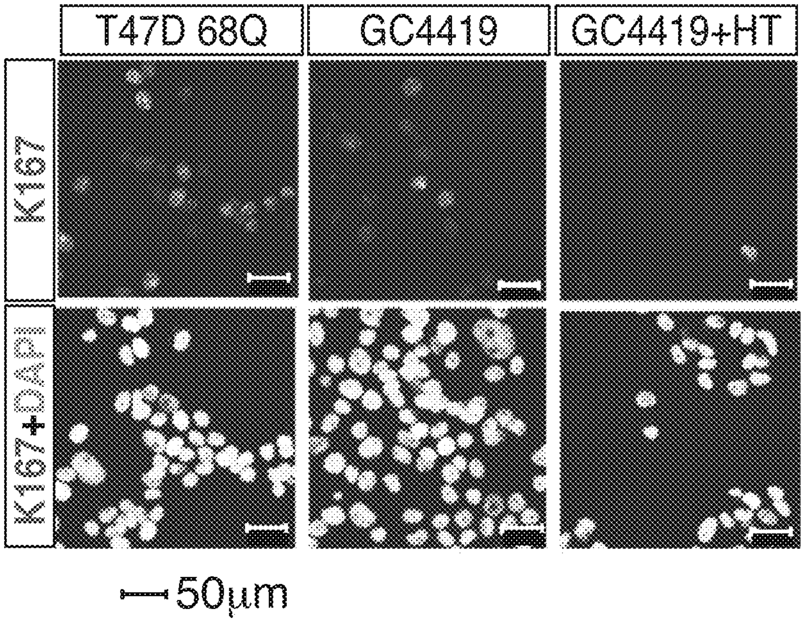

MCF7-HTR (FIG. 7*i* and FIG. 16*a*) and T47D-HTR cells (FIG. 16*b, c*), which display a MnSOD-K68-Ac signature (FIG. 6*d*), exhibit increased Ki-67 levels, similar to luminal B breast malignancies, similar to MCF7-MnSOD$^{K68Q}$ and T47D-MnSOD$^{K68Q}$ cells (FIG. 2*c, d*). In addition, MCF7-HTR (FIG. 16*d, e*) and T47D-HTR (FIG. 16*f, g*) cells treated with the MnPAM dismutase mimetic GC4419 exhibited decreased Ki-67 IHC staining and hydroxy-Tam plus GC4419 further decreased Ki-67. GC4419 or hydroxy-Tam and GC4419 also reversed the increase in Ki-67 IHC staining in MCF7-MnSOD$^{K68Q}$ (FIG. 17*a, b*) and T47D-MnSOD$^{K68Q}$ (FIG. 17*c, d*) cell lines, suggesting that pharmacologically mimicking the activity of deacetylated lysine 68 MnSOD reverses the increase in Ki-67. Accordingly, it was shown that Ki-67 levels were increased in hydroxy-Tam resistant (HTR) breast cancer cells, and that pharmacologically mimicking the activity of deacetylated lysine 68 MnSOD with a manganese pentaazamacrocyclic dismutase mimetic decreased Ki-67 levels in the HTR cells and made them sensitive to hydroxy-Tam cytotoxicity.

Figure 7J:
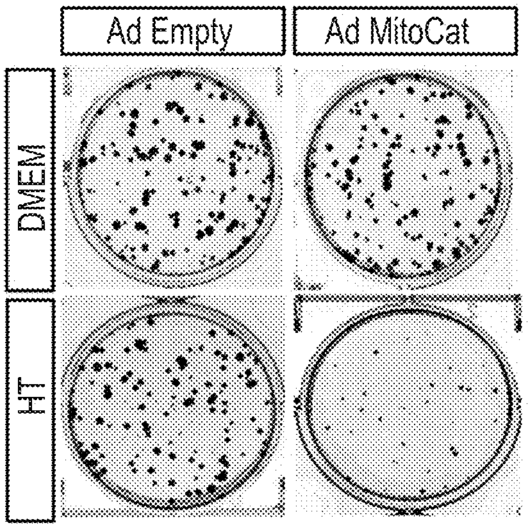
Figure 7K:
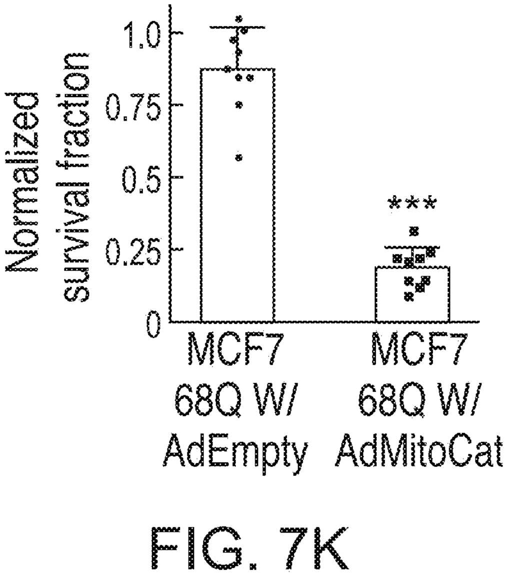

To determine if hydrogen peroxide is necessary for the HTR observed in the MCF7-MnSOD$^{K68Q}$ cells, we infected these cells with AdMitoCat, which removed and/or significantly reduced mitochondrial hydrogen peroxide levels, a critical and necessary substrate for peroxidase enzymatic activity. The results of clonogenic cell survival experiments demonstrated that decreased mitochondrial hydrogen peroxide levels reversed the HTR observed in MCF7 cells that constitutively express MnSOD$^{K68Q}$ (FIG. 7*j, k*). These results suggest that, either indirectly or directly, cells expressing the MnSOD acetylation mutant require hydrogen peroxide to maintain resistance to Tam. Accordingly, it was shown that hydroxy-Tam exposure-induced resistance to hydroxy-Tam (HTR) is associated with loss of the tetrameric MnSOD and activity, increased monomeric form, increased oxidative stress, and increased proliferation, while mimicking perpetually deacetylated lysine with MnSOD$^{K68R}$ in the HTR cancer cells reversed these effects.

Tam-Resistant Xenografts Exhibit a More Aggressive Phenotype.

Figure 8A:
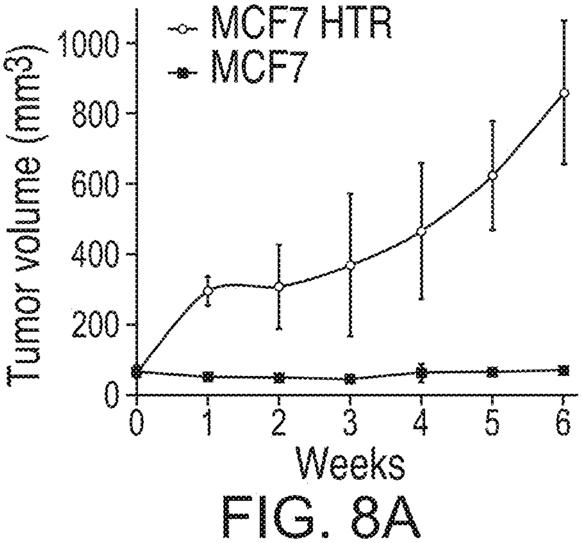
FIG. 8*c* is a plot showing results for MCF7-HTR doxycycline-inducible MnSODK68R cells that were implanted into hind limbs of nude mice and the tumor volumes were monitored for 4 weeks, and error bars represent±1 SEM.
FIG. 8*d* shows luminal breast cancer sample TMA stained with anti-MnSOD-K68-Ac or anti-SIRT3 antibodies.
FIGS. 8*e* and 8*f* show quantified TMA consisting of luminal A (n=37) and luminal B (n=38) samples immunostained for, with respect to FIG. 8*e*, MnSOD-K68-Ac, and with respect to FIG. 8*f*, SIRT3. The shaded boxes represent the interquartile range; whiskers represent the 10th-90th percentile range. Experiments were done in triplicate. *p<0.05. A t-test was used to compare data between the two groups.
FIG. 8*g* is a schematic of the dichotomous role for MnSOD in normal cells (i.e., protection) versus tumor promoter and/or and Tam resistance.
Figure 8B:
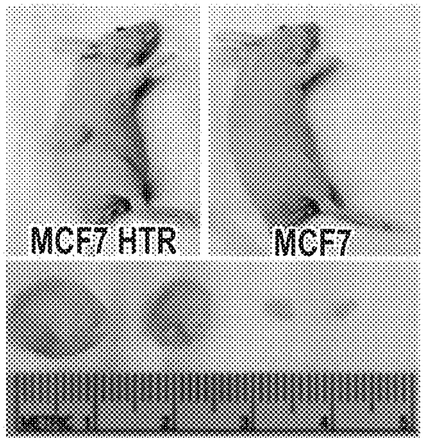
Figure 8C:
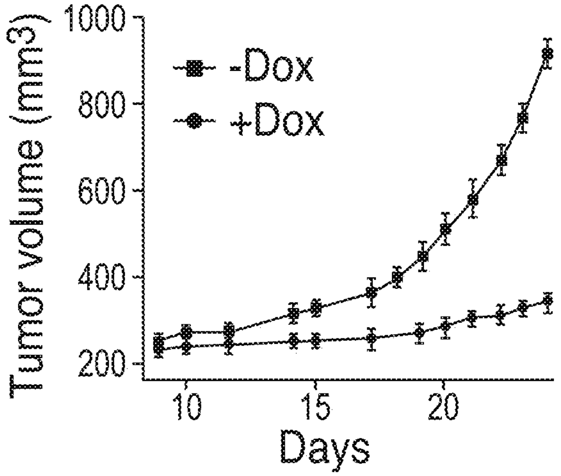
Figures 17D, 17E:
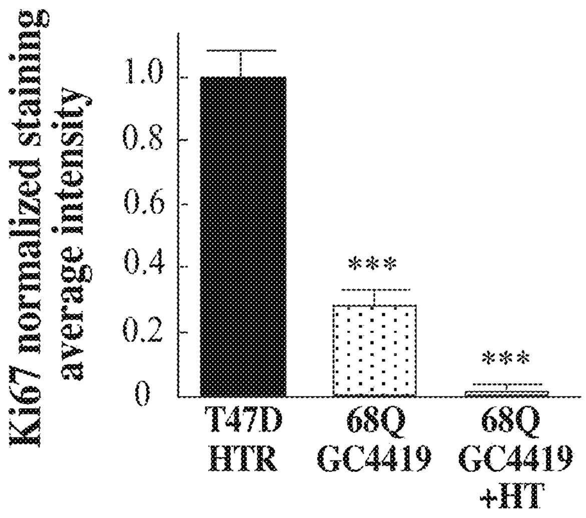
Figure 18A:
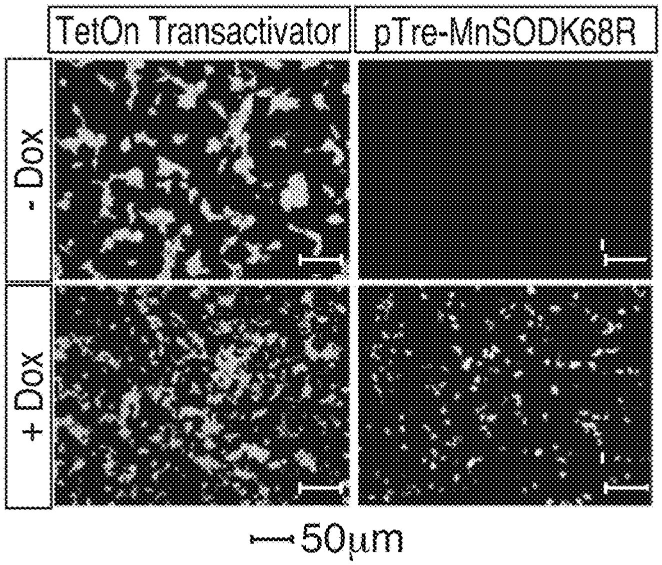
FIGS. 18*a*-18*b* are images and plots that illustrate that mimicking deacetylation of MnSOD-K68 with Tet-On induced expression of MnSOD$^{K68R}$ inhibits xenograft growth in MCF7-HTR cells.
Figure 18B:
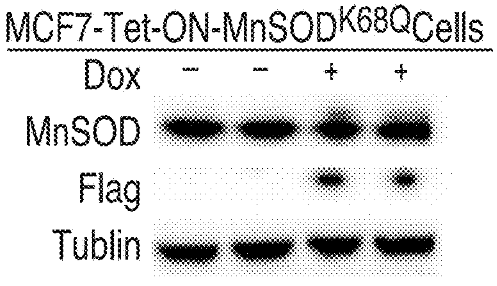

To test if MCF7-HTR cells, which exhibit a MnSOD-K68-Ac signature (FIG. 6*d*), form more aggressive in vivo xenograft tumors, MCF7 and MCF7-HTR cells were injected into immunodeficient mice, and tumor growth was monitored. Without estrogen supplementation, control MCF7 cells were not able to form tumors in vivo, as expected. In contrast, MCF7-HTR cells formed tumors averaging 859 $mm^3$ in 6 weeks without estrogen supplementation (FIG. 8*a, b*), and xenograft engraftment was 100% (FIG. 17*e*), indicating that these cells exhibited a highly tumorigenic phenotype. Finally, the MCF7-HTR cells were used to construct a Tet-On expression system for the inducible expression of the deacetylation mimic mutant (MnSOD$^{K68R}$). As such, MCF7-HTR cells were initially infected with pTet-DualOn (Clontech) and selected with puromycin, followed by infection with pTre-Dual2-MnSODK68R and hygromycin selection, and finally, these cells were validated for MnSOD$^{K68R}$ Tet-induction (FIG. 18*a, b*). MCF7-HTR-Dual2-MnSOD$^{K68R}$ xenografts were grown to 100 mm, and mice were exposed to doxycycline to induce MnSOD$^{K68R}$ expression. These experiments showed that enforced expression of MnSOD$^{K68R}$ inhibited in vivo MCF7-HTR xenograft tumor cell growth (FIG. 8*c*). Accordingly, it was shown that mimicking deacetylation of MnSOD-K68 with Tet-On induced expression of MnSOD$^{K68R}$ inhibits xenograft growth in MCF7-HTR cells.

Human Luminal B Tumors Exhibit High Levels of MnSOD-K68-Ac.

Figure 8D:
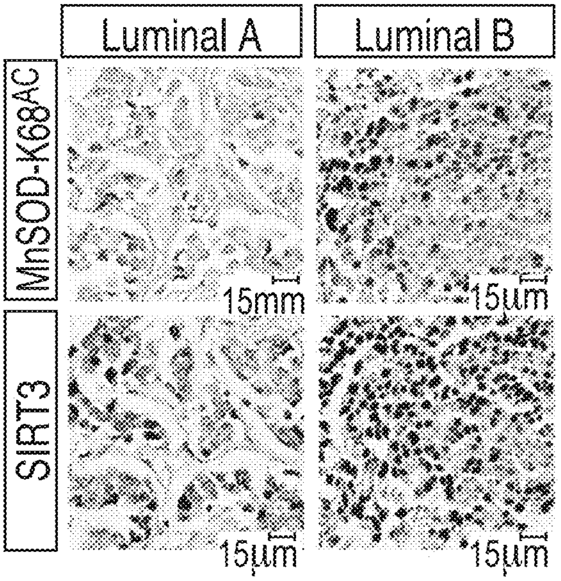
Figure 18C:
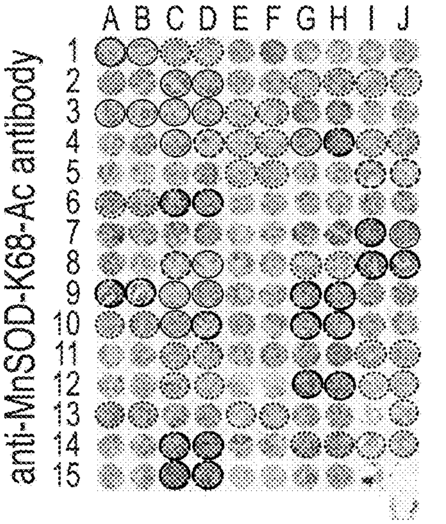
FIGS. 18*c*-18*d* are images that show a human breast cancer TMA consisting of luminal A (n=37) and luminal B (n=38) samples that were dewaxed and immunostained with either anti-MnSOD-K68-Ac (in FIG. 18*c*) or anti-SIRT3 antibodies (in FIG. 18*d*). MnSOD-K68-Ac and SIRT3 staining was grouped into low, intermediate, and high levels, and the number of samples that fell into each of these groups is presented in the table under each TMA. Circled tumor samples contain high MnSOD-K68-Ac staining. All experiments were done in triplicate. Representative images are shown.
Figure 18D:
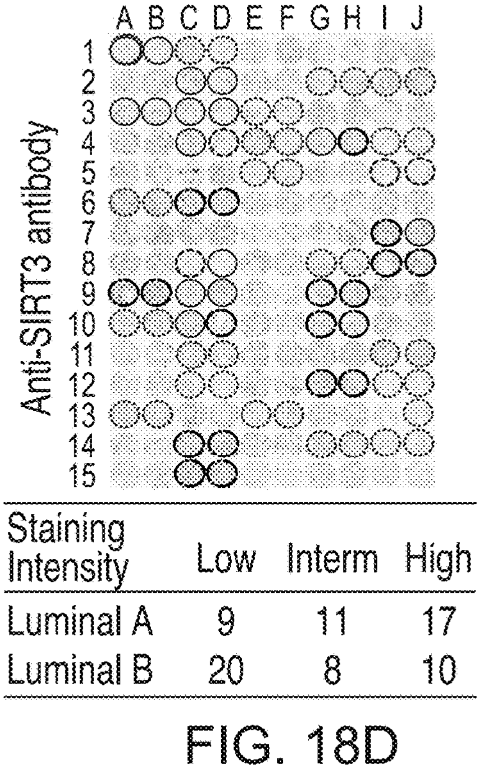

Mice lacking Sirt3 develop mammary tumors with a luminal B-like phenotype that are ER+, poorly differentiated, and display high levels of Ki-67[5,7,33]. To determine if there is a subgroup of human ER+ tumors that display a loss of SIRT3/MnSOD-Ac signature, breast cancer patient tissue microarray (TMA) slides containing all four subtypes of breast malignancies were analyzed. The TMA was stained using anti-MnSOD-K68-Ac (see FIG. 12*a, b* for antibody specificity) and anti-SIRT3 antibodies, and representative IHC images for luminal A and B tumor samples are shown (FIG. 8*d* and FIG. 18*c, d*). Staining intensity was subsequently quantified using automated HistoQuest software that revealed that MnSOD-K68-Ac levels are significantly higher (FIG. 8*e*), and SIRT3 protein levels are markedly lower (FIG. 8*f*) in the luminal B samples, as compared to luminal A tumor samples. In addition, stratification of the staining intensities from the luminal A versus luminal B TMAs into low, intermediate, and high staining suggests that there may be a subgroup of luminal B tumors that exhibit significant MnSOD-K68-Ac staining (FIG. 18*c, d*). These results suggest that the SIRT3/MnSOD-Ac signature is a useful marker to identify a specific subgroup of women with luminal B breast cancer and who might most benefit from pharmacologic intervention to cause or mimick lysine 68 deacetylation.

Methods

Cell lines. The ER+ MCF7 and T47D human breast cells, which were all obtained from ATCC, authenticated using STR profiling with CellCheck 9 Plus by IDEXX Bioresearch, and tested for *mycoplasma* using *Mycoplasma* Detection Kit, InvivoGen, Inc in April 2016, were cultured in Dulbecco's Modified Eagle's Medium (DMEM, Gibco) supplemented with 10% fetal bovine serum (FBS; Sigma) and Antimycotic solution (Sigma). Cells were maintained in a humidified 37° C. environment with 5% $CO_2$. pMEFs were isolated from E14.5 isogenic SIRT3+/+ mice (through a protocol that was approved by the Institutional Animal Care and Use Committee (IACUC) and complied with related animal research ethical regulations) and maintained in a 37° C. incubator with 5% $CO_2$ and 6% oxygen, except when otherwise noted. MCF7 and T47D cells were grown for 3 months in 1 μM hydroxy-Tam to create MCF7-HTR and T47D-HTR permanent cell lines, and several different subclones were frozen. MCF7-HTR and T47D-HTR were not used for >5 passages, and new cell lines were used. All experiments were done using exponentially growing cell cultures at 50% confluence.

Virus Plasmids and Short-Hairpin RNA (shRNA) Constructs and Mutagenesis.

To package lentivirus, 293T cells (obtained from ATCC) were transfected with 5 μg DNA, 5 μg psPAX2 packaging plasmid, and 500 ng VSV. G envelope plasmid. Viral supernatant was collected after 72 h and filtered through a 0.45 μm filter (Corning). Lenti-SIRT3$^{WT}$ and the deacetylation-null mutant (lenti-SIRT3$^{DN}$) were gifts from Dr. Toren Finkel (NIDDK). pLKO.1 human SIRT3 shRNA was purchased from OpenBiosystem. *Lenti*-MnSOD plasmid (human) was used as the MnSOD$^{WT}$ plasmid and for site-directed mutagenesis, i.e., K68 to arginine (R: deacetyl mimic) or glutamine (Q: acetyl mimic) (Bioinnovatise). MCF7, T47D, and NIH3T3 cells were infected with 5 MOI of lentivirus and selected with DMEM containing 2 μg/mL puromycin (Invitrogen) or 100 μg/mL G418 sulfate (Invitrogen) for 14 days. After a 2-week selection period, cells were grown in DMEM with 10% FBS.

Transduction of antioxidant enzymes. Replication-incompetent adenoviral vectors, AdCMV Bgl II (AdBgIII) and AdCMV Mito-Catalase (AdMitoCat) were received as a gift from Dr. Douglas Spitz (University of Iowa) and Dr. Marcelo Bonini (Medical College of Wisconsin, WI). Cells were plated the day before virus administration. The desired number of viral particles was added for 24 h, and then the media was changed to fresh media and left for another 48 h prior to each experiment.

In vitro cell transformation assay. For this study, spontaneous immortalization of pMEFs is the ability to continue dividing past passage 15. For in vitro immortalization experiments, MnSOD, or one of its site-directed mutants (K-R or K-Q), was co-infected with c-Myc and/or Kras into third-passage pMEFs. Cells were cultured and split every 2 days to prevent confluency and plated onto a new 100 mm dish at $3.0\times10^5$ cells. After 15 additional passages (18 total), cells were considered immortalized.

Clonogenic cell survival assay. For the clonogenic survival analysis, exponentially growing cells were replated using appropriate dilutions, and clonogenic survival was evaluated after 14 days in regular growth medium. Cells were stained with crystal violet, and colonies of >50 cells were counted and utilized to calculate clonogenic survival[46].

Soft-agar colony formation assay analysis. Ten-thousand cells were plated on 0.3% agar in growth medium over a 0.6% base agar foundation layer in growth medium[7,8]. After 21 days, the colonies were visualized under a ×20 microscope (Zeiss), and images were acquired.

Xenograft in vivo tumorigenesis analysis. Five million MCF7, MCF7-HTR, or MCF7 cells (obtained from ATCC) expressing MnSOD$^{K68WT}$, MnSOD$^{K68R}$ or MnSOD$^{K68Q}$ were injected into Foxn1 nu athymic nude mice (Jackson Laboratory) that were 6-weeks-old (through a protocol that was approved by the Institutional Animal Care and Use Committee (IACUC) and complied with related animal research ethical regulations). Tumor sizes were examined using a Vernier caliper every 2-3 days, and the volumes were calculated using V=½×W2×L. When the sizes of tumors reached an average of 1000 $mm^3$, the mice were sacrificed, and the tumors were collected for weight and size analysis.

TetOn inducible system for MCF-HTR MnSOD$^{K68R}$ xenografts. MCF7-HTR cells were infected with pLenti-CMV-IE-Tet-On Advanced-IRES2-ZsGreen1-P2A-Puro plasmid (Clontech, Mountain View, CA, modified by Bioinnovatise, Inc., Baltimore, MD) and selected under puromycin (1 μg/mL) and for green color (MCF7-HTR TetOn). Subsequently, MCF7-HTR TetOn cells were infected with pLenti-SV40 promotor-HygroR-SV40 poly(A)/pTreDual2MnSOD$^{K68R}$-mCherry (MCF7-HTR TetOn MnSOD$^{K68R}$; Clontech, Inc.) and were selected for mCherry and with hygromycin (50 μg/mL). To confirm the activation of the TetOn system, 1 μg/mL of doxycycline (Acros Organics, New Jersey) was added and after 24 h, expression was verified by the presence of mCherry, and fluorescent images were taken. Western blots for were used to validate that expression of MnSOD$^{K68R}$ was activated. Eight-week-old nude mice (Jackson Labs) were injected with 5×106 MCF7-HTR TetOn MnSOD$^{K68R}$ cells into the right hind flank at the time of tamoxifen pellet placement (5 mg pellet, Innovative Research of America, Sarasota, FL). The experimental group was given feed containing doxycycline (625 ppm, Envigo Teklad Diets, Madison, WI); the control group remained on standard feed provided by Northwestern's Animal Facility. Feed was changed every three days for the duration of the experiment. Tumors were measured every other day, and at the end of the experiment, tumors were removed for analysis through a protocol that was approved by the Institutional Animal Care and Use Committee (IACUC) and complied with related animal research ethical regulations.

Immunohistochemistry staining and analysis. Breast cancer tissue array slides (Biomax) were immersed twice in 100% xylene (Sigma) for 5 min and 100% ethanol (Sigma) for 5 min. Slides were sequentially immersed with 95%, 80 and 50% ethanol for 5 min before immersion in water and fixation in 95 mL of 95% ethanol and 5 mL of 37% formaldehyde for 2 min. Slides were then treated with 1% Triton X-100 in 1×PBS (Corning) for 20 min, washed three times in 1×PBS for 5 min, and quenched in 0.3% $H_2O_2$ in 1×PBS for 20 min. Slides were blocked with 10% donkey serum (Sigma), 1% bovine serum albumin (BSA; Sigma) and 0.3% Triton X-100 (Sigma) in 1×PBS for 2 h before treatment with an anti-MnSOD-K68-Ac antibody (1:250 dilution, Abcam #ab137037) for 48 h at 4° C. These slides were subsequently incubated at room temperature for 1 h before being washed three times with 1×PBS for 5 min. Rabbit secondary antibody (1:200 dilution, A0545, Sigma) was diluted in antibody solution and applied to slides for 1 h before being washed three times with 1× PBS for 5 min each. The slides were treated with VECTASTAIN ABC kit (Vector Laboratories) for 45 min following the manufacturer's protocol to detect avidin/biotinylated enzyme complexes. Slides were treated using the DAB peroxidase substrate kit (Vector Laboratories), per the manufacturer's protocol, and stained in hematoxylin (Sigma) for 10 min. Then slides were destained with 100 mL of 70% ethanol and 1 mL of 37% hydrochloric acid before dehydration. The intensities were quantified using HistoQuest software (Tissuegnostics).

Peroxidase Activity Assay.

One-million cells expressing Flag-tagged $MnSOD^{WT}$, $MnSOD^{K68R}$, and $MnSOD^{K68Q}$ were lysed for 30 min in 25 mM Tris-HCl pH 7.4, 150 mM NaCl, 1 mM EDTA, 0.1% NP-40, 5% glycerol, protease inhibitors (BioTool) and TSA (Trichostatin A, Sigma). Lysates were quantified with the Bradford assay (BioRad) and IPed using anti-Flag antibody (Sigma). The peroxidase enzymatic activities of these IPed proteins were determined by using pyrogallol as the substrate. In the reaction mix, the final concentrations were 14 mM potassium phosphate (Sigma), 0.027% (v/v) hydrogen peroxide (Sigma), and 0.5% (w/v) pyrogallol (Sigma). The plate was tapped to mix the sample and reaction reagent, incubated for 10 min at room temperature, and then read at OD 420 nm. The increase in A420 was recorded every 3 min. The AA420/20s was obtained using the maximum linear rate or 0.5-min interval for all the test samples and blanks. The peroxidase activity was calculated using this equation:

Units/mL=[(ΔA420/20 s Test Sample—ΔA420/20 s Blank)(reaction volume)(dilution factor)]/[(12)(0.1)].

Glutathione Analysis.

One-million cells at 70-80% confluency were lysed in 1.34 mM diethylenetriaminepenta-acetic acid (DETAPAC, Sigma) and dissolved in 143 mM sodium phosphate (Sigma). Then 6.3 mM EDTA (Sigma) and 5% 5-sulfosalicylic acid (Sigma) were added to the lysates. Fifty microliters of lysate were mixed with 700 μL 0.298 mM NADPH (Sigma) dissolved in sodium phosphate buffer, 100 μL 6 mM 5,5'-dithio-bis-2-nitrobenzoic acid (DTNB, Sigma) in sodium phosphate buffer, 100 μL water, and 50 μL 0.023 U/μL glutathione reductase (GR) dissolved in water (Sigma). Kinetic absorbance was read at 412 nm every 15 s for 2.5 min using an xMark™ microplate absorbance spectrophotometer (BioRad), and the rates were compared to a standard curve. Tumors were lysed in DETAPAC buffer before being assayed, and protein concentrations were measured for standardization of GSH levels that were normalized using the BCA method.

MnSOD/SOD Enzymatic Activity.

Total SOD and MnSOD activity were determined by an indirect competitive inhibition assay[47]. Superoxide is generated from xanthine by xanthine oxidase and detected by recording the rate of reduction of nitroblue tetrazolium (NBT). SOD scavenges superoxide and competitively inhibits the reduction of NBT. One unit of SOD activity is defined as the amount of protein required to inhibit 50% of the maximal NBT reduction. To obtain the amount of MnSOD activity, 5 mM sodium cyanide was added to inhibit the CuZnSOD enzyme activity. The protein levels in each sample were measured using the BCA protein assay[48,49,50,51].

Western Blot Analysis.

Cells and tissues were washed three times with cold 1×PBS, harvested, and lysed for 30 min in 25 mM Tris-HCl pH 7.4, 150 mM NaCl, 1 mM EDTA, 0.1% NP-40, 5% glycerol with protease inhibitors (BioTool) and TSA (Sigma), then quantified by Bradford assay and immunoblotted with: anti-MnSOD (1:1000 dilution, Millipore, #06-984), anti-MnSOD-K68-Ac (1:1000 dilution, Abcam, #Ab137037), anti-MnSOD-K122-Ac (1:500, Abcam, #Ab214675), anti-SIRT3 (1:1000 dilution, Cell Signaling, #D22A3), anti-IDH2 (1:1000 dilution, Cell Signaling, #56439), anti-IDH2-K413-Ac (1:1000 dilution, Epitomics, Inc, Burlingame, CA (this company has been bought by Abcam, Inc.)), anti-OSCP (1:1000 dilution, Santa Cruz Biotechnology, # sc-365162), anti-OSCP-K139-Ac (1:1000 dilution, Epitomics, Inc, Burlingame, CA), and anti-actin (1:10,000 dilution, Cell Signaling, #4970). Secondary antibody includes anti-rabbit and anti-mouse (1:10,000 dilution, Cell Signaling, #7074, #7076). For the MnSOD tetramerization assay, lysed cells were treated with 0.1% glutaraldehyde for 10 min at room temperature before samples were immunoblotted with anti-MnSOD antibody.

Determination of Cellular Superoxide Levels Using MitoSox.

Steady-state levels of mitochondrial superoxide were estimated using the oxidation of a fluorescent dye, dihydroethidium (DHE) (Life Technologies). Cells were trypsinized, washed, and then labeled in 5 mM pyruvate containing 1×PBS with MitoSox Red (2 μM in 0.1% DMSO) for 20 min at 37° C. After labeling, cells were kept on ice. Samples were analyzed using a Fortessa flow cytometer (Becton Dickinson Immunocytometry System, Inc., Mountain View, California; excitation 488 nm, emission 585, 25 nm band-pass filter). The mean fluorescence intensity (MFI) of 10,000 cells was analyzed in each sample and corrected for autofluorescence from unlabeled cells. The MFI data were normalized to control levels.

Estimation of Cellular $H_2O_2$ Levels Using $CDCFH_2$ Oxidation.

Steady-state levels of $H_2O_2$ were estimated using the oxidation-sensitive 5-(and 6)-carboxy-2',7'-dichlorodihydrofluorescein diacetate ($CDCFH_2$) (Life Technologies). The cells were trypsinized and washed with 1×PBS once and then labeled with $CDCFH_2$ or CDCF (10 μg/mL, in 0.1% DMSO, 15 min) at 37° C. After being labeled, the cells were kept on ice. Samples were analyzed using a Fortessa flow cytometer (Becton Dickinson Immunocytometry System, Inc., Mountain View, California; excitation 488 nm, emission 530 nm, 25 nm band-pass filter). The MFI of 10,000 cells was analyzed in samples and corrected for autofluorescence from unlabeled cells. The MFI data were normalized to control levels.

Cell Survival Experiments Using MnSOD Mimetic GC4419 Treatments.

To test parameters indicative of oxidative stress, a clonogenic assay with hydroxy-Tam and MnPAM dismutase mimetic treatments was performed. Cells were plated at a density of 50,000 cells per 60-mm dish and treated with 1 μM hydroxy-Tam (Sigma) and 5 μM GC4419 (Galera Therapeutics) for a total of 120 h. This protocol was repeated with a fresh medium change every 24 h for 5 days. On day 6, the cells were trypsinized, counted, and replated in control medium using appropriate dilutions, and clonogenic survival was evaluated.

Incorporation of N-(ε)-acetyl-lysine into K68.

BL21 (DE3) pMAGIC chemically competent *E. coli* cells, which were a kind gift from Andrzej Joachimiak, Argonne National Labs, were co-transformed with pEVOL-AcKRS and pET21a-$MnSOD^{K68TAG}$ plasmids or pET21a-wtMnSOD to express MnSOD-K68-Ac and MnSOD-WT proteins. The cells harboring pEVOL-AcKRS and pET21a-MnSOD$^{K68TAG}$ plasmids were incubated in 100 mL LB with 300 μg/mL ampicillin, 50 μg/mL kanamycin, and 50 μg/mL chloramphenicol (37° C., 220 rpm) for 3 h at 37° C., and 50 mM nicotinamide (Sigma) was added to this culture. When OD600 reached 1.1, 2 mM Nε-acetyl-lysine (Sigma) was added to the culture and cells were induced by the addition of 0.4 mM IPTG and 0.2% arabinose (25° C., 180 rpm) for another 20 h. (The bacterial MnSOD expression and lysine acetylation tRNA mutant plasmids used to make physically acetylated MnSOD-K68-Ac were a kind gift from Dr. Jiangyun Wang, Institute of Biophysics, Chinese Academy of Sciences, Beijing, China).

The BL21 (DE3) cells harboring pET21a-wtMnSOD plasmid were cultured in 5 mL LB media with 300 μg/mL ampicillin and 50 μg/mL kanamycin and 1 mL of this culture was incubated in 100 mL LB with 300 μg/mL ampicillin and 50 μg/mL kanamycin (37° C., 200 rpm) overnight. The next day, 1 L of LB with 300 μg/mL ampicillin and 50 μg/mL kanamycin was inoculated with 10 mL of overnight culture, for ~2.5 h until OD600=0.6, and then cells were induced with 0.4 mM IPTG (25° C. 180 rpm) overnight. All purification steps were performed on ice. *E. coli* cells in 1 L LB were harvested by centrifugation (6000 rpm, 10 min, 4° C.) and washed with 50 mL Buffer I containing 20 mM imidazole, 50 mM Tris-HCl, 200 mM NaCl, 5 mM $MgCl_2$, 50 mM nicotinamide, pH=8.0. Then pellets after centrifugation were suspended with 50 mL Buffer I supplemented with 1 mM PMSF and −1 mg/mL lysozyme, and the lysates were incubated at 4° C. for 10 min. Then protein was extracted by sonication cycling (5 s on, 6 s off, 25 min). The extract was clarified by centrifugation (13,000×g, 30 min, 4° C.) and the pellet discarded. In all, 0.2 mL Ni2+-NTA beads were added to the supernatant and incubated with agitation at 4° C. for 1 h.

Beads were transferred into a column and washed three times with Buffer I containing increasing imidazole gradient (50, 75, 100 mM) and protein was eluted in 1 mL Buffer I supplemented with 200 mM imidazole. The proteins were analyzed by SDS-PAGE and then concentrated using Ultra-15 Centrifugal Filter Unit (10 kDa, Millipore Amicon™, USA UFC800324). The eluted protein was then re-buffered to Buffer 11 (50 mM Tris-HCl, 200 mM NaCl, 5 mM $MgCl_2$, 50 mM nicotinamide, pH 8.0) and loaded onto an equilibrated Ni2+-NTA ÄKTA FPLC Purifier system with GE HisTrap HP columns (Product #GE17524701) and further purified by a Superdex 200 Increase 10/300 GL column (GE Healthcare, Product #GE28-9909-44) in a buffer containing 50 mM potassium phosphate (pH=7.8). Peak fractions were collected using an automated fraction collector. A280 as a function of elution volume/time was also recorded[13,27,28]. The peak protein fraction concentrations were determined and immunoblotted with anti-MnSOD and anti-MnSOD-K68-Ac. The remaining purified proteins were measured for peroxidase activity and MnSOD activity. The eluted fractions were then subjected to further analysis. A calibration curve was generated using a gel filtration low and high molecular weight kit (GE Healthcare) according to the manufacturer's instructions and is shown FIG. 4*e*, which was used to determine the relative size of peak 1 and peak 2.

Immunofluorescence Sample Preparation and Image Acquisition.

Cells seeded on glass coverslips were fixed in 4% paraformaldehyde and then blocked with 1% BSA and 10% normal goat serum in 1× PBS. Cells were incubated with anti-Ki-67 (c-bioscience) antibody in 1×PBS followed by incubation with goat anti-rabbit IgG conjugated with Alexa Fluor 647 (Invitrogen) in 1×PBS with 5% goat serum. Cells were washed in 1×PBS, mounted, and imaged with a fluorescence microscope. Fluorescence images were captured using a laser scanning confocal microscope (Nikon A1R). The paired images in all the figures were collected at the same gain and offset settings. Post-collection processing was applied uniformly to all paired images. The images were either presented as a single optic layer after acquisition in z-series stack scans from individual fields or displayed as maximum intensity projections to represent confocal stacks.

Statistical Analysis.

Statistical analysis was performed using GraphPad Prism for Windows (GraphPad Software, San Diego, CA). Error bars indicate mean±SEM. One-way ANOVA analysis with Tukey's post-analysis was used to study the differences among three or more groups. For two column bar graphs (i.e., is a significant difference between the means of two groups), a t-test was used. All experiments were repeated at least three times. Statistical significance was assumed at $p<0.05$.

Example 2

Most men diagnosed with metastatic castration-resistant prostate cancer (mCRPC) will initially exhibit an excellent response to androgen-deprivation therapy (ADT) and/or androgen receptor inhibition, including enzalutamide (ENZ), both of which target the Androgen Receptor (AR) Signaling pathwaya. However, with time nearly most men will exhibit progression of their disease. As such, the lethality in men with AR pathway therapy resistance is due, at least in significant part, to the development of resistance against these agents and importantly, a lack of effective alternate systemic therapies[82]. Thus, the identification of the specific processes leading to lack of response to AR pathway inhibition, including ADT (ADTR) and ENZ (ENZR) resistance, the underlying mechanism, new therapeutic interventions, and predictive signatures is of importance. In this regard, multiple mechanisms have been identified that contribute to ADTR/ENZR, which are mainly focused on the AR, including AR amplification and hypersensitivity, AR mutations leading to promiscuity, mutations in coactivators/co-repressors, and AR-independent intratumoral androgen production[81,83,84], used as escape pathways that provide alternative proliferative and survival stimuli. While most men develop ADTR through a mechanism involving altered AR signaling, an emerging mechanism of resistance centers on the development of lineage plasticity properties[85-87].

In an NCI white paper (Beltran, 2019) and a seminal review (Yuan, 2019, Cancer Discovery)[88] it was proposed that cellular lineage plasticity (or stemness), due to microenvironmental cues, stochastic genetic and/or epigenetic alterations, or treatment-imposed selective pressures, contributes to tumor heterogeneity and the development of resistant tumor cell phenotypes. The development of a lineage plasticity phenotype has recently emerged as an important mechanism of treatment resistance in prostate cancer[81,84] that occurs in roughly 20% of advanced prostate cancer patients, representing important clinical and therapeutic implications[86,87]. In this regard, prolonged exposure to ADT is associated with a subset of tumor cells exhibiting a loss of AR signaling dependence and luminal prostate markers, and the induction of stem cell-like developmental programs[85,86]. Disrupted mitochondrial metabolism, including aberrant ROS levels, is one potential mechanism leading to a drug resistance phenotypes rooted in the development of lineage plasticity-like properties[87]. Thus, lineage plasticity is defined as CRPC associated with the loss of AR-regulated lineage characteristics that, where plasticity is driven by the disruption of the cells' normal metabolic physiology, leads to the acquisition of new phenotypes, including AR independence, sustained tumor cell proliferation, and ENZR.

Detoxification activity of antioxidant enzymes is dysregulated in tumors[89,90], and the subsequent loss of metabolic homeostasis corresponds with tumors that exhibit resistance to anticancer agents, including ADT/ENZ[89-91]. MnSOD is a mitochondrial detoxification enzyme (i.e., a superoxide dismutase) that, when either deleted or dysregulated, plays a role in metabolism, oncogenesis, and a therapeutic resistance phenotype. MnSOD-Ac may act as a nexus between the metabolic and bioenergetic balance and tumor cell growth and/or survival, and, under specific cellular conditions, it can function as an in vivo driver of an ENZR tumor phenotype. A mitochondrial signaling axis centered on MnSOD-Ac has been identified which when dysregulated, disrupts cell metabolism, leading to aberrant ROS (Zhu, 2019, Nature Commun.)[52] and also abnormally stabilized $HIF2_{\alpha}$ activates dedifferentiation programs (He, 2019; Proc. Natl. Acad. Sci.)[55]. In certain cases, when MnSOD-K68-Ac exists outside of its normal physiological context, modeled by $MnSOD^{K68Q}$ expression, it disrupts cellular metabolism, increases ROS levels, and stabilizes $HIF2_{\alpha}$, leading to a lineage plasticity phenotype and ENZR tumors cells[89,90]. Accordingly, targeting the MnSOD-K68-Ac axis with appropriate therapeutic agents (i.e., MnPAM dismutase mimetics such as GC4419) may decrease lineage plasticity/stemness and provide an effective therapeutic option.

Figure 19A:
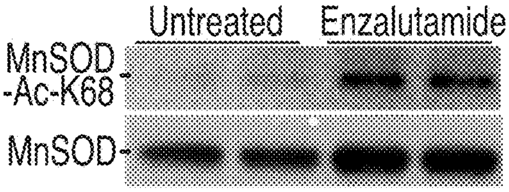
FIGS. 19*a*-19*c* are images and a plot showing that enzalutamide-resistant prostate cancer cells (LNCaP-ENZR) showed increased acetylation of lysine 68 on MnSOD, and decreased levels of MnSOD tetramer form and activity.
Figure 19B:
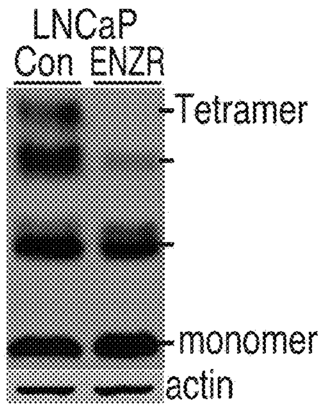

ENZR Prostate Tumor Cells Exhibit Increased MnSOD-K68-Ac and Decreased MnSOD Activity To address whether there is a link between MnSOD-K68-Ac and ENZR, two ENZ sensitive prostate tumor cell lines were used, LNCaP or 22RV1, which were cultured in 5 μM of ENZ for 3 weeks and then continuously grown at 10 μM, using an established method[91] to select for ENZR cells. Immunoblotting of LNCaP-ENZR (FIG. 19*a*) or 22RV1-ENZR (data not shown) cells showed an increase in MnSOD-K68-Ac, implying altered MnSOD biology may be one potential mechanism driving ENZR. Since lysine 68 acetylation alters the surface charge at the MnSOD tetramerization interface, we assessed the oligomerization state of MnSOD in LNCaP-ENZR cells. Cross-linking experiments showed a decrease in the tetramer complex (FIG. 19*b*). This gel also showed trimer and dimer bands, which are not observed using a semi-native separation method, which imply these are artifacts bands likely due to the harsh glutaraldehyde crosslinking isolation method.

Figure 19C:
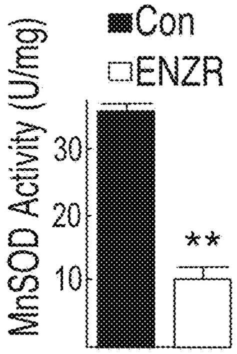

LNCaP-ENZR (FIG. 19*c*) and 22RV1-ENZR (data not shown) cells exhibited a decrease in MnSOD activity, and increased cellular ROS levels (data not shown). These results imply that when MnSOD-K68-Ac is increased due to chronic ENZ exposure, or with enforced expression of the MnSOD K68 acetylation mimic mutant gene ($MnSOD^{K68Q}$), it disrupts cell metabolism, including aberrant ROS levels, leading to an ENZR phenotype in prostate tumor tissue culture cells. Finally, these are pooled cells and thus, it seems likely that subsets of cells have different mechanisms of ENZR, however, it also appears that dysregulated MnSOD biology is at least one mechanism. Accordingly, it was shown that enzalutamide-resistant prostate cancer cells (LNCaP-ENZR) showed increased acetylation of lysine 68 on MnSOD, and decreased levels of MnSOD tetramer form and activity.

Expression of $MnSOD^{K68R}$ Reversed ENZR, while in Contrast, $MnSOD^{K68Q}$ Induced ENZR in PCa Cells To determine if the MnSOD-K68-Ac-ROS axis plays a role in the ENZR phenotype, ENZR tissue culture model cells were infected with the MnSOD deacetylation mimic mutant ($MnSOD^{K68R}$), which enriches for tetrameric MnSOD and increases MnSOD activity. Clonogenic cell survival experiments, done 72 hrs. after infection in cells cultured in 10 μm ENZ, showed LNCaP-ENZR (FIG. 20*a*, bar 1 vs. 2) and 22RV1-ENZR (data not shown) cells infected with lenti-$MnSOD^{K68R}$, converted from ENZR to a sensitive phenotype. $MnSOD^{K68R}$ levels were confirmed via immunoblotting with an anti-Flag antibody. $MnSOD^{K68R}$ expression also decreased cellular ROS levels (data not shown), implying that when MnSOD-K68-Ac exists outside of its normal physiological context it disrupts cell metabolism leading to an ENZR phenotype. Thus, expression of an acetylation mimic, which would also disrupt MnSOD biology, should also induce an ENZR phenotype. Indeed, LNCaP cells infected with lentivirus expressing the acetylation mimic mutant gene ($MnSOD^{K68Q}$) previously shown to mimic MnSOD-K68-Ac (Zhu, 2019*, Nature Commun.*) also exhibited an ENZR phenotype. Accordingly, it was shown that mimicking deacetylation of MnSOD-K68 with $MnSOD^{K68R}$ expression reversed the ENZR in LNCaP-ENZR cells while mimicking acetylation of MnSOD-K68 with $MnSOD^{K68Q}$ induces enzalutamide resistance in LNCaP cells.

ENZR Resistance is Reversed by Mimicking Lysine 68 Deacetylation with MnPAM Dismutase Mimetic.

Figure 20A:
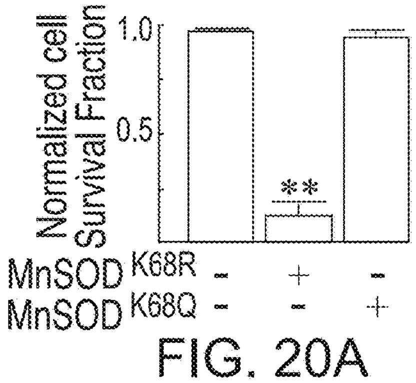
FIGS. 20*a*-20*b* are plots showing that mimicking deacetylation of MnSOD-K68 with MnSOD$^{K68R}$ expression reversed the ENZR in LNCaP-ENZR cells while mimicking acetylation of MnSOD-K68 with MnSOD$^{K68Q}$ induces enzalutamide resistance in LNCaP cells.
Figure 20B:
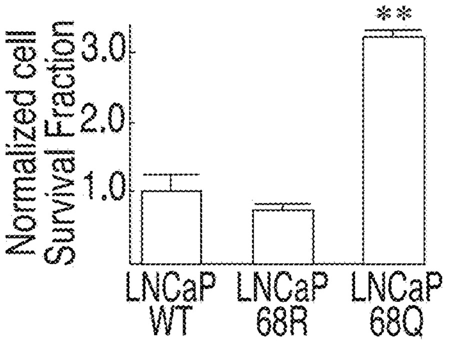
Figure 21A:
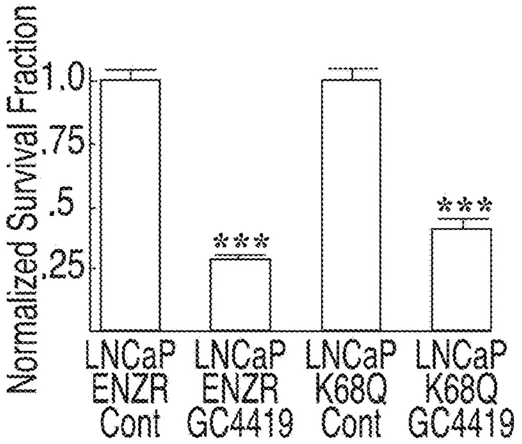
FIGS. 21*a*-21*b* are a chart and graph showing that pharmacologically mimicking the activity of deacetylated lysine 68 MnSOD with a manganese pentaazamacrocyclic dismutase mimetic both inhibited the growth of LNCaP-ENZR tumors and reversed the enzalutamide resistance in LNCaP-ENZR/LNCaP-MnSOD$^{K68Q}$ cells and tumors.
Figure 21B:
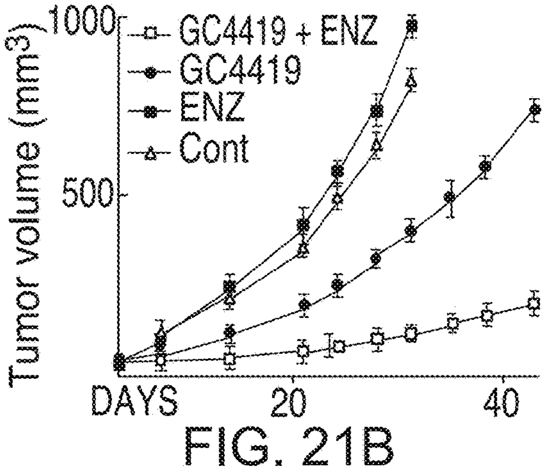

The data in FIGS. 20*a*-20*b* suggests that the disruption of MnSOD biology, due to aberrant MnSOD-K68-Ac and ROS levels, may play a role, at least in part, in the development of the ENZR phenotype. Thus, it was surmised that restoring MnSOD activity, using the manganese pentaaza macrocyclic ring complex (MnPAM) dismutase mimetic GC4419, an agent that catalytically converts superoxide to hydrogen peroxide via same the catalytic mechanism used by homotetrameric MnSOD, would reverse/convert the ENZR to a sensitive phenotype. Indeed, LNCaP-ENZR cells, treated with GC4419, exhibited a significant decrease in tumor cell survival in the presence of ENZ, measured by clonogenic survival experiments (FIG. 21*a*, left two bars). In addition, the ENZR seen in LNCaP-$MnSOD^{K68Q}$ cells (FIG. 21*a*, left two bars) was also converted to a sensitive phenotype by GC4419 exposure (right two bars). LNCaP-$MnSOD^{K68Q}$ cells, which exhibited ENZR (FIG. 20*b*, bar 3), were also used for in vivo murine hind limb xenografts experiments with exposure to GC4419. The dose and pharmacokinetics for GC4419 were based on data for murine models[92-93]. LNCaP-$MnSOD^{K68Q}$ cells grown in mice with or without ENZ treatment (FIG. 21*b* top plot of boxes in graph) exhibited similar growth characteristics, consistent with LNCaP-$MnSOD^{K68Q}$ xenografts being ENZR. In contrast, treatment of LNCaP-$MnSOD^{K68Q}$ murine xenografts with GC4419 (second from bottom plot of boxes in graph), and to a greater extent GC4419+ENZ (bottom plot of boxes in graph), led to a significant inhibition of xenograft growth. Accordingly, it was shown that pharmacologically mimicking the activity of deacetylated lysine 68 MnSOD with a manganese pentaazamacrocyclic dismutase mimetic both inhibited the growth of LNCaP-ENZR tumors and reversed the enzalutamide resistance in LNCaP-ENZR/LNCaP-$MnSOD^{K68Q}$ cells and tumors.

This result may explain surprising clinical data showing that MnSOD levels, under specific conditions, positively correlate with more aggressive breast cancers, implying that MnSOD can also act as a tumor promoter, instead of its more established function as a tumor suppressor (TS)[95-97]. These studies, and previous data[52,55], suggest a dichotomous role for MnSOD where the tetramer acts as a TS, theoretically during the early, proliferative stage of tumor initiation. However, once carcinogenesis progresses, monomeric MnSOD-K68-Ac may establish more aggressive tumor phenotypes. Thus, MnSOD may switch from a tetrameric SOD to a monomeric peroxidase, under specific conditions, such as nutrient status, genetic damage, or cell stress. In this model, we surmise that the cellular and/or mitochondrial stress from normal metabolic requirements for energy generation, however, continuous ENZ exposure disrupts MnSOD biology, due to MnSOD-K68-Ac, shifting the balance towards higher levels of the monomer form the MnSOD. Thus, this process may play a role directly leading to ENZR, and more broadly AR pathway directed therapy resistance, as well as other mechanisms promoting tumor growth. In addition, the analogous observations in Example 1 of MnSOD-K68-Ac supporting estrogen pathway directed therapy resistance, such as TamR, suggest that this is a shared mechanism of resistance to anti-cancer hormone pathway directed therapy. Lastly, restoring normal deacetylated lysine 8 MnSOD activity with MnPAM dismutase mimetics such as GC4419 may restore cellular metabolism, and importantly, reversing the ENZR, and more generally hormone pathway directed therapy resistance, tumor cell phenotype.

Prostate Tumor Grade Correlates with Increased MnSOD-K68-Ac Levels

Figure 22A:
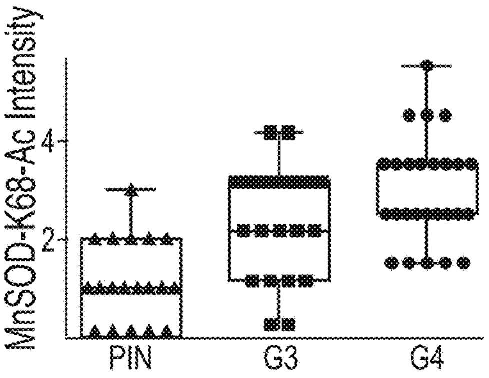
FIGS. 22*a*-22*b* are a plot and images showing MnSOD-K68-Ac staining correlates with increasing Gleason grade in human prostate cancer tissue samples.
Figure 22B:
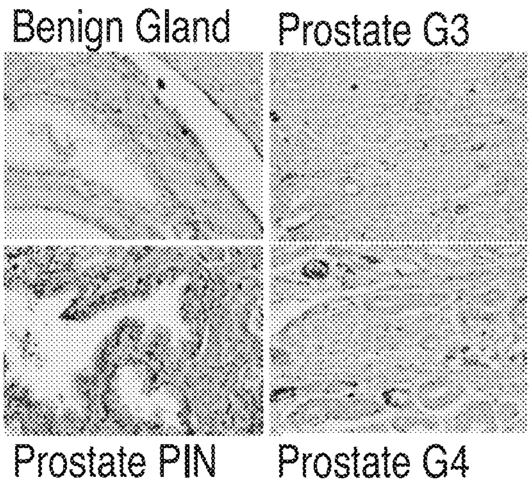

Using genomics, a correlative link has been shown between MnSOD-Ac and prostate cancer[98]. To extend this data, a tissue microarray (TMA) containing twenty-one PIN, 28 grade 3, and 25 grade 4 prostate tumors, was stained with our anti-MnSOD-K68-Ac antibody, and samples were scored by staining intensity. Quantification by Tissue-Gnostics software showed a significant increase in MnSOD-K68-Ac staining that correlated with increasing tumor grade (FIGS. 22*a,b*). These results show there are human prostate tumors that exhibit a MnSOD-K68-Ac (AcK68) signature, and that intensity of that AcK signature is associated with more aggressive and more progressed disease.

Dysregulation of the MnSOD-K68-Ac/ROS/HIF$2_\alpha$ Axis Directs a Lineage Plasticity ENZR Tumor Phenotype.

Figure 23A:
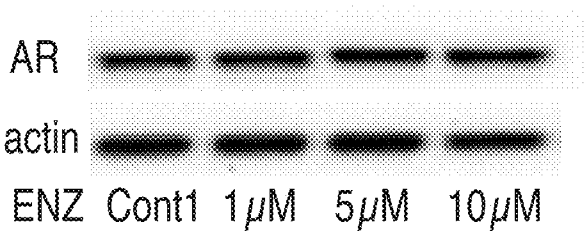
FIGS. 23*a*-23*b* are an image and plot showing that LNCaP-MnSOD$^{K68Q}$ cells do not exhibit changes in expression or activity of androgen receptor (AR).
Figure 23B:
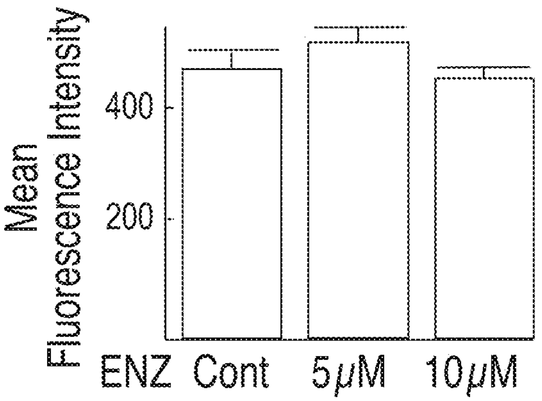
Figure 24A:
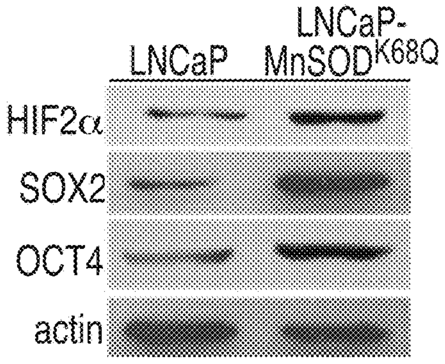
FIGS. 24*a*-24*b* are an image and plot showing that dysregulation of the MnSOD-Ac-K68-ROS-$HIF2_{\alpha}$ axis directs a stemness phenotype in prostate cancer cells, that is also associated with resistance to androgen pathway therapy.
Figure 24B:
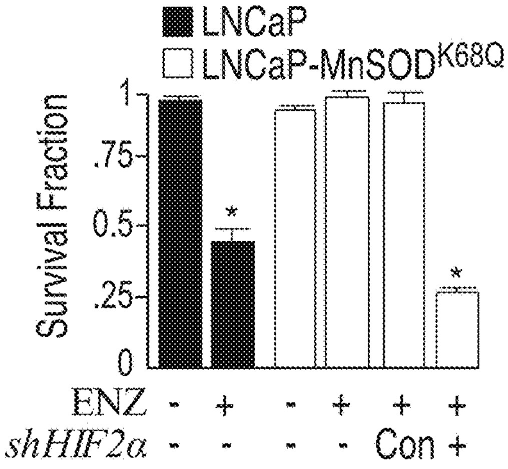

While mechanisms of ENZR include a wide range of genetic mutations, AR splice variants, dysregulation of AR, and AR-related signaling pathways, there are a subset of metastatic prostate tumors that exhibit ENZR, via a stem cell-like mechanism, which is independent of AR-signaling[87]. To determine if the mechanism by which MnSOD$^{K68Q}$ expression leads to ENZR, is via dysregulation of AR signaling, LNCaP-3×AR-LNCaP cells were used that contain a mCherry reporter gene downstream of 3×AR binding sites associated with a minimal promoter, which is a proxy to assay AR signaling. These cells were infected with lenti-MnSOD$^{K68Q}$ and the subsequent cells (LNCaP-3×AR-Cherry-MnSOD$^{K68Q}$) exhibited ENZR, similar to the LNCaP-MnSOD$^{K68Q}$ cells (see FIG. 20*b*, bar 3). Surprisingly, these cells did not exhibit any changes in AR protein levels (FIG. 23*a*) or AR transcriptional activity as measure by mCherry expression (FIG. 23*b*), compared to control cells. Rather, these cells exhibited an increase in HIF$2_\alpha$, SOX2, and Oct4 levels, three downstream biomarkers linked to lineage plasticity (FIG. 24*a*). This is of importance since HIF$2_\alpha$ stabilization can induce a lineage plasticity phenotype, and ENZR. Lastly, HIF$2_\alpha$ knockdown decreased both SOX2 and Oct4 levels (data not shown) and reverted ENZR tumor cells to a sensitive phenotype (FIG. 24*b*, bar 5 vs. 6). Thus, it is surmised that disrupted cell metabolism, due to expression of MnSOD$^{K68Q}$, stabilizes HIF$2_\alpha$ leading to lineage plasticity properties, that is a potentially novel mechanism for the ENZR phenotype in a subset of prostate tumors. Thus, these results suggest the MnSOD-K68-Ac/ROS/HIF$2_\alpha$ axis may be a therapeutic target for new interventions. Accordingly, it was shown that LNCaP-MnSOD$^{K68Q}$ cells do not exhibit any changes in expression or activity of androgen receptor (AR). It was also shown that dysregulation of the MnSOD-Ac-K68/ROS/HIF$2_\alpha$ axis directs a stemness phenotype in prostate cancer cells, that is also associated with resistance to androgen pathway therapy.

Example 3

Estrogen receptor positive (ER+) invasive ductal cancers (IDCs), the most common type of breast cancer, are commonly treated with selective estrogen receptor modulators (SERMs), which have been shown in multiple studies to improve clinical outcomes[99,100]. ER+ IDCs are classified as luminal A versus luminal B cancer (LuBCa). LuBCa's, which account for most breast cancer deaths in America, exhibit aggressive tumor characteristics including an elevated proliferative index (high Ki-67), poorly differentiation (high grade), and an increased risk of recurrence and metastasis[101,102]. The lethality in women with LuBCa is due, at least in part, to the development of resistance against selective estrogen receptor modulators (SERMs) and a lack of alternative systemic therapies[103]. Thus, the identification of mechanism(s) of SERM resistance is of great clinical importance.

While the ER pathway plays a pivotal role in breast cancer, and endocrine therapy blocking ER signaling is highly effective, over time, a small subset of ER+ women recur due to the development of endocrine resistance[99,100]. Multiple mechanisms of endocrine resistance have been identified, including deregulation of various components of the ER signaling pathway, altered cell cycle and cell survival processes, and the activation of escape pathways that provide tumors with alternative proliferative and survival stimuli[99,104]. While most resistance to SERMs involves one of these processes, an increasingly accepted mechanism involves the development lineage plasticity. In this regard, a recent NCI white paper (Beltran, 2019)[86] and a seminal review (Yuan, 2019, *Cancer Discovery*)[88] stated lineage plasticity, due to microenvironmental cues, stochastic genetic/epigenetic, metabolic alterations, or other therapy-imposed selective pressures, contributes to tumor heterogeneity and importantly, to the development of resistant phenotypes. Lineage plasticity is understood as a reversible or irreversible reprogramming where a mature somatic cell can display plasticity, via a change in cell "identity", by dedifferentiation to a progenitor-like state or by transdifferentiation to an alternative differentiated cell type, leading to the emergence of new phenotypes[105-109]. Disruption of mitochondrial physiology may be a novel mechanism leading to lineage plasticity and how tumor cells establish resistant phenotypes to therapeutic interventions[110,111]. Lineage plasticity may thus also lead to a therapy resistance phenotype in a subgroup of ER+ LuBCa IDCs.

Antioxidant enzymes are dysregulated in tumors[108,109], and the subsequent loss of metabolic homeostasis corresponds with tumor cells exhibiting therapy resistance[108-110]. Manganese superoxide dismutase (MnSOD) is a key mitochondrial enzyme that, when deleted or dysregulated, plays a role in oncogenesis, and, importantly, therapy resistance.

While a mechanistic link between the dysregulation of mitochondrial ROS, MnSOD activity, and tumor cell resistance has long been suggested, rigorous models to support this idea are limited. Levels of MnSOD acetylation (Ac) may, at least in some part, connect metabolic and bioenergetic balance and tumor cell growth and/or survival, and, under specific cellular conditions, function as an in vivo driver of tumor resistance by inducing lineage plasticity. For example, a mitochondrial signaling axis centered on MnSOD-Ac exists, which when dysregulated, disrupts cell metabolism, leading to aberrant ROS levels (Zhu, 2019, *Nature Commun.*)[52] and abnormally stabilizes $HIF2_{\alpha}$, which activates dedifferentiation programs (He, 2019; *Proc. Natl. Acad. Sci.*)[55] Thus, it appears MnSOD exhibits a dichotomous function, based on its lysine 68 (K68) acetylation status, where the deacetylated homotetrameric form acts as a protective detoxification enzyme against persistent/aberrant ROS. In contrast, K68-Ac inhibits homotetramer formation and shifts the MnSOD equilibrium towards a predominantly monomeric form of MnSOD that functions as a peroxidase and/or oncoprotein. Thus, when MnSOD-K68-Ac exists outside of its normal physiological context, for example as modeled by $MnSOD^{K68Q}$ expression, it disrupts cellular metabolism, increases ROS levels, stabilizes $HIF2_{\alpha}$, and promotes lineage plasticity and a PanR (multi-therapy resistance) phenotype[112,113]. Accordingly, displacing the MnSOD-K68-Ac axis with a suitable MnPAM dismutase mimetic (e.g., GC4419) may provide an effective new therapeutic option to address resistance to multiple therapies.

MCF7-$MnSOD^{K68Q}$ Cells Exhibited Resistance to Fulvestrant (Fulv) and Palbociclib (Palb)

Figure 25A:
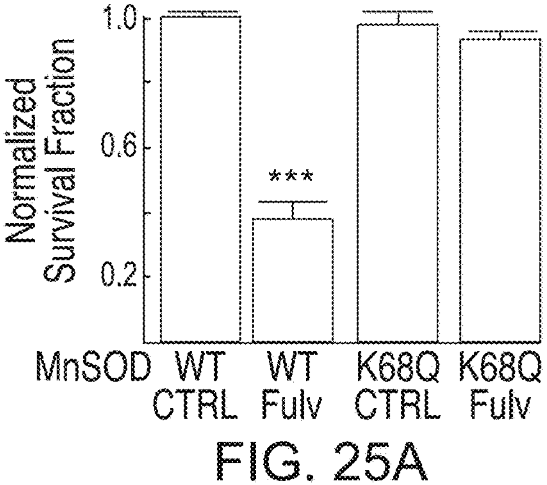
FIGS. 25*a*-25*c* are graphs showing that mimicking acetylation of MnSOD-K68 with $MnSOD^{K68Q}$ expression in breast cancer cells induces fulvestrant resistance (Fulv-R) and palbociclib resistance (Palb-R), and that pharmacologically mimicking the activity of deacetylated lysine 68 MnSOD with a manganese pentaazamacrocyclic dismutase mimetic both inhibited the growth of $MnSOD^{K68Q}$ breast cancer cells and restores their response to palbociclib.
Figure 25B:
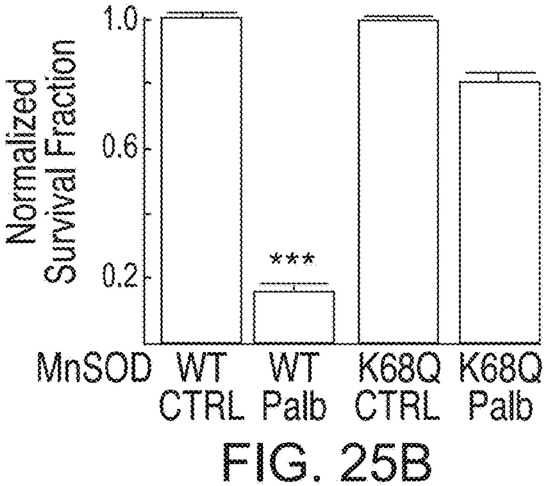
Figure 25C:
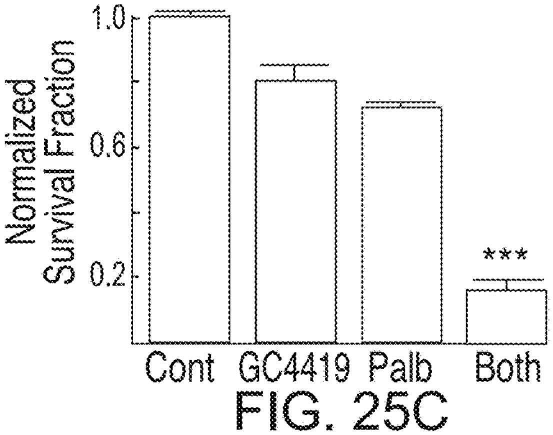

The PALOMA-3[114] study showed that a combination of Fulv, an estrogen receptor disruptor, and Palb, a cell cycle inhibitor, improved progression-free survival (PFS), compared to Fulv alone, yet no survival benefit was observed in endocrine-resistant women. To assess whether cells expressing $MnSOD^{K68Q}$ would exhibit resistance to these agents, clonogenic tumor cell survival studies were performed that that showed MCF7- $MnSOD^{K68Q}$ cells exhibited resistance to Fulv (Fulv-R, FIG. 25*a*) and Palb (Palb-R, FIG. 25*b*), compared to MCF7 cells expressing $MnSOD^{WT}$ (bars 2 vs. 4). It was also shown that combining the MnPAM dismutase mimetic GC4419 and Palb led to increased MCF7-$MnSOD^{K68Q}$ tumor cell killing (FIG. 25*c*). Accordingly, it was shown that mimicking acetylation of MnSOD-K68 with $MnSOD^{K68Q}$ expression in breast cancer cells induces fulvestrant resistance (Fulv-R) and palbociclib resistance (Palb-R), and that pharmacologically mimicking the activity of deacetylated lysine 68 MnSOD with a manganese pentaazamacrocyclic dismutase mimetic both inhibited the growth of $MnSOD^{K68Q}$ breast cancer cells and restores their response to palbociclib.

Figure 26A:
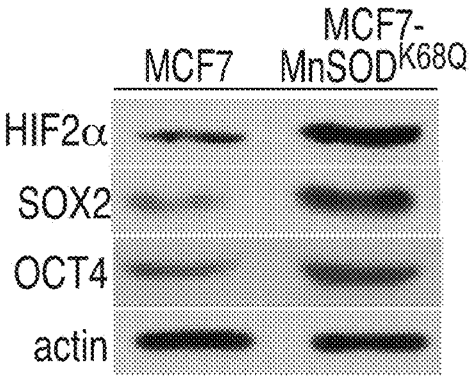
FIGS. 26*a*-26*b* are an image and a graph showing that dysregulation of the MnSOD-Ac-K68/ROS/$HIF2_{\alpha}$ axis directs a stemness phenotype in breast cancer cells, that is also associated with resistance to estrogen pathway therapy.
Figure 26B:
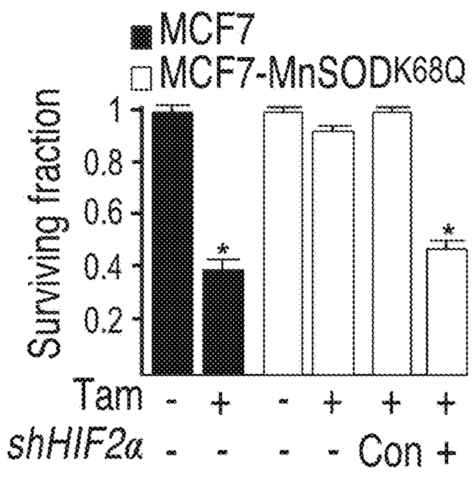

Disrupting the MnSOD-Ac-K68/$HIF2_{\alpha}$ Axis Leads to Lineage Plasticity in Breast Cancer Cells Disrupting mitochondrial metabolism can reprogram tumors, including breast cancers, to exhibit lineage plasticity[115], a cellular developmental process leading to alternative cell "fates" and tumor resistance phenotypes, due to changes in cell environments, e.g., genetic/epigenetic damage or exposure to therapeutic agents[104,116]. MCF7-$MnSOD^{K68Q}$ and T47D-$MnSOD^{K68Q}$ cells did not exhibit changes in ER signaling, or ER-related pathways, implying that TamR emerges via an ER-independent mechanism[54]. However, it is also shown that MCF7-$MnSOD^{K68Q}$ cells exhibited increased $HIF2_{\alpha}$ levels (FIG. 26*a*), known to promote lineage plasticity properties. In addition, levels of OCT4 and SOX2, two established stemness markers, were also increased (FIG. 26*a*). Importantly, $HIF2_{\alpha}$ knockdown also decreased SOX2 and OCT4 levels (data not shown) as well as converted the TamR cells to a sensitive tumor cell phenotype (FIG. 26*b*, bar 5 vs. 6). These results are consistent with published data where $HIF2_{\alpha}$ correlates with increased risk of distant recurrence and poor outcomes. This indicates that induction of lineage plasticity may be a mechanism leading to more aggressive tumors and a TamR phenotype in breast tumor cells expressing $MnSOD^{K68}$Q. Accordingly, it was shown that dysregulation of the MnSOD-Ac-K68/ROS/$HIF2_{\alpha}$ axis directs a stemness phenotype in breast cancer cells, that is also associated with resistance to estrogen pathway therapy.

Aberrant $HIF2_{\alpha}$ Levels Promote Lineage Plasticity, Leading to Chemoresistance and Metastasis.

Figure 27A:
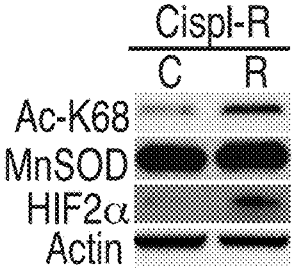
FIGS. 27*a*-27*c* are an image and graphs showing that MnSOD-Ac-K68/ROS/$HIF2_{\alpha}$ dysregulation directs PanR (multi-therapy resistance to cancer therapeutics).
Figure 27B:
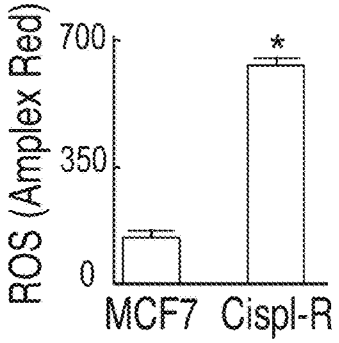
Figure 27C:
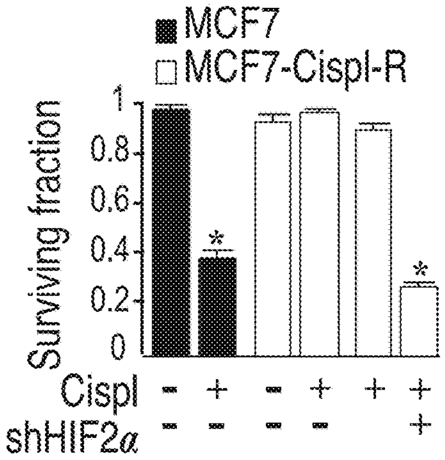

Breast tumor cells expressing $MnSOD^{K68Q}$ may exhibit a PanR tumor cell phenotype of resistance to multiple agents commonly used to treat women with LuBCa. Thus, MCF7 cells were selected for cisplatin resistance (Cispl-R) by 3 months of exposure to 5 μM Cispl. These MCF7-Cispl-R cells exhibited an increase in MnSOD-K68-Ac and $HIF2_{\alpha}$ levels (FIG. 27*a*) and also exhibited increased ROS levels (FIG. 27*b*), implying aberrant MnSOD-K68-Ac, via increased ROS levels, leads to $HIF2_{\alpha}$ stabilization. To test this idea, we showed that pharmacologically mimicking the activity of deacetylated lysine 68 MnSOD with GC4419 or $HIF2_{\alpha}$ knockdown decreased cell ROS levels (data not shown). Lastly, MCF7-Cispl-R treated with GC4419 or $shHIF2_{\alpha}$ showed decreased SOX2 and OCT4 levels (data not shown), and converted the Cispl-R cells to a sensitive phenotype (FIG. 27*c*). This data implies that $HIF2_{\alpha}$ stabilization, due to aberrant MnSOD-K68-Ac and ROS levels, leads to lineage plasticity and a Cispl-R phenotype. Accordingly, it was shown that MnSOD-Ac-K68/ROS/$HIF2_{\alpha}$ dysregulation directs PanR (multi-therapy resistance to cancer therapeutics). Based on this data, we propose that MnSOD-K68-Ac promotes aberrant ROS and $HIF2_{\alpha}$ levels, leading to the enrichment of stemness properties that induce a breast tumor cell PanR phenotype that is sensitive to, and may be reversed by, pharmacologically mimicking the activity of deacetylated lysine 68 MnSOD with a manganese pentaazamacrocyclic dismutase mimetic.

Example 4

Manganese superoxide dismutase (MnSOD) acetylation (Ac) is a key post-translational modification that has important regulator detoxification activity in various disease models. MnSOD lysine-68 (K68) acetylation (AcK68) leads to a change in function from a superoxide-scavenging homotetramer to a peroxidase-directed monomer. Estrogen receptor positive (ER+) breast cancer cell lines (MCF7 and T47D), selected for continuous growth in cisplatin (CDDP) and doxorubicin (DXR), exhibited a concentration dependent increase in MnSOD-K68-Ac. In addition, MnSOD-K68-Ac, as modeled by the expression of a validated acetylation mimic mutant gene ($MnSOD^{K68Q}$) also leads to therapy resistance to CDDP and DXR, loss of tetrameric MnSOD, altered mitochondrial structure and morphology, and aberrant cellular metabolism. $MnSOD^{K68Q}$ expression in mouse embryo fibroblasts (MEFs) induced an in vitro transformation permissive phenotype.

Figure 28A:
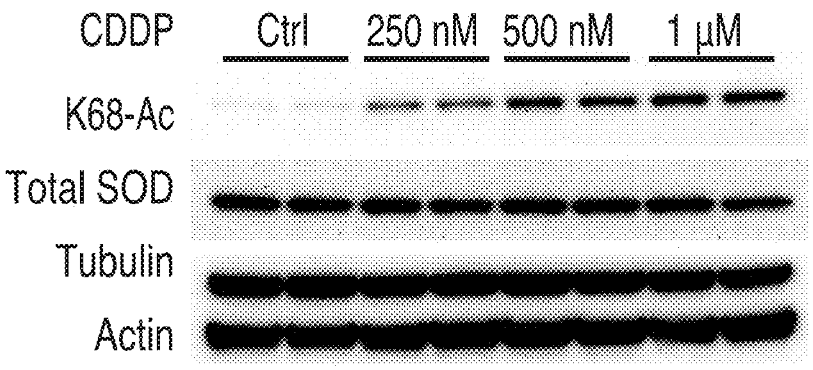
FIGS. 28*a*-28*f* are images and a graph showing that cisplatin and doxorubicin-resistant breast cancer cells as an example of multi-therapy resistance exhibit an increase in MnSOD-K68-Ac and that mimicking acetylation of MnSOD-K68 with $MnSOD^{K68Q}$ expression in non-resistant breast cancer cells increases their resistance to chemotherapy consistent with the PanR phenotype.
Figure 28B:
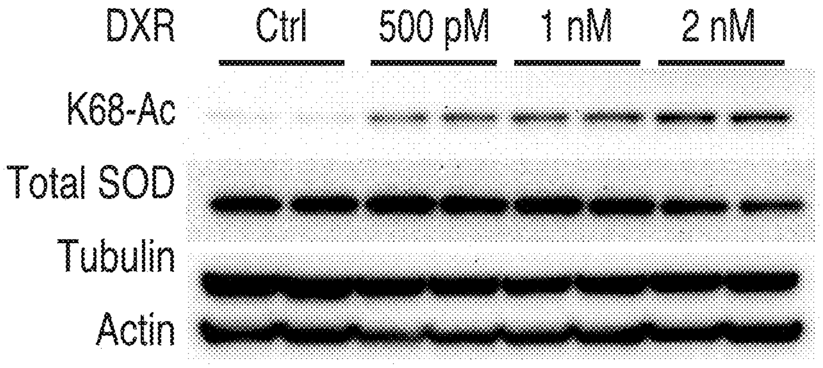
Figure 28C:
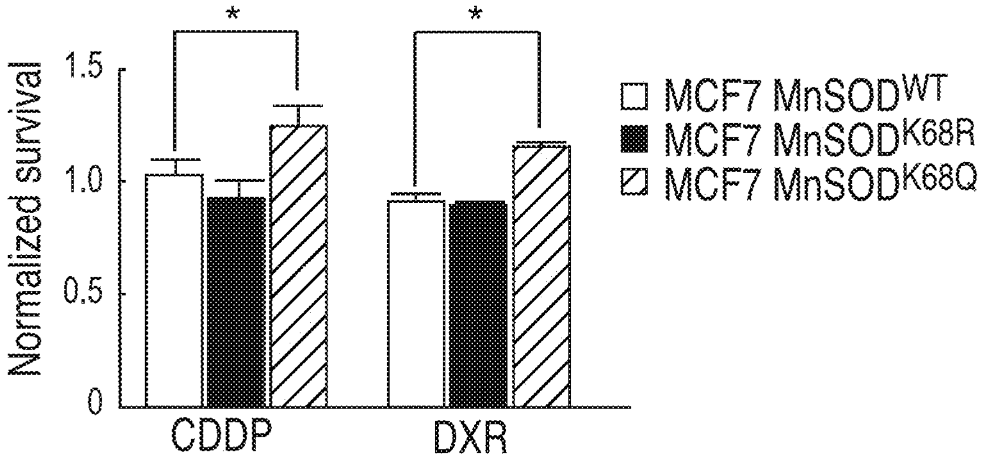
Figure 28D:
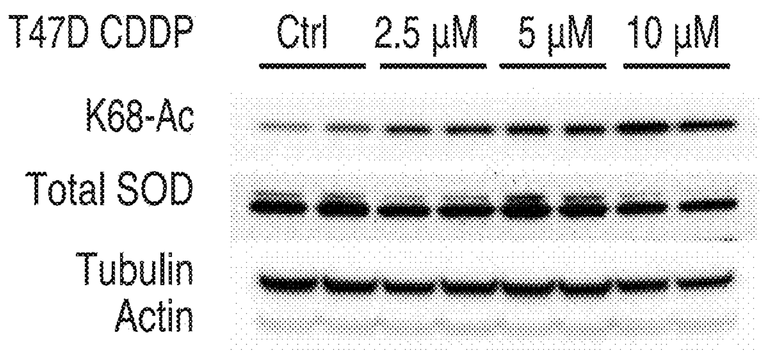
Figure 28E:
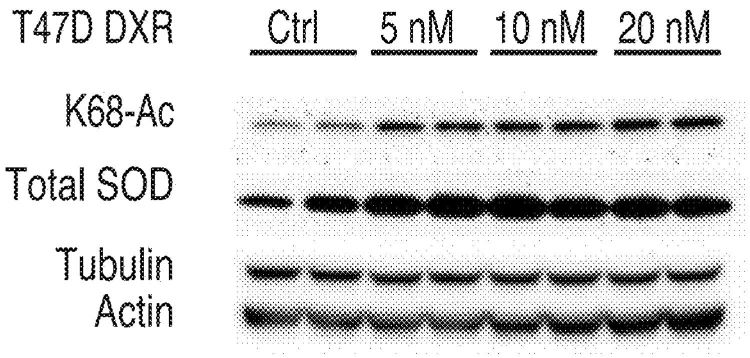
Figure 28F:
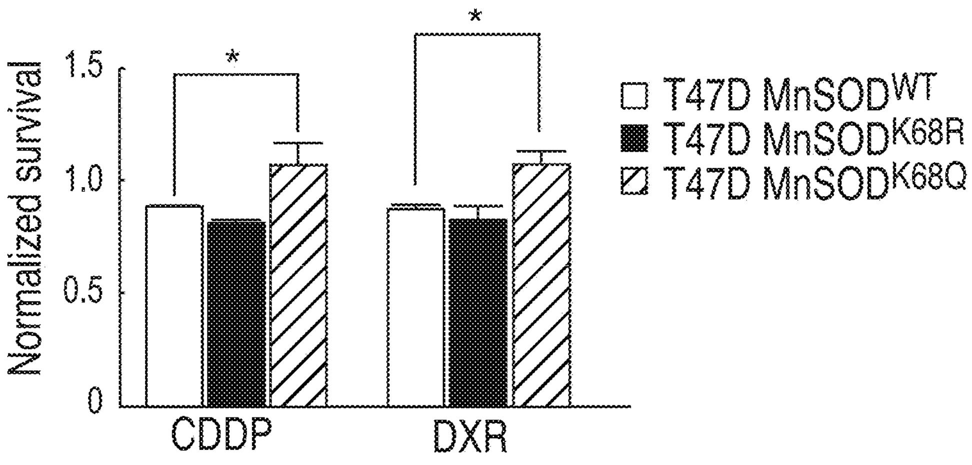

Cisplatin and Doxorubicin-Resistant Breast Cancer Cells Exhibit An Increase in MnSOD-K68-Ac MnSOD-K68-Ac is enriched in women with luminal B breast malignancies[52], which commonly recur with endocrine therapy, and is a mitochondrial based signaling network for the development of tamoxifen resistance (TamR), as determined using breast cancer tissue culture cells. In this example, it was explored whether this resistance phenotype could be extended to a broader application in other standard treatments in women with luminal B breast cancer, including cisplatin (CDDP) and doxorubicin (DXR). To address this question, a standard method was used to select tissue culture for resistance to anticancer agents in both MCF7 and T47D, two established ER+ breast cancer cell lines[53]. MCF7 cells were selected for resistance with three different doses of CDDP (250 nM, 500 nM, 1 μM) and DXR (500 μM, 1 nM, and 2 nM) for 3 months. T47D cells were selected for resistance with three different doses of CDDP (2.5 μM, 5 μM, 10 μM) and DXR (5 nM, 10 nM, and 20 nM) for 3 months. Both CDDP-resistant and DXR-resistant MCF7 and T47D cells showed a dose-dependent increase in MnSOD-K68-Ac (FIGS. 28*a*28*b* and 28*d*-28*e*), without changes in total MnSOD protein levels. In order to study specifically on the effect of K68 acetylation on drug resistance, K68 acetylation mimic ($MnSOD^{K68Q}$) and deacetylation mimic ($MnSOD^{K68R}$) mutants were made where the substitution of a lysine (K) with a glutamine (Q) mimics an constitutively acetylated amino acid state, while the substitution with an arginine (R) mimics constitutive deacetylation[54,52,55]. MCF7 and T47D cells overexpressing $MnSOD^{K68Q}$ exhibited higher resistance to the short-term treatment (48 hours) of the highest dose of CDDP (1 μM for MCF7 and 10 μM for T47D) and DXR (2 nM for MCF7 and 20 nM for T47D) (FIGS. 28*c* and 28*f*). These results clearly suggest a role for the disruption of MnSOD biology, through dysregulated MnSOD-Ac, in a PanR tumor cell phenotype in MCF7 and T47D breast cancer cells. Consistent with this, in Examples 1 and 3 MCF7 and/or T47D breast cancer cells overexpressing $MnSOD^{K68Q}$ exhibited resistance to treatment with hydroxy-Tam, Fulv and Palb. Accordingly, it was shown that cisplatin and doxorubicin-resistant breast cancer cells as an example of multi-therapy resistance exhibit an increase in MnSOD-K68-Ac and that mimicking acetylation of MnSOD-K68 with $MnSOD^{K68Q}$ expression in non-resistant breast cancer cells increases their resistance to chemotherapy consistent with the PanR phenotype.

Cell Lines

The wild-type ER+ MCF7 human breast cancer cells and immortalized MnSOD[1] mouse embryonic fibroblast cells (MEF) were cultured at 37° C. with 5% $CO_2$ in regular growth medium, which is composed of Dulbecco's Modified Eagle's Medium (DMEM, Gibco) with 10% fetal bovine serum (FBS; Sigma) and 1% Antibiotic Antimycotic solution (Sigma). Primary MEFs were isolated from isogenic mouse embryos (E13.5) and cultured at 37° C. with 5% $CO_2$ and 6% oxygen. *Lenti*-virally infected MCF7 and MEFs were grown in media with 1 μg/ml puromycin. Cisplatin and doxorubicin resistant MCF7 cells were treated for over 3 months to establish permanent cell lines. All experiments were done using exponentially growing cells at 50%-70% confluence.

Lentiviral Infection

Human Lenti-MnSOD plasmid was used for site-directed mutagenesis where lysine at location 68 is mutated to either arginine (deacetylation mimetic) or glutamine (acetylation mimetic) (Bioinnovatise). 293T cells were transfected with 5 μg DNA of interest, 5 μg psPAX2 packaging plasmid, and 300 ng VSV. G envelope plasmid. Fresh medium was added after overnight incubation and viral supernatant was collected after an additional 48 h and filtered using a 0.45 μm filter (Corning). MCF7 and MEFs were lenti-virally infected at 40% confluence with 10 μg/ml polybrene for 72 h. Cells were subsequently recovered with regular medium for 24 h and then selected with 1 μg/ml puromycin.

Clonogenic Cell Survival Assay

To evaluate clonogenic cell survival by testing cell growth at low density, 500 exponentially growing cells were plated in triplicate in 6-well plates using serial dilution, and the growth of the cells was examined throughout 14 days in regular growth medium. Cells were fixed with 70% ethanol for 5 minutes and then stained with 0.5% crystal violet (in 25% methanol) for 20 minutes. Photos of stained plates were taken, and colonies of more than 50 cells were counted and used to calculate clonogenic survival.

Soft Agar Colony Formation Assay 10,000 cells were plated in triplicate on 0.3% agar in growth medium 1× over a 0.6% base agar foundation layer in growth medium 1× (growth medium 2× consisted of DMEM supplemented with 20% FBS, 2% penicillin-streptomycin, 1% 2.5M glucose and 2% GlutaMax 100×). The size of colonies was monitored over a period of 3 weeks, and by the end of 3 weeks, colony growth was visualized via microscope and images were acquired.

MTT Cell Proliferation Assay

Cell proliferation was measured using MTT proliferation assay kit (ab211091). 10,000 exponentially growing cells were plated in regular growth medium per well into 96-well plates in triplicate. Cells were treated with specified drugs after overnight and incubated for 48 hours. The treatment media was then discarded and a mixture of 50 μl MTT reagent and 50 μl serum-free media was added into each well and incubated for 3 hours at 37° C. 150 μl of MTT solvent was then added, and the plate was shaken for 15 minutes avoiding light. The absorbance was read at OD=590 nm and used to evaluate cell proliferation.

Incorporation and Isolation of N-(ε)-Acetyl-Lysine into MnSOD-K68

BL21 (DE3) pMAGIC bacteria were co-transformed with pEVOL-AcKRS, which expresses an acetyl-lysyl-tRNA synthetase/$tRNA^{CUA}$ pair from *M. barkeri*, and pET21a-$MnSOD^{K68TAG}$ which expresses a site-specific mutation that allows incorporation of N-(ε)-acetyl-1-lysine (AcK) into K68. BL21(DE3) pMAGIC cells were transformed with pEVOL-AcKRS and pET21a-MnSODK68TAG were cultured in 3 ml of sterile LB media with 300 μg/ml ampicillin, 50 μg/ml kanamycin and 50 μg/ml chloramphenicol, and 1 ml of the culture was then cultured in 100 ml of LB media with 300 μg/ml ampicillin, 50 μg/ml kanamycin and 50 μg/ml chloramphenicol overnight (200 rpm, 37° C.). 1 ml of the overnight culture was inoculated in 100 ml of LB media with the same antibiotic concentration and shaken at 220 rpm, 37° C. until OD=600 nm reaches 0.6. Bacterial culture was induced with 0.4 mM IPTG, nicotinamide, arabinose and N-acetyl lysine and shaken overnight at 180 rpm, room temperature.

BL21(DE3) pMAGIC cells were transformed with pEVOL-AcKRS and pET21a-MnSODK68TAG were cultured in 3 ml of sterile LB media with 300 μg/ml ampicillin, 50 μg/ml kanamycin and 50 μg/ml chloramphenicol, and 1 ml of the culture was then cultured in 100 ml of LB media with 300 μg/ml ampicillin, 50 μg/ml kanamycin and 50 μg/ml chloramphenicol overnight (200 rpm, 37° C.). 1 ml of the overnight culture was inoculated in 100 ml of LB media with the same antibiotic concentration and shaken at 220 rpm, 37° C. until OD¬600 reaches 0.6. Bacterial culture was induced with 0.4 mM IPTG, nicotinamide, arabinose and N-acetyl lysine and shaken overnight at 180 rpm, room temperature.

Protein was lysed in buffer (20 mM imidazole, 50 mM Tris-HCl, 200 mM NaCl, pH=8) with 1.5 mg/ml PMSF and 1 mg/ml lysozyme. Lysates were incubated on ice for 10 minutes, sonicated for 20 min (10s on, 5s off, 50% amplitude), and centrifuged for supernatant (13,000 g, 30 min). 0.2 mL Ni2+ NTA beads were added to the collected supernatant and rotated for 1 hour at 4° C. Protein was filtered via passing the supernatant through Probond Purification System filter column. The column was washed three times using the lysing buffer. Then the protein was eluted with elution buffer (250 mM imidazole, 50 mM Tris-HCl, 200 mM NaCl, pH=8) and quantified for further experiments.

Peroxidase Activity Assay

One million cells expressing Flag-tagged MnSODw, $MnSOD^{K68R}$ and $MnSOD^{K68}Q$ were lysed for 30 min in 25 mM Tris-HCl pH 7.4, 150 mM NaCl, 1 mM EDTA, 0.1% NP-40, 5% glycerol, protease inhibitors (BioTool) and TSA (Tri chostatin A, Sigma). Lysates were quantified with the Bradford assay (BioRad) and IPed using anti-Flag antibody (company). The peroxidase enzymatic activities of these IPed proteins were determined by using pyrogallol as the substrate. In the reaction mix, the final concentrations were 14 mM potassium phosphate (Sigma), 0.027% (v/v) hydrogen peroxide (Sigma), and 0.5% (w/v) pyrogallol (Sigma). The plate was tapped to mix the sample and reaction reagent, incubated for 10 min at room temperature, and then read at OD=420 nm. The increase in A420 was recorded every 3 min. The AA420/20 sec was obtained using the maximum linear rate or 0.5-minute interval for all the test samples and blanks. The peroxidase activity was calculated using the following equation:

$$\text{Units/mL}=[(\Delta A420/20\text{ sec Test Sample}-\Delta A420/20\text{ sec Blank})(\text{reaction volume})(\text{dilution factor})]/[(12)(0.1)].$$

Statistical Analysis

Statistical analysis was performed using GraphPad Prism for Windows (GraphPad Software, San Diego, CA). Data were expressed as mean SEM unless otherwise specified. One-way ANOVA analysis with Tukey's post-analysis was used to study the differences among three or more means. Significance was determined at $p<0.05$ and the 95% confidence interval.

Example 5

Figure 29A:
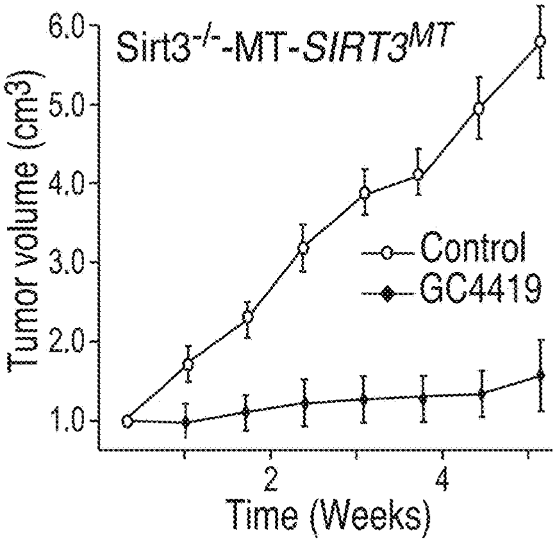
FIGS. 29*a*-29*b* are plots showing that the growth of murine mammary allograft tumors is inhibited by exposure to the MnSOD mimic GC4419 much more in cells without expression of deacetylation competent SIRT3.
Figure 29B:
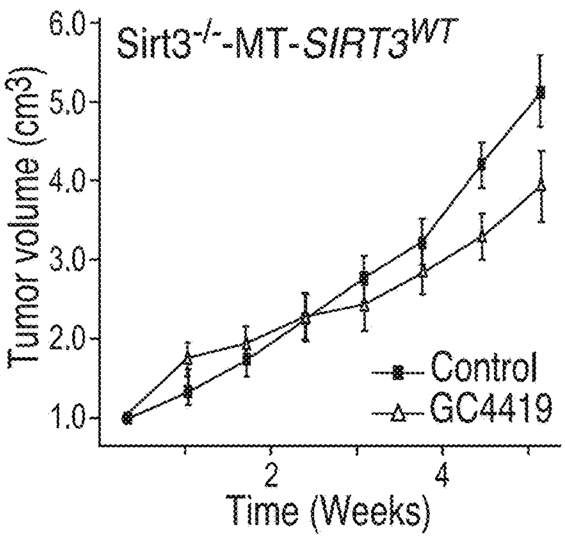

Allograft Mammary Tumors Isolated from Mice Lacking Sirt3 Exhibit Significant Cytotoxic Sensitivity to MnPAM Dismutase Mimetics It was evaluated whether agents that pharmacologically mimicking deacetylated lysine 68 MnSOD might be cytotoxic and/or reverse the Tam resistance in tumors exhibiting a SIRT3-MnSOD-Ac signature. IP injection with 2 mg/kg GC4419 (a MnPAM selective dismutase mimetic) 30 minutes before IR attenuated liver damage in mice lacking Sirt3 (Coleman et al., 2014, Antioxid. Redox Signal.) To address whether Tam resistance could be reversed in vivo, tumor cell lines were used derived from a mammary tumor that developed spontaneously in Sirt3 knockout mouse, referred to as $Sirt3^{-/-}$-mammary tumor cells ($Sirt3^{-/-}$-MT). These cell lines were subsequently infected with and selected to express either a SIRT3 wild-type ($Sirt3^{-/-}$-MT-$SIRT3^{WT}$) or deacetylation activity null ($Sirt3^{-/-}$-MT-$SIRT3^{DN}$) gene and a lenti-luciferase to assess tumor growth by bioluminescence. Allograft tumor mice were split into four groups: (1) control, untreated $Sirt3^{-/-}$-MT-$SIRT3^{DN}$; (2) GC4419 treated $Sirt3^{-/-}$-MT-$SIRT3^{DN}$; (3) control, untreated $Sirt3^{-/-}$-MT-$SIRT3^{WT}$; and (4) GC4419 treated $Sirt3^{-/-}$-MT-$SIRT3^{WT}$. These experiments demonstrated that the $Sirt3^{-/-}$-MT-$SIRT3^{DN}$ allografts injected with GC4419 by IP every other day for five weeks exhibited an anti-proliferative effect, as measured by a significant decrease in tumor growth, as compared to control mice (FIG. 29*a*, top line control vs. bottom line with GC4419). In contrast, little change in tumor growth was observed in $Sirt3^{-/-}$-MT-$SIRT3^{WT}$ allografts exposed to GC4419 (FIG. 29*b*), though these tumors did grow slightly slower (FIGS. 29*a-b*, line ending highest on the y axis after 4 weeks in FIG. 7*b* is control, line ending lower on y axis after 6 weeks is with GC4419). In vitro data with different Tam resistant as well as loss of Sirt3 tumor cell lines also shows that GC4419 reverses Tam resistance (data not shown). Accordingly, it was shown that the growth of murine mammary allograft tumors is inhibited by pharmacologically mimicking the activity of deacetylated lysine 68 MnSOD with a manganese pentaazamacrocyclic dismutase mimetic much more in tumors without deacetylation competent SIRT3. Further, this supports that selection of tumors displaying an AcK68 signature could increase response to treatment with a MnPAM dismutase mimetic (or other methods) alone or in combination with other therapies.

Example 6

Figure 30A:
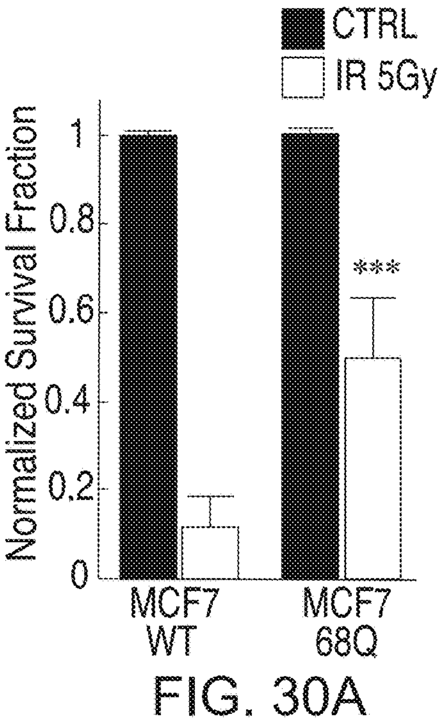
FIGS. 30*a*-30*b* are plots showing that mimicking acetylation of MnSOD-K68 with $MnSOD^{K68Q}$ expression induces ionizing radiation resistance (IRR) in breast cancer cells, and that pharmacologically mimicking the activity of deacetylated lysine 68 MnSOD with a manganese pentaazamacrocyclic dismutase mimetic reverses this IRR.
Figure 30B:
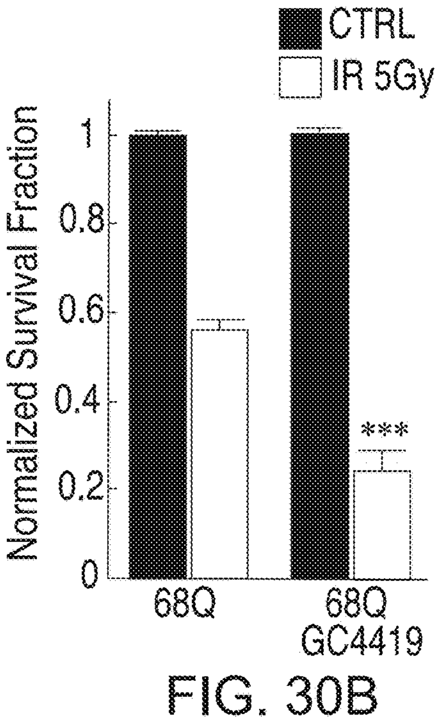

Expression of $MnSOD^{K68Q}$ (i.e., the K68-Ac Mimic Mutant) Induces Ionizing Radiation Resistance (IRR) in MCF7 Cells To determine if the MnSOD-K68-Ac-ROS axis plays a role in IRR, it was hypothesized that MnSOD acetylation might play a role in how tumor cells are reprogrammed to produce a IRR phenotype. To address this idea, an established tumor cell line MCF-7 was infected with lenti-$MnSOD^{K68Q}$ to induce $MnSOD^{K68Q}$ expression, which was validated. MCF-7-$MnSOD^{WT}$ and MCF-7-$MnSOD^{K68Q}$ cells were treated without or with 5 Gy of IR. Clonogenic cell survival experiments showed that enforced $MnSOD^{K68Q}$ expression in MCF7 cells led to decreased IR-induced cell killing (FIG. 30*a*, black bar vs. checked bar). In addition, it was surmised that pharmacologically mimicking deacetylated lysine 68 MnSOD with the MnPAM dismutase mimetic GC4419 would reverse the IRR phenotype in the MCF-7-$MnSOD^{K68Q}$ cells. Indeed, clonogenic cell survival studies showed that exposure to GC4419 reversed the IRR phenotype (FIG. 30*b*, checked bar 2 vs. bar 4). These experiments suggest that the IRR observed in the MCF-7-$MnSOD^{K68Q}$ cells was converted to a sensitive phenotype due to exposure to GC4419, indicating that replacement of SOD activity is a mechanism in this process. These results clearly suggest a role for the disruption of MnSOD biology, through dysregulated MnSOD-Ac, in a PanR (multi-therapy resistant) tumor cell phenotype in breast cancer cells. Consistent with this, in Examples 1, 3 and 4 breast cancer cells overexpressing $MnSOD^{K68Q}$ exhibited resistance to treatment with hydroxy-Tam, Fulv, Palb, CDDP and DXR, and in Example 2 prostate cancer cells overexpressing MnSODK68Q exhibited resistance to treatment with ENZ. Induction of resistance to these multiple therapies also increased native expression of MnSOD AcK68 with all of the related downstream effects, which could be reduced or reversed in several by pharmacologic MnPAM dismutase mimetic. Accordingly, it was shown that mimicking acetylation of MnSOD-K68 with $MnSOD^{K68Q}$ expression induces ionizing radiation resistance (IRR) and PanR in breast cancer cells, and that pharmacologically mimicking the activity of deacetylated lysine 68 MnSOD with a manganese pentaazamacrocyclic dismutase mimetic reverses this IRR and PanR.

Figure 31A:
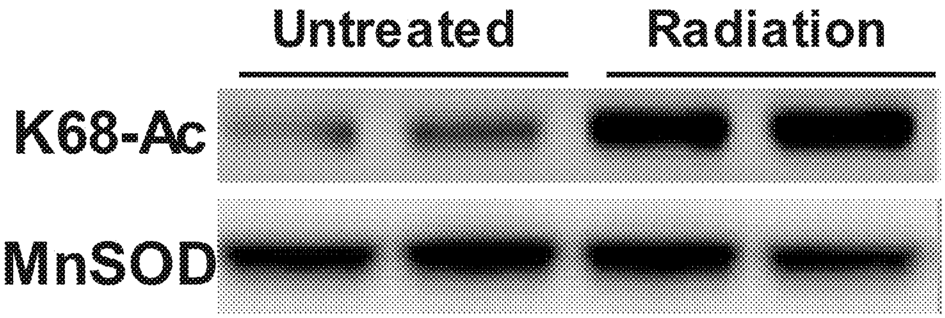
FIGS. 31*a*-31*b* are an image and graph showing that LNCaP-IRR (ionizing radiation resistant) cells exhibited increased MnSOD-K68-Ac.
Figure 31B:
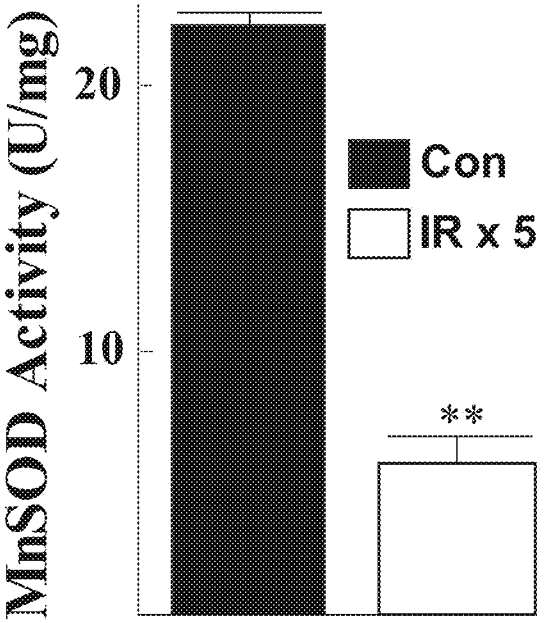

IRR Prostate Tumor Cell Lines Exhibit Increased MnSOD-K68-Ac And Decreased MnSOD Activity To further assess whether the MnSOD-K68-Ac-ROS axis plays a role in IRR, we used two hormone-sensitive prostate tumor cell lines, LNCaP and 22RV1, which were treated with 5 Gy IR for 5 consecutive days to select for IRR. LNCaP-IRR cells showed an increase in MnSOD-K68-Ac (FIG. 31*a*), as did 22RV1-IRR cells (data not shown) cultured identically. LNCaP-IRR cells also exhibited a decrease in MnSOD activity (FIG. 31*b*) and an increase in ROS levels (data not shown). Accordingly, it was shown that IRR in prostate cancer cells is associated with an increase in AcK68 signature, just as in Example 5 for IRR in breast cancer. Further this is consistent with the PanR phenotype demonstrated in the other Examples in breast and prostate cancer cells for radiation resistance, cytotoxic chemotherapy resistance and targeted therapy resistance (hormone and non-hormone pathways). In all of these, development of resistance may be associated with increased acetylation of lysine 68 of MnSOD and increased lineage plasticity/stemness, and engineering, forcing or mimicking acetylation of lysine 68 imparts specific and multi-therapy resistance, while engineering, forcing or mimicking de-acetylation of lysine 68, including by pharmacologic methods, reverses that resistance. Acetylation of lysine 68 (AcK68) is also associated in both experimental cancer models and human tumor samples with disease grade/aggressiveness and progression.

Example Protocols

The example protocols below show methods of determining levels of target proteins, including AcK68, SIRT3 and $HIF2_{\alpha}$, in tissue samples containing tumor cell.

Breast Tissue Protocol

Breast cancer tissue and normal breast tissue slides (n>=6) were immersed twice in 100% xylene (Sigma) for 5 min and 100% ethanol (Sigma) for 5 min. Slides were sequentially immersed with 95%, 80 and 50% ethanol for 5 min before immersion in water and fixation in 95 mL of 95% ethanol and 5 mL of 37% formaldehyde for 2 min. Slides were then treated with 1% Triton X-100 in 1×PBS (Corning) for 20 min, washed three times in 1×PBS for 5 min, and quenched in 03% $H_2O_2$ in 1×PBS for 20 min. Slides were blocked with 10% donkey serum (Sigma), 1% bovine serum albumin (BSA: Sigma) and 0.3% Triton X-100 (Sigma) in 1×PBS for 2 h before treatment with an anti-MnSOD-K68-Ac antibody (1:250 dilution) for 48 h at 4° C. These slides were subsequently incubated at room temperature for 1 h before being washed three times with 1×PBS for 5 min. Rabbit secondary antibody (1:200 dilution, A0545, Sigma) was diluted in antibody solution and applied to slides for 1 h before being washed three times with 1×PBS for 5 min each. The slides were treated with VECTASTAIN ABC kit (Vector Laboratories) for 45 min following the manufacturer's protocol to detect avidin/biotinylated enzyme complexes. Slides were treated using the DAB peroxidase substrate kit (Vector Laboratories), per the manufacturer's protocol, and stained in hematoxylin (Sigma) for 10 min. Then slides were destained with 100 mL of 70% ethanol and 1 mL of 37% hydrochloric acid before dehydration. The intensities were quantified using HistoQuest software (Tissuegnostics). Each tissue received a score between 0-250 according to the signal intensity. Any tissue slide received score that is lower than 1 standard deviation of the normal breast tissue average score was considered low. Any tissue slide received score that is higher than 1 standard deviation of the normal breast tissue average score was considered high. The normal breast tissue average score was determined by assessing at least 6 non-cancerous breast tissue samples from different individuals.

Prostate Tissue Protocol

Prostate cancer tissue and normal prostate tissue slides (n>=6) were immersed twice in 100% xylene (Sigma) for 5 min and 100% ethanol (Sigma) for 5 min. Slides were sequentially immersed with 95%, 80 and 50% ethanol for 5 min before immersion in water and fixation in 95 mL of 95% ethanol and 5 mL of 37% formaldehyde for 2 min. Slides were then treated with 1% Triton X-100 in 1×PBS (Corning) for 20 min, washed three times in 1×PBS for 5 min, and quenched in 0.3% $H_2O_2$ in 1×PBS for 20 min. Slides were blocked with 10% donkey serum (Sigma), 1% bovine serum albumin (BSA, Sigma) and 0.3% Triton X-100 (Sigma) in 1×PBS for 2 h before treatment with an anti-MnSOD-K68-Ac antibody (1:250 dilution) for 48 h at 4° C. These slides were subsequently incubated at room temperature for 1 h before being washed three times with 1×PBS for 5 min. Rabbit secondary antibody (1:200 dilution, A0545, Sigma) was diluted in antibody solution and applied to slides for 1 h before being washed three times with 1×PBS for 5 min each. The slides were treated with VECTASTAIN ABC kit (Vector Laboratories) for 45 min following the manufacturer's protocol to detect avidin/biotinylated enzyme complexes. Slides were treated using the DAB peroxidase substrate kit (Vector Laboratories), per the manufacturer's protocol, and stained in hematoxylin (Sigma) for 10 min. Then slides were destained with 100 mL of 70% ethanol and 1 mL of 37% hydrochloric acid before dehydration. The intensities were quantified using HistoQuest software (Tissuegnostics). Each tissue received a score between 0-250 according to the signal intensity. Any tissue slide received score that is lower than 1 standard deviation of the normal prostate tissue average score was considered low. Any tissue slide received score that is higher than 1 standard deviation of the normal prostate tissue average score was considered high. The normal prostate tissue average score was determined by assessing at least 6 non-cancerous prostate tissue samples from different individuals.

REFERENCES

Each of the references referred to herein are hereby incorporated by reference in their entireties.

1. Qiu, X., Brown, K., Hirschey, M. D., Verdin, E. & Chen, D. Calorie restriction reduces oxidative stress by SIRT3-mediated SOD2 activation. Cell Metab. 12, 662-667 (2010).
2. Tao, R., Vassilopoulos, A., Parisiadou, L., Yan, Y. & Gius, D. Regulation of MnSOD enzymatic activity by Sirt3 connects the mitochondrial acetylome signaling networks to aging and carcinogenesis. Antioxid. Redox Signal. 20, 1646-1654 (2013).
3. Zhu, Y. et al. Exploring the electrostatic repulsion model in the role of Sirt3 in directing MnSOD acetylation status and enzymatic activity. Free Radic. Biol. Med. 53, 828-833 (2012).
4. Ozden, O. et al. Acetylation of MnSOD directs enzymatic activity responding to cellular nutrient status or oxidative stress. Aging 3, 102-107 (2011).

5. Zou, X., Santa-Maria, C. A., O'Brien, J., Gius, D. & Zhu, Y. Manganese superoxide dismutase acetylation and dysregulation, due to loss of SIRT3 activity, promote a luminal B-Like breast carcinogenic-permissive phenotype. Antioxid. Redox. Signal. 25, 326-336 (2016).
6. Chen, Y. et al. Tumour suppressor SIRT3 deacetylates and activates manganese superoxide dismutase to scavenge ROS. EMBO Rep. 12, 534-541 (2011).
7. Kim, H. S. et al. SIRT3 is a mitochondria-localized tumor suppressor required for maintenance of mitochondrial integrity and metabolism during stress. Cancer Cell 17, 41-52 (2010).
8. Tao, R. et al. Sirt3-mediated deacetylation of evolutionarily conserved lysine 122 regulates MnSOD activity in response to stress. Mol. Cell 40, 893-904 (2010).
9. Haigis, M. C., Deng, C. X., Finley, L. W., Kim, H. S. & Gius, D. SIRT3 is a mitochondrial tumor suppressor: a scientific tale that connects aberrant cellular ROS, the Warburg effect, and carcinogenesis. Cancer Res. 72, 2468-2472 (2012).
10. Borgstahl, G. E. et al. The structure of human mitochondrial manganese superoxide dismutase reveals a novel tetrameric interface of two 4-helix bundles. Cell 71, 107-118 (1992).
11. Brown, K. et al. SIRT3 reverses aging-associated degeneration. Cell Rep. 3, 319-327 (2013).
12. Vassilopoulos, A. et al. SIRT3 deacetylates ATP synthase F1 complex proteins in response to nutrient- and exercise-induced stress. Antioxid. Redox Signal. 21, 551-564 (2014).
13. Knyphausen, P. et al. Insights into lysine deacetylation of natively folded substrate proteins by sirtuins. J. Biol. Chem. 291, 14677-14694 (2016).
14. Hart, P. C. et al. MnSOD upregulation sustains the Warburg effect via mitochondrial ROS and AMPK-dependent signalling in cancer. Nat. Commun. 6, 6053 (2015).
15. Vidimar, V. et al. Dysfunctional MnSOD leads to redox dysregulation and activation of prosurvival AKT signaling in uterine leiomyomas. Sci. Adv. 2, e1601132 (2016).
16. Van Remmen, H. et al. Life-long reduction in MnSOD activity results in increased DNA damage and higher incidence of cancer but does not accelerate aging. Physiol. Genom. 16, 29-37 (2003).
17. Oberley, L. W. Mechanism of the tumor suppressive effect of MnSOD overexpression. Biomed. Pharmacother. Biomed. Pharmacother. 59, 143-148 (2005).
18. Venkataraman, S. et al. Manganese superoxide dismutase overexpression inhibits the growth of androgen-independent prostate cancer cells. Oncogene 24, 77-89 (2005).
19. Cullen, K. J. et al. Glutathione S-transferase pi amplification is associated with cisplatin resistance in head and neck squamous cell carcinoma cell lines and primary tumors. Cancer Res. 63, 8097-8102 (2003).
20. Kattan, Z., Minig, V., Leroy, P., Dauca, M. & Becuwe, P. Role of manganese superoxide dismutase on growth and invasive properties of human estrogen-independent breast cancer cells. Breast Cancer Res. Treat. 108, 203-215 (2008).
21. Torrens-Mas, M., Pons, D. G., Sastre-Serra, J., Oliver, J. & Roca, P. SIRT3 silencing sensitizes breast cancer cells to cytotoxic treatments through an increment in ROS production. J. Cell Biochem. 118, 397-406 (2017).
22. Cook, K. L. et al. Knockdown of estrogen receptor-alpha induces autophagy and inhibits antiestrogen-mediated unfolded protein response activation, promoting ROS-induced breast cancer cell death. FASEB J. 28, 3891-3905 (2014).
23. Nass, N., Sel, S., Ignatov, A., Roessner, A. & Kalinski, T. Oxidative stress and glyoxalase I activity mediate dicarbonyl toxicity in MCF-7 mamma carcinoma cells and a tamoxifen resistant derivative. Biochim. Biophys. Acta 1860, 1272-1280 (2016).
24. Sotgia, F., Fiorillo, M. & Lisanti, M. P. Mitochondrial markers predict recurrence, metastasis and tamoxifen-resistance in breast cancer patients: Early detection of treatment failure with companion diagnostics. Oncotarget 8, 68730-68745 (2017).
25. Land, H., Chen, A. C., Morgenstern, J. P., Parada, L. F. & Weinberg, R. A. Behavior of myc and ras oncogenes in transformation of rat embryo fibroblasts. Mol. Cell Biol. 6, 1917-1925 (1986).
26. Ansenberger-Fricano, K. et al. The peroxidase activity of mitochondrial superoxide dismutase. Free Radic. Biol. Med. 54, 116-124 (2013).
27. Lammers, M. Expression and purification of site-specifically lysine-acetylated and natively-folded proteins for biophysical investigations. Methods Mol. Biol. 1728, 169-190 (2018).
28. de Boor, S. et al. Small GTP-binding protein Ran is regulated by posttranslational lysine acetylation. Proc. Natl Acad. Sci. USA 112, E3679-E3688 (2015).
29. Cho, S. K., Pedram, A., Levin, E. R. & Kwon, Y. J. Acid-degradable core-shell nanoparticles for reversed tamoxifen-resistance in breast cancer by silencing manganese superoxide dismutase (MnSOD). Biomaterials 34, 10228-10237 (2013).
30. Fu, A. et al. High expression of MnSOD promotes survival of circulating breast cancer cells and increases their resistance to doxorubicin. Oncotarget 7, 50239-50257 (2016).
31. Razandi, M., Pedram, A., Jordan, V. C., Fuqua, S. & Levin, E. R. Tamoxifen regulates cell fate through mitochondrial estrogen receptor beta in breast cancer. Oncogene 32, 3274-3285 (2013).
32. Cook, K. L. & Clarke, R. Estrogen receptor-alpha signaling and localization regulates autophagy and unfolded protein response activation in ER+ breast cancer. Receptors Clin. Investig. 1, e316 (2014).
33. Desouki, M. M., Doubinskaia, I., Gius, D. & Abdulkadir, S. A. Decreased mitochondrial SIRT3 expression is a potential molecular biomarker associated with poor outcome in breast cancer. Hum. Pathol. 45, 1071-1077 (2014).
34. Fu, Y. et al. Aging promotes sirtuin 3-dependent cartilage superoxide dismutase 2 acetylation and osteoarthritis. Arthritis Rheuma. 68, 1887-1898 (2016). [00450]35. Shi, H. et al. Sirt3 protects dopaminergic neurons from mitochondrial oxidative stress. Hum. Mol. Genet. 26, 1915-1926 (2017).
36. Dikalova, A. E. et al. Sirt3 impairment and SOD2 hyperacetylation in vascular oxidative stress and hypertension. Circ. Res. 121, 564-574 (2017).
37. Gao, J. et al. Deacetylation of MnSOD by PARP-regulated SIRT3 protects retinal capillary endothelial cells from hyperglycemia-induced damage. Biochem. Biophys. Res. Commun. 472, 425-431 (2016).
38. Quiros, I. et al. Upregulation of manganese superoxide dismutase (SOD2) is a common pathway for neuroendocrine differentiation in prostate cancer cells. Int J. Cancer 125, 1497-1504 (2009).

39. Yang, X. J. Lysine acetylation and the bromodomain: a new partnership for signaling. Bioessays 26, 1076-1087 (2004).

40. Lu, J. et al. A small molecule activator of SIRT3 promotes deacetylation and activation of manganese superoxide dismutase. Free Radic. Biol. Med 112, 287-297 (2017).

41. Aykin-Burns, N., Ahmad, I. M., Zhu, Y., Oberley, L. W. & Spitz, D. R. Increased levels of superoxide and $H_2O_2$ mediate the differential susceptibility of cancer cells versus normal cells to glucose deprivation. Biochem J. 418, 29-37 (2009).

42. Hanahan, D. & Weinberg, R. A. The hallmarks of cancer. Cell 100, 57-70 (2000).

43. Spitz, D. R., Azzam, E. I., Li, J. J. & Gius, D. Metabolic oxidation/reduction reactions and cellular responses to ionizing radiation: a unifying concept in stress response biology. Cancer Metastas. Rev. 23, 311-322 (2004).

44. Hanahan, D. & Weinberg, R. A. Hallmarks of cancer: the next generation. Cell 144, 646-674 (2011).

45. Guarente, L. Mitochondria—a nexus for aging, calorie restriction, and sirtuins? Cell 132, 171-176 (2008).

46. Culotta, V. C., Yang, M. & O'Halloran, T. V. Activation of superoxide dismutases: putting the metal to the pedal. Biochim. Biophys. Acta 1763, 747-758 (2006).

47. Naranuntarat, A., Jensen, L. T., Pazicni, S., Penner-Hahn, J. E. & Culotta, V. C. The interaction of mitochondrial iron with manganese superoxide dismutase. J. Biol. Chem. 284, 22633-22640 (2009).

48. Kang, Y., He, Y. X., Zhao, M. X. & Li, W. F. Structures of native and Fe-substituted SOD2 from Saccharomyces cerevisiae. Acta Crystallogr Sect. F. Struct. Biol. Cryst. Commun. 67, 1173-1178 (2011).

49. Ozden, O. et al. SIRT3 deacetylates and increases pyruvate dehydrogenase activity in cancer cells. Free Radic. Biol. Med. 76, 163-172 (2014).

50. Scarbrough, P. M. et al. Simultaneous inhibition of glutathione- and thioredoxin-dependent metabolism is necessary to potentiate 17AAG-induced cancer cell killing via oxidative stress. Free Radic. Biol. Med. 52, 436-443 (2012).

51. Lin, X. et al. 2-Deoxy-D-glucose-induced cytotoxicity and radiosensitization in tumor cells is mediated via disruptions in thiol metabolism. Cancer Res. 63, 3413-3417 (2003).

52. Zhu, Y., et al. Lysine 68 acetylation directs MnSOD as a tetrameric detoxification complex versus a monomeric tumor promoter. *Nat Commun* 10, 2399 (2019).

53. McDermott, M., et al. In vitro Development of Chemotherapy and Targeted Therapy Drug-Resistant Cancer Cell Lines: A Practical Guide with Case Studies. *Front Oncol* 4, 40 (2014).

54. Tao, R., et al. Sirt3-mediated deacetylation of evolutionarily conserved lysine 122 regulates MnSOD activity in response to stress. *Mol Cell* 40, 893-904 (2010).

55. He, C., et al. SOD2 acetylation on lysine 68 promotes stem cell reprogramming in breast cancer. *Proc Natl Acad Sci USA* (2019).

56. Oberley, L. W. & Oberley, T. D. Role of antioxidant enzymes in cell immortalization and transformation. *Molecular and cellular biochemistry* 84, 147-153 (1988).

57. Gius, D. & Spitz, D. R. Redox signaling in cancer biology. *Antioxid Redox Signal* 8, 1249-1252 (2006).

58. Fridovich, I. Superoxide dismutases: defence against endogenous superoxide radical. *Ciba Found Symp,* 77-93 (1978).

59. Brawn, K. & Fridovich, I. Superoxide radical and superoxide dismutases: threat and defense. *Acta Physiol Scand* Suppl 492, 9-18 (1980).

60. Bresciani, G., da Cruz, I. B. & Gonzalez-Gallego, J. Manganese superoxide dismutase and oxidative stress modulation. *Adv Clin Chem* 68, 87-130 (2015).

61. Zou, X., et al. Manganese superoxide dismutase (SOD2): is there a center in the universe of mitochondrial redox signaling? *J Bioenerg Biomembr* (2017).

62. Fridovich, I. Superoxide radical and superoxide dismutases. *Annu Rev Biochem* 64, 97-112 (1995).

63. Liochev, S. I. & Fridovich, I. How does superoxide dismutase protect against tumor necrosis factor: a hypothesis informed by effect of superoxide on "free" iron. *Free Radic Biol Med* 23, 668-671 (1997).

64. Dhar, S. K. & St Clair, D. K. Manganese superoxide dismutase regulation and cancer. *Free Radic Biol Med* 52, 2209-2222 (2012).

65. Miriyala, S., Holley, A. K. & St Clair, D. K. Mitochondrial superoxide dismutase—signals of distinction. *Anticancer Agents Med Chem* 11, 181-190 (2011).

66. Ahn, B. H., et al. A role for the mitochondrial deacetylase Sirt3 in regulating energy homeostasis. *Proc Natl Acad Sci USA* 105, 14447-14452 (2008).

67. Hirschey, M. D., et al. SIRT3 regulates mitochondrial fatty-acid oxidation by reversible enzyme deacetylation. *Nature* 464, 121-125 (2010).

68. Sarsour, E. H., et al. Manganese superoxide dismutase regulates a metabolic switch during the mammalian cell cycle. *Cancer Res* 72, 3807-3816 (2012).

69. Lu, J., et al. A small molecule activator of SIRT3 promotes deacetylation and activation of manganese superoxide dismutase. *Free Radic Biol Med* 112, 287-297 (2017).

70. Lu, J., et al. Novel mechanisms for superoxide-scavenging activity of human manganese superoxide dismutase determined by the K68 key acetylation site. *Free Radic Biol Med* 85, 114-126 (2015).

71. Lone, M. U., et al. Physical interaction of estrogen receptor with MnSOD: implication in mitochondrial O2·− upregulation and mTORC2 potentiation in estrogen-responsive breast cancer cells. *Oncogene* 36, 1829-1839 (2017).

72. Finley, L. W., et al. SIRT3 opposes reprogramming of cancer cell metabolism through HIF1alpha destabilization. *Cancer Cell* 19, 416-428 (2011).

73. Park, S. H., et al. Sirt3, Mitochondrial ROS, Ageing, and Carcinogenesis. *International journal of molecular sciences* 12, 6226-6239 (2011).

74. Beyer, W. F., Jr. & Fridovich, I. In vivo competition between iron and manganese for occupancy of the active site region of the manganese-superoxide dismutase of *Escherichia coli. J Biol Chem* 266, 303-308 (1991).

75. Vance, C. K. & Miller, A. F. Novel insights into the basis for *Escherichia coli* superoxide dismutase's metal ion specificity from Mn-substituted FeSOD and its very high E(m). *Biochemistry* 40, 13079-13087 (2001).

76. Privalle, C. T. & Fridovich, I. Transcriptional and maturational effects of manganese and iron on the biosynthesis of manganese-superoxide dismutase in *Escherichia coli. J Biol Chem* 267, 9140-9145 (1992).

77. Zhao, Y., et al. Manganese superoxide dismutase deficiency enhances cell turnover via tumor promoter-induced alterations in AP-1 and p53-mediated pathways in a skin cancer model. *Oncogene* 21, 3836-3846 (2002).

78. Kim, Y. S., Gupta Vallur, P., Phaeton, R., Mythreye, K. & Hempel, N. Insights into the Dichotomous Regulation of SOD2 in Cancer. *Antioxidants* (*Basel*) 6(2017).

79. Wang, C., Tian, L., Popov, V. M. & Pestell, R. G. Acetylation and nuclear receptor action. *J Steroid Biochem Mol Biol* 123, 91-100 (2011).

80. Saitou, M., et al. Mitochondrial ultrastructure-associated chemotherapy response in ovarian cancer. *Oncology reports* 21, 199-204 (2009).

81. Vander Ark, A., Cao, J. & Li, X. Mechanisms and Approaches for Overcoming Enzalutamide Resistance in Prostate Cancer. *Front Oncol* 8, 180 (2018).

82. Sotgia, F., Fiorillo, M. & Lisanti, M. P. Mitochondrial markers predict recurrence, metastasis and tamoxifen-resistance in breast cancer patients: Early detection of treatment failure with companion diagnostics. *Oncotarget* 8, 68730-68745 (2017).

83. Prekovic, S., et al. Molecular underpinnings of enzalutamide resistance. *Endocr Relat Cancer* 25, R545-R557 (2018).

84. Culig, Z. Molecular Mechanisms of Enzalutamide Resistance in Prostate Cancer. *Curr Mol Biol Rep* 3, 230-235 (2017).

85. Blee, A. M. & Huang, H. Lineage plasticity-mediated therapy resistance in prostate cancer. *Asian J Androl* 21, 241-248 (2019).

86. Beltran, H., et al. The role of lineage plasticity in prostate cancer therapy resistance. *Clin Cancer Res* (2019).

87. Davies, A. H., Beltran, H. & Zoubeidi, A. Cellular plasticity and the neuroendocrine phenotype in prostate cancer. *Nat Rev Urol* 15, 271-286 (2018).

88. Yuan, S., Norgard, R. J. & Stanger, B. Z. Cellular Plasticity in Cancer. *Cancer Discov* 9, 837-851 (2019).

89. Ellis, L. Understanding cancer lineage plasticity: reversing therapeutic resistance in metastatic prostate cancer. *Pharmacogenomics* 18, 597-600 (2017).

90. Han, B., Qu, Y., Yu-Rice, Y., Johnson, J. & Cui, X. FOXC1-induced Gli2 activation: A non-canonical pathway contributing to stemness and anti-Hedgehog resistance in basal-like breast cancer. *Mol Cell* Oncol 3, e1131668 (2016).

91. Kregel, S., et al. Acquired resistance to the second-generation androgen receptor antagonist enzalutamide in castration-resistant prostate cancer. *Oncotarget* 7, 26259-26274 (2016).

92. Vidimar, V., et al. Dysfunctional MnSOD leads to redox dysregulation and activation of prosurvival AKT signaling in uterine leiomyomas. *Sci Adv* 2, e1601132 (2016).

93. Heer, C. D., et al. Superoxide Dismutase Mimetic GC4419 Enhances the Oxidation of Pharmacological Ascorbate and Its Anticancer Effects in an H(2)O(2)-Dependent Manner. *Antioxidants* (*Basel*) 7(2018).

94. Batinic-Haberle, I., Tovmasyan, A. & Spasojevic, I. Mn porphyrin-based redox-active drugs—Differential effects as cancer therapeutics and protectors of normal tissue against oxidative injury. *Antioxid Redox Signal* (2018).

95. He, T., et al. Redox factor-1 contributes to the regulation of progression from G0/G1 to S by PDGF in vascular smooth muscle cells. *Am J Physiol Heart Circ Physiol* 285, H804-812 (2003).

96. Kattan, Z., Minig, V., Leroy, P., Dauca, M. & Becuwe, P. Role of manganese superoxide dismutase on growth and invasive properties of human estrogen-independent breast cancer cells. *Breast Cancer Res Treat* 108, 203-215 (2008).

97. Hart, P. C., et al. MnSOD upregulation sustains the Warburg effect via mitochondrial ROS and AMPK-dependent signalling in cancer. *Nat Commun* 6, 6053 (2015).

98. Kim, H. S., et al. SIRT3 is a mitochondria-localized tumor suppressor required for maintenance of mitochondrial integrity and metabolism during stress. *Cancer Cell*17, 41-52 (2010).

99. Osborne, C. K. & Schiff, R. Mechanisms of endocrine resistance in breast cancer. *Annu Rev Med* 62, 233-247 (2011).

100. Szostakowska, M., Trebinska-Stryjewska, A., Grzybowska, E. A. & Fabisiewicz, A. Resistance to endocrine therapy in breast cancer: molecular mechanisms and future goals. *Breast Cancer Res Treat* 173, 489-497 (2019).

101. Ades, F., et al. Luminal B breast cancer: molecular characterization, clinical management, and future perspectives. *J Clin Oncol* 32, 2794-2803 (2014).

102. Creighton, C. J. The molecular profile of luminal B breast cancer. *Biologics* 6, 289-297 (2012).

103. Sotgia, F., Fiorillo, M. & Lisanti, M. P. Mitochondrial markers predict recurrence, metastasis and tamoxifen-resistance in breast cancer patients: Early detection of treatment failure with companion diagnostics. *Oncotarget* 8, 68730-68745 (2017).

104. Rodriguez, D., et al. The Central Contributions of Breast Cancer Stem Cells in Developing Resistance to Endocrine Therapy in Estrogen Receptor (ER)-Positive Breast Cancer. *Cancers* (*Basel*) 11(2019).

105. Witt, A. E., et al. Identification of a cancer stem cell-specific function for the histone deacetylases, HDAC1 and HDAC7, in breast and ovarian cancer. *Oncogene* 36, 1707-1720 (2017).

106. Wahl, G. M. & Spike, B. T. Cell state plasticity, stem cells, EMT, and the generation of intra-tumoral heterogeneity. *NPJ Breast Cancer* 3, 14 (2017).

107. Spike, B. T., et al. A mammary stem cell population identified and characterized in late embryogenesis reveals similarities to human breast cancer. *Cell Stem Cell* 10, 183-197 (2012).

108. Lee, K. M., et al. MYC and MCL1 Cooperatively Promote Chemotherapy-Resistant Breast Cancer Stem Cells via Regulation of Mitochondrial Oxidative Phosphorylation. *Cell Metab* 26, 633-647 e637 (2017).

109. Yan, Y., et al. HIF-2alpha promotes conversion to a stem cell phenotype and induces chemoresistance in breast cancer cells by activating Wnt and Notch pathways. *J Exp Clin Cancer Res* 37, 256 (2018).

110. Hanahan, D. & Weinberg, R. A. Hallmarks of cancer: the next generation. *Cell* 144, 646-674 (2011).

111. Hanahan, D. & Weinberg, R. A. The hallmarks of cancer. *Cell* 100, 57-70 (2000).

112. Han, B., Qu, Y., Yu-Rice, Y., Johnson, J. & Cui, X. FOXC1-induced Gli2 activation: A non-canonical pathway contributing to stemness and anti-Hedgehog resistance in basal-like breast cancer. *Mol Cell Oncol* 3, e1131668 (2016).

113. Kim, T., et al. A basal-like breast cancer-specific role for SRF-IL6 in YAP-induced cancer stemness. *Nat Commun* 6, 10186 (2015).

114. Turner, N.C., et al. Overall Survival with Palbociclib and Fulvestrant in Advanced Breast Cancer. *N Engl J Med* 379, 1926-1936 (2018).

115. Davies, A. H., Beltran, H. & Zoubeidi, A. Cellular plasticity and the neuroendocrine phenotype in prostate cancer. *Nat Rev Urol* 15, 271-286 (2018).

116. Nugud, A., Sandeep, D. & El-Serafi, A. T. Two faces of the coin: Minireview for dissecting the role of reactive oxygen species in stem cell potency and lineage commitment. *J Adv Res* 14, 73-79 (2018).

117. Sachdev, J. C., Sandoval, A. C. & Jahanzeb, M. Update on Precision Medicine in Breast Cancer. *Cancer Treat Res* 178, 45-80 (2019).

118. Tsuchida, J., et al. Clinical target sequencing for precision medicine of breast cancer. *Int J Clin Oncol* 24, 131-140 (2019).

119. Meisel, J. L., Venur, V. A., Gnant, M. & Carey, L. Evolution of Targeted Therapy in Breast Cancer: Where Precision Medicine Began. *Am Soc Clin Oncol* Educ Book 38, 78-86 (2018).

120. Naito, Y. & Urasaki, T. Precision medicine in breast cancer. *Chin Clin Oncol* 7, 29 (2018).

121. Zhu, Y., et al. Exploring the electrostatic repulsion model in the role of Sirt3 in directing MnSOD acetylation status and enzymatic activity. *Free Radic Biol Med* 53, 828-833 (2012).

122. Lu, J., et al. A small molecule activator of SIRT3 promotes deacetylation and activation of manganese superoxide dismutase. *Free Radic Biol Med* 112, 287-297 (2017).

123. Lu, J., et al. Novel mechanisms for superoxide-scavenging activity of human manganese superoxide dismutase determined by the K68 key acetylation site. *Free Radic Biol Med* 85, 114-126 (2015).

124. Ganini, D., Santos, J. H., Bonini, M. G. & Mason, R. P. Switch of Mitochondrial Superoxide Dismutase into a Prooxidant Peroxidase in Manganese-Deficient Cells and Mice. *Cell Chem Biol* 25, 413-425 e416 (2018).

125. Ansenberger-Fricano, K., et al. The peroxidase activity of mitochondrial superoxide dismutase. *Free Radic Biol Med* 54, 116-124 (2013).

126. Kattan, Z., Minig, V., Leroy, P., Dauca, M. & Becuwe, P. Role of manganese superoxide dismutase on growth and invasive properties of human estrogen-independent breast cancer cells. *Breast Cancer Res Treat* 108, 203-215 (2008).

127. Hart, P. C., et al. MnSOD upregulation sustains the Warburg effect via mitochondrial ROS and AMPK-dependent signalling in cancer. *Nat Commun* 6, 6053 (2015).

128. Vidimar, V., et al. Dysfunctional MnSOD leads to redox dysregulation and activation of prosurvival AKT signaling in uterine leiomyomas. *Sci Adv* 2, e1601132 (2016).

129. Heer, C. D., et al. Superoxide Dismutase Mimetic GC4419 Enhances the Oxidation of Pharmacological Ascorbate and Its Anticancer Effects in an H(2)O(2)-Dependent Manner. *Antioxidants* (*Basel*) 7(2018).

130. Batinic-Haberle, I., Tovmasyan, A. & Spasojevic, I. Mn porphyrin-based redox-active drugs—Differential effects as cancer therapeutics and protectors of normal tissue against oxidative injury. *Antioxid Redox Signal* (2018).

131. Oronsky, B., et al. A Review of Clinical Radioprotection and Chemoprotection for Oral Mucositis. *Transl Oncol* 11, 771-778 (2018).

132. Anderson, C. M., et al. Phase 1b/2a Trial of the Superoxide Dismutase Mimetic GC4419 to Reduce Chemoradiotherapy-Induced Oral Mucositis in Patients With Oral Cavity or Oropharyngeal Carcinoma. *Int J Radiat Oncol Biol Phys* (2017).

133. Kim, H. S., et al. SIRT2 maintains genome integrity and suppresses tumorigenesis through regulating APC/C activity. *Cancer Cell* 20, 487-499 (2011).

134. Sorlie, T., et al. Repeated observation of breast tumor subtypes in independent gene expression data sets. *Proc Natl Acad Sci USA* 100, 8418-8423 (2003).

135. Brenton, J. D., Carey, L. A., Ahmed, A. A. & Caldas, C. Molecular classification and molecular forecasting of breast cancer: ready for clinical application?*J Clin Oncol* 23, 7350-7360 (2005).

136. Gyorffy, B. & Schafer, R. Meta-analysis of gene expression profiles related to relapse-free survival in 1,079 breast cancer patients. *Breast Cancer Res Treat* 118, 433-441 (2009).

137. Turner, N.C., et al. Cyclin E1 Expression and Palbociclib Efficacy in Previously Treated Hormone Receptor-Positive Metastatic Breast Cancer. *J Clin Oncol* 37, 1169-1178 (2019).

138. Helczynska, K., et al. Hypoxia-inducible factor-2alpha correlates to distant recurrence and poor outcome in invasive breast cancer. *Cancer Res* 68, 9212-9220 (2008).

139. Mimeault, M. & Batra, S. K. Hypoxia-inducing factors as master regulators of sternness properties and altered metabolism of cancer- and metastasis-initiating cells. *J Cell Mol Med* 17, 30-54 (2013).

140. Gordan, J. D. & Simon, M. C. Hypoxia-inducible factors: central regulators of the tumor phenotype. *Curr Opin Genet Dev* 17, 71-77 (2007).

141. Saitou, M., et al. Mitochondrial ultrastructure-associated chemotherapy response in ovarian cancer. *Oncol Rep* 21, 199-204 (2009).

142. Luo, B., Groenke, K., Takors, R., Wandrey, C. & Oldiges, M. Simultaneous determination of multiple intracellular metabolites in glycolysis, pentose phosphate pathway and tricarboxylic acid cycle by liquid chromatography-mass spectrometry. *J ChromatogrA* 1147, 153-164 (2007).

143. Tang, B., et al. A flexible reporter system for direct observation and isolation of cancer stem cells. *Stem Cell Reports* 4, 155-169 (2015).

144. Kuroda, T., et al. Octamer and Sox elements are required for transcriptional cis regulation of Nanog gene expression. *Mol Cell Biol* 25, 2475-2485 (2005).

145. Rahbari, M., et al. Hydrogen peroxide dynamics in subcellular compartments of malaria parasites using genetically encoded redox probes. *Sci Rep* 7, 10449 (2017).

146. Zhang, K., et al. Current Stem Cell Biomarkers and Their Functional Mechanisms in Prostate Cancer. *Int J Mol Sci* 17(2016).

147. Nazio, F., Bordi, M., Cianfanelli, V., Locatelli, F. & Cecconi, F. Autophagy and cancer stem cells: molecular mechanisms and therapeutic applications. *Cell Death Differ* 26, 690-702 (2019).

148. Zhu, C., et al. Hypoxia-inducible factor-2 alpha promotes the proliferation of human placenta-derived mesenchymal stem cells through the MAPK/ERK signaling pathway. *Sci Rep* 6, 35489 (2016).

149. Han, S., et al. Association Between Hypoxia-Inducible Factor-2alpha (HIF-2alpha) Expression and Colorectal Cancer and Its Prognostic Role: a Systematic Analysis. *Cell Physiol Biochem* 48, 516-527 (2018).

150. Razandi, M., Pedram, A., Jordan, V. C., Fuqua, S. & Levin, E. R. Tamoxifen regulates cell fate through mitochondrial estrogen receptor beta in breast cancer. *Oncogene* 32, 3274-3285 (2013).

151. Li, M., et al. Estrogen receptor beta upregulated by lncRNA-H19 to promote cancer stem-like properties in papillary thyroid carcinoma. *Cell Death Dis* 9, 1120 (2018).

152. Kocaturk, B. & Versteeg, H. H. Orthotopic injection of breast cancer cells into the mammary fat pad of mice to study tumor growth. *J Vis Exp* (2015).
153. Visonneau, S., Cesano, A., Torosian, M. H., Miller, E. J. & Santoli, D. Growth characteristics and metastatic properties of human breast cancer xenografts in immunodeficient mice. *Am J Pathol* 152, 1299-1311 (1998).
154. Anderson, C. M., et al. Phase IIb, Randomized, Double-Blind Trial of GC4419 Versus Placebo to Reduce Severe Oral Mucositis Due to Concurrent Radiotherapy and Cisplatin For Head and Neck Cancer. *J Clin Oncol* 37, 3256-3265 (2019).
155. Zhou, H., Yuan, Y. & Nie, L. Accuracy, Safety, and Reliability of Novel Phase I Trial Designs. *Clin Cancer Res* 24, 4357-4364 (2018).
156. Yuan, Y., Hess, K. R., Hilsenbeck, S. G. & Gilbert, M. R. Bayesian Optimal Interval Design: A Simple and Well-Performing Design for Phase I Oncology Trials. *Clin Cancer Res* 22, 4291-4301 (2016).
157. Cornen, S., et al. Candidate luminal B breast cancer genes identified by genome, gene expression and DNA methylation profiling. *PLoS One* 9, e81843 (2014).
158. Zhang, X., Yang, H. & Zhang, R. Challenges and future of precision medicine strategies for breast cancer based on a database on drug reactions. *Biosci Rep* (2019).
159. Kim, T., et al. A basal-like breast cancer-specific role for SRF-IL6 in YAP-induced cancer stemness. *Nat Commun* 6, 10186 (2015).
160. Anderson, C. M., et al. Phase 1b/2a Trial of the Superoxide Dismutase Mimetic GC4419 to Reduce Chemoradiotherapy-Induced Oral Mucositis in Patients With Oral Cavity or Oropharyngeal Carcinoma. *Int J Radiat Oncol Biol Phys* (2017).
161. Land, H., Chen, A. C., Morgenstern, J. P., Parada, L. F. & Weinberg, R. A. Behavior of myc and ras oncogenes in transformation of rat embryo fibroblasts. *Mol Cell Biol* 6, 1917-1925 (1986).
162. Sarsour, E. H., Venkataraman, S., Kalen, A. L., Oberley, L. W. & Goswami, P. C. Manganese superoxide dismutase activity regulates transitions between quiescent and proliferative growth. *Aging Cell* 7, 405-417 (2008).
163. Lammers, M. Expression and Purification of Site-Specifically Lysine-Acetylated and Natively-Folded Proteins for Biophysical Investigations. *Methods Mol Biol* 1728, 169-190 (2018).
164. Oronsky, B., et al. A Review of Clinical Radioprotection and Chemoprotection for Oral Mucositis. *Transl Oncol* 11, 771-778 (2018)
165. Kuroda, T., et al. Octamer and Sox elements are required for transcriptional cis regulation of Nanog gene expression. *Mol Cell Biol* 25, 2475-2485 (2005).
166. Rahbari, M., et al. Hydrogen peroxide dynamics in subcellular compartments of malaria parasites using genetically encoded redox probes. *Sci Rep* 7, 10449 (2017).
167. Namekawa, T., Ikeda, K., Horie-Inoue, K. & Inoue, S. Application of Prostate Cancer Models for Preclinical Study: Advantages and Limitations of Cell Lines, Patient-Derived Xenografts, and Three-Dimensional Culture of Patient-Derived Cells. *Cells* 8(2019).
168. Njoroge, R. N., et al. Organoids model distinct Vitamin E effects at different stages of prostate cancer evolution. *Sci Rep* 7, 16285 (2017).
169. Unno, K., et al. Modeling African American prostate adenocarcinoma by inducing defined genetic alterations in organoids. *Oncotarget* 8, 51264-51276 (2017).
170. Han, H., et al. Small-Molecule MYC Inhibitors Suppress Tumor Growth and Enhance Immunotherapy. *Cancer Cell* 36, 483-497 e415 (2019).
171. Anderson, P. D., et al. Nkx3.1 and Myc crossregulate shared target genes in mouse and human prostate tumorigenesis. *J Clin Invest* 122, 1907-1919 (2012).
172. Wang, J., et al. Pim1 kinase synergizes with c-MYC to induce advanced prostate carcinoma. *Oncogene* 29, 2477-2487 (2010).
173. Zhang, K., et al. Current Stem Cell Biomarkers and Their Functional Mechanisms in Prostate Cancer. *International journal of molecular sciences* 17(2016).
174. Nazio, F., Bordi, M., Cianfanelli, V., Locatelli, F. & Cecconi, F. Autophagy and cancer stem cells: molecular mechanisms and therapeutic applications. *Cell death and differentiation* 26, 690-702 (2019).
175. Yoo, Y. A., et al. Bmil marks distinct castration-resistant luminal progenitor cells competent for prostate regeneration and tumour initiation. *Nat Commun* 7, 12943 (2016).
176. Holder, S. L. & Abdulkadir, S. A. PIM1 kinase as a target in prostate cancer: roles in tumorigenesis, castration resistance, and docetaxel resistance. *Curr Cancer Drug Targets* 14, 105-114 (2014).
177. Kirschner, A. N., et al. PIM kinase inhibitor AZD1208 for treatment of MYC-driven prostate cancer. *J Natl Cancer Inst* 107(2015).
178. Coleman, M. C., et al. Superoxide mediates acute liver injury in irradiated mice lacking sirtuin 3. *Antioxid Redox Signal* 20, 1423-1435 (2014).
179. Mapuskar, K. A., et al. Mitochondrial Superoxide Increases Age-Associated Susceptibility of Human Dermal Fibroblasts to Radiation and Chemotherapy. *Cancer Res* 77, 5054-5067 (2017).
180. Saitou, M., et al. Mitochondrial ultrastructure-associated chemotherapy response in ovarian cancer. *Oncol Rep* 21, 199-204 (2009).
181. Luo, B., Groenke, K., Takors, R., Wandrey, C. & Oldiges, M. Simultaneous determination of multiple intracellular metabolites in glycolysis, pentose phosphate pathway and tricarboxylic acid cycle by liquid chromatography-mass spectrometry. *J Chromatogr A* 1147, 153-164 (2007).
182. Lee, M. C., et al. Genome-wide analysis of HIF-2alpha chromatin binding sites under normoxia in human bronchial epithelial cells (BEAS-2B) suggests its diverse functions. *Sci Rep* 6, 29311 (2016).
183. Jacobus, J. A., et al. Low-dose radiation-induced enhancement of thymic lymphomagenesis in Lck-Bax mice is dependent on LET and gender. *Radiat Res* 180, 156-165 (2013).
184. Cramer-Morales, K., Heer, C. D., Mapuskar, K. A. & Domann, F. E. SOD2 targeted gene editing by CRISPR/Cas9 yields Human cells devoid of MnSOD. *Free Radic Biol Med* 89, 379-386 (2015).
185. Zhu, C., et al. Hypoxia-inducible factor-2 alpha promotes the proliferation of human placenta-derived mesenchymal stem cells through the MAPK/ERK signaling pathway. *Sci Rep* 6, 35489 (2016).
186. Han, S., et al. Association Between Hypoxia-Inducible Factor-2alpha (HIF-2alpha) Expression and Colorectal Cancer and Its Prognostic Role: a Systematic Analysis. *Cell Physiol Biochem* 48, 516-527 (2018).
187. Yan, Y., et al. HIF-2alpha promotes conversion to a stem cell phenotype and induces chemoresistance in breast cancer cells by activating Wnt and Notch pathways. *J Exp Clin Cancer Res* 37, 256 (2018).

Certain examples herein were adapted from the article "Lysine 68 Acetylation Directs MnSOD as a Tetrameric Detoxification Complex Versus a Monomeric Tumor Promoter" by Zhu et al., Nature Communications (2019) 10:2399, published online Jun. 3, 2019. This article was published under a Creative Commons Attribution 4.0 International License, a copy of which can be viewed at http://creativecommons.org/licenses/by/4.0/.

What is claimed is:

1. A method for treating a cancer in a mammalian subject, wherein the method comprises administering to the subject in need thereof a therapeutically effective amount of:

(a) an anticancer therapy selected from the group consisting of a cell cycle inhibitor, a chemotherapeutic agent, a dose of ionizing radiation, a therapeutic agent that inhibits a hormone receptor pathway associated with growth of the cancer, and a therapeutic agent that inhibits a hormone receptor pathway associated with progression of the cancer; and (b) Compound (4419):

(4419)

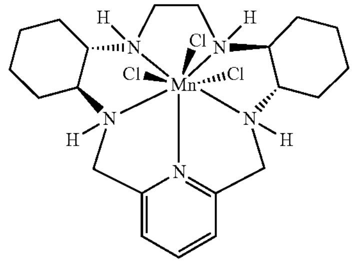

wherein the mammalian subject is afflicted with the cancer and has resistance to the anti-cancer therapy, or the mammalian subject is afflicted with the cancer and has a tumor signature indicative of dysregulation of the MnSOD-Ac-K68/ROS/HIF2α axis;

wherein the therapeutically effective amount of the anticancer therapy is administered to the subject in need thereof prior to, concomitantly with, or after administration of the therapeutically effective amount of Compound (4419); and wherein the cancer and/or tumor is selected from the group consisting of breast cancer, a desmoid tumor, endometrial cancer, glioblastoma, glioma, head and neck cancer, hepatocellular carcinoma, melanoma, ovarian cancer, pancreatic carcinoma, prostate cancer, renal cell carcinoma, and testicular cancer.

2. The method of claim 1, wherein the method comprises administering to the subject in need thereof a therapeutically effective amount of (a) an anticancer therapy comprising a cell cycle inhibitor.

3. The method of claim 1, wherein the method comprises administering to the subject in need thereof a therapeutically effective amount of (a) an anticancer therapy comprising a chemotherapeutic agent.

4. The method of claim 3, wherein the chemotherapeutic agent is:

(i) at least one platinum-containing chemotherapeutic agent selected from the group consisting of cisplatin, carboplatin, dicycloplatin, heptaplatin, LA-12, lipoplatin, lobaplatin, nedaplatin, oxaliplatin, phenanthriplatin, phosphaplatin, picoplatin, prolindac, satraplatin, and triplatin tetranitrate; or (ii) at least one anthracycline chemotherapeutic agent selected from the group consisting of daunorubicin, doxorubicin, epirubicin, and idarubicin.

5. The method of claim 1, wherein the method comprises administering to the subject in need thereof a therapeutically effective amount of (a) an anticancer therapy comprising a dose of ionizing radiation.

6. The method of claim 1, wherein the method comprises administering to the subject in need thereof a therapeutically effective amount of (a) an anticancer therapy comprising a therapeutic agent that inhibits a hormone receptor pathway associated with growth of the cancer or a therapeutic agent that inhibits a hormone receptor pathway associated with progression of the cancer.

7. The method of claim 6, wherein the therapeutic agent that inhibits a hormone receptor pathway associated with growth of the cancer or the therapeutic agent that inhibits a hormone receptor pathway associated with progression of the cancer is selected from the group consisting of an aromatase inhibitor, a cyclin dependent kinase 4 (CDK4) inhibitor, a cyclin dependent kinase 6 (CDK6) inhibitor, an estrogen receptor degrader, an estrogen receptor downregulator, an estrogen receptor inhibitor, a gonadotropin-releasing hormone (GnRH) agonist, and a selective estrogen receptor modulator (SERM), or a combination thereof.

8. The method of claim 7, wherein the aromatase inhibitor, cyclin dependent kinase 4 (CDK4) inhibitor, cyclin dependent kinase 6 (CDK6) inhibitor, estrogen receptor degrader, estrogen receptor downregulator, estrogen receptor inhibitor, gonadotropin-releasing hormone (GnRH) agonist, or selective estrogen receptor modulator (SERI), or combination thereof, is selected from the group consisting of abemaciclib, bazedoxifene, brilanestrant, clomifene, elacestrant, fulvestrant, lasofoxifene, nafoxidine, ospemifene, palbociclib, raloxifene, ribociclib, tamoxifen, 4-hydroxytamoxifen, and toremifene.

9. The method of claim 8, wherein:

(a) the cancer and/or tumor is breast cancer; and (b) the cyclin dependent kinase 4 (CDK4) inhibitor and/or cyclin dependent kinase 6 (CDK6) inhibitor is palbociclib.

10. The method of claim 1, wherein the cancer and/or tumor is breast cancer or prostate cancer.

11. The method of claim 1, wherein the cancer and/or tumor is breast cancer.

* * * * *